United States Patent
Sinha

(10) Patent No.: US 10,993,418 B2
(45) Date of Patent: May 4, 2021

(54) METHOD FOR MEASURING TUMOR BURDEN IN PATIENT DERIVED XENOGRAFT (PDX) MICE

(71) Applicant: Life Genetics Lab, LLC, New Orleans, LA (US)

(72) Inventor: Sudhir Sinha, New Orleans, LA (US)

(*) Notice: Subject to any disclaimer, the term of this patent is extended or adjusted under 35 U.S.C. 154(b) by 85 days.

(21) Appl. No.: 15/967,397

(22) Filed: Apr. 30, 2018

(65) Prior Publication Data

US 2018/0288982 A1  Oct. 11, 2018

Related U.S. Application Data

(63) Continuation-in-part of application No. 14/983,397, filed on Dec. 29, 2015, and a continuation-in-part of application No. 13/964,970, filed on Aug. 12, 2013, now Pat. No. 9,957,557.

(60) Provisional application No. 62/562,287, filed on Sep. 22, 2017, provisional application No. 62/118,666, filed on Feb. 20, 2015, provisional application No. 62/097,400, filed on Dec. 29, 2014, provisional application No. 61/793,595, filed on Mar. 15, 2013, provisional application No. 61/767,668, filed on Feb. 21, 2013, provisional application No. 61/682,507, filed on Aug. 13, 2012.

(51) Int. Cl.
| | |
|---|---|
| *C12Q 1/6886* | (2018.01) |
| *C12Q 1/6809* | (2018.01) |
| *C12Q 1/6827* | (2018.01) |
| *C12Q 1/686* | (2018.01) |
| *C12Q 1/6851* | (2018.01) |
| *A01K 67/027* | (2006.01) |
| *C12Q 1/6811* | (2018.01) |

(52) U.S. Cl.
CPC ...... *A01K 67/0271* (2013.01); *A01K 67/0276* (2013.01); *C12Q 1/686* (2013.01); *C12Q 1/6809* (2013.01); *C12Q 1/6811* (2013.01); *C12Q 1/6827* (2013.01); *C12Q 1/6886* (2013.01); *A01K 2207/12* (2013.01); *A01K 2207/15* (2013.01); *A01K 2217/075* (2013.01); *A01K 2217/15* (2013.01); *A01K 2227/105* (2013.01); *A01K 2267/0331* (2013.01); *C12N 2320/10* (2013.01); *C12Q 1/6851* (2013.01); *C12Q 2561/101* (2013.01); *C12Q 2561/113* (2013.01); *C12Q 2600/112* (2013.01); *C12Q 2600/16* (2013.01)

(58) Field of Classification Search
CPC .... C12Q 1/686; C12Q 1/6886; C12Q 1/6851; C12Q 2561/101; C12Q 2561/113; C12Q 2600/112
See application file for complete search history.

(56) References Cited

U.S. PATENT DOCUMENTS

| | | | |
|---|---|---|---|
| 5,210,015 | A | 5/1993 | Gelfand et al. |
| 5,487,972 | A | 1/1996 | Gelfand et al. |
| 5,925,517 | A | 7/1999 | Tyagi et al. |
| 6,103,476 | A | 8/2000 | Tyagi et al. |
| 6,268,130 | B1 | 7/2001 | Kleyn et al. |
| 6,569,627 | B2 | 5/2003 | Wittwer et al. |
| 7,991,558 | B2 | 8/2011 | Kurnik |
| 8,551,707 | B2 | 10/2013 | Oeth et al. |
| 8,741,573 | B2 | 6/2014 | Sjoblom et al. |
| 8,835,110 | B2 | 9/2014 | Wang et al. |
| 2005/0009048 | A1 | 1/2005 | Sagner et al. |
| 2006/0099620 | A1 | 5/2006 | Walker et al. |
| 2006/0199217 | A1 | 9/2006 | Sinha et al. |
| 2006/0289312 | A1 | 12/2006 | Tremblay et al. |
| 2008/0206755 | A1 | 8/2008 | Sinha et al. |
| 2009/0068660 | A1 | 3/2009 | Hoon et al. |

(Continued)

FOREIGN PATENT DOCUMENTS

| | | |
|---|---|---|
| CN | 102134595 | 7/2011 |
| WO | 2004081186 | 9/2004 |

(Continued)

OTHER PUBLICATIONS

Schneider et al. Quantification of human Alu sequences by real-time PCR—an improved method to measure therapeutic efficacy of anti-metastatic drugs in human xenotransplants. Clinical & Experimental Metastasis 2002; 19: 571-582). (Year: 2002).*

(Continued)

*Primary Examiner* — Angela M. Bertagna
(74) *Attorney, Agent, or Firm* — Stonebridge IP, PLLC

(57) ABSTRACT

Kits and methods providing measurement of tumor burden in a patient derived xenograft (PDX) mouse are described. Exemplary embodiments contemplate taking a sample, typically a blood sample, from a PDX mouse and using a real-time polymerase chain reaction (PCR) system to quantitate both human patient circulating tumor DNA (ctDNA) and mouse DNA. In preferred embodiments, both PCR amplifications are done simultaneously in a multiplex, and a highly polymorphic human DNA target sequence is amplified for high sensitivity, allowing for small volume samples, typically 50-100 μL, of mouse blood. Serial evaluations are possible because the mouse can survive withdrawal of these small volumes of blood. A related method allows for quantitation of ctDNA in the presence of human immune cells added to a "humanized" mouse. These relatively quick and easy methods of determining tumor burden in PDX mice can have predictive value for the efficacy of cancer treatments in human patients.

14 Claims, 48 Drawing Sheets
(47 of 48 Drawing Sheet(s) Filed in Color)
Specification includes a Sequence Listing.

(56) References Cited

U.S. PATENT DOCUMENTS

| | | | |
|---|---|---|---|
| 2009/0280479 | A1 | 11/2009 | Hoon et al. |
| 2011/0021974 | A1 | 1/2011 | Shantha et al. |
| 2011/0151465 | A1 | 6/2011 | Hoon et al. |
| 2011/0159502 | A1 | 6/2011 | Hoon et al. |
| 2013/0143213 | A1 | 6/2013 | Oliphant et al. |
| 2014/0095080 | A1 | 4/2014 | Kurnik |
| 2016/0186239 | A1* | 6/2016 | Sinha ............... C12Q 2531/113 506/9 |

FOREIGN PATENT DOCUMENTS

| | | | |
|---|---|---|---|
| WO | 2006128192 | A2 | 11/2006 |
| WO | 2007100530 | | 9/2007 |
| WO | 2011042920 | | 4/2011 |
| WO | 2011153254 | A2 | 12/2011 |
| WO | 2012038503 | | 3/2012 |
| WO | 2012048113 | A2 | 4/2012 |
| WO | 2014143616 | A1 | 9/2014 |
| WO | 2014201092 | A1 | 12/2014 |

OTHER PUBLICATIONS

Schubert et al. Agonists and antagonists of GnRH-I and -II reduce metastasis formation by triple-negative human breast cancer cells in vivo. Breast Cancer Research and Treatment 2011; 130: 783-790. (Year: 2011).*

Becker et al. Sensitive PCR method for the detection and real-time quantification of human cells in xenotransplantation systems. British Journal of Cancer 2002; 87: 1328-1335. (Year: 2002).*

Rago et al. Serial Assessment of Human Tumor Burdens in Mice by the Analysis of Circulating DNA. Cancer Research 2007; 67: 9364-9370.. (Year: 2007).*

Arya et al. Basic principles of real-time quantitative PCR. Expert Review in Molecular Diagnostics 2005; 5: 209-219. (Year: 2005).*

Kubista et al. The real-time polymerase chain reaction. Molecular Aspects of Medicine 2006; 27: 95-125 (Year: 2006).*

Ginzinger, D.G. Gene quantification using real-time quantitative PCR: An emerging technology hits the mainstream. Experimental Hematology 2002; 30: 503-512 (Year: 2002).*

Ostertag, E.M. & Kazazian, H.H. Biology of mammalian L1 retrotransposons. Annual Review of Genetics 2001; 35: 501-538 (Year: 2001).*

Choi et al. Development of real-time PCR assays for detection and quantification of human bocavirus. Journal of Clinical Virology 2008; 42: 249-253 (Year: 2008).*

Versage et al. Development of a Multitarget Real-Time TaqMan PCR Assay for Enhanced Detection of Francisella tularensis in Complex Specimens. Journal of Clinical Microbiology 2003; 41: 5492-5499 (Year: 2003).*

Thurman et al. Detection of *Mycoplasma pneumoniae, Chlamydia pneumoniae,* and *Legionella* spp. in clinical specimens using a single-tube multiplex real-time PCR assay. Diagnostic Microbiology and Infectious Disease 2011; 70: 1-9 (Year: 2011).*

Tentler et al. Patient-derived tumour xenografts as models for oncology drug development. Nature Reviews Clinical Oncology 2012; 9: 338-350 (Year: 2012).*

Moro et al. Patient-Derived Xenografts of Non Small Cell Lung Cancer: Resurgence of an Old Model for Investigation of Modern Concepts of Tailored Therapy and Cancer Stem Cells. Journal of Biomedicine and Biotechnology 2012; Article ID 568567; doi: 10.1155/2012/568567 (Year: 2012).*

Nehmann et al. Comparison of two techniques for the screening of human tumor cells in mouse blood: Quantitative real-time polymerase chain reaction (qRT-PCR) versus laser scanning cytometry (LSC). Acta Histochemica 2010; 112: 489-496 (Year: 2010).*

Walker et al., Human DNA quantitation using Alu element-based polymerase chain reaction, Analytical Biochemistry, 315, 122-128, 2003 (Cited in Office action (Paper No. 7/2015) dated Jul. 29, 2015 of the parent U.S. Appl. No. 13/964,970, filed Aug. 12, 2013).

Wang et al., SVA Elements: A Hominid-specific Retroposon Family, J. Mol. Biol., 354, 994-1007, 2005 (Cited in Office action (Paper No. 7/2015) dated Jul. 29, 2015 of the parent U.S. Appl. No. 13/964,970, filed Aug. 12, 2013).

Hughes et al., Genomics and Genetics of Human and Primate Y Chromosomes, Annu. Rev. Genomics Hum. Genet., 13, 83-108, 2012 (Cited in Office action (Paper No. 7/2015) dated Jul. 29, 2015 of the parent U.S. Appl. No. 13/964,970, filed Aug. 12, 2013).

Matuk, Retinitis pigmentosa and retinal degeneration in animals: a review, Can. J. Biochem. Cell Biol., 62(6): 535-546, 1984, abstract (Cited in IDS filed on Oct. 29, 2015 of the parent U.S. Appl. No. 13/964,970, filed Aug. 12, 2013).

Nicklas et al., Development of an Alu-based, real-time PCR method for quantitation of human DNA in forensic samples, J. Forensic. Sci., 48(5): 936-944, 2003 (Cited in Office action (Paper No. 2/2016) dated Feb. 11, 2016 of the parent U.S. Appl. No. 13/964,970, filed Aug. 12, 2013).

Nicklas et al., Development of a Real-Time Method to Detect DNA Degradation in Forensic Samples, J. Forensic Sci., 57(2): 466-471, 2012 (Cited in Office action (Paper No. 2/2016) dated Feb. 11, 2016 of the parent U.S. Appl. No. 13/964,970, filed Aug. 12, 2013).

Chinese Office Action issued by Chinese Patent Office dated Mar. 21, 2016 in connection with Chinese Patent Application No. 201380052972.9 corresponding to U.S. Appl. No. 13/964,970 and Request for Entry of the Accompanying Office Action attached herewith (Cited in IDS filed on Apr. 26, 2016 of the parent U.S. Appl. No. 13/964,970, filed Aug. 12, 2013).

Swango et al., A quantitative PCR assay for the assessment of DNA degradation in forensic samples, Forensic Science International, 158, pp. 14-26, 2006 (Cited in IDS filed on Apr. 26, 2016 of the parent U.S. Appl. No. 13/964,970, filed Aug. 12, 2013).

Hudlow et al., A quadruplex real-time qPCR assay for the simultaneous assessment of total human DNA, human male DNA, DNA degradation and the presence of PCR inhibitors in forensic samples: A diagnostic tool for STR typing, Forensic Science International: Genetics 2, pp. 108-125, 2008 (Cited in IDS filed on Apr. 26, 2016 of the parent U.S. Appl. No. 13/964,970, filed Aug. 12, 2013).

European Search Report dated Mar. 15, 2016 by the European Patent Office in connection with European Patent Application No. 13829192.7 corresponding to U.S. Appl. No. 13/964,970 (Cited in IDS filed on Apr. 26, 2016 of the parent U.S. Appl. No. 13/964,970, filed Aug. 12, 2013).

Stangegaard et al., Evaluation of Four Automated Protocols for Extraction of DNA from FTA Cards, Journal of Laboratory Automation, 18(5): pp. 404-410, 2013 (Cited in IDS filed on Jun. 9, 2016 of the parent U.S. Appl. No. 13/964,970, filed Aug. 12, 2013).

Lee et al., Allelic discrimination by nick-translation PCR with fluorogenic probes, Nucleic Acids Research, 21(16): 3761-3766, 1993 (Cited in IDS filed on Apr. 11, 2017 of the parent U.S. Appl. No. 13/964,970, filed Aug. 12, 2013).

Tyagi et al., Molecular Beacons: Probes that Fluoresce upon Hybridization, Nature Biotechnology, 14, pp. 303-308, 1996 (Cited in IDS filed on Apr. 11, 2017 of the parent U.S. Appl. No. 13/964,970, filed Aug. 12, 2013).

Butler et al., The Development of Reduced Size STR Amplicons as Tools for Analysis of Degraded DNA, J. Forensic Sci., 48(5): 1054-1064, 2003 (Cited in IDS filed on Apr. 11, 2017 of the parent U.S. Appl. No. 13/964,970, filed Aug. 12, 2013).

Parsons et al., Application of novel "mini-amplicon" STR multiplexes to high volume casework on degraded skeletal remains, Forensic Science International: Genetics 1, 175-179, 2007 (Cited in IDS filed on Apr. 11, 2017 of the parent U.S. Appl. No. 13/964,970, filed Aug. 12, 2013).

Nicklas et al., Development of a Real-Time Method to Detect DNA Degradation in Forensic Samples, J. Forensic Sci., 57(2): 466-471, 2012 (Cited in IDS filed on Apr. 11, 2017 of the parent U.S. Appl. No. 13/964,970, filed Aug. 12, 2013).

Walker et al., Multiplex polymerase chain reaction for simultaneous quantitation of human nuclear, mitochondrial, and male Y-chromosome DNA: application in human identification, Analytical Biochemistry, 337, pp. 89-97, 2005 (Cited in IDS filed on Apr. 11, 2017 of the parent U.S. Appl. No. 13/964,970, filed Aug. 12, 2013).

(56) References Cited

OTHER PUBLICATIONS

Carter et al., Genome-wide analysis of the human Alu Yb-lineage, Human Genomics, 1(3): 167-178, 2004 (Cited in IDS filed on Apr. 11, 2017 of the parent U.S. Appl. No. 13/964,970, filed Aug. 12, 2013).

Shen et al., Structure and Genetics of the Partially Duplicated Gene RP Located Immediately Upstream of the Complement C4A and the C4B Genes in the HLA Class III Region, J. Biol. Chem., 269(11): 8466-8476, 1994 (Cited in IDS filed on Apr. 11, 2017 of the parent U.S. Appl. No. 13/964,970, filed Aug. 12, 2013).

Stewart et al., A Comprehensive Map of Mobile Element Insertion Polymorphisms in Humans, PLoS Genetics, 7(8): e1002236, 2011 (Cited in Notice of Allowance (Paper No. 11/2017) dated Dec. 13, 2017 of the parent U.S. Appl. No. 13/964,970, filed Aug. 12, 2013).

Hao et al., "Circulating cell-free DNA in serum as a biomarker for diagnosis and prognostic prediction of colorectal cancer", British Journal of Cancer (Oct. 14, 2014); 111(8), pp. 1482-1489, (Feb. 26, 2002), www.bjcancer.com, DOIL10.1038/bjc.2014.470, UK.

Garcia-Olmo et al., "Circulating nucleic acids in plasma and serum (CNAPS): applications in oncology", OncoTargets and Therapy (2013), vol. 2016:6, pp. 819-832, DOI: http://dx.doi.org/10.2147/OTT.S44668.

Nicklas et al., "Development of an Alu-based, Real-Time PCR Method for Quantitation of Human DNA in Forensic Samples", J Forensic Sci, Sep. 2003, vol. 48, No. 5, Paper ID JFS2002414_485, pp. 936-944, West Conshohocken, PA.

Yu et al., "Recent Advances in Clinical Applications of Circulating Cell-free DNA Integrity", Lab Med. 2014; 45 (1): 6-12, US, www.medscape.com/viewarticle/823418_print.

Sunami et al., "Multimarker Circulating DNA Assay for Assessing Blood of Prostate Cancer Patients", Clinical Chemistry (2009), vol. 55:3, pp. 559-567, USA.

Roth et al., "Circulating microRNAs as blood-based markers for patients with primary and metastatic breast cancer", Breast Cancer Research (2010) vol. 12, Issue 6:R90, Germany, http://breast-cancer-research.com/content/12/6/R90.

Agostini et al., "Circulating Cell-Free DNA: A Promising Marker of Pathologic Tumor Response in Rectal Cancer Patients Receiving Preoperative Chemoradiotherapy", Annals of Surgical Oncology, 2011, 18:2461-2468, DOI 10.1245/s10434-011-1638-y, USA.

Mead et al., "Circulating tumour markers can define patients with normal colons, benign polyps, and cancers", British Journal of Cancer (2011) 105, pp. 239-245, UK.

Shen et al., "Diagnosis of lung cancer in individuals with solitary pulmonary nodules by plasma microRNA biomarkers", BioMed Central Cancer (2011), 11:374, pp. 1-9, Baltimore, MD USA, http://www.biomedcentral.com/1471-2407/11/374.

Hassanein et al., "The State of Molecular Biomarkers for the Early Detection of Lung Cancer", Cancer Prev Res (Phila), Aug. 2012; 5(8): 992-1006. doi:10.01158/1940-6207.CAPR-11-0441, Nashville, TN.

Schwarzenbach et al., "Cell-free nucleic acids as biomarkers in cancer patients", Nature Reviews Cancer, May 12, 2011; doi:10.1038/nrc3066, pp. 426-437, USA.

Umetani et al., "Increased Integrity of Free Circulating DNA in sera of Patients with Colorectal or Periampullary Cancer: Direct Quantitative PCR for ALU Repeats", Clinical Chemistry (2006), 52:6, pp. 1062-1069, USA.

Umetani et al., "Prediction of Breast Tumor Progression by Integrity of Free Circulating DNA in Serum", Journal of Clinical Oncology, vol. 24, No. 26, Sep. 10, 2006, pp. 4270-4276, USA.

\* cited by examiner

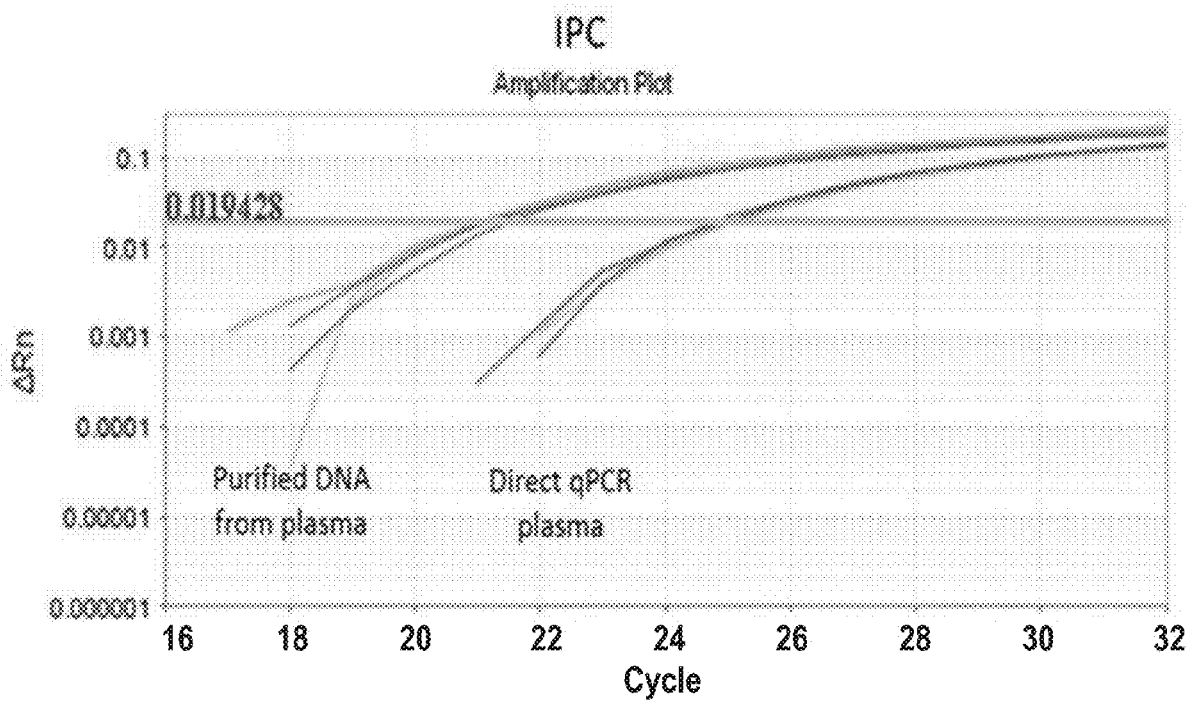
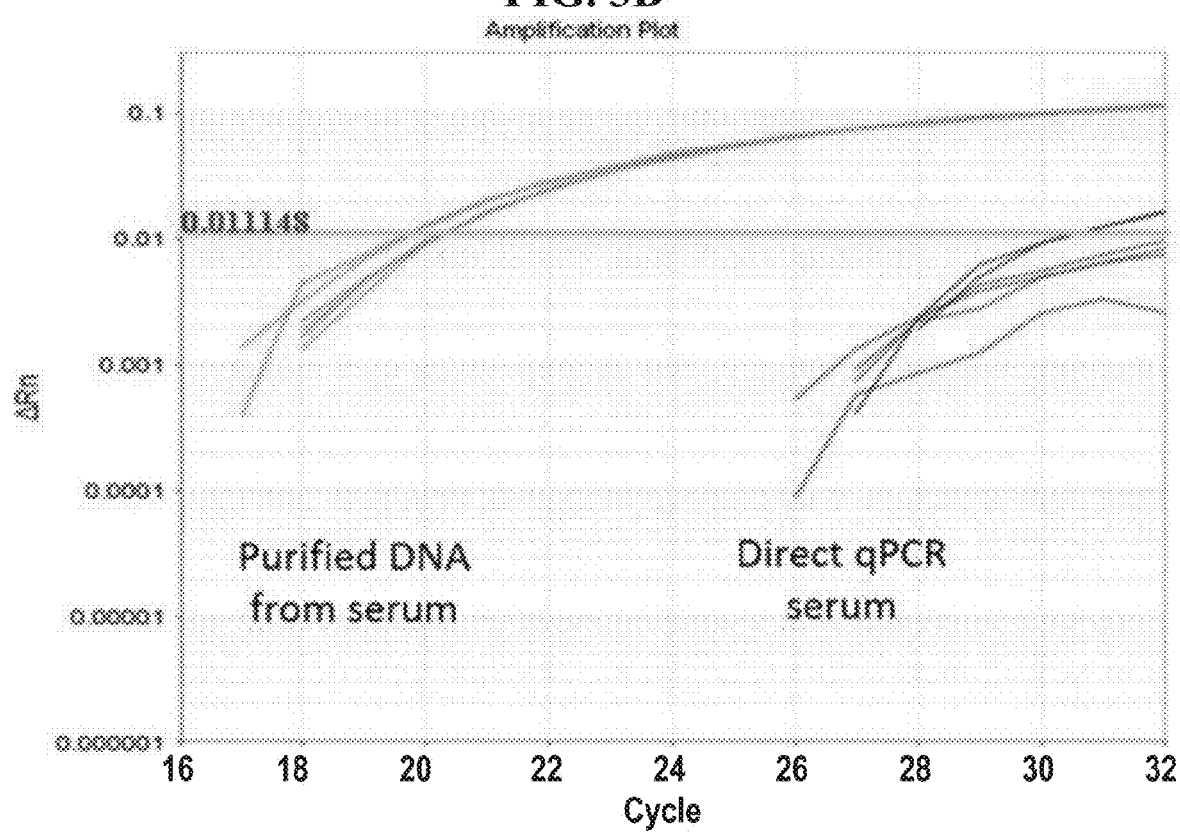

*Degradation ratios > 99%

FIG. 19
DEGRADATION GP
Control-
13% DR
1 hour-
85% DR
3 hour-
99% DR
FIG. 20
Control-
13% DR
5 min
25% DR
15 min
81% DR
30 min
96% DR
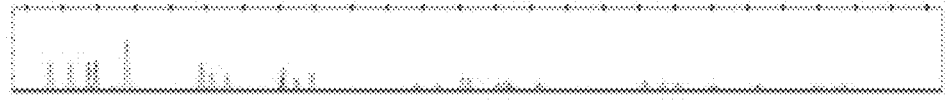

DEGRADATION GP

Amplification Plot

Standard Curve

METHOD FOR MEASURING TUMOR BURDEN IN PATIENT DERIVED XENOGRAFT (PDX) MICE

CLAIM OF PRIORITY

This application makes reference to, claims all benefits accruing under 35 U.S.C. § 120 from, and is a Continuation-in-Part of a U.S. non-provisional patent application for DEVELOPMENT OF A HIGHLY SENSITIVE QUANTIFICATION SYSTEM FOR ASSESSING DNA DEGRADATION AND QUALITY IN FORENSIC SAMPLES, earlier filed in the United States Patent and Trademark Office under 35 U.S.C. § 111(a) on 12 Aug. 2013 and duly assigned Ser. No. 13/964,970, which is incorporated into this application by reference, and which in turn, timely made reference to, incorporated the same therein and claimed all benefits accruing under 35 U.S.C. § 119(e) from other applications of the same title earlier filed in the United States Patent and Trademark Office as provisional applications under 35 U.S.C. § 111(b) on 13 Aug. 2012 and duly assigned Ser. No. 61/682,507, on 21 Feb. 2013 and duly assigned Ser. No. 61/767,668 and on 15 Mar. 2013 and duly assigned Ser. No. 61/793,595, makes reference to, incorporates the same herein and claims all benefits accruing under 35 U.S.C. § 120 from, and is a Continuation-in-Part of a U.S. non-provisional patent application for MULTIPLEXED ASSAY FOR QUANTITATING AND ASSESSING INTEGRITY OF CELL-FREE DNA IN BIOLOGICAL FLUIDS FOR CANCER DIAGNOSIS, PROGNOSIS AND SURVEILLANCE, earlier filed in the United States Patent and Trademark Office under 35 U.S.C. § 111(a) on 29 Dec. 2015 and duly assigned Ser. No. 14/983,397, which is incorporated into this application by reference, and which in turn, timely made reference to, incorporated the same therein and claimed all benefits accruing under 35 U.S.C. § 119(e) from other applications of the same title earlier filed in the United States Patent and Trademark Office as provisional applications under 335 U.S.C. § 111(b) on 29 Dec. 2014 and duly assigned Ser. No. 62/097,400 and on 20 Feb. 2015 and duly assigned Ser. No. 62/118,666, and makes reference to, incorporates the same herein and claims all benefits accruing under 35 U.S.C. § 119(e) from another application entitled A METHOD TO MEASURE TUMOR BURDEN IN PATIENT DERIVED XENOGRAPH (PDX) MICE, earlier filed in the United States Patent and Trademark Office as a provisional application under 35 U.S.C. § 111(b) on 22 Sep. 2017 and duly assigned Ser. No. 62/562,287.

STATEMENT REGARDING FEDERALLY SPONSORED RESEARCH OR DEVELOPMENT

This invention was made with U.S. Government support under SBIR grant #1230352 awarded by the National Science Foundation. The U.S. Government has certain rights in this invention.

NUCLEOTIDE SEQUENCE LISTING

An ASCII text file including nucleotide sequences of interest in the present application is being filed concurrently with the present application in the United States Patent and Trademark Office and is hereby incorporated by reference. The aforementioned ASCII text file is named primersprobesPDX_ST25.txt, was created on 30 Apr. 2018 and has a size of 17 kilobytes.

STATEMENT OF APPLICABILITY OF AMERICA INVENTS ACT

This application claims the benefit of the filing date of a provisional application filed prior to 16 Mar. 2013 and also contains claim(s) to a claimed invention that has an effective filing date as defined in 37 C.F.R. § 1.109 that is on or after 16 Mar. 2013.

BACKGROUND OF THE INVENTION

Field of the Invention

A highly sensitive method for measuring tumor burden in patient derived xenograft (PDX) mice by quantitating patient circulating tumor DNA (ctDNA) and/or circulating tumor cell DNA (ctcDNA) using a quantitative polymerase chain reaction (qPCR) technique. The accuracy, precision and sensitivity made possible by the disclosed qPCR method using newly identified target elements allows for reliable quantitation of ctDNA and/or ctcDNA, and thus tumor burden, from a small volume of mouse blood, serial measurements using samples from the same mouse and characterization of an extent of degradation of ctDNA.

Description of the Related Art

PDX Mice

Animal models have been used in predicting efficacy and evaluating toxicity for cancer chemotherapeutic agents for the last two decades. Morton, et al., *Establishment of human tumor xenografts in immunodeficient mice*, Nature Protocols 2007, 2(2): 247-50. Many different animal models have been developed over the years to accomplish these tasks of predicting efficacy and evaluating toxicity. The discovery of T-cell deficient nude athymic mice made it possible to allow transplantation and propagation of human tumor tissues (xenografts) in mice. An athymic mouse is a laboratory mouse that lacks a thymus gland. Athymic mice have no T cells and are therefore useful in research because they do not reject tumor or other cells transplanted from mice, humans or other species. Several types of immune-deficient mice have been established using either various tumor cell lines or patient derived human tumor tissues obtained from biopsy or autopsy.

A patient derived xenograft (PDX) mouse is created when cancerous tissue from a patient's primary tumor is implanted directly into an immunodeficient mouse. Although early PDX models provided solutions to the challenges that researchers faced in cancer drug research, such as by providing positive tumor responses in mouse models, these successes were frequently not reflected in successful treatment of human cancers. The development of the immune-deficient nude mouse was a key factor in reversing this trend. Today, PDX cancer models are popular models for use in cancer drug research. PDX models offer a powerful tool for studying tumor biology and evaluating oncologic therapy, and include preclinical research, screening platforms for clinical drug trials, personalized cancer therapy ("Mouse Avatars"), and enable the discovery of biomarkers predicting oncologic drug sensitivity and resistance.

Impetus for the Invention

Cancer is one of the leading causes of death in developed, and increasingly also developing, nations. According to the World Health Organization, in 2012, over 14 million new cases were reported and over 8 million people died worldwide (Atlanta: American Cancer Society, Cancer Facts & FIGs, 2014). Colorectal cancer (CRC) is the third most commonly diagnosed cancer and third-leading cause of cancer deaths in the United States. In 2014, nearly 140,000 diagnoses and 50,000 deaths are expected in the U.S. (Atlanta: American Cancer Society, Colorectal Cancer: Facts & FIGS. 2014-2016). CRC is often curable if detected early, and outcomes can be improved with post-treatment monitoring and surveillance for recurrence.

Effective cancer management depends on early diagnosis, accurate tumor staging, and consistent monitoring.

SUMMARY OF THE INVENTION

One object of the present invention is to detect human ctDNA against a background of mouse cfDNA in a qPCR multiplex, thereby measuring a tumor burden in a PDX mouse and facilitating observation of the growth of a human tumor in a PDX mouse.

Another object of the invention is to perform useful qPCR using samples of small microliter volumes (e.g., 100 µL) of mouse blood, enabling serial monitoring of DNA concentrations and thus tumor burden without killing the mouse.

Another object of the invention is to perform qPCR reactions to quantitate DNA with high enough PCR efficiency and sensitivity to obtain accurate quantitation results using volumes of mouse blood of about 200 microliters or less.

Another object of the invention is to quantitate both human DNA and mouse DNA in a mixture of the two, thus facilitating an assessment of a tumor burden in a PDX mouse.

Another object of the invention is to ensure that qPCR reactions to quantitate human and mouse DNAs proceed without cross reactivity between human and mouse DNAs.

Another object of the invention is to measure a tumor burden in a humanized PDX mouse by selectively monitoring specific human patient DNA markers in the blood of the mouse, where the specific human patient DNA markers are not amplified when the human immune cells that were used to form the humanized mouse are subjected to PCR amplification conditions.

Another object of the invention is to allow the identification of tumors that are growing in PDX mice based on the presence of human ctDNA in the corresponding xenograft models.

Another object of the invention is to provide researchers with a means for deciding how long to keep PDX mouse models waiting in anticipation of tumor growth.

Another object of the invention is to assist in the development of a new quality management regime for actively managing scientific decisions relating to cancer diagnosis or treatment.

Another object of the invention is to assist in the development of a new process for building PDX mouse models.

Another object of the invention is to assist researchers in evaluating the efficacies of prospective oncologic drugs being studied in PDX models by plotting ctDNA and/or ctcDNA levels in PDX mouse models versus time.

Another object of the invention is to provide a way to quantitatively characterize an extent of degradation of cfDNA and ctDNA, thereby allowing researchers a means for characterizing the type of cell disruption (i.e., cell death) that released the respective DNAs into a mouse bloodstream.

Another object of the invention is to provide a method for measuring tumor burden in a patient derived xenograft (PDX) mouse, the method comprising: providing a sample taken from a patient derived xenograft (PDX) mouse; using a real-time polymerase chain reaction system to separately quantitate within the sample human DNA including a first retrotransposon interspersed element and mouse DNA including a mouse retrotransposon interspersed element, the first retrotransposon interspersed element being an Alu element found in the human genome or an SVA element of the human retinitis pigmentosa (RP) gene, the mouse retrotransposon interspersed element being found in the genome of the mouse; and assessing a tumor burden based on said quantitations. Another object of the invention is to provide a kit for measuring tumor burden in a PDX mouse according to the latter method.

Another object of the invention is to provide a method for measuring circulating tumor cell DNA derived from the tumor cells metastasizing by way of the plasma in the PDX mouse, the method comprising: providing a sample taken from a patient derived xenograft (PDX) mouse; using a real-time polymerase chain reaction system to separately quantitate within the sample human DNA from cells including a first retrotransposon interspersed element and mouse DNA including a mouse retrotransposon interspersed element, the first retrotransposon interspersed element being an *Alu* element found in the human genome or an SVA element of the human retinitis pigmentosa (RP) gene, the mouse retrotransposon interspersed element being found in the genome of the mouse; and assessing a tumor burden from cells based on said quantitations. Another object of the invention is to provide a kit for measuring tumor burden in cells in a PDX mouse according to the latter method.

In one embodiment of the present invention, the sample taken from the PDX mouse may be a blood sample.

In another embodiment of the present invention, the blood sample taken from the PDX mouse may have a volume of about 200 µL or less. In other embodiments, the blood sample taken from the PDX mouse may have a volume of from about 25 µL to about 100 µL. In still other embodiments, the blood sample taken from the PDX mouse may have a volume of 50 µL, 75 µL, 100 µL, 125 µL, 150 µL, 175 µL, or 200 µL.

In preferred embodiments of the present invention, the *Alu* element may be an *Alu* Yb8 target genetic sequence.

In certain embodiments of the present invention, the real-time polymerase chain reaction system may make use of a first set of nucleic acid sequences for quantitation of the *Alu* element, the first set of nucleic acid sequences including a forward primer having a structure defined as 5'-GGAAGCGGAGCTTGCAGTGA-3' (SEQ ID NO: 5), a reverse primer having a structure defined as 5'-AGACGGAGTCTCGCTCTGTCGC-3' (SEQ ID NO: 6) and a probe including a structure defined as 5'-AGATTGCGCCACTGCAGTCCGCAGT-3' (SEQ ID NO: 36), where a fluorescent label may reside on the probe (SEQ ID NO: 37). In some embodiments, the real-time polymerase chain reaction system may make use of a first set of nucleic acid sequences for quantitation of the SVA element, the first set of nucleic acid sequences including one of the following groups of nucleic acid sequences, where one group includes a forward primer having a structure defined as 5'-CTGTGTCCACTCAGGGTTAAAT-3' (SEQ ID NO: 38), a reverse primer having a structure defined as 5'-GAGGGAAGGTCAGCAGATAAAC-3' (SEQ ID NO: 39) and a probe including a structure defined as 5'-AAGGGCGGTGCAAGATGTGCTTTGTT-3' (SEQ ID NO: 10), another group includes a forward primer having a structure defined as 5'-CCTGTGCTCTCTGAAA-CATGTGCT-3' (SEQ ID NO: 41), a reverse primer having a structure defined as 5'-GATTTGGCAGGGT-CATGGGACAAT-3' (SEQ ID NO: 9) and a probe including a structure defined as 5'-AAGGGCGGTGCAA-GATGTGCTTTGTT-3' (SEQ ID NO: 10), and another group includes a forward primer having a structure defined as 5'-ATGTGCTGTGTCCACTCAGGGTTA-3' (SEQ ID NO: 11), a reverse primer having a structure defined as 5'-ATTCTTGGGTGTTTCTCACAGAGG-3' (SEQ ID NO: 13) and a probe including a structure defined as 5'-AAGGGCGGTGCAAGATGTGCTTTGTT-3' (SEQ ID NO: 10).

In certain embodiments of the present invention, the real-time polymerase chain reaction system may make use of a second set of nucleic acid sequences for quantitation of the mouse retrotransposon interspersed element, the second set of nucleic acid sequences including a forward primer having a structure defined as 5'-GACCAAGACTCGTGAG-GATAAC-3' (SEQ ID NO: 28), a reverse primer having a structure defined as 5'-CCAGTGTTGGGTCAGGTTTA-3' (SEQ ID NO: 29) and a probe including a structure defined as 5'-AGTCGTGGAGGTAGAAATATGGCAGAGA-3' (SEQ ID NO: 30), where a fluorescent label may reside on the probe (SEQ ID NO: 31).

In preferred embodiments of the present invention, the first retrotransposon interspersed element and the mouse retrotransposon interspersed element do not exhibit any significant cross reactivity with respect to real-time polymerase chain reaction amplification.

In embodiments of the present invention, the method for measuring tumor burden in a patient derived xenograft (PDX) mouse may further comprise determining a ratio of human DNA to mouse DNA in the sample using quantitation results provided by the real-time polymerase chain reaction system; and considering the ratio as an indication of an extent of tumor growth intensity in the mouse.

In embodiments of the present invention, the providing, using, determining and considering steps of the above method for measuring tumor burden in a patient derived xenograft (PDX) mouse may be performed multiple times in repetition over a time interval, the samples being taken serially from the same PDX mouse, the resulting ratios serving to characterize tumor growth in the mouse over time.

In embodiments of the present invention, the providing, using, determining and considering steps of the above method for measuring tumor burden in a patient derived xenograft (PDX) mouse may be performed on each of a series of samples, each sample being taken from a different PDX mouse, the resulting ratios serving to assist a researcher in selecting one or more PDX mice for further study.

In embodiments of the present invention, the above method for measuring tumor burden in a patient derived xenograft (PDX) mouse may further comprise treating the PDX mouse with a putative or potential anti-cancer drug prior to the providing step; and accepting the ratio as a predictor of likely efficacy of the drug in a human patient.

In preferred embodiments of the present invention, a PDX mouse may survive the taking of a sample for DNA analysis.

In preferred embodiments of the present invention, quantitation of the human DNA and quantitation of the mouse DNA may be performed simultaneously.

In some embodiments of the present invention, the sample taken from the PDX mouse in performance of a method for measuring tumor burden in a PDX mouse may be derived from circulating tumor cells metastasizing by way of the plasma in the PDX mouse, the assessed tumor burden being attributed to circulating tumor cells.

Certain embodiments of the present invention may comprise a method for measuring an extent of degradation of ctDNA in PDX mouse models, the method comprising: providing a sample that is taken from a PDX mouse; quantitating an amount of DNA based on a first retrotransposon interspersed element in the sample using a real-time polymerase chain reaction (PCR) technique, and quantitating an amount of DNA based on a second retrotransposon interspersed element in the sample using a real-time PCR technique, the first retrotransposon interspersed element being an *Alu* element found in the human genome, the second retrotransposon interspersed element being an SVA element of the human retinitis pigmentosa (RP) gene; determining a ratio of the amount of DNA based on the first retrotransposon interspersed element to the amount of DNA based on the second retrotransposon interspersed element in the sample; and assessing an extent of degradation of the human ctDNA in the sample based on said ratio. Embodiments of the present invention may include a kit for measuring an extent of degradation of ctDNA in a PDX mouse model according to the latter method.

Certain embodiments of the present invention may comprise a kit for assessing an extent of degradation of human DNA in a sample comprising human DNA, the kit comprising: a primer mixture including a primer set corresponding to an *Alu* element found in the human genome and a primer set corresponding to an SVA element of the human retinitis pigmentosa (RP) gene, each primer set comprising a forward primer and a reverse primer and producing a corresponding amplicon using a real-time polymerase chain reaction system; and instructions indicating use of the primer mixture with the real-time polymerase chain reaction system to amplify human DNA in a sample comprising human DNA, determination of quantitative amounts of DNA in the sample based separately on amplification of the *Alu* element and amplification of the SVA element, calculation of a ratio of the quantity of DNA based on amplification of the *Alu* element to the quantity of DNA based on amplification of the SVA element, and use of said ratio as a measure of an extent of degradation of the human DNA in the sample. In such a kit, the sample may be a blood sample taken from a PDX mouse model, and the ratio may serve as an indication of an integrity of the human DNA in the sample.

In certain embodiments, the above-described kit may comprise a primer set corresponding to the *Alu* element including a forward primer having a structure defined as 5'-GGAAGCGGAGCTTGCAGTGA-3' (SEQ ID NO: 5) and a reverse primer having a structure defined as 5'-AGACGGAGTCTCGCTCTGTCGC-3' (SEQ ID NO: 6) and may comprise a primer set corresponding to the SVA element including a forward primer having a structure defined as 5'-CCTGTGCTCTCTGAAACATGTGCT-3' (SEQ ID NO: 41) and a reverse primer having a structure defined as 5'-GATTTGGCAGGGTCATGGGACAAT-3' (SEQ ID NO: 9).

Other embodiments of the present invention may comprise a kit enabling measurement of tumor burden in a PDX mouse, the kit comprising: a primer/probe mixture including at least one of a primer/probe set corresponding to an *Alu* target element found in the human genome and a primer/probe set corresponding to an SVA target element of the human retinitis pigmentosa (RP) gene and including a primer/probe set corresponding to a mouse retrotransposon interspersed element being found in the genome of the mouse, each primer/probe set comprising a forward primer, a reverse primer and a probe and forming a corresponding amplicon with a real-time polymerase chain reaction system; and instructions indicating use of the primer/probe mixture with the real-time polymerase chain reaction system for amplifying DNA from a sample taken from the PDX mouse, determination of a quantitative amount of DNA based separately on amplification of at least one of the *Alu* element and the SVA element and on amplification of the mouse retrotransposon interspersed element, calculation of a ratio of the quantity of DNA based on amplification of one of the human target element(s) to the quantity of DNA based on amplification of the mouse retrotransposon interspersed element, and use of said ratio as a measure of a tumor burden in the PDX mouse.

In certain embodiments, the aforementioned kit may include a primer/probe set corresponding to the *Alu* element including a forward primer having a structure defined as 5'-GGAAGCGGAGCTTGCAGTGA-3' (SEQ ID NO: 5), a reverse primer having a structure defined as 5'-AGACGGAGTCTCGCTCTGTCGC-3' (SEQ ID NO: 6) and a probe including a structure defined as 5'-AGATTGCGCCACTGCAGTCCGCAGT-3' (SEQ ID NO: 36) and/or a primer/probe set corresponding to the SVA element including one of the following groups of nucleic acid sequences, where one group includes a forward primer having a structure defined as 5'-CTGTGTCCACTCAGGGTTAAAT-3' (SEQ ID NO: 38), a reverse primer having a structure defined as 5'-GAGGGAAGGTCAGCAGATAAAC-3' (SEQ ID NO: 39) and a probe including a structure defined as 5'-AAGGGCGGTGCAAGATGTGCTTTGTT-3' (SEQ ID NO: 10), another group includes a forward primer having a structure defined as 5'-CCTGTGCTCTCTGAAACATGTGCT-3' (SEQ ID NO: 41), a reverse primer having a structure defined as 5'-GATTTGGCAGGGTCATGGGACAAT-3' (SEQ ID NO: 9) and a probe including a structure defined as 5'-AAGGGCGGTGCAAGATGTGCTTTGTT-3' (SEQ ID NO: 10), and another group includes a forward primer having a structure defined as 5'-ATGTGCTGTGTCCACTCAGGGTTA-3' (SEQ ID NO: 11), a reverse primer having a structure defined as 5'-ATTCTTGGGTGTTTCTCACAGAGG-3' (SEQ ID NO: 13) and a probe including a structure defined as 5'-AAGGGCGGTGCAAGATGTGCTTTGTT-3' (SEQ ID NO: 10).

In certain embodiments, the aforementioned kit may include a primer/probe set corresponding to the mouse including a forward primer having a structure defined as 5'-GACCAAGACTCGTGAGGATAAC-3' (SEQ ID NO: 28), a reverse primer having a structure defined as 5'-CCAGTGTTGGGTCAGGTTTA-3' (SEQ ID NO: 29) and a probe including a structure defined as 5'-AGTCGTGGAGGGTAGAAATATGGCAGAGA-3' (SEQ ID NO: 30).

Another object of the present invention is to provide a method of quantifying the extent of degradation present in a human DNA sample.

Another object of the invention is to provide a method for quantitating the total amount of human DNA as well as the male DNA in a sample.

Another object of the invention is to provide an internal positive control that will offer increased confidence in the results of the tumor burden determination and the results of the DNA degradation determination by providing an additional assessment for the presence of PCR inhibitors in the sample.

Another object of the invention is to provide a convenient means for analysts to choose from among multiple DNA samples the best one for further analytical attention.

Another object of the invention is to provide an improved means for selecting the optimum analytical method to employ on a particular DNA sample, based on the extent of its degradation.

Another object of the invention is to provide a means of assessing the extent of admixture of non-human DNA with the human DNA sample being tested.

Another object of the invention is to provide a means of assessing the extent of admixture of male and female DNA in the sample being tested.

These and other objects may be attained, in one embodiment of the present invention, from a process for quantitating a human DNA in a sample in order to assess the extent of degradation of the DNA or DNA Integrity (DII) therein by providing a sample to be analyzed, using a real time polymerase chain reaction system to separately quantitate within the sample a first retrotransposon interspersed element and a second retrotransposon interspersed element, the first retrotransposon interspersed element being an *Alu* element and the second retrotransposon interspersed element being an SVA element of the RP gene, and calculating a ratio of an occurrence within the sample of the first retrotransposon interspersed element to an occurrence of the second retrotransposon interspersed element.

In certain embodiments, the quantitation of the first retrotransposon interspersed element and the second retrotransposon interspersed element may be performed simultaneously.

In certain embodiments, the ratio of an occurrence within the sample of the first retrotransposon interspersed element to an occurrence of the second retrotransposon interspersed element may be used to determine an extent of degradation, or the DNA integrity of the DNA in the sample.

In certain embodiments, the second retrotransposon interspersed element may comprise at least two times as many base pairs as are comprised by the first retrotransposon interspersed element. In other embodiments, the second retrotransposon interspersed element may comprise at least three times as many base pairs as are comprised by the first retrotransposon interspersed element.

In certain embodiments, the process of the invention may further comprise the steps of providing a first probe comprising a first moiety capable of fluorescence at a first diagnostic wavelength and a first quencher capable of quenching the first moiety fluorescence, the first probe being targeted to a first retrotransposon interspersed element, providing a second probe comprising a second moiety capable of fluorescence at a second diagnostic wavelength and a second quencher capable of quenching the second moiety fluorescence, the second probe being targeted to a second retrotransposon interspersed element, providing at least one primer that is useful in the real-time polymerase chain reaction system, the system being capable of amplification of a DNA sample, providing a Taq polymerase enzyme capable of catalyzing the formation of a nucleic acid sequence that is complementary to one present in the sample, the polymerase enzyme being capable both of cleaving the first probe to separate the first fluorescent moiety from the first quencher and of cleaving the second probe to separate the second fluorescent moiety from the second quencher, treating the sample with the first probe and the second probe, amplifying the sample using the at least one primer and the Taq polymerase enzyme by means of the real-time polymerase chain reaction system, the real time polymerase chain reaction system including a plurality of polymerase chain reaction cycles, illuminating the sample during each real time polymerase chain reaction cycle using an excitation source capable of inducing fluorescence in both the first moiety and the second moiety, measuring the fluorescence emitted from the first moiety and the fluorescence emitted from the second moiety for each real time polymerase chain reaction cycle, determining a threshold cycle number for the first retrotransposon interspersed element and the second retrotransposon interspersed element, and comparing the determined threshold cycle numbers with standard curves for each of the first retrotransposon interspersed element and the second retrotransposon interspersed element to determine a concentration for each of the first retrotransposon interspersed element and the second retrotransposon interspersed element within the sample. When the DNA is degraded due to exposure to the environment, the amount of available longer target sequence for amplification will be less than a shorter target sequence, hence the ratio of quantities of the longer fragment to the shorter fragment in a given DNA sample is diagnostic of the extent of DNA degradation. In case of DNA which is not degraded or minimally degraded, the ratio of the two target amounts in the sample will be close to one.

In certain embodiments, the process for quantitating human DNA in a sample may further comprise providing at least one primer selected from the group consisting of a forward primer labeled SEQ ID NO: 5 and a reverse primer labeled SEQ ID NO: 6 (primers for the 80 base pair Yb8 *Alu* fragment) and providing at least one primer selected from the group consisting of forward primers labeled SEQ ID NOS: 11 and 41 and reverse primers labeled SEQ ID NO: 9 and 13 (primers for the 257 base pair and 265 base pair human SVA fragments):

```
5' GGAAGCGGAGCTTGCAGTGA 3'         (SEQ ID NO: 5)

5' AGACGGAGTCTCGCTCTGTCGC 3'       (SEQ ID NO: 6)

5' CCTGTGCTCTCTGAAACATGTGCT 3'     (SEQ ID NO: 41)

5' GATTTGGCAGGGTCATGGGACAAT 3'     (SEQ ID NO: 9)

5' ATGTGCTGTGTCCACTCAGGGTTA 3'     (SEQ ID NO: 11)

5' ATTCTTGGGTGTTTCTCACAGAGG 3'     (SEQ ID NO: 13)
```

Alternatively, in other embodiments, the approximately 80 base pair Yb8 *Alu* fragment may be paired with either a 207 base pair human SVA fragment or a 265 base pair SVA fragment to form a pair of target elements in the inventive process. In these embodiments, the process for quantitating human DNA in a sample may further comprise providing at least one primer selected from the group consisting of a forward primer labeled SEQ ID NO: 5 and a reverse primer labeled SEQ ID NO: 6 (primers for the 80 base pair Yb8 *Alu* fragment) and providing at least one primer selected from the group consisting of a forward primer labeled SEQ ID NO: 38, a reverse primer labeled SEQ ID NO: 39 (primers for the 207 base pair SVA fragment), a forward primer labeled SEQ ID NO: 11 and a reverse primer labeled SEQ ID NO: 13 (primers for the 265 base pair SVA fragment):

```
5' CTGTGTCCACTCAGGGTTAAAT 3'       (SEQ ID NO: 38)

5' GAGGGAAGGTCAGCAGATAAAC 3'       (SEQ ID NO: 39)
```

```
5' ATGTGCTGTGTCCACTCAGGGTTA 3'     (SEQ ID NO: 11)

5' ATTCTTGGGTGTTTCTCACAGAGG 3'     (SEQ ID NO: 13)
```

In certain embodiments, the first probe may have a sequence labeled SEQ ID NO: 37, where the fluorescent label may be HEX or FAM (for the 80 base pair Yb8 *Alu* fragment; fluorescent labels defined infra), and the second probe may have a sequence labeled SEQ ID NO: 40, where the fluorescent label may be Cy5, HEX, or FAM (for the SVA fragment):

```
                                       (SEQ ID NO: 37)
    5' [Label]AGATTGCGCCACTGCAGTCCGCAGT 3'

(SEQ ID NO: 40)
    5' [Label]AAGGGCGGTGCAAGATGTGCTTTGTT 3'
```

Alternatively, in another embodiment, the approximately 80 base pair Yb8 Alu fragment may be paired with the approximately 250 base pair *Alu* Ya5 fragment as target elements in the inventive process. In these embodiments, the process for quantitating human DNA in a sample may further comprise providing at least one primer selected from the group consisting of a forward primer labeled SEQ ID NO: 5 and a reverse primer labeled SEQ ID NO: 6 (primers for the 79 base pair Yb8 *Alu* fragment) and providing at least one primer selected from the group consisting of a forward primer labeled SEQ ID NO: 1, a forward primer labeled SEQ ID NO: 2 and a reverse primer labeled SEQ ID NO: 3 (primers for the 250 base pair *Alu* Ya5 fragment):

```
5' GGAAGCGGAGCTTGCAGTGA 3'         (SEQ ID NO: 5)

5' AGACGGAGTCTCGCTCTGTCGC 3'       (SEQ ID NO: 6)

5' TCACGCCTGTAATCCCAGCACTT 3'      (SEQ ID NO: 1)

5' ACGCCTGTAATCCCAGCACTTTG 3'      (SEQ ID NO: 2)

5' TCTGTCGCCCAGGCTGGAGT 3'.        (SEQ ID NO: 3)
```

In certain embodiments, the first probe may have a sequence labeled SEQ ID NO: 7 (for the 79 base pair Yb8 *Alu* fragment), and the second probe may be selected from the group consisting of a sequence labeled SEQ ID NO: 4 (for the 250 base pair *Alu* Ya5 fragment) and a sequence labeled SEQ ID NO: 10 (for the 290 base pair SVA fragment):

```
5' ATCACGAGGTCAGGAGATCGAGACCAT 3'  (SEQ ID NO: 4)

5' AGATTGCGCCACTGCAGTCCGCAG 3'     (SEQ ID NO: 7)

5' AAGGGCGGTGCAAGATGTGCTTTGTT 3'.  (SEQ ID NO: 10)
```

In certain embodiments, the real-time polymerase chain reaction system may operate under the following approximate conditions: 95° C. for 10 minutes; 32-40 cycles of: 95° C. for 15 seconds, 61° C. for 70-120 seconds.

In certain embodiments, an internal positive control may be added to the sample to form a sample mixture. A real-time polymerase chain reaction system may then be used to quantitate the internal positive control within the sample mixture, and this quantitation can be compared with the corresponding quantitation of the internal positive control without the sample. The latter comparison may then be used to determine an extent to which the process was affected by the presence of an inhibitor in the sample.

In certain embodiments, the quantitation of the first retrotransposon interspersed element, the second retrotransposon interspersed element and the internal positive control may be performed simultaneously.

In some embodiments, the internal positive control may comprise a synthetic nucleotide sequence.

In certain embodiments, the process for quantitating human DNA in a sample may comprise providing a primer for the internal positive control, the primer for the internal positive control being selected from the group consisting of a sequence labeled SEQ ID NO: 18 and a sequence labeled SEQ ID NO: 22:

```
5' GCATAAAGATCCTGCCAACAG 3'    (SEQ ID NO: 18)

5' GCCCGAACTTCCAACACTAT 3'    (SEQ ID NO: 22)
```

In certain embodiments, the process for quantitating human DNA in a sample may comprise providing a third probe, the third probe comprising a third moiety capable of fluorescence at a third diagnostic wavelength and a third quencher capable of quenching the third moiety fluorescence, the third probe being targeted to the positive internal control, the Taq polymerase enzyme being further capable of cleaving the third probe to separate the third fluorescent moiety from the third quencher, the third probe having a sequence labeled SEQ ID NO: 42, where the fluorescent label may be HEX, ROX, or TMR:

```
                                        (SEQ ID NO: 42)
    5' [Label]ACAGTGTCAGGCAGAGATTGCACT 3'
```

In certain embodiments, the process for quantitating human DNA in a sample may comprise providing a primer for the internal positive control, the primer for the internal positive control being selected from the group consisting of a sequence labeled SEQ ID NO: 16, a sequence labeled SEQ ID NO: 17, a sequence labeled SEQ ID NO: 18 and a sequence labeled SEQ ID NO: 19:

```
5' AAAGATCCTGCCAACAGGACAGTG 3'   (SEQ ID NO: 16)

5' ACAGACGGTATAGAGACCAATCAG 3'   (SEQ ID NO: 17)

5' GCATAAAGATCCTGCCAACAG 3'      (SEQ ID NO: 18)

5' ACCAAAGTGCTGCAGAAATAC 3'.     (SEQ ID NO: 19)
```

In certain embodiments, the process for quantitating human DNA in a sample may comprise providing a third probe, the third probe comprising a third moiety capable of fluorescence at a third diagnostic wavelength and a third quencher capable of quenching the third moiety fluorescence, the third probe being targeted to the positive internal control, the Taq polymerase enzyme being further capable of cleaving the third probe to separate the third fluorescent moiety from the third quencher, the third probe having a sequence labeled SEQ ID NO: 20:

```
5' AGGCAGAGATTGCACTGCCTTAAAGTGG 3'.  (SEQ ID NO: 20)
```

In certain embodiments, the first retrotransposon interspersed element and the second retrotransposon interspersed element may independently be one of a SINE target sequence, a LINE (long interspersed elements) target sequence and a SVA target sequence.

In certain embodiments, the first retrotransposon interspersed element may consist of 40 to 150 base pairs, and the second retrotransposon interspersed element may consist of 120 to 400 base pairs.

In certain embodiments, the sensitivity of the human DNA quantitation may be about 0.6 pg and the sensitivity of the mouse DNA quantitation may be about 12 pg.

In other embodiments the sensitivity of the human DNA quantitation may be in the range of from about 5 pg to about 9 pg.

In certain embodiments, the efficiency of the real time polymerase chain reaction system with respect to each of the first retrotransposon interspersed element and the second retrotransposon interspersed element may be at least about 90%. In other embodiments, these efficiencies may be at least about 80%.

In certain embodiments, the process step of using a real time polymerase chain reaction system may include the preparation of standard curves for the quantitation of the first retrotransposon interspersed element and the quantitation of the second retrotransposon interspersed element. The standard curves may each be a plot of a threshold cycle vs. a quantity of DNA, and each may have an $R^2$ value of at least 0.99.

In preferred embodiments, the real time polymerase chain reaction system that is used in the inventive process for quantitating human DNA in a sample may be substantially unreactive to non-primate DNA in the sample.

In certain embodiments, the DNA in a tested sample may have been degraded by one of mechanical means, chemical means and environmental means.

In embodiments of the invention, the real time polymerase chain reaction system may be one of SYBR® Green, TaqMan® and AmpliFluor®.

In certain other embodiments, a process for quantitating total human DNA and male specific DNA in a sample in order to assess the extent of degradation of the DNA therein according to the present invention may comprise the steps of providing a sample to be analyzed, using a real time polymerase chain reaction system to separately quantitate within the sample a male specific DNA sequence, a first retrotransposon interspersed element and a second retrotransposon interspersed element, the male specific DNA sequence being a 90 bp Y-chromosome specific DNA sequence, the first retrotransposon interspersed element being an *Alu* element, the second retrotransposon interspersed element being an SVA element of the RP gene, and calculating a ratio of an occurrence within the sample of the first retrotransposon interspersed element to an occurrence of the second retrotransposon interspersed element.

In certain embodiments of the process for quantitating total human DNA and male DNA in a sample, the first retrotransposon interspersed element may be one of a SINE target sequence, a LINE target sequence and a SVA target sequence consisting of 40 to 150 base pairs, the second retrotransposon interspersed element may be one of a SINE target sequence, a LINE target sequence and a SVA target sequence consisting of 120 to 400 base pairs, and the male target may be a region of a human Y chromosome DNA containing a 90 base pair sequence which is deleted on a human X-chromosome in an X-Y chromosome homologous region.

In certain embodiments of the process for quantitating total human DNA and male specific DNA in a sample, the first retrotransposon interspersed element may be a target sequence that has about 80 base pairs and is an *Alu* element of subfamily Yb8, the second retrotransposon interspersed element may be a target sequence that has about 290 base pairs and is an SVA element of the RP gene, and the male specific DNA sequence may be a region of a human Y chromosome DNA containing a 90 base pair sequence which is deleted on a human X-chromosome in an X-Y chromosome homologous region.

In certain embodiments, the process for quantitating total human DNA and male specific DNA in a sample may further comprise providing at least one primer selected from the group consisting of a forward primer labeled SEQ ID NO: 5 and a reverse primer labeled SEQ ID NO: 6 (primers for the Yb8 *Alu* fragment), providing at least one primer selected from the group consisting of a forward primer labeled SEQ ID NO: 8, a forward primer labeled SEQ ID NO: 11, a forward primer labeled SEQ ID NO: 14, a reverse primer labeled SEQ ID NO: 9, a reverse primer labeled SEQ ID NO: 12, a reverse primer labeled SEQ ID NO: 13 and a reverse primer labeled SEQ ID NO: 15 (primers for the SVA sequence):

| | |
|---|---|
| 5' GGAAGCGGAGCTTGCAGTGA 3' | (SEQ ID NO: 5) |
| 5' AGACGGAGTCTCGCTCTGTCGC 3' | (SEQ ID NO: 6) |
| 5' TGGGATCCTGTTGATCTGTGACCT 3' | (SEQ ID NO: 8) |
| 5' GATTTGGCAGGGTCATGGGACAAT 3' | (SEQ ID NO: 9) |
| 5' ATGTGCTGTGTCCACTCAGGGTTA 3' | (SEQ ID NO: 11) |
| 5' TTCTTGGGTGTTTCTCACAGAGGG 3' | (SEQ ID NO: 12) |
| 5' ATTCTTGGGTGTTTCTCACAGAGG 3' | (SEQ ID NO: 13) |
| 5' CCAACCCTGTGCTCTCTGAAAC 3' | (SEQ ID NO: 14) |
| 5' TTTGGCAGGGTCATGGGACAA 3', | (SEQ ID NO: 15) | and providing at least one primer selected from the group consisting of a forward primer labeled SEQ ID NO: 25 and a reverse primer labeled SEQ ID NO: 26:

| | |
|---|---|
| 5' CAATGTG/CTAGGCTCTAGGAATAC 3' | (SEQ ID NO: 25) |
| 5' AAGAGTGTCATGGCTCAAAGAG 3'. | (SEQ ID NO: 26) |

In certain embodiments, the process for quantitating total human DNA and male specific DNA in a sample may further comprise providing a probe for the male specific DNA target sequence, the probe having a sequence labeled SEQ ID NO: 27:

| | |
|---|---|
| 5' AGAGAGTATGACAAACATGGCATGGGC 3'. | (SEQ ID NO: 27) |

In certain embodiments, the process for quantitating total human DNA and male specific DNA in a sample may further comprise adding an internal positive control to the sample to form a sample mixture, using the real time polymerase chain reaction system to quantitate the internal positive control within the sample mixture, comparing an expected occurrence of the internal positive control with an occurrence within the sample mixture of the internal positive control, and using the comparison to determine an extent to which the process was affected by the presence of an inhibitor in the sample.

In certain embodiments, the process for quantitating total human DNA and male specific DNA in a sample may further comprise providing at least one primer selected from the group consisting of a forward primer labeled SEQ ID NO: 21, a reverse primer labeled SEQ ID NO: 22, and a reverse primer labeled SEQ ID NO: 23 (primers for a specifically tailored internal positive control):

| | |
|---|---|
| 5' GCATAAAGATCCTGCCAACAG 3' | (SEQ ID NO: 21) |
| 5' GCCCGAACTTCCAACACTAT 3' | (SEQ ID NO: 22) |
| 5' ATTGTTCCTCCTGCCTGATT 3'. | (SEQ ID NO: 23) |

In certain embodiments, the process for quantitating total human DNA and male specific DNA in a sample may further comprise providing a probe for the positive internal control, the probe having a sequence labeled SEQ ID NO: 24:

5' ACAGTGTCAGGCAGAGATTGCACT 3' (SEQ ID NO: 24).

The present application describes a process whereby retrotransposon interspersed element ('RE') markers can be simultaneously assayed in a single, highly sensitive multiplex qPCR reaction, with the inclusion of an internal positive control to monitor the presence of PCR inhibitors potentially present in blood serum or plasma. This method enables development of an accurate, rapid, affordable, minimally invasive, high throughput, cost effective clinical test with the potential to complement or replace existing procedures and improve cancer diagnosis, prognosis, surveillance and/or treatment monitoring.

Accordingly, one object of the invention is to develop a multiplexed qPCR method that accurately quantitates cfDNA in biological fluids including blood plasma or serum.

Another object of the invention is to develop a multiplexed qPCR method that accurately provides a determination of the extent of fragmentation or integrity of cfDNA in biological fluids including blood plasma or serum.

Another object of the invention is to develop a three target (one short RE target, one long RE target, and one internal positive control synthetic target) multiplex RE-qPCR assay to accurately and robustly obtain cfDNA concentration and DNA integrity values from normal and CRC patients by direct qPCR from plasma/serum samples without DNA purification.

One embodiment of the invention takes the form of a multiplexed method to quantitate the integrity of circulating cell free human DNA, comprising providing a sample of serum, plasma, urine, or other biological fluid, the sample comprising cell free human DNA, the cell free human DNA comprising a short nucleic acid fragment including less than 180 bp and a long nucleic acid fragment including more than 180 bp, the short nucleic acid fragment and the long nucleic acid fragment being retrotransposable element (RE) genomic targets that are independent of each other, using a quantitative polymerase chain reaction (qPCR) method to separately and simultaneously quantitate the short nucleic acid fragment and the long nucleic acid fragment, obtaining for each quantitated nucleic acid fragment a threshold cycle number, comparing each threshold cycle number with a standard curve to determine for each quantitated nucleic acid fragment a quantity of the DNA fragment that was present in the sample, and calculating a ratio of the quantity of the long nucleic acid fragment to the quantity of the short nucleic acid fragment, but the present invention is not limited thereto.

In certain embodiments of the multiplexed method of the present invention, the retrotransposable element genomic targets may be each independently an interspersed ALU, SVA, or LINE element. In certain embodiments, these retrotransposable element genomic targets may each have a copy number in excess of 1000 copies per genome.

Some embodiments of the multiplexed method of the present invention further comprise a step of adding a synthetic DNA sequence as an internal positive control prior to the using step, quantitating the internal positive control in the using step, and utilizing the quantitative internal positive control result in the comparing step to improve the accuracy and reliability of the comparing step.

In embodiments of the multiplexed method of the present invention, the use of an internal positive control enables a determination of the concentration of cell free DNA in the sample.

In some embodiments of the multiplexed method of the present invention, the sample of serum, plasma, urine, or other biological fluid may be placed in a single tube, and the qPCR reactions for quantitation of the nucleic acid fragments may be carried out in that same single tube.

In some embodiments of the multiplexed method of the present invention, the ratio of the quantity of the long nucleic acid fragment to the quantity of the short nucleic acid fragment may serve as an integrity value of circulating cell free DNA for diagnostic applications. These diagnostic applications may include one or more of the detection, diagnosis, prognosis, treatment monitoring, and surveillance of cancer.

In certain embodiments, the multiplexed method of the present invention may include a step of deactivating or eliminating proteins that bind to the short nucleic acid fragment or the long nucleic acid fragment. This may be done by mixing the sample with a buffer including a surfactant and chelating agent, enzymatically digesting the protein, then using heat to deactivate and insolubilize the digested protein, followed by centrifugation. Alternatively, dilution of the sample using 40 parts sterile water to one part sample by volume may have the effect of deactivating or eliminating these proteins.

In certain embodiments, the multiplexed method of the present invention may include a step of providing a hybridization probe corresponding to the short nucleic acid fragment and a probe corresponding to the long nucleic acid fragment. In certain embodiments, each probe may include an observable label. In some embodiments, the observable labels may be fluorescent labels that are distinct from each other.

In some embodiments, the multiplexed method of the present invention may include a step of separating amplification products obtained from the qPCR reaction using electrophoresis.

In some embodiments, the multiplexed method of the present invention may include a step of determining an optimum temperature for the qPCR reaction.

The multiplexed method of the present invention may include a sample that comes from an individual who is suffering from cancer or who is at risk for developing cancer.

In certain embodiments, the present invention may take the form of a multiplexed system for characterizing cancer in humans including a sample of serum, plasma, urine, or other biological fluid, the sample comprising cell free DNA, the cell free DNA comprising two retrotransposable element targets, the first target being a multi-copy retrotransposon having less than 180 bp, the second target being another multi-copy retrotransposon having more than 180 bp, the first target and the second target being independent of each other, the sample further comprising an added third target, the third target being an internal positive control comprising synthetic DNA; a TaqMan probe corresponding to each of the first target, the second target and the third target, each probe comprising a detectable label that is distinct from the labels incorporated into the other probes; a forward primer and a reverse primer for amplifying each of the first target, the second target and the third target; a DNA standard for generating standard curves for the first target and the second target; a qPCR system for simultaneously amplifying the first target, the second target and the third target and for producing a threshold cycle number for each target; and a qPCR data analysis system for producing DNA quantitation values for each target by interpolation using threshold cycle numbers and linear standard curves and for using the DNA quantitation values to produce an indication of the integrity of the cell free DNA.

In other embodiments of the multiplexed system of the present invention, the first target is a multi-copy retrotransposon having less than N bp, and the second target is another multi-copy retrotransposon having more than N bp, where N is 125 bp, 130 bp, 140 bp, 150 bp, 160 bp, 170 bp, 190 bp, 200 bp, or 205 bp.

In some embodiments of the multiplexed system of the present invention, the detectable labels corresponding to the first target, the second target and the third target may be fluorophores that are distinct from each other.

In some embodiments of the multiplexed system of the present invention, the qPCR system may amplify the first target, the second target and the third target without prior purification of the first, second, or third DNA targets.

In some embodiments, the multiplexed system of the present invention may include DNA polymerase, and the qPCR system may amplify a template DNA fragment of each of the first target, the second target and the third target after deactivation or elimination of protein bound to at least one of a template DNA and DNA polymerase.

In certain embodiments of the multiplexed system of the present invention, the retrotransposable element genomic targets may be each independently an interspersed ALU, SVA, or LINE element.

In certain embodiments of the multiplexed system of the present invention, the first target may be an ALU element having a size selected from the group consisting of 80 bp, 119 bp, 120 bp and 123 bp, and the second target may be an SVA element having a size selected from the group consisting of 207 bp, 257 bp, 265 bp, 290 bp, 355 bp, 367 bp, 399 bp and 411 bp.

In some embodiments of the multiplexed system of the present invention, the first target may be an ALU element of the Yb8 subfamily having a size of about 80 bp, and the second target may be an SVA element having a size of about 207 bp, but the first target and the second target are not limited thereto. In other embodiments, the first target Yb8 ALU element may have a size of about 119 bp, about 120 bp, or about 123 bp, and the second target SVA element may have a size of about 257 bp, about 265 bp, about 290 bp, about 355 bp, about 367 bp, about 399 bp, or about 411 bp. Embodiments of the present invention may be formed from any possible pairing of a suitable first target ALU element with a suitable second target SVA element.

In some embodiments of the multiplexed system of the present invention, the third target, which is an internal positive control comprising synthetic DNA, may have a size of about 172 base pairs, but the size of the internal positive control sequence is not limited thereto.

In some embodiments of the multiplexed system of the present invention, the first retrotransposable element target and the second retrotransposable element target may each have a copy number in excess of 1000 copies per genome.

In some embodiments of the multiplexed system of the present invention, one or more additional retrotransposable element targets found in the cell free DNA may be added to the multiplex. Such multiplexed systems may further comprise a distinctly labeled TaqMan probe corresponding to each target and a forward and reverse primer set corresponding to each target, the qPCR system simultaneously amplifying each target.

In some embodiments, the present invention may include a kit for determining concentration and integrity of cell free DNA in biological fluids, the kit comprising a set of primers corresponding to each of a short retrotransposable element genomic target sequence and a long retrotransposable element genomic target sequence, the short retrotransposable element being shorter than 180 bp in length, the long retrotransposable element being longer than 180 bp in length, the short retrotransposable element and the long retrotransposable element being independent of each other, each set of primers comprising a forward primer and a reverse primer; a synthetic genomic sequence suitable for use as an internal positive control; and one or more reagents for performing quantitative real-time polymerase chain reaction (PCR) amplification.

In some embodiments, the kit of the present invention may include a vacuum-filled test tube for collecting a sample of whole blood or an anticoagulant-treated tube for collecting a sample of whole blood and producing a plasma sample.

In some embodiments, the kit of the present invention may include a probe corresponding to the short target sequence and/or a probe corresponding to the long target sequence. Each probe may include an observable label. The observable labels may be fluorescent organic dyes.

BRIEF DESCRIPTION OF THE FIGURES

The patent or application file contains at least one drawing executed in color. Copies of this patent or patent application publication with color drawing(s) will be provided by the Office upon request and payment of the necessary fee.

A more complete appreciation of the invention, and many of the attendant advantages thereof, will be readily apparent as the same becomes better understood by reference to the following detailed description when considered in conjunction with the accompanying Figures, wherein:

FIG. 3A shows qPCR amplification plots for blood plasma samples, showing behavior both for purified DNA and for the case of using direct qPCR. The horizontal lines show the automatic cycle threshold setting.

FIG. 3B shows qPCR amplification plots for serum samples, showing behavior both for purified DNA and for the case of using direct qPCR. The horizontal lines show the automatic cycle threshold setting.

FIG. 19 shows STR results for 1 ng targeted sonicated samples.

FIG. 20 shows STR results for 1 ng targeted DNase I treated samples.

R2: 0.999; efficiency: 95.427%. Target: Human; slope: −3.404; y-intercept: 15.158; R²: 0.999; efficiency: 96.67%.

Figure 25:
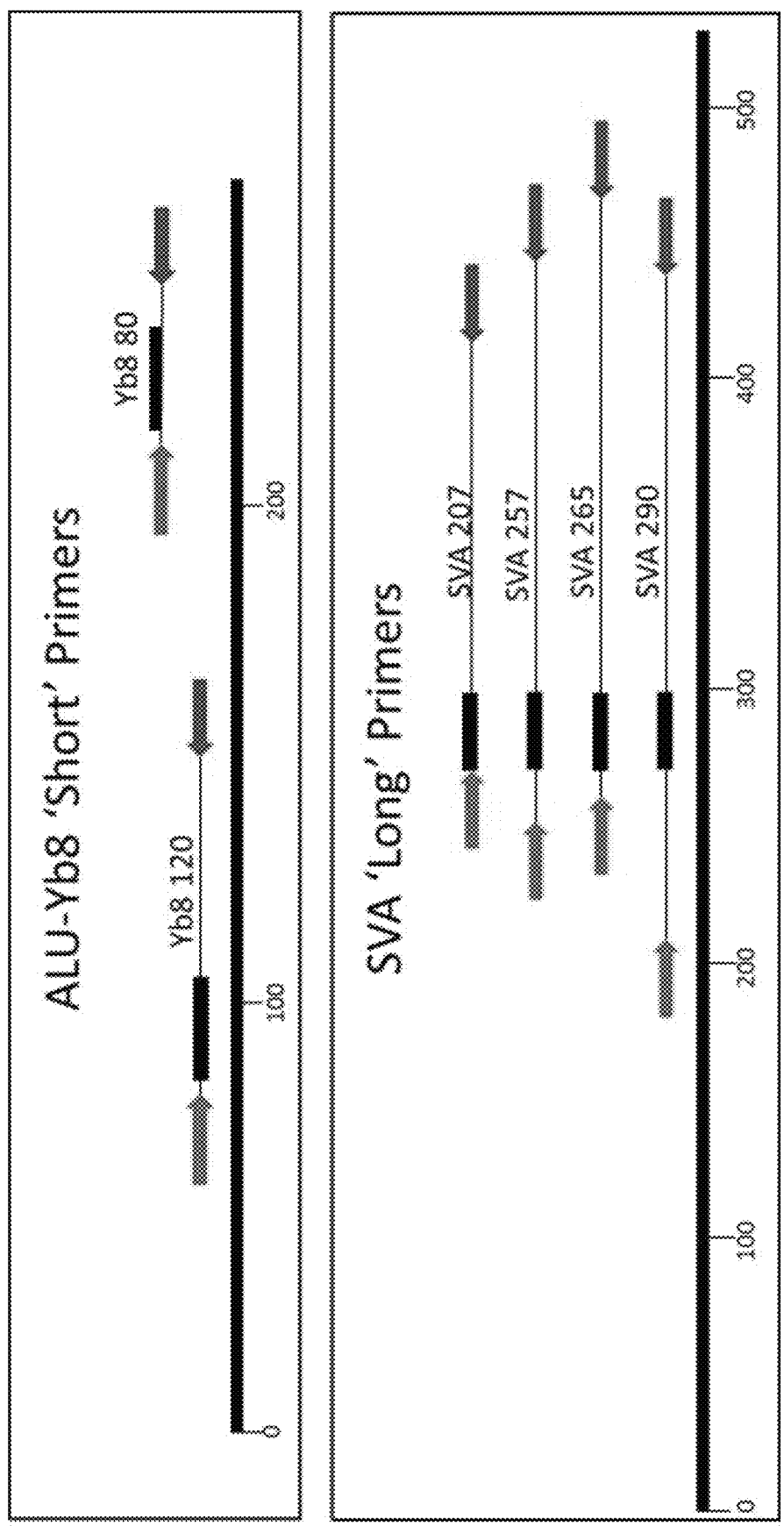

FIG. 25 shows a schematic representation of relative positions of the forward and reverse primers as well as the double labeled probes for qPCR analysis. The two short targets designed within the Yb8 sequence are 80 and 120 bp in size. The four long targets designed within the SVA sequence are 207, 257, 265, and 290 bp in size.

Figure 26A:
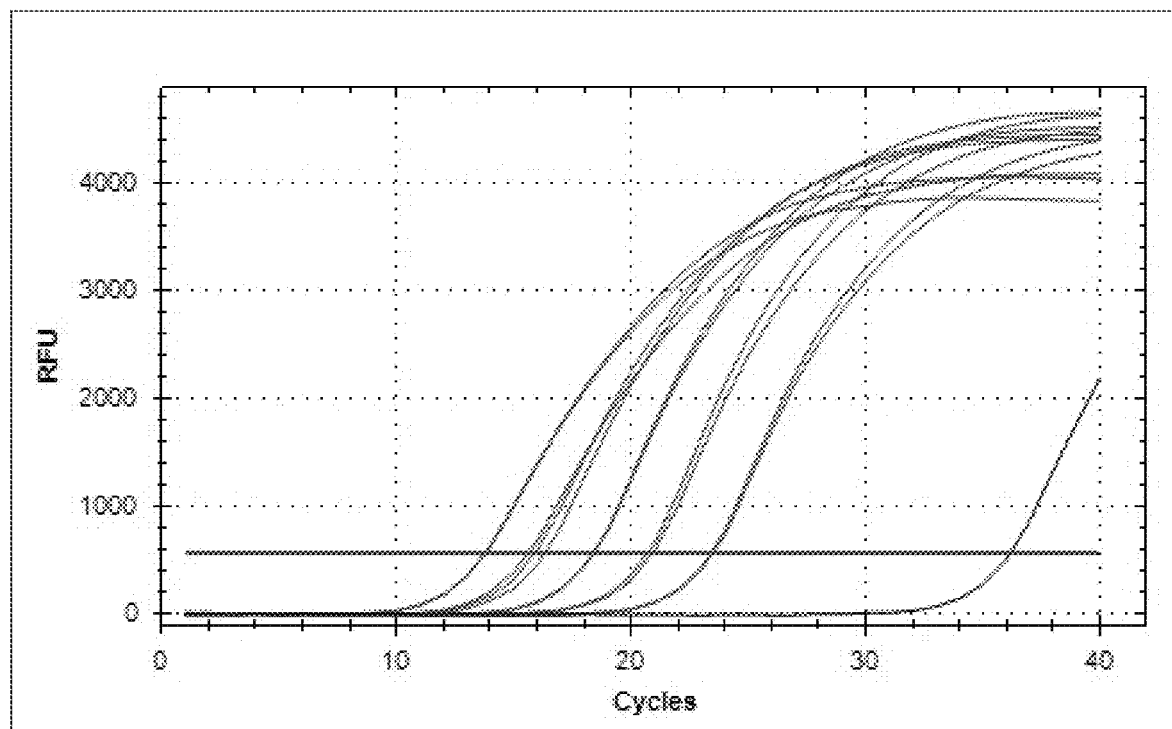

FIG. 26A shows an amplification plot for the SYBR qPCR analysis of the Yb8-119 target using standard DNA (1 ng, 200 pg, 40 pg, 8 pg, and 1.6 pg) in green, with positive control in red and no template control in black.

Figure 26B:
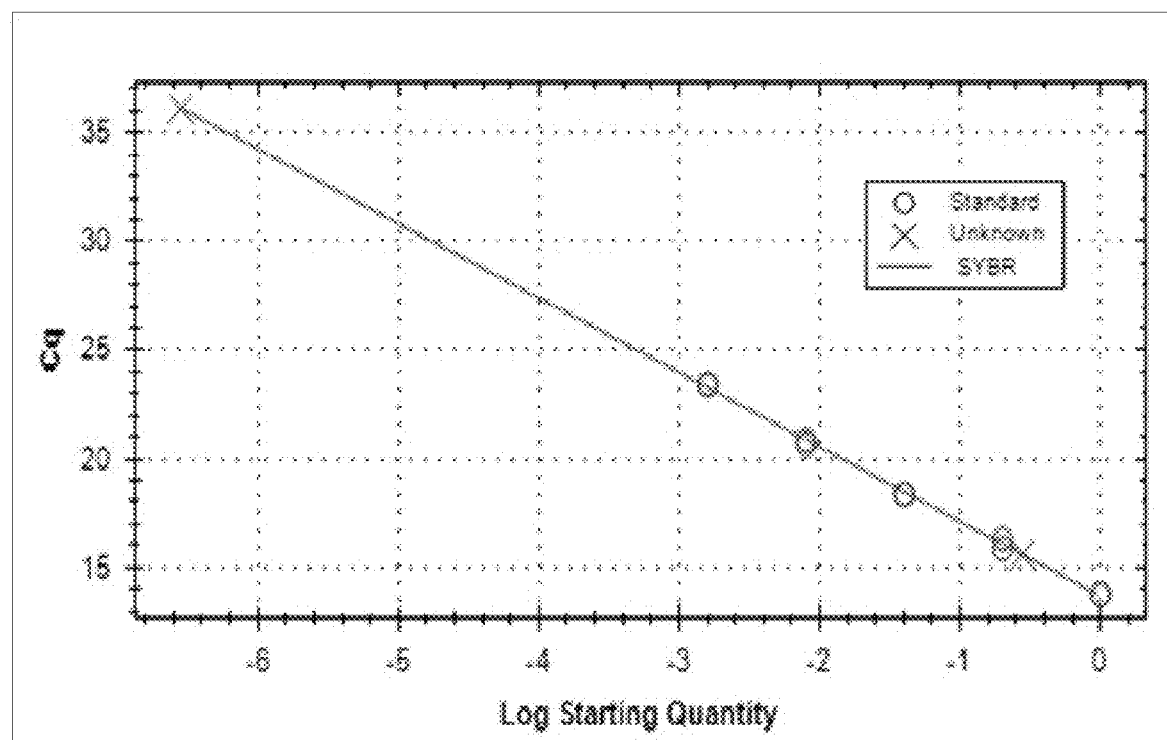

FIG. 26B shows a standard curve for the SYBR qPCR analysis of the Yb8-119 target using standard DNA (1 ng, 200 pg, 40 pg, 8 pg, and 1.6 pg). Efficiency: 95.7%; R²: 0.998; slope: 3.430; y-intercept: 13.682.

Figure 26C:
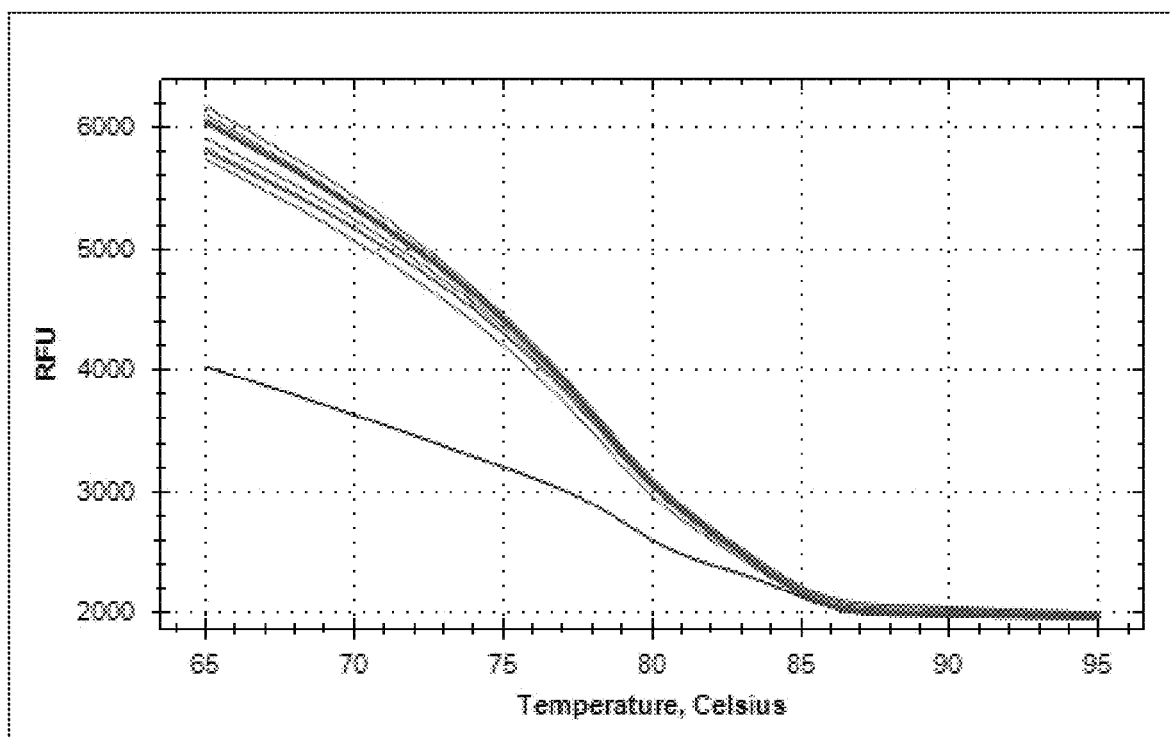

FIG. 26C shows a melt curve for the SYBR qPCR analysis of the Yb8-119 target using standard DNA (1 ng, 200 pg, 40 pg, 8 pg, and 1.6 pg) in green, with positive control in red and no template control in black.

Figure 26D:
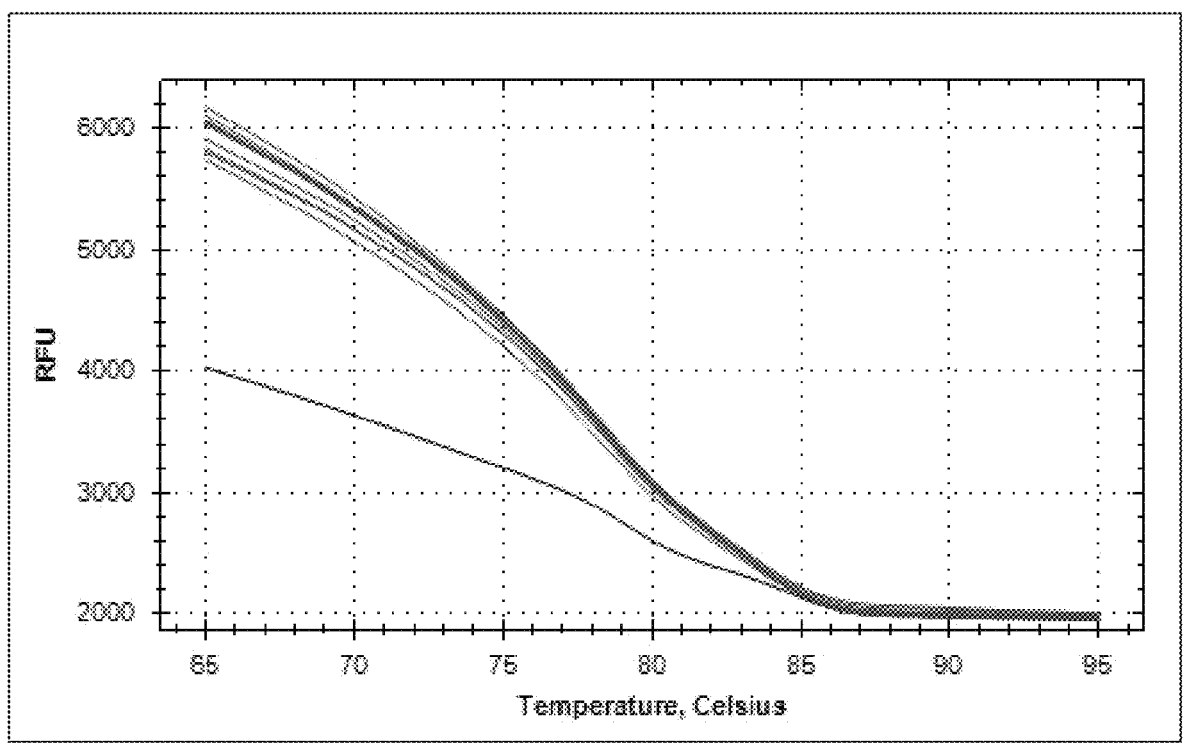

FIG. 26D shows a melt peak plot for the SYBR qPCR analysis of the Yb8-119 target using standard DNA (1 ng, 200 pg, 40 pg, 8 pg, and 1.6 pg) in green, with positive control in red and no template control in black.

Figure 27A:
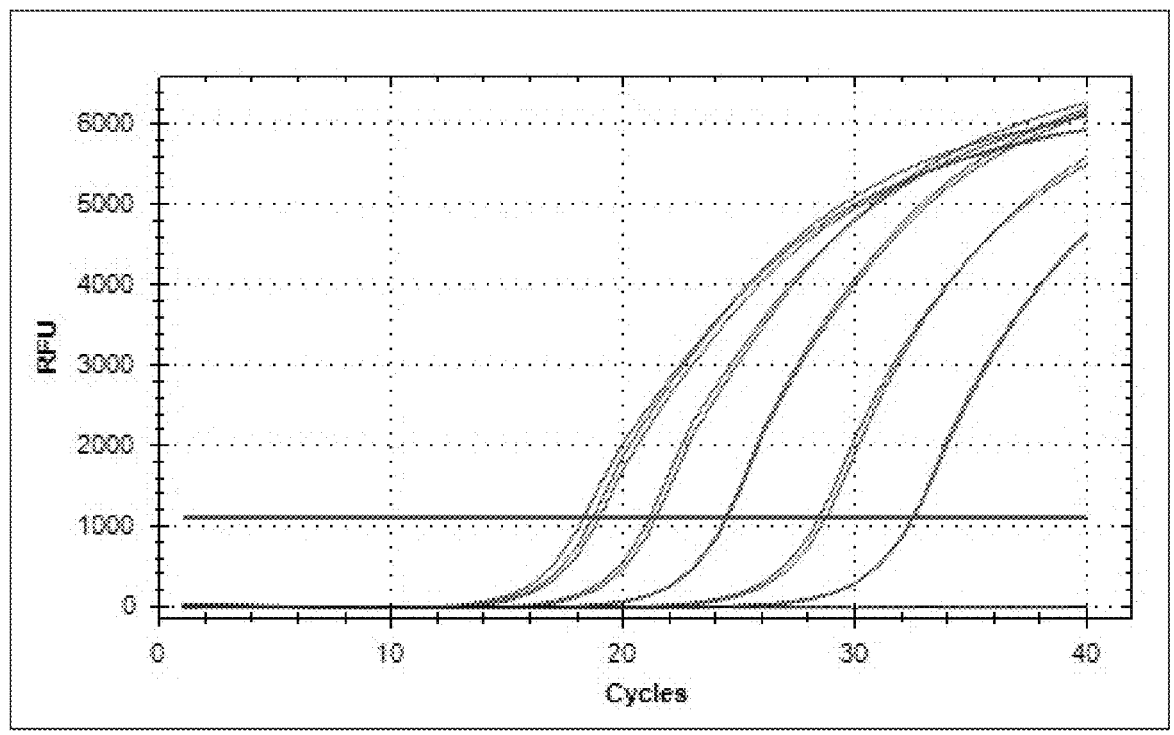

FIG. 27A shows an amplification plot for the SYBR qPCR analysis of the SVA-399 target using standard DNA (1 ng, 200 pg, 40 pg, 8 pg, and 1.6 pg) in green, with positive control in red and no template control in black.

Figure 27B:
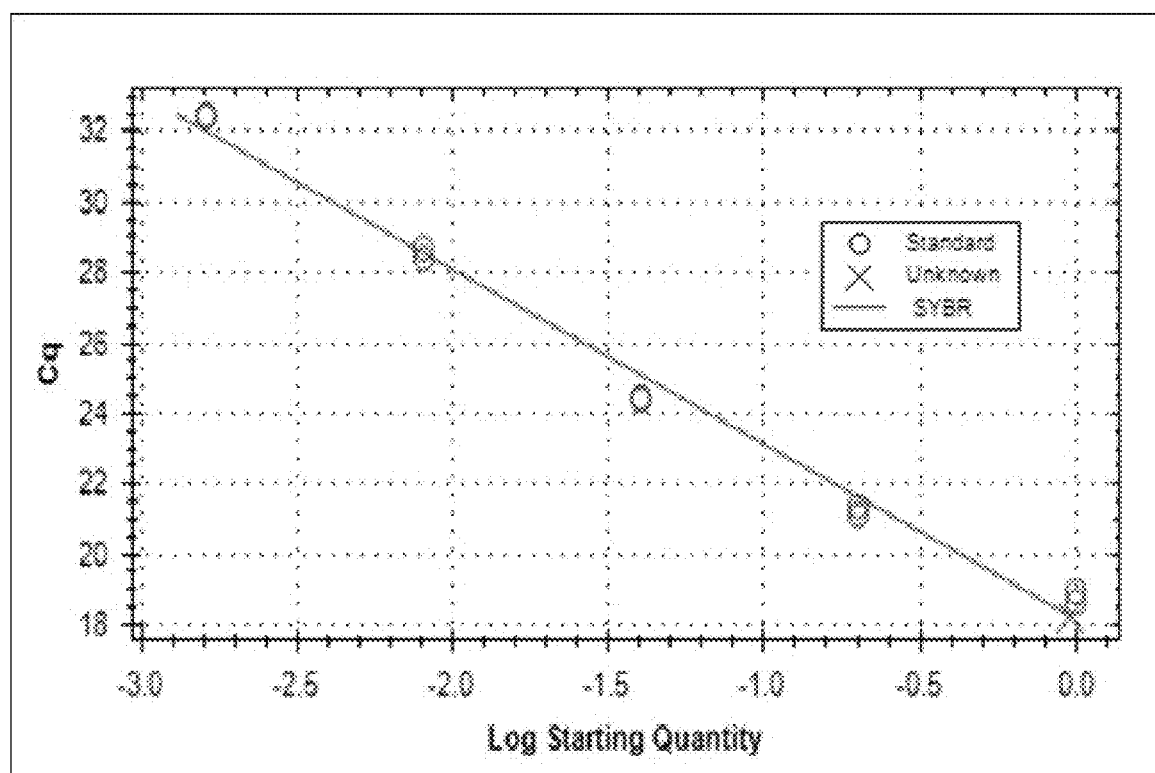

FIG. 27B shows a standard curve for the SYBR qPCR analysis of the SVA-399 target using standard DNA (1 ng, 200 pg, 40 pg, 8 pg, and 1.6 pg). Efficiency: 59.2%; R²: 0.990; slope: −4.954; y-intercept: 18.174.

Figure 27C:
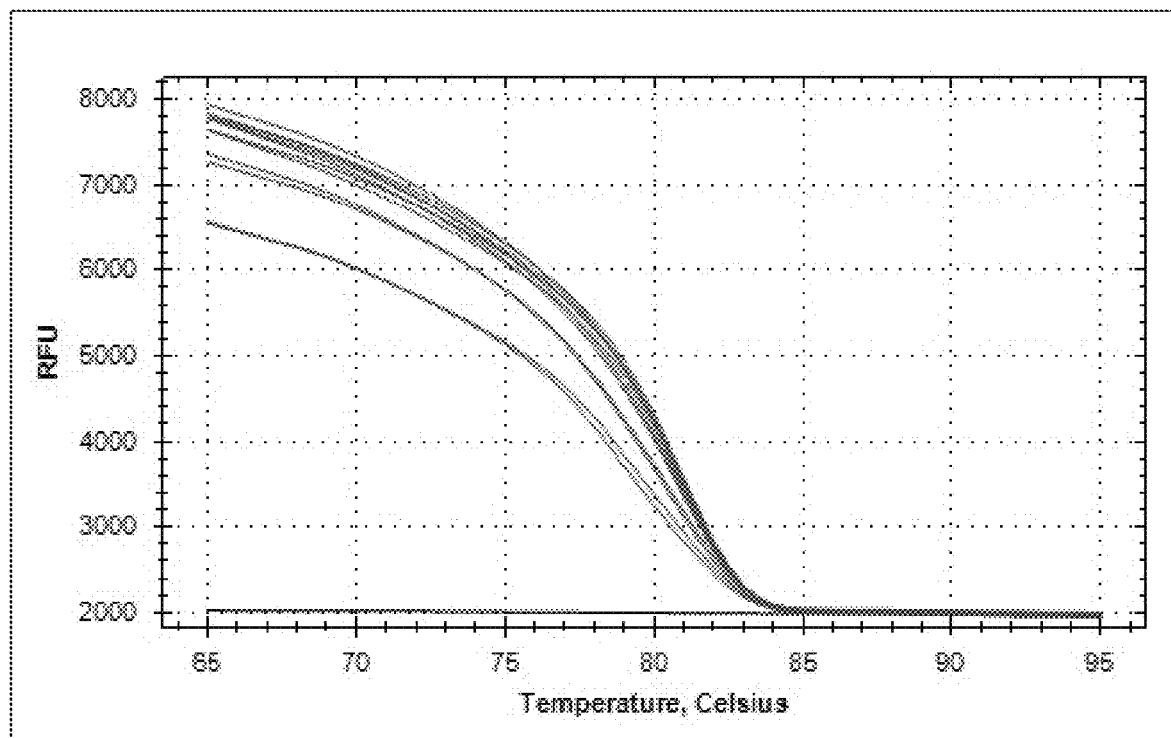

FIG. 27C shows a melt curve for the SYBR qPCR analysis of the SVA-399 target using standard DNA (1 ng, 200 pg, 40 pg, 8 pg, and 1.6 pg) in green, with positive control in red and no template control in black.

Figure 27D:
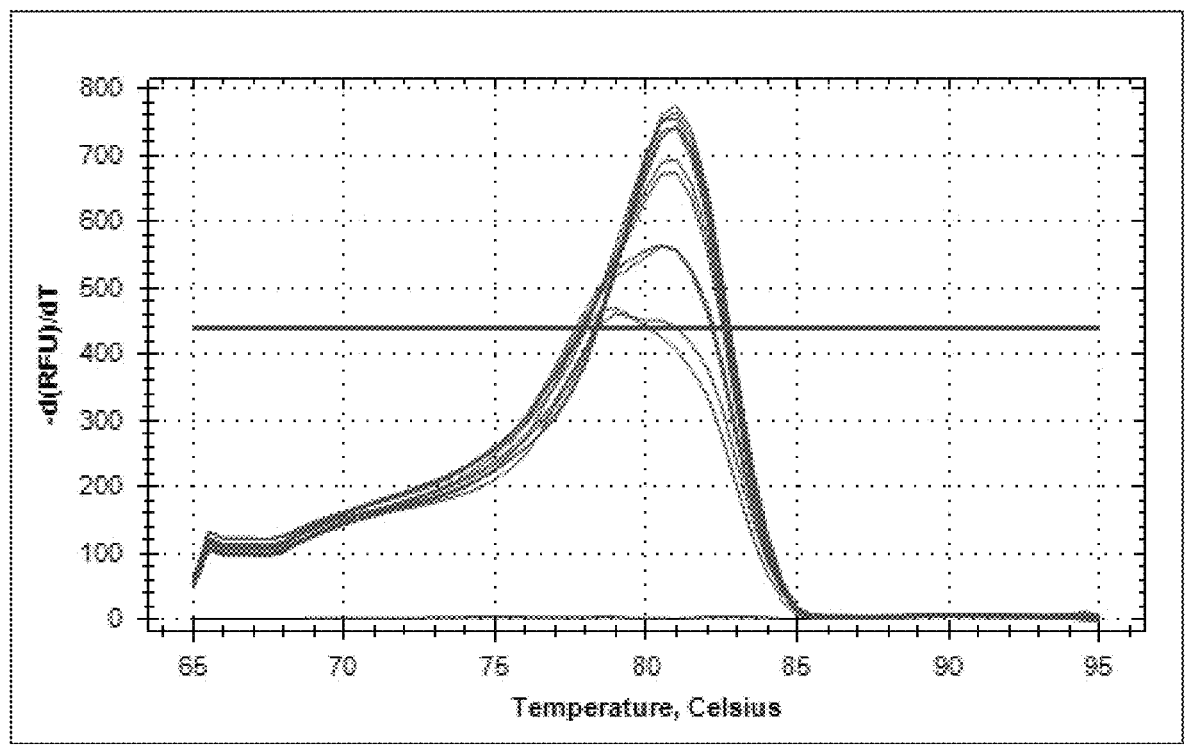

FIG. 27D shows a melt peak plot for the SYBR qPCR analysis of the SVA-399 target using standard DNA (1 ng, 200 pg, 40 pg, 8 pg, and 1.6 pg) in green, with positive control in red and no template control in black.

Figure 28A:
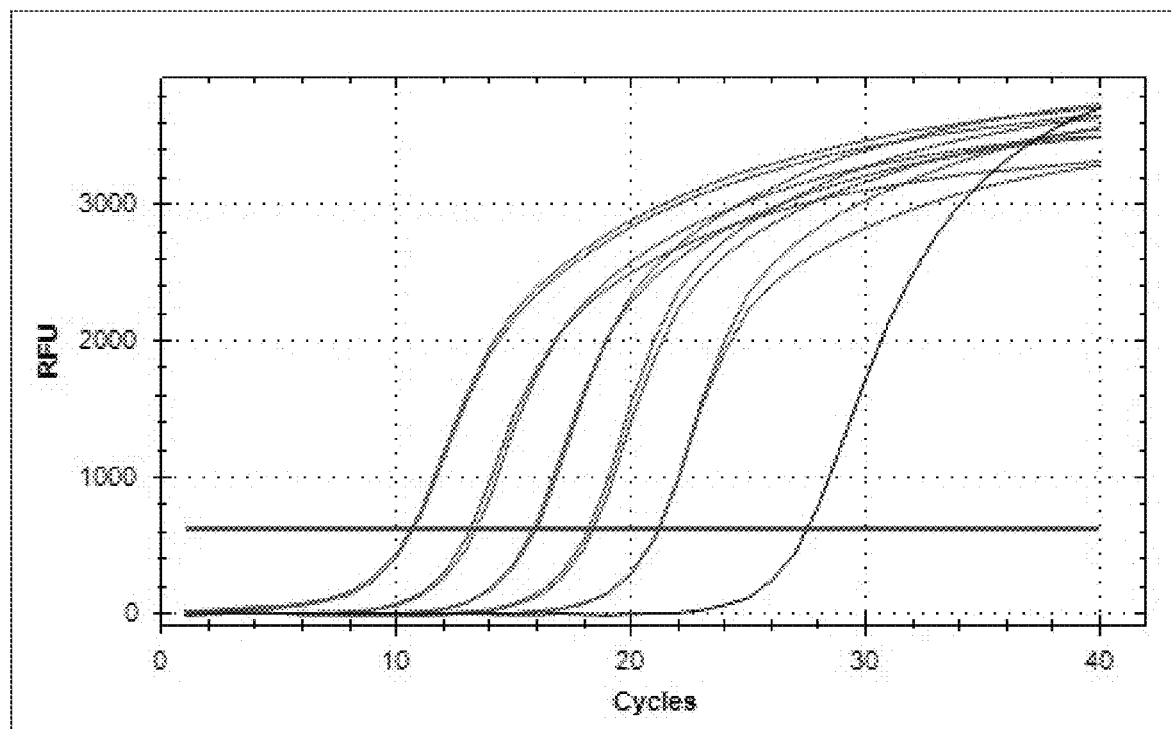

FIG. 28A shows an amplification plot for the SYBR qPCR analysis of the Alu-115 target using standard DNA (5 ng, 1 ng, 200 pg, 40 pg, and 8 pg) in green, with positive control in red and no template control in black.

Figure 28B:
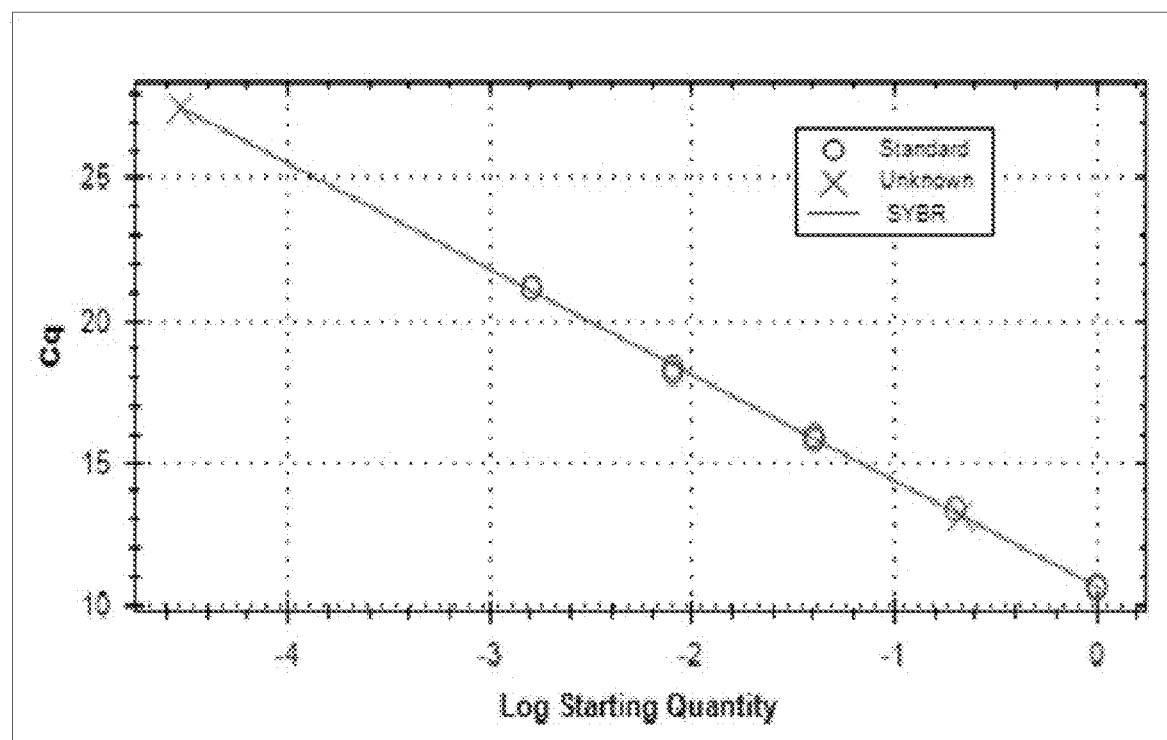

FIG. 28B shows a standard curve for the SYBR qPCR analysis of the Alu-115 target using standard DNA (5 ng, 1 ng, 200 pg, 40 pg, and 8 pg). Efficiency: 85.5%; R²: 0.999; slope: −3.718; y-intercept: 10.667.

Figure 28C:
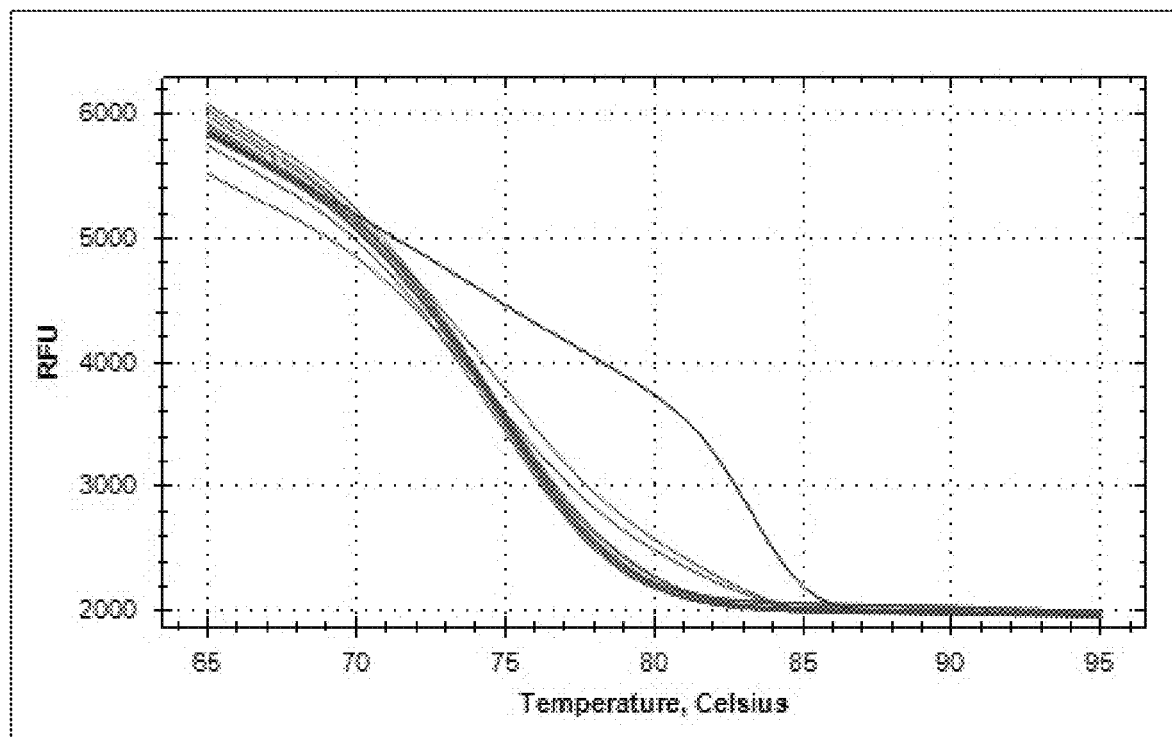

FIG. 28C shows a melt curve for the SYBR qPCR analysis of the Alu-115 target using standard DNA (5 ng, 1 ng, 200 pg, 40 pg, and 8 pg) in green, with positive control in red and no template control in black.

Figure 28D:
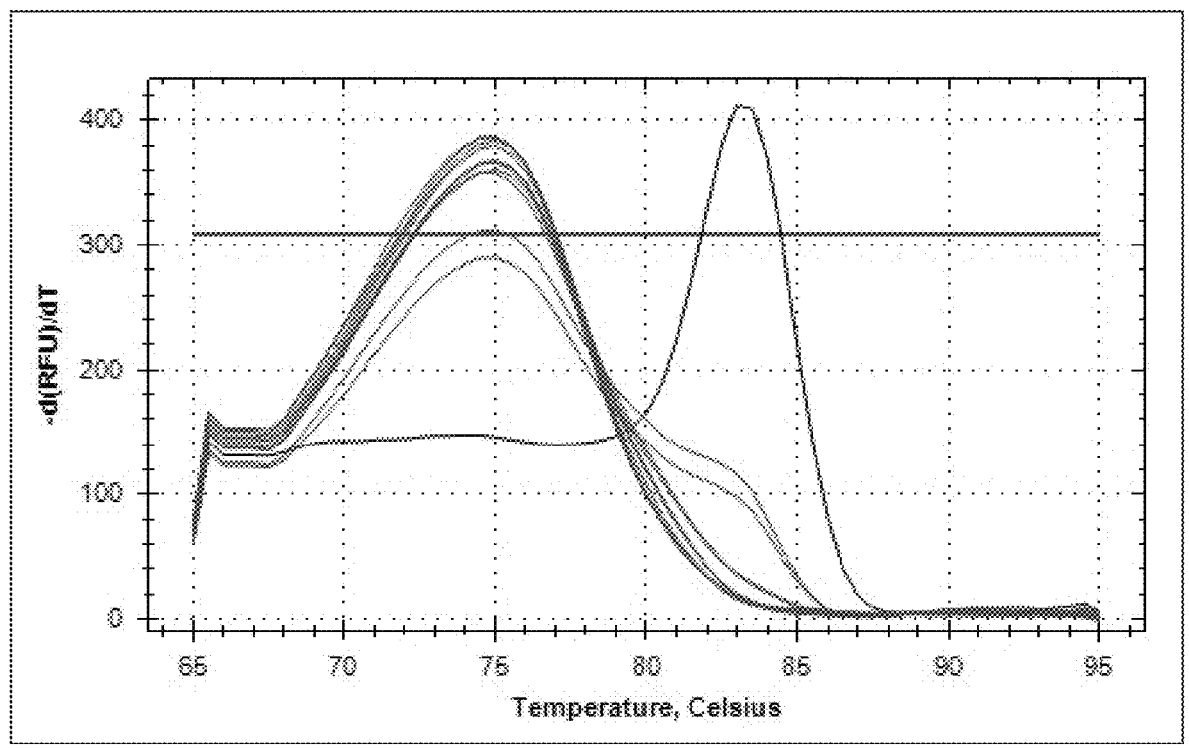

FIG. 28D shows a melt peak plot for the SYBR qPCR analysis of the Alu-115 target using standard DNA (5 ng, 1 ng, 200 pg, 40 pg, and 8 pg) in green, with positive control in red and no template control in black.

Figure 29A:
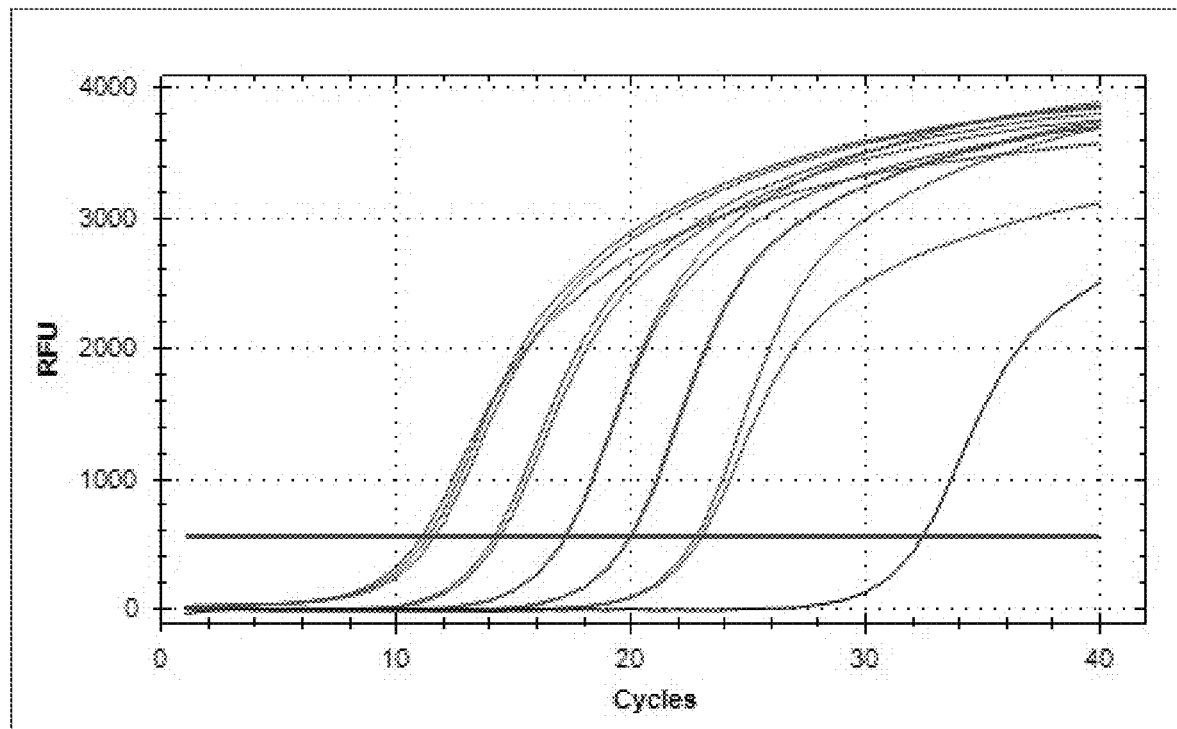

FIG. 29A shows an amplification plot for the SYBR qPCR analysis of the Alu-247 target using standard DNA (5 ng, 1 ng, 200 pg, 40 pg, and 8 pg) in green, with positive control in red and no template control in black.

Figure 29B:
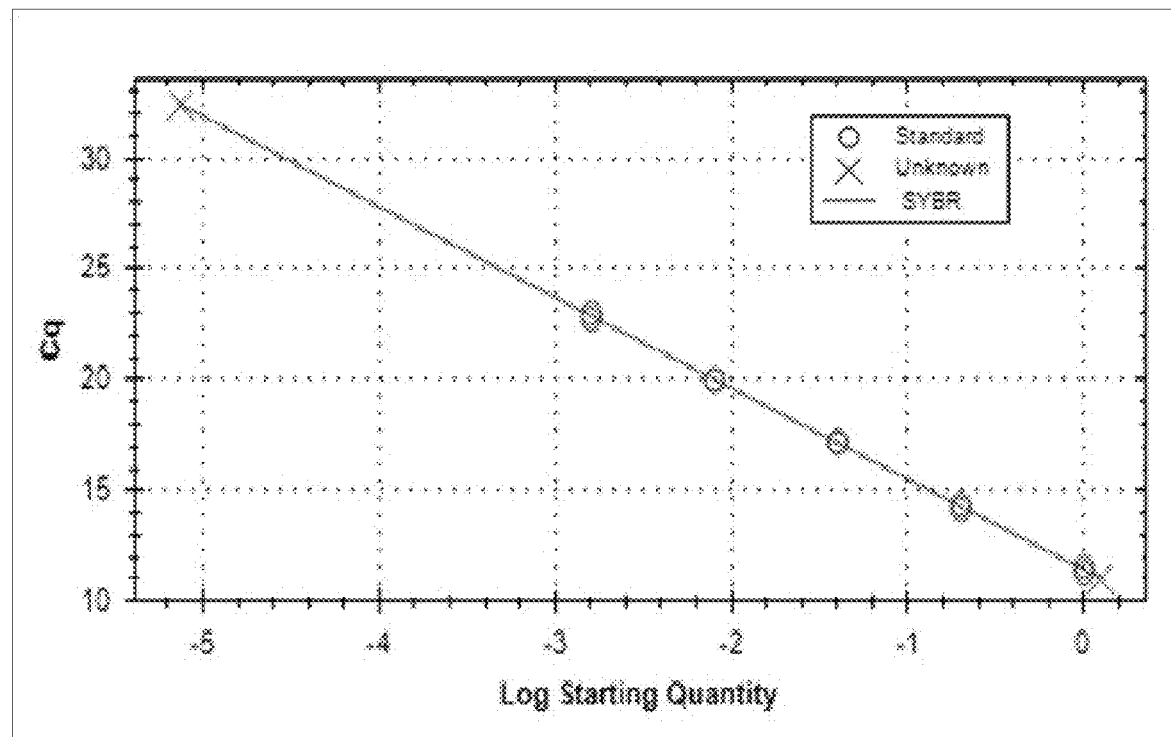

FIG. 29B shows a standard curve for the SYBR qPCR analysis of the Alu-247 target using standard DNA (5 ng, 1 ng, 200 pg, 40 pg, and 8 pg). Efficiency: 75.6%; R²: 0.999; slope: −4.089; y-intercept: 11.447.

Figure 29C:
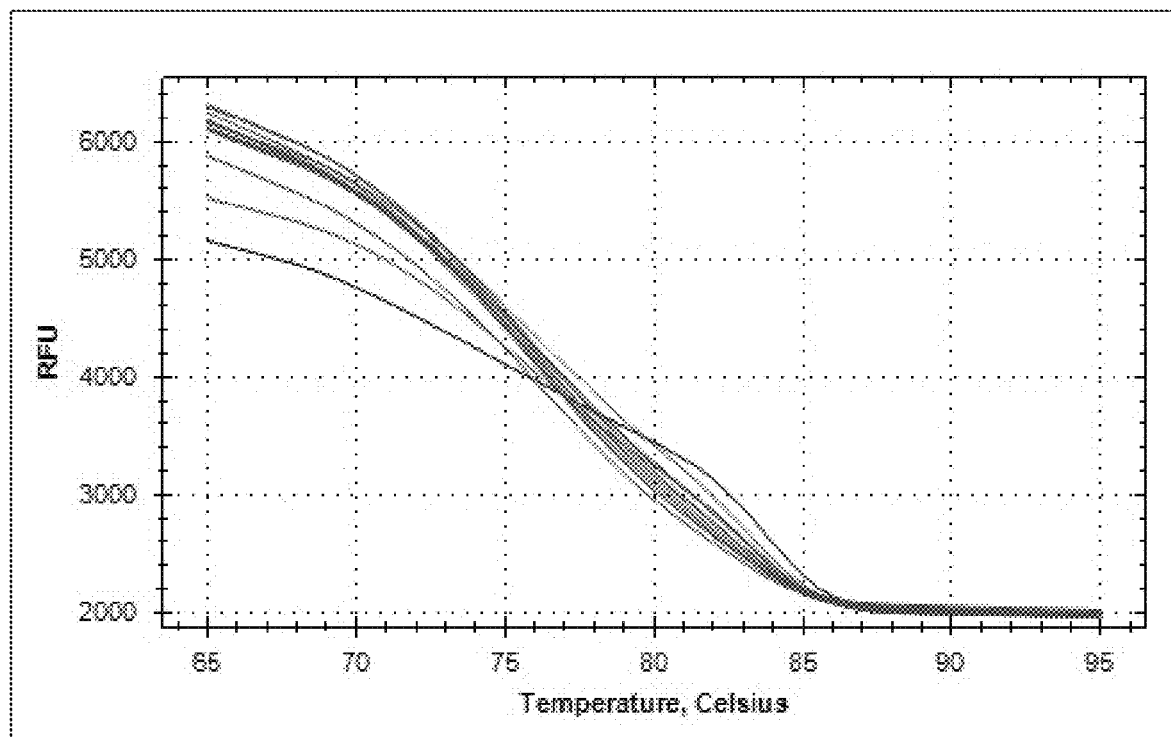

FIG. 29C shows a melt curve for the SYBR qPCR analysis of the Alu-247 target using standard DNA (5 ng, 1 ng, 200 pg, 40 pg, and 8 pg) in green, with positive control in red and no template control in black.

Figure 29D:
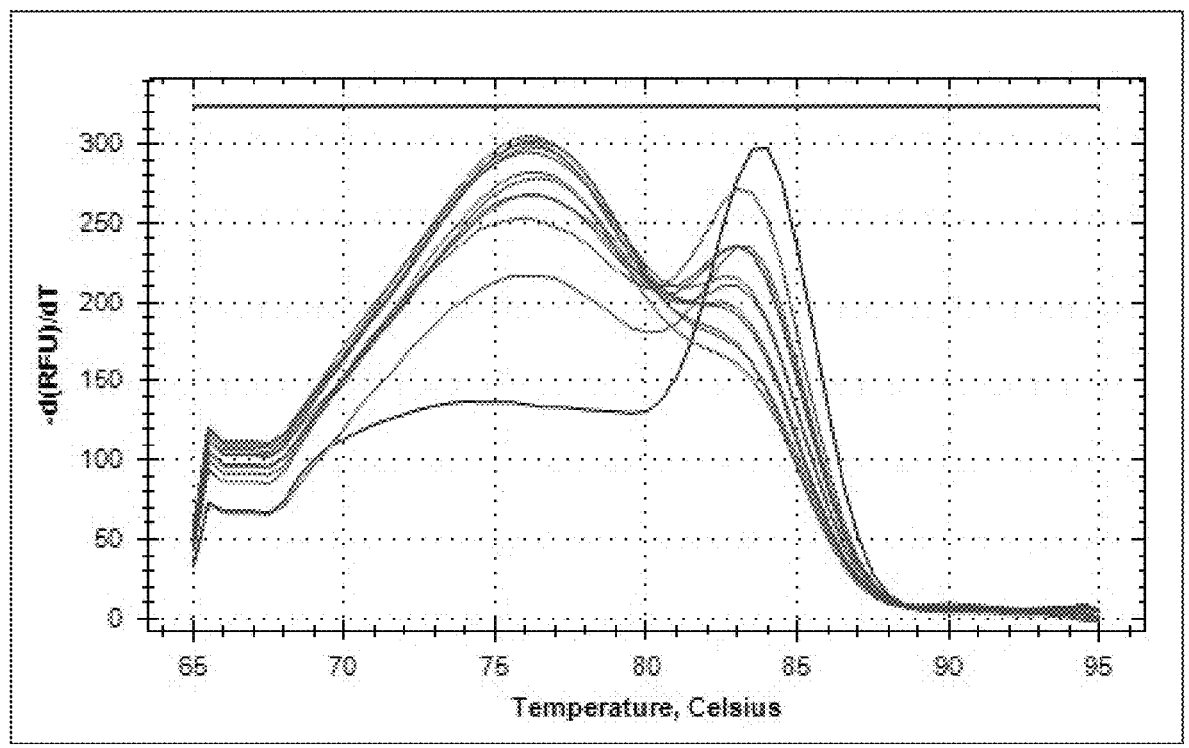

FIG. 29D shows a melt peak plot for the SYBR qPCR analysis of the Alu-247 target using standard DNA (5 ng, 1 ng, 200 pg, 40 pg, and 8 pg) in green, with positive control in red and no template control in black.

Figure 30A:
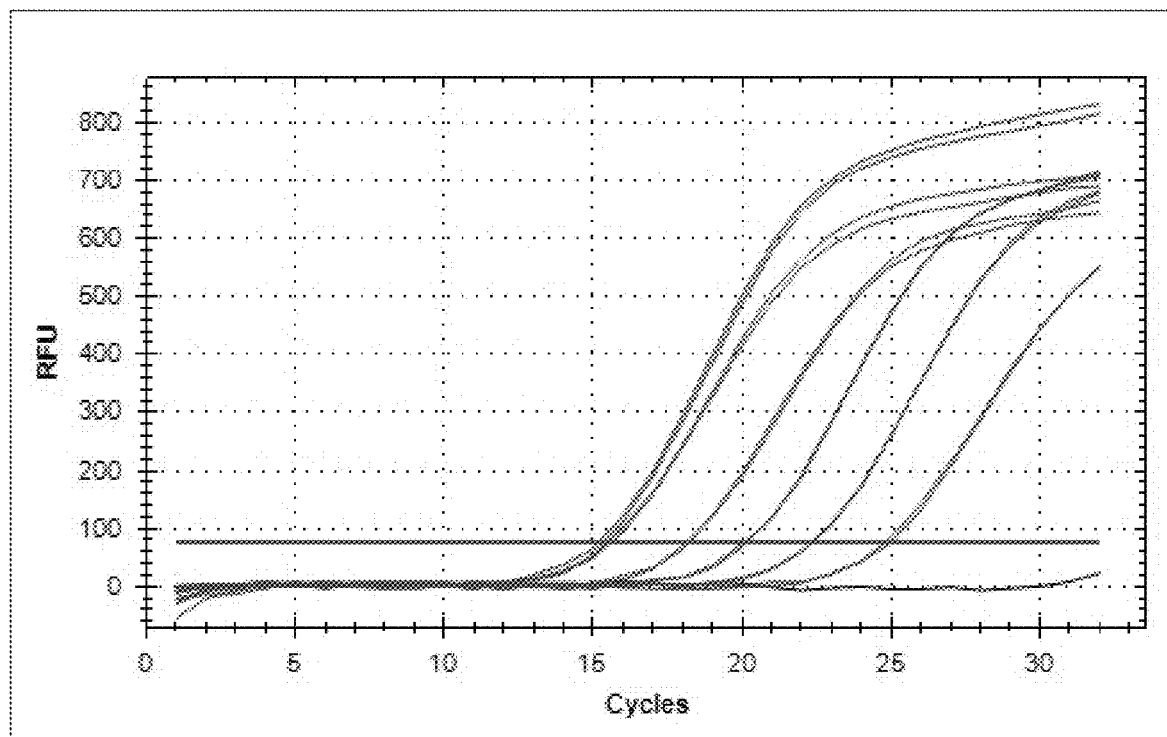

FIG. 30A shows an amplification plot for the Yb8-80 target of a real-time PCR multiplex of the Yb8-80 and SVA-207 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.

Figure 30B:
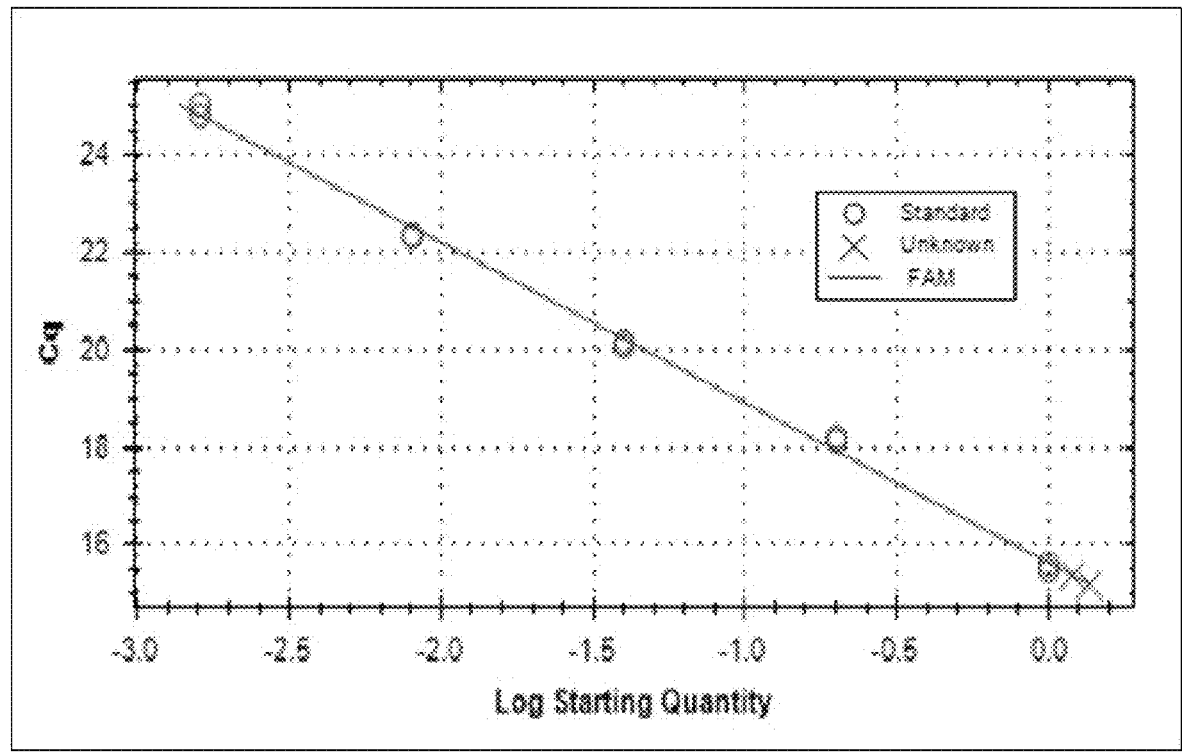

FIG. 30B shows a standard curve for the Yb8-80 target of a real-time PCR multiplex of the Yb8-80 and SVA-207 targets. Efficiency: 101.8%; R²: 0.997; slope: −3.280; y-intercept: 15.643.

Figure 30C:
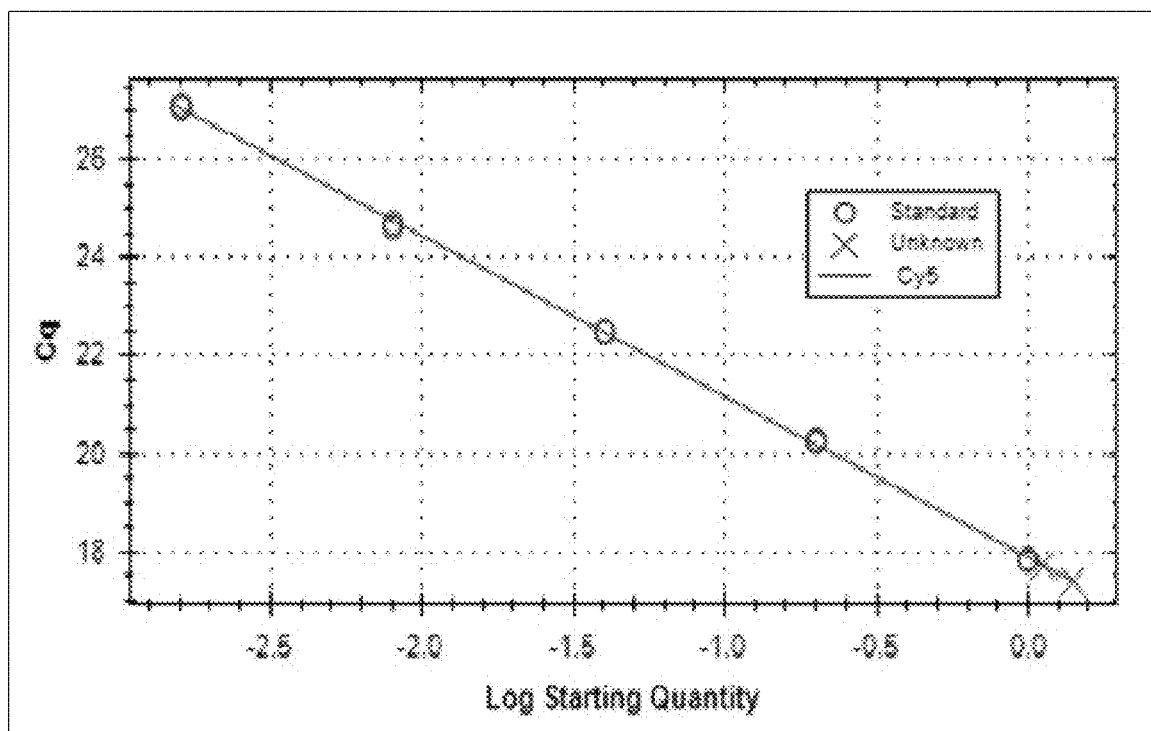

FIG. 30C shows an amplification plot for the SVA-207 target of a real-time PCR multiplex of the Yb8-80 and SVA-207 targets, the quantification of DNA in each sample being determined by use of a calibration curve with serial dilutions (1 ng, 200 pg, 40 pg, 8 pg, and 1.6 pg), with amplification of the SVA-207 target in purple, positive control in red and no template control in black. Efficiency: 101.7%; R²: 1.000; slope: −3.281; y-intercept: 17.888.

Figure 30D:
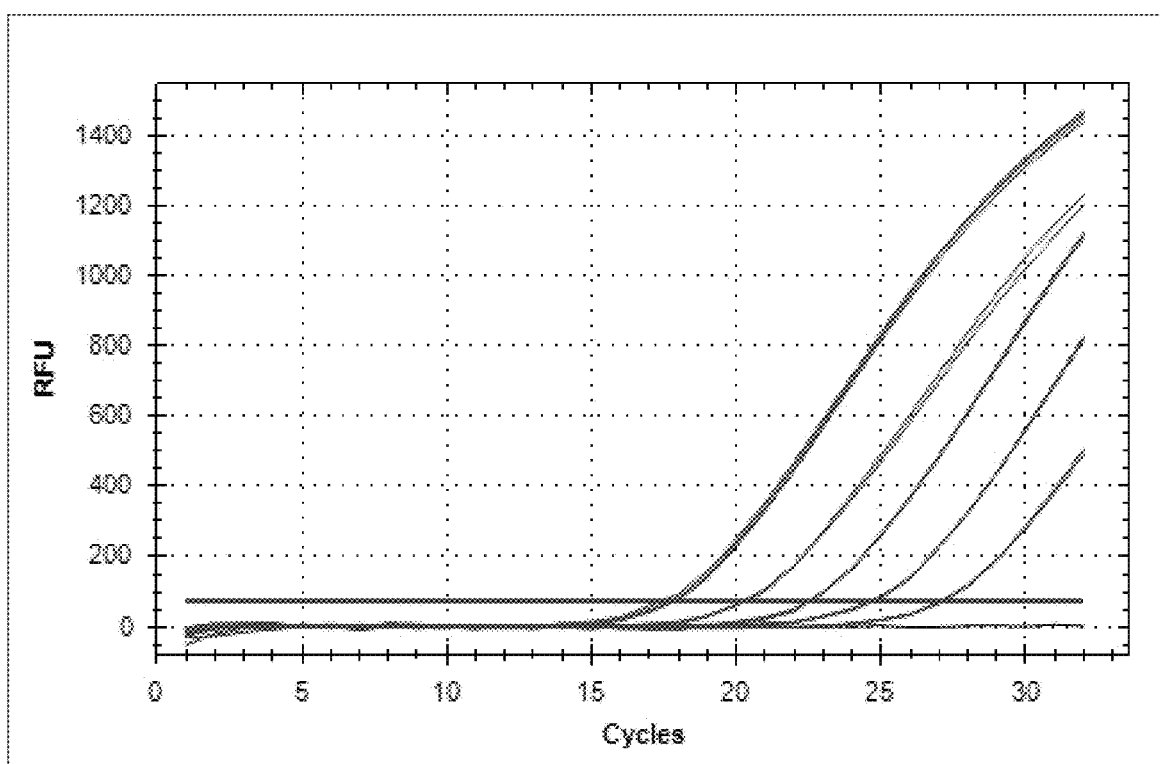

FIG. 30D shows a standard curve for the SVA-207 target of a real-time PCR multiplex of the Yb8-80 and SVA-207 targets.

Figure 30E:
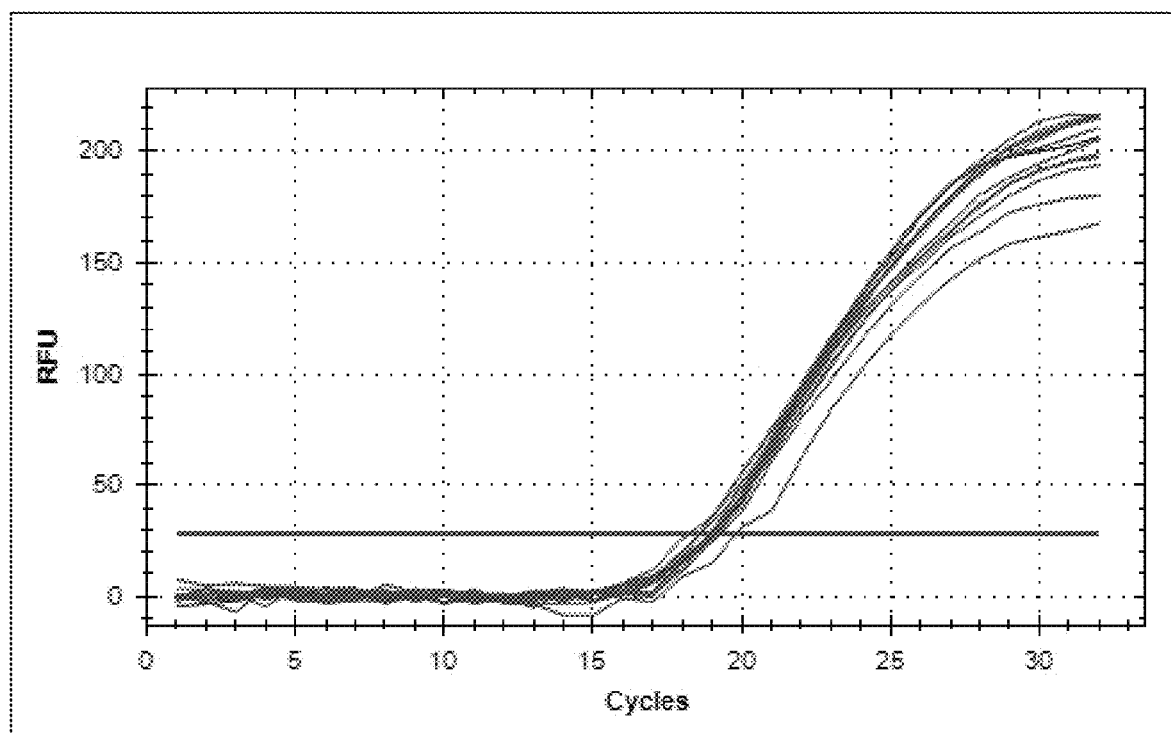

FIG. 30E shows an amplification plot of the internal positive control target within a real-time PCR multiplex of the Yb8-80 and SVA-207 targets, with amplification of the internal positive control target in blue.

Figure 31A:
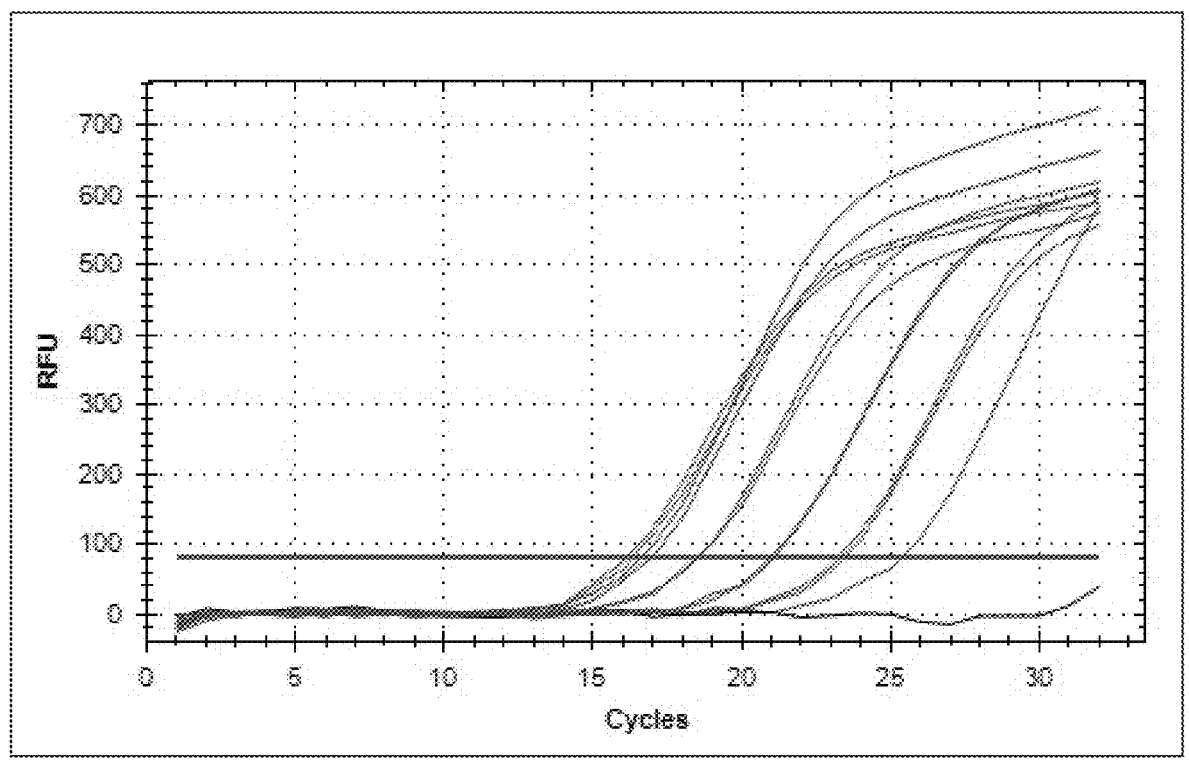

FIG. 31A shows an amplification plot for the Yb8-80 target of a real-time PCR multiplex of the Yb8-80 and SVA-257 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.

Figure 31B:
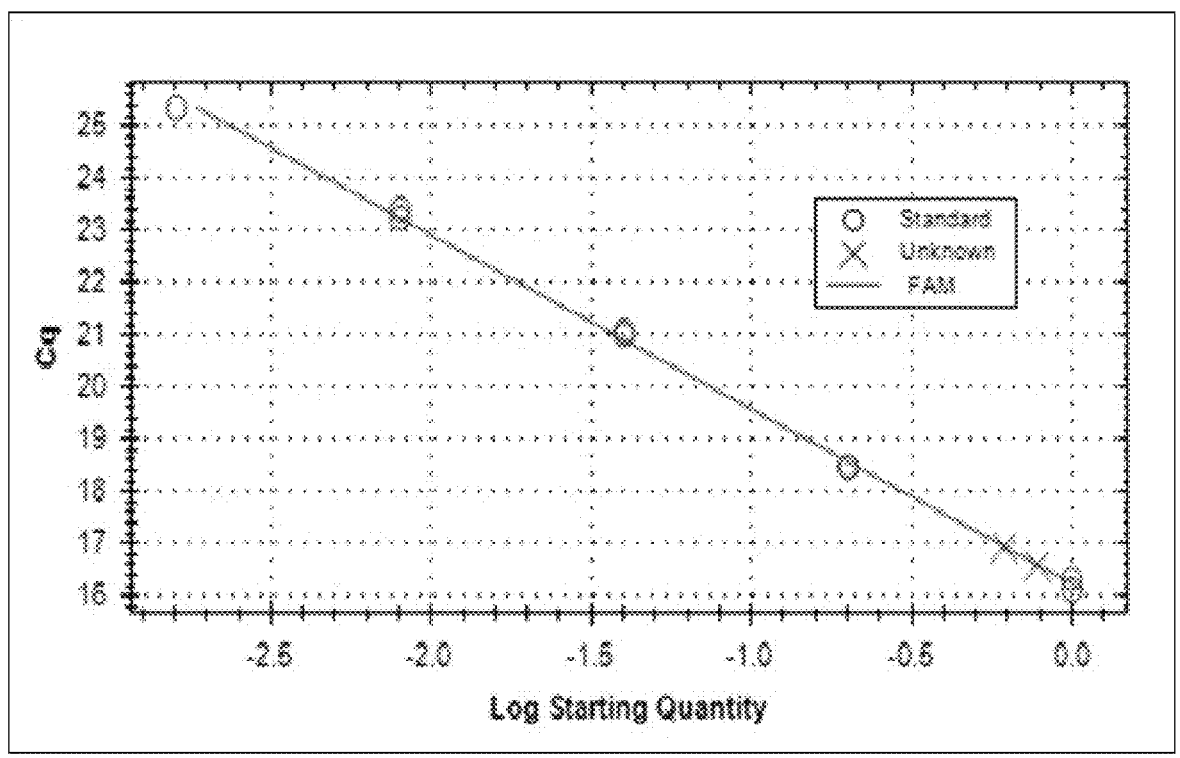

FIG. 31B shows a standard curve for the Yb8-80 target of a real-time PCR multiplex of the Yb8-80 and SVA-257 targets. Efficiency: 99.4%; R²: 0.998; slope: −3.336; y-intercept: 16.246.

Figure 31C:
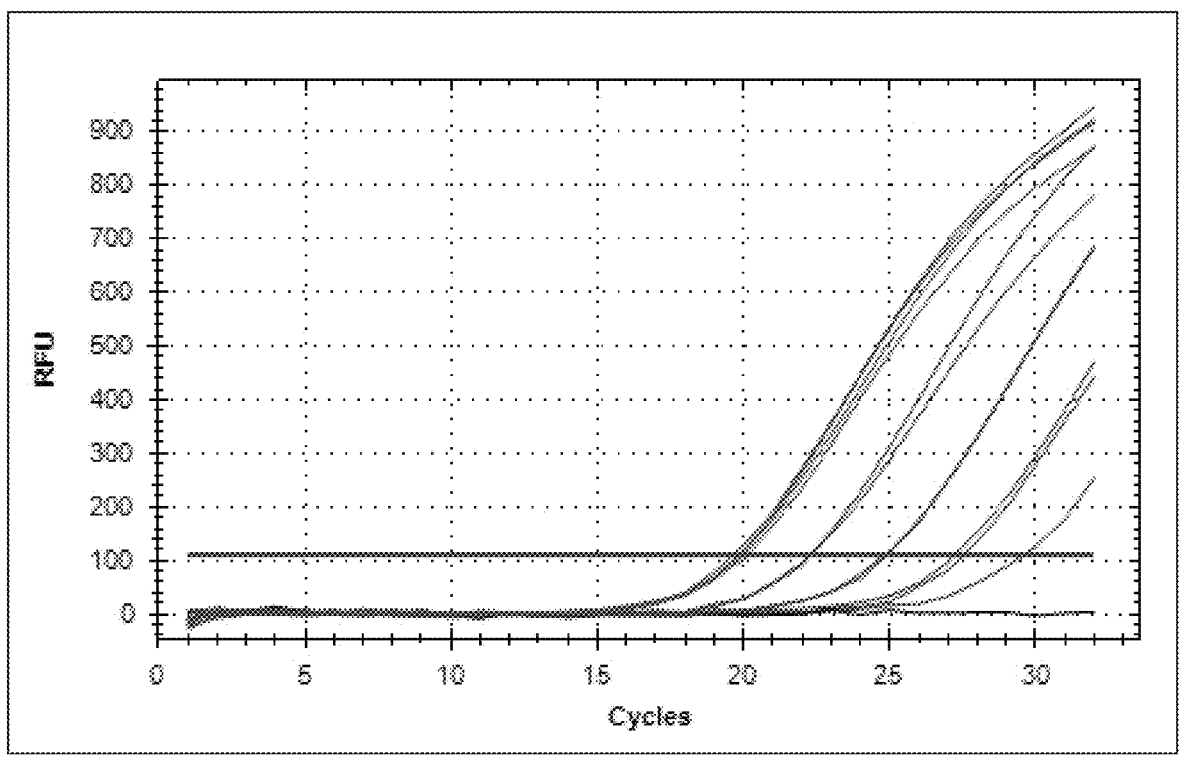

FIG. 31C shows an amplification plot for the SVA-257 target of a real-time PCR multiplex of the Yb8-80 and SVA-257 targets, the quantification of DNA in each sample being determined by use of a calibration curve with serial dilutions (1 ng, 200 pg, 40 pg, 8 pg, and 1.6 pg), with amplification of the SVA-257 target in purple, positive control in red and no template control in black.

Figure 31D:
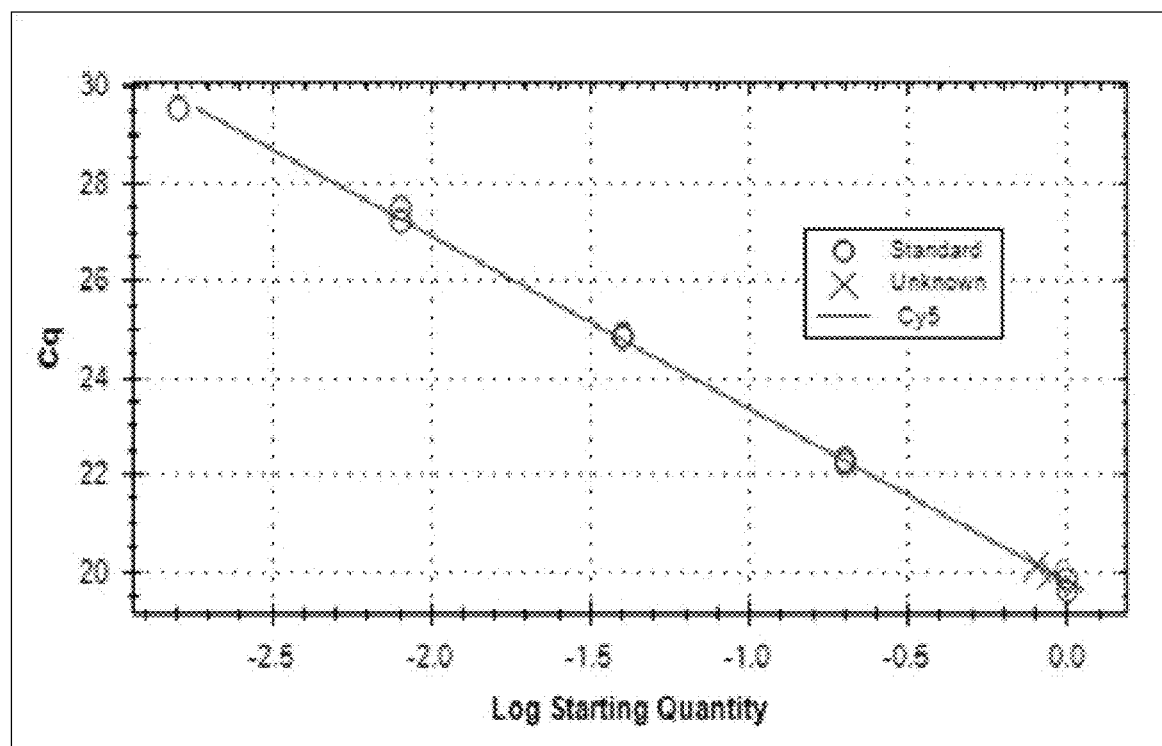

FIG. 31D shows a standard curve for the SVA-257 target of a real-time PCR multiplex of the Yb8-80 and SVA-257 targets. Efficiency: 90.5%; R²: 0.998; slope: −3.573; y-intercept: 19.787.

Figure 31E:
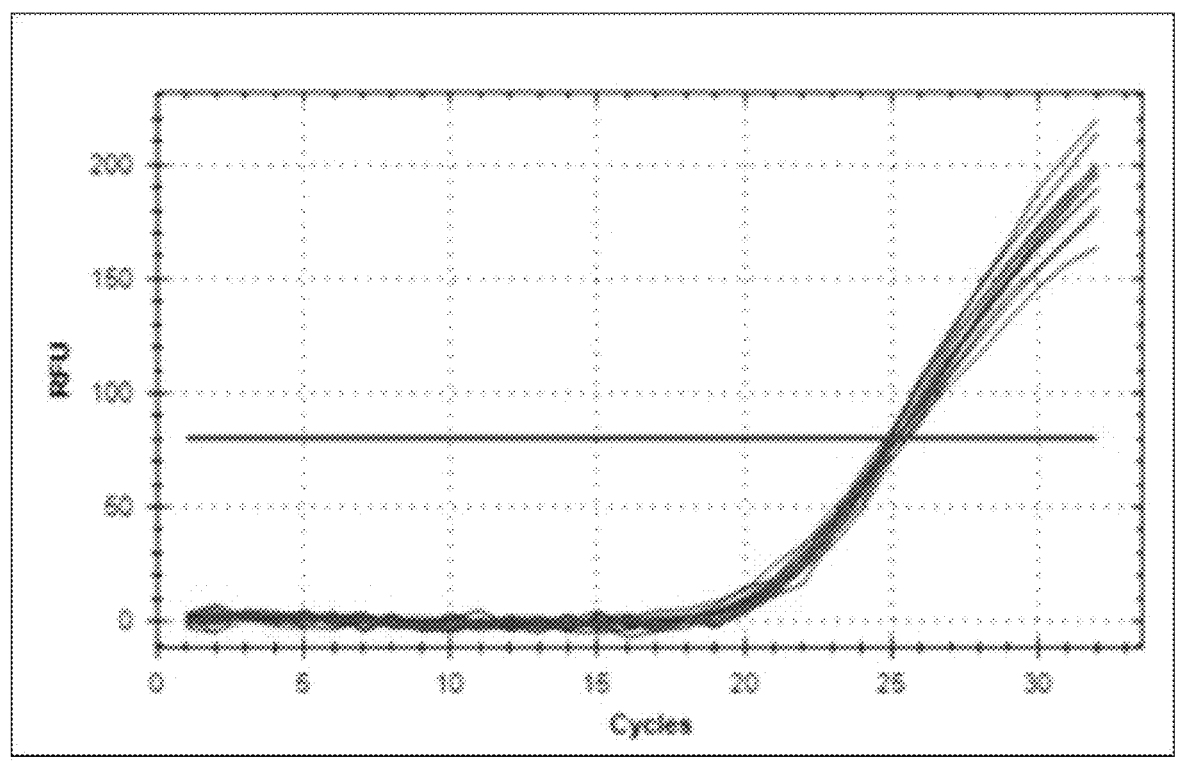

FIG. 31E shows an amplification plot of the internal positive control target within a real-time PCR multiplex of the Yb8-80 and SVA-257 targets, with amplification of the internal positive control target in blue.

Figure 32A:
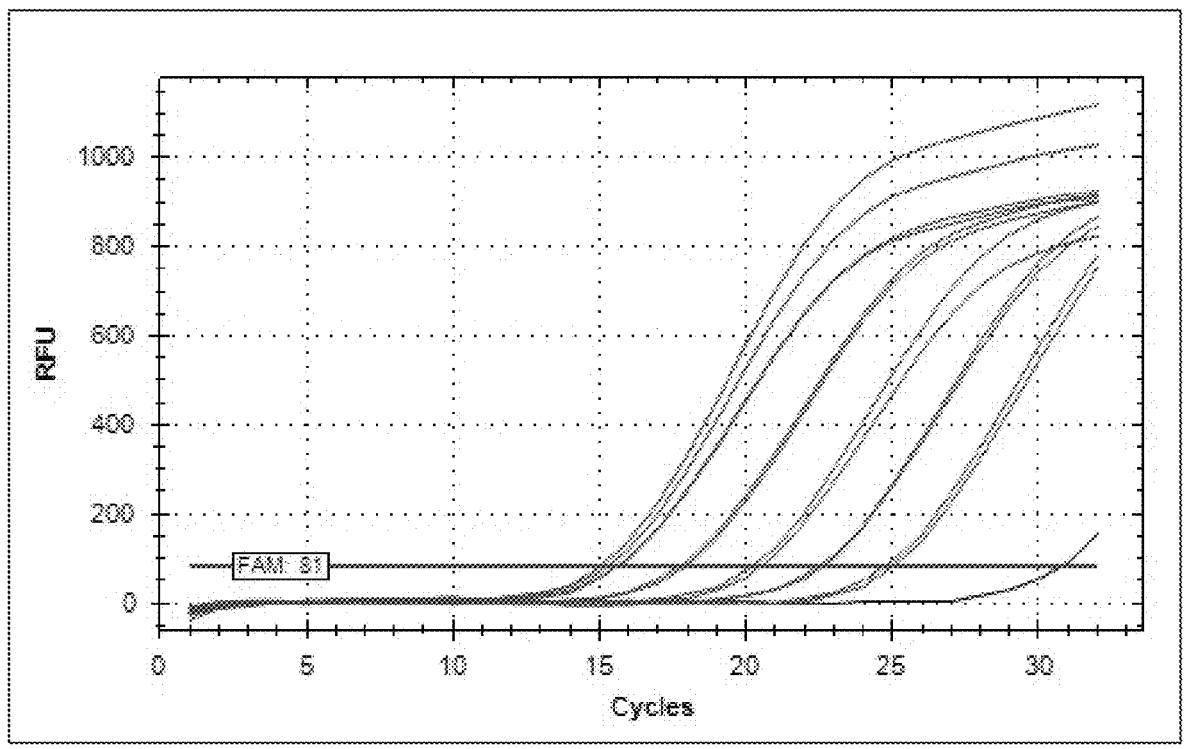

FIG. 32A shows an amplification plot for the Yb8-80 target of a real-time PCR multiplex of the Yb8-80 and SVA-265 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.

Figure 32B:
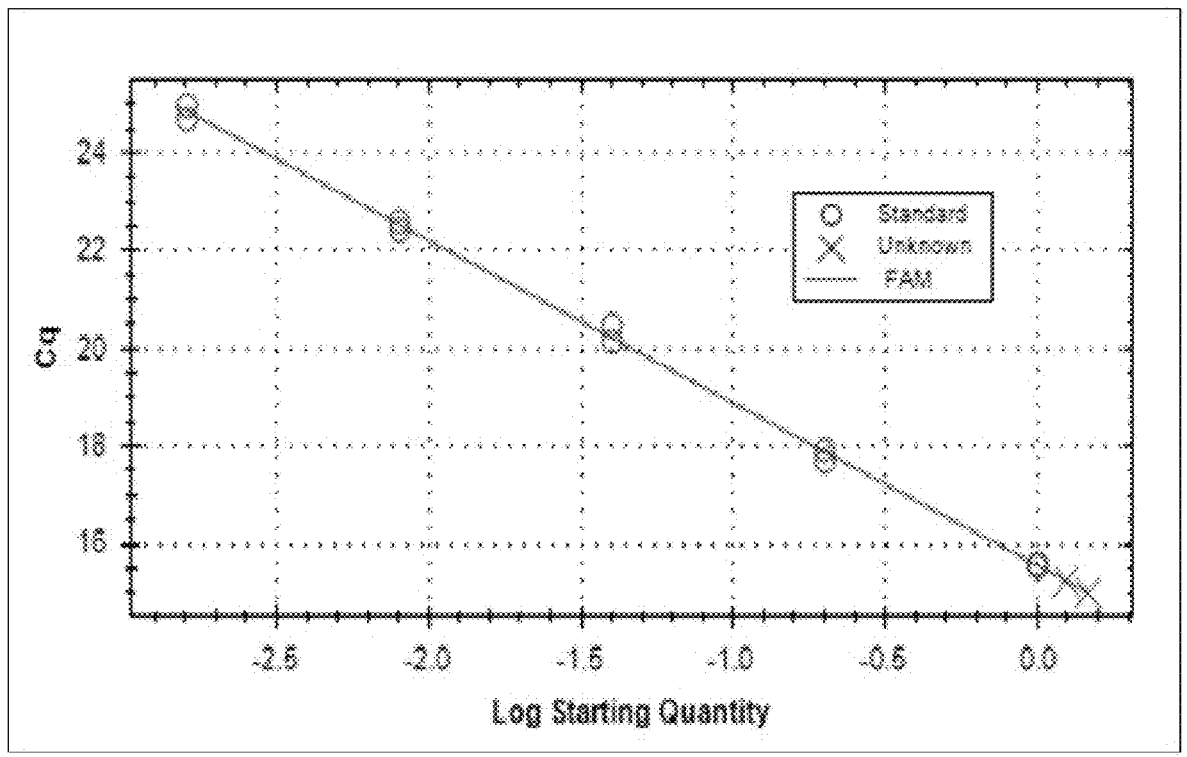

FIG. 32B shows a standard curve for the Yb8-80 target of a real-time PCR multiplex of the Yb8-80 and SVA-265 targets. Efficiency: 99.9%; $R^2$: 0.998; slope: −3.324; y-intercept: 15.565.

Figure 32C:
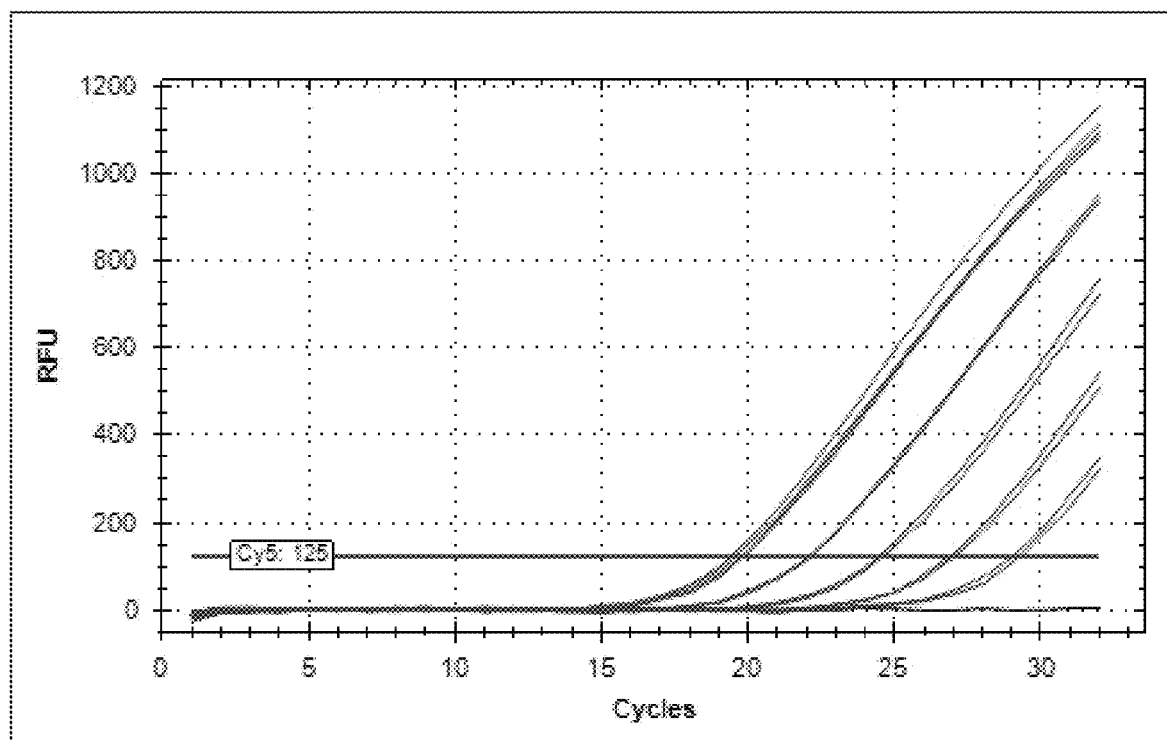

FIG. 32C shows an amplification plot for the SVA-265 target of a real-time PCR multiplex of the Yb8-80 and SVA-265 targets, the quantification of DNA in each sample being determined by use of a calibration curve with serial dilutions (1 ng, 200 pg, 40 pg, 8 pg, and 1.6 pg), with amplification of the SVA-265 target in purple, positive control in red and no template control in black.

Figure 32D:
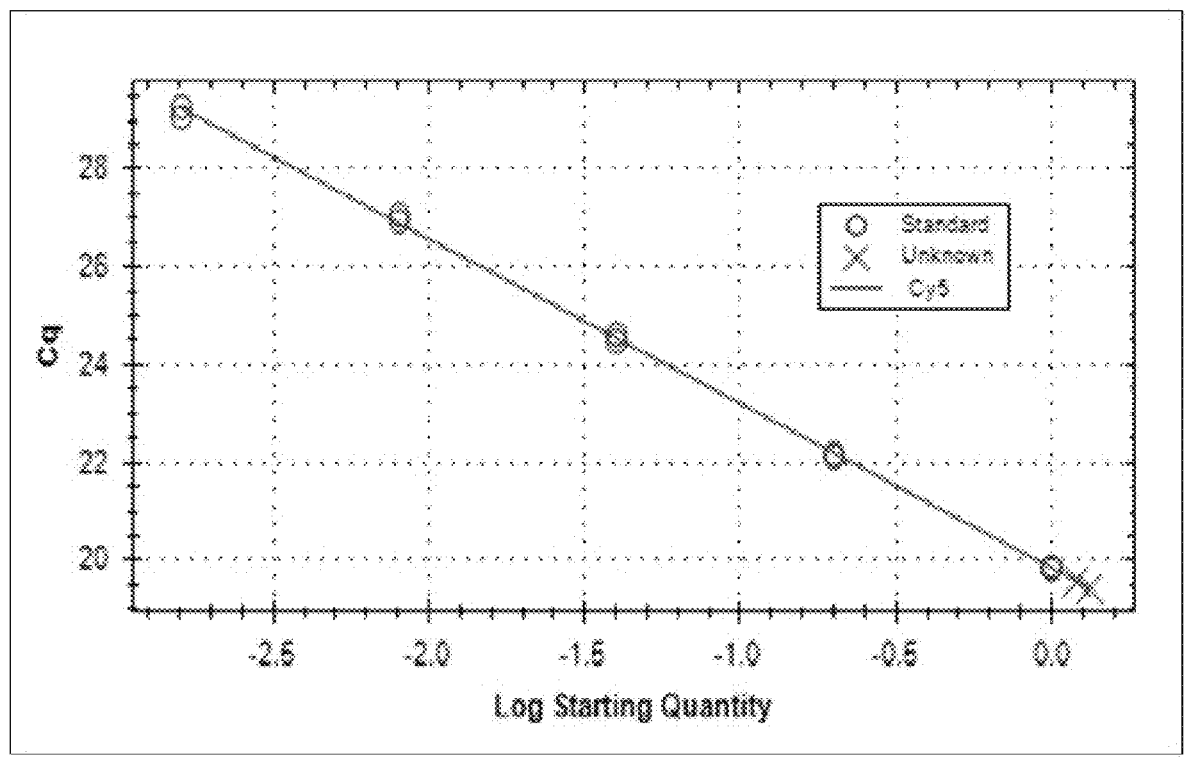

FIG. 32D shows a standard curve for the SVA-265 target of a real-time PCR multiplex of the Yb8-80 and SVA-265 targets. Efficiency: 98.3%; $R^2$: 0.999; slope: −3.363; y-intercept: 19.848.

Figure 32E:
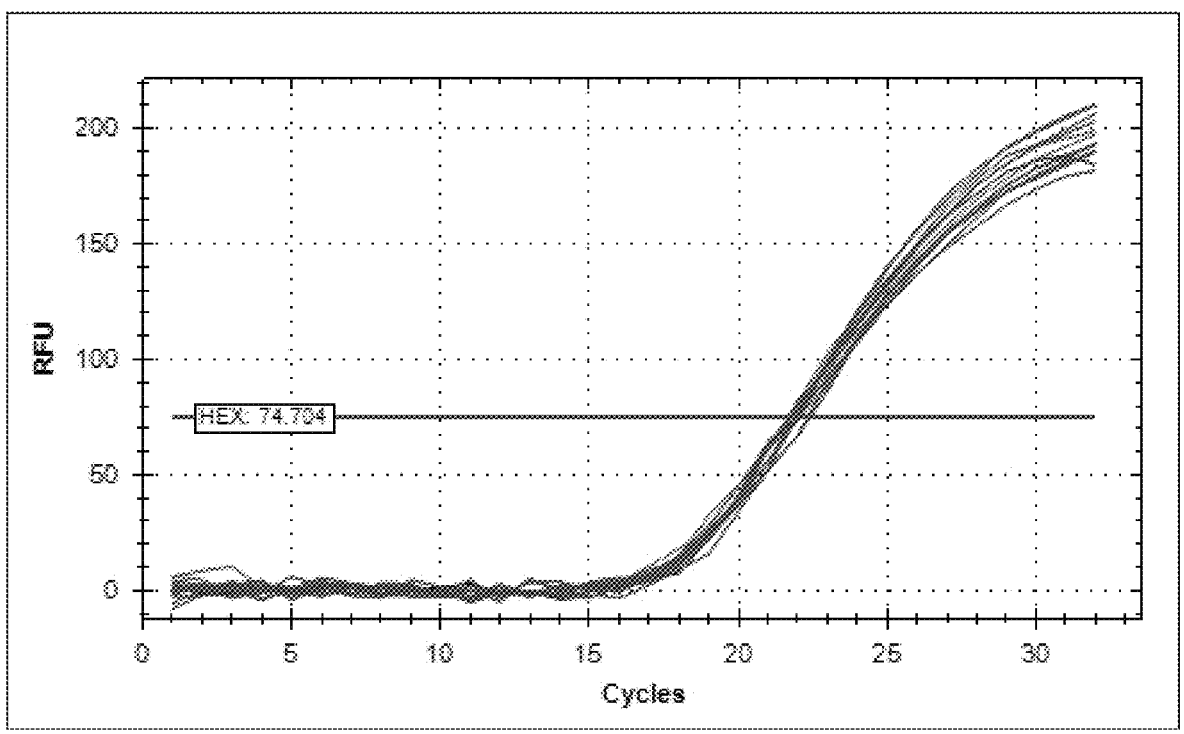

FIG. 32E shows an amplification plot of the internal positive control target within a real-time PCR multiplex of the Yb8-80 and SVA-265 targets, with amplification of the internal positive control target in blue.

Figure 33A:
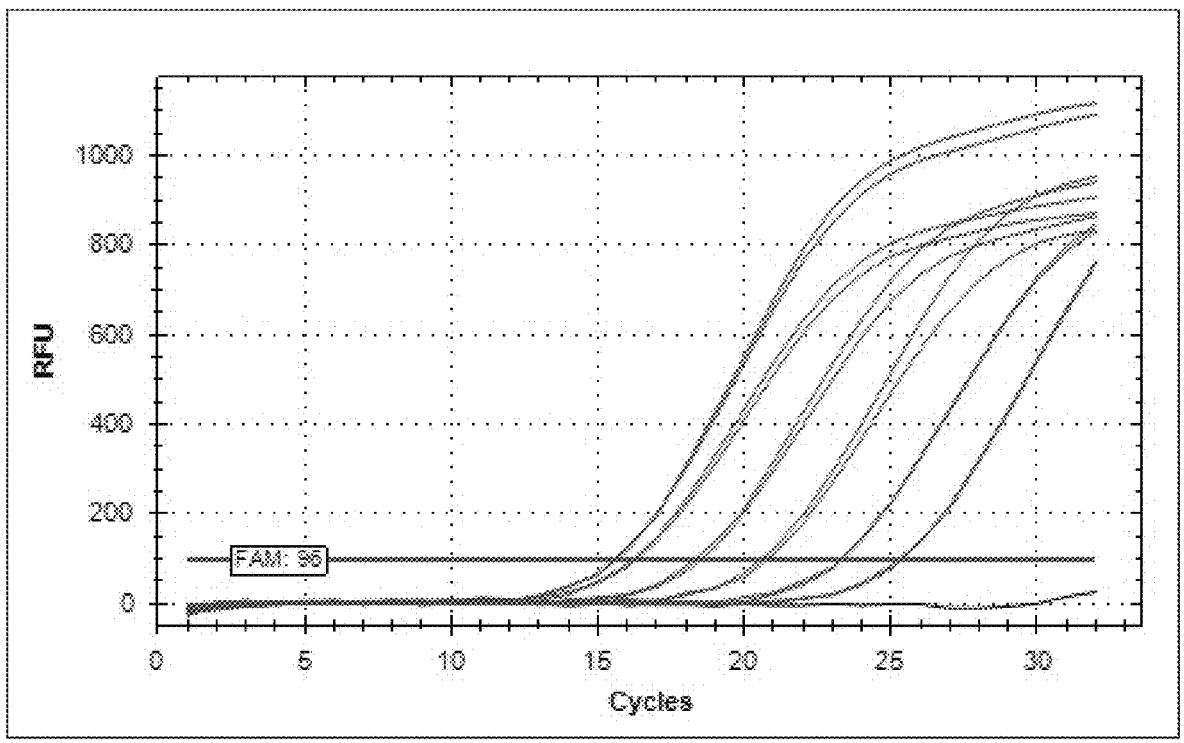

FIG. 33A shows an amplification plot for the Yb8-80 target of a real-time PCR multiplex of the Yb8-80 and SVA-290 targets, the quantification of DNA in each sample being determined by use of a calibration curve with serial dilutions (1 ng, 200 pg, 40 pg, 8 pg, and 1.6 pg), with amplification of the Yb8-80 target in green, positive control in red and no template control in black.

Figure 33B:
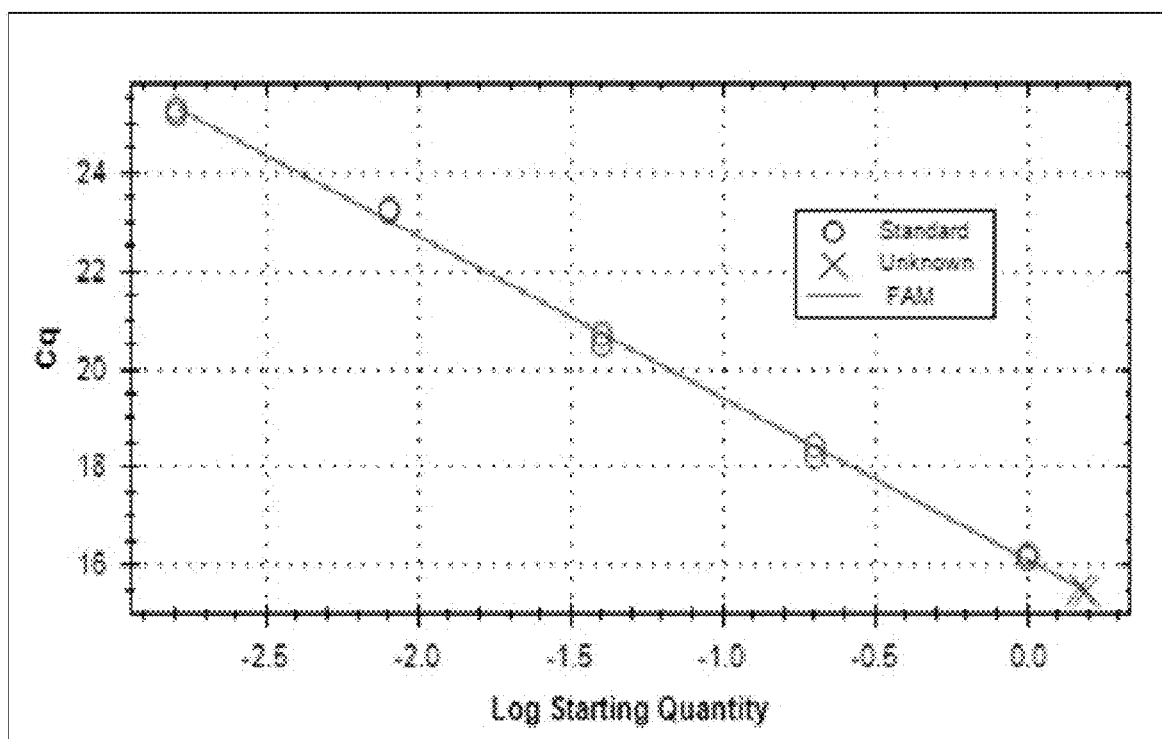

FIG. 33B shows a standard curve for the Yb8-80 target of a real-time PCR multiplex of the Yb8-80 and SVA-290 targets. Efficiency: 101.2%; $R^2$: 0.998; slope: −3.294; y-intercept: 16.120.

Figure 33C:
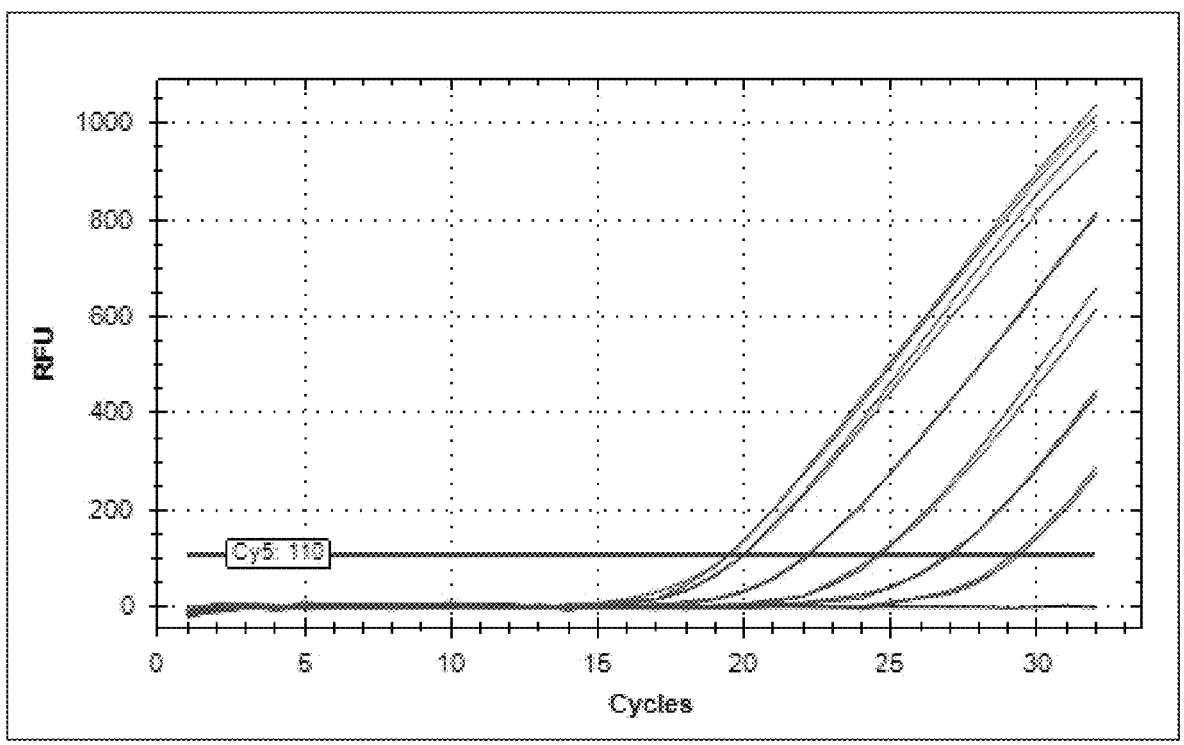

FIG. 33C shows an amplification plot for the SVA-290 target of a real-time PCR multiplex of the Yb8-80 and SVA-290 targets, the quantification of DNA in each sample being determined by use of a calibration curve with serial dilutions (1 ng, 200 pg, 40 pg, 8 pg, and 1.6 pg), with amplification of the SVA-290 target in purple, positive control in red and no template control in black.

Figure 33D:
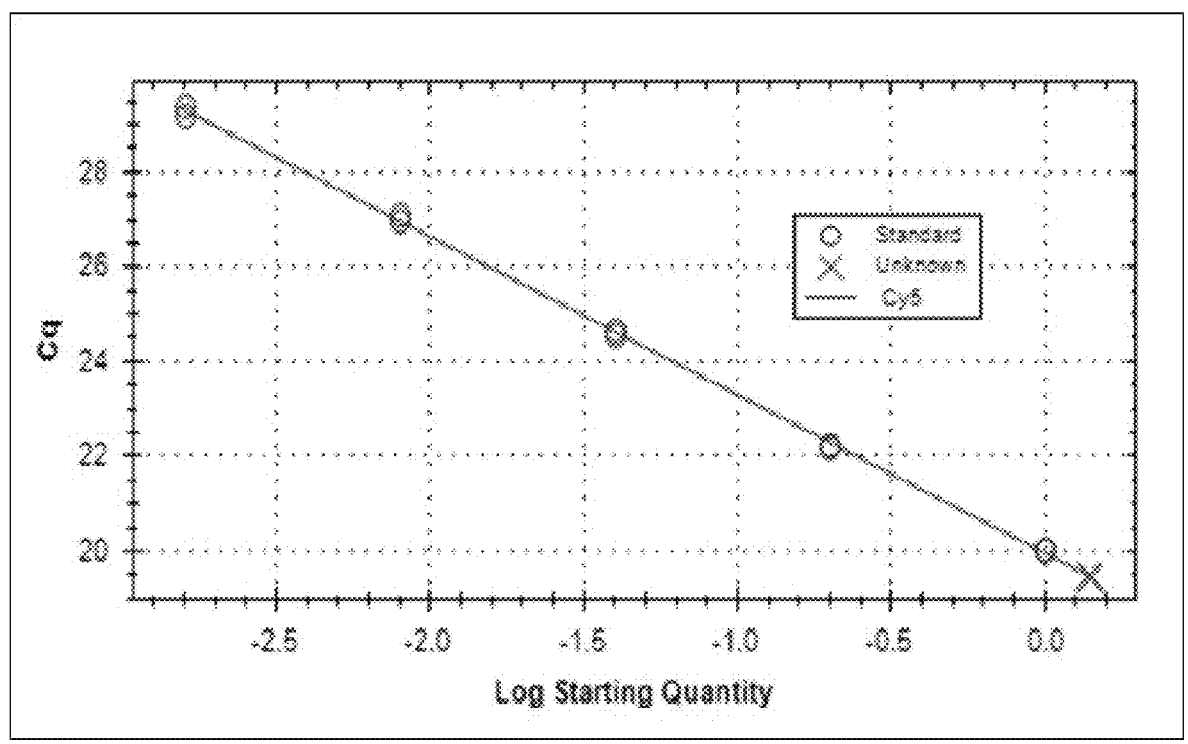

FIG. 33D shows a standard curve for the SVA-290 target of a real-time PCR multiplex of the Yb8-80 and SVA-290 targets. Efficiency: 99.3%; $R^2$: 0.999; slope: −3.340; y-intercept: 19.958.

Figure 33E:
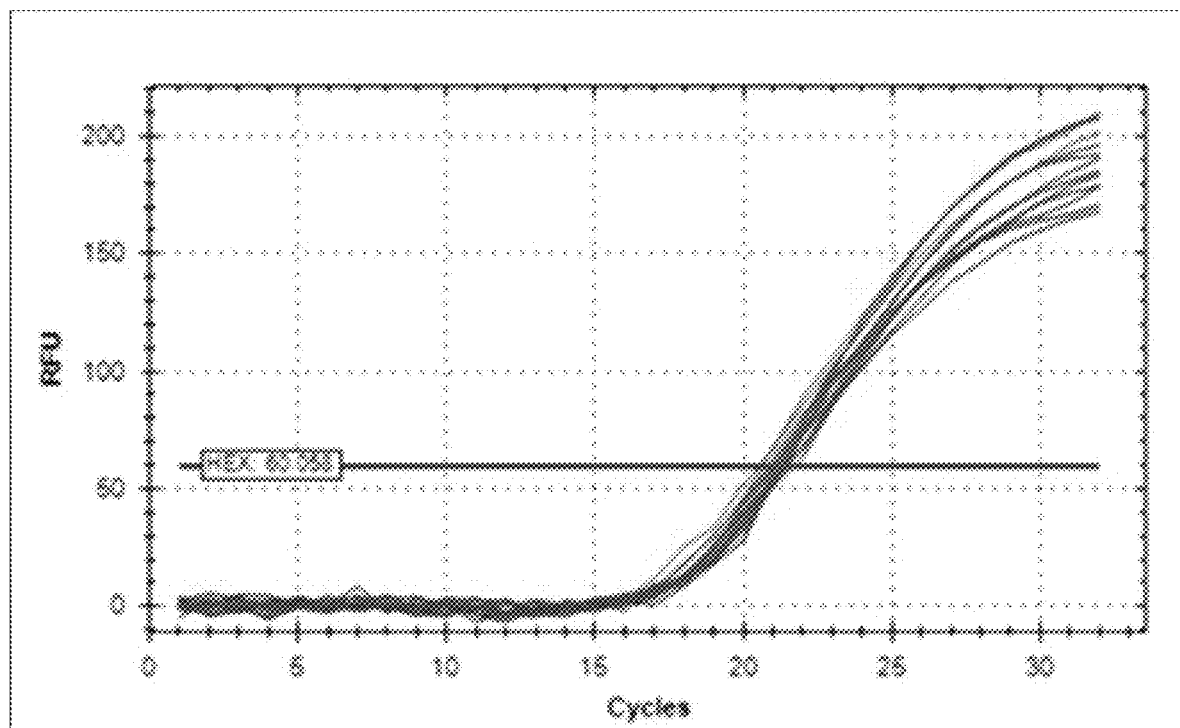

FIG. 33E shows an amplification plot of the internal positive control target within a real-time PCR multiplex of the Yb8-80 and SVA-290 targets, with amplification of the internal positive control target in blue.

Figure 34A:
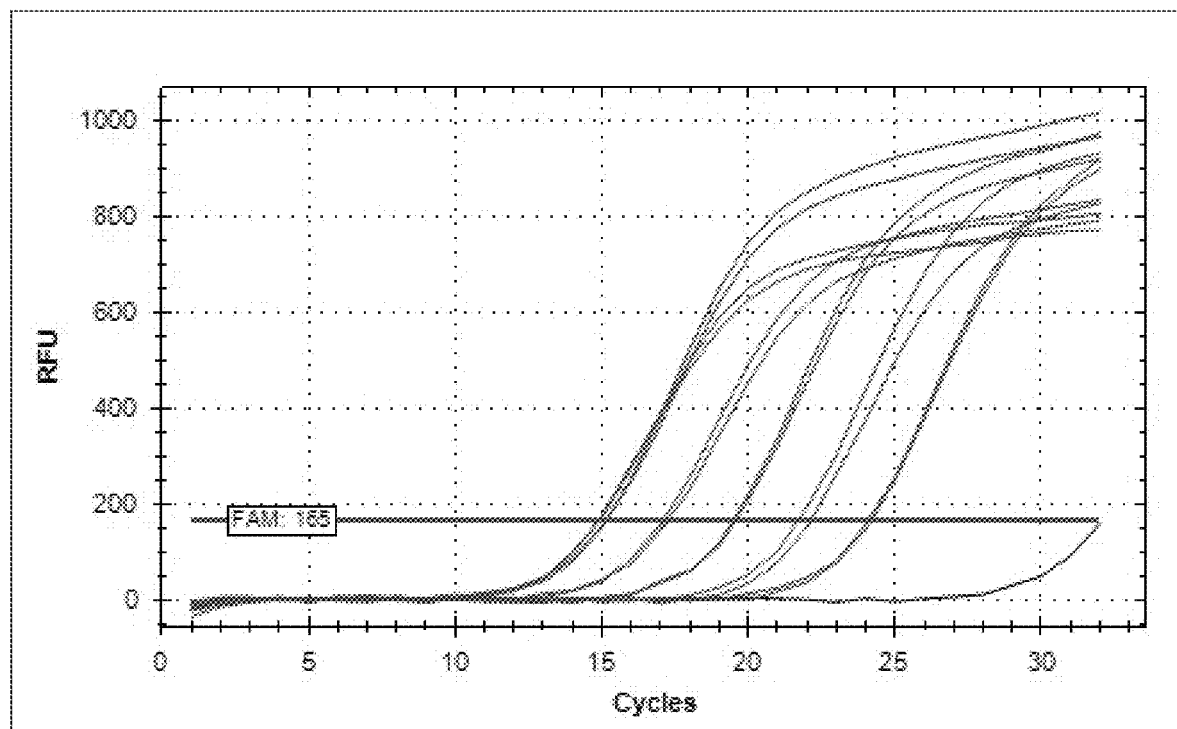

FIG. 34A shows an amplification plot for the Yb8-120 target of a real-time PCR multiplex of the Yb8-120 and SVA-207 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.

Figure 34B:
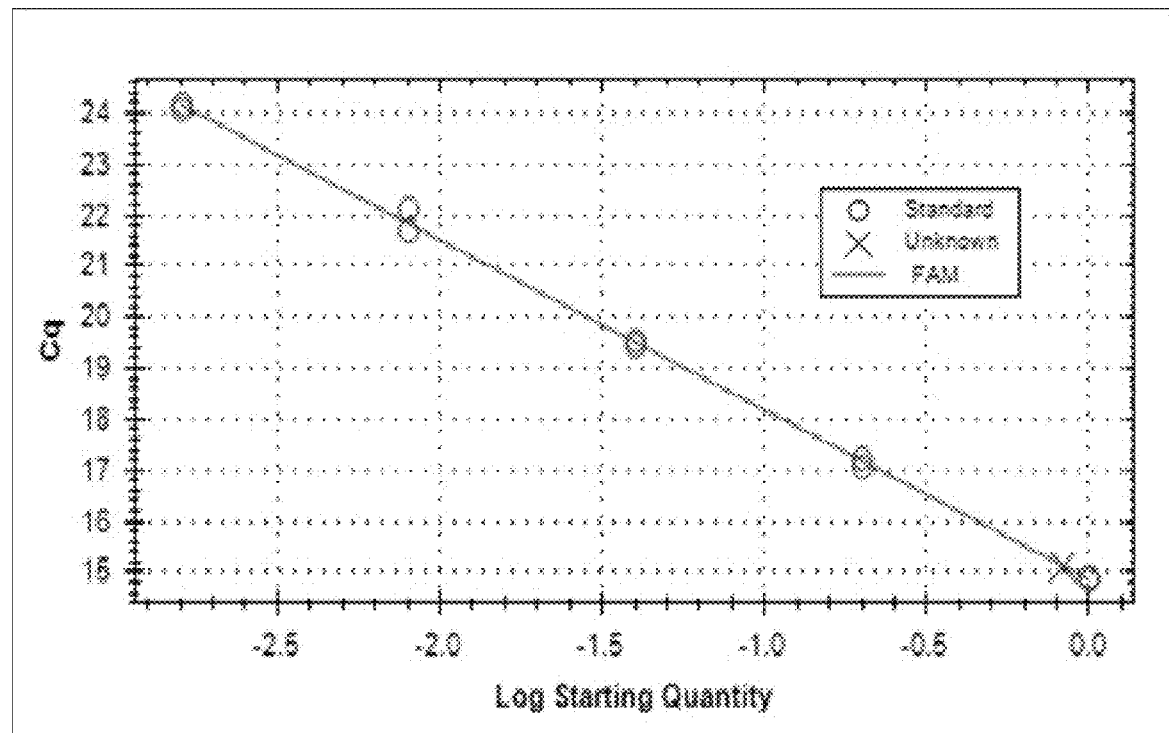

FIG. 34B shows a standard curve for the Yb8-120 target of a real-time PCR multiplex of the Yb8-120 and SVA-207 targets. Efficiency: 99.9%; $R^2$: 0.999; slope: −3.324; y-intercept: 14.864.

Figure 34C:
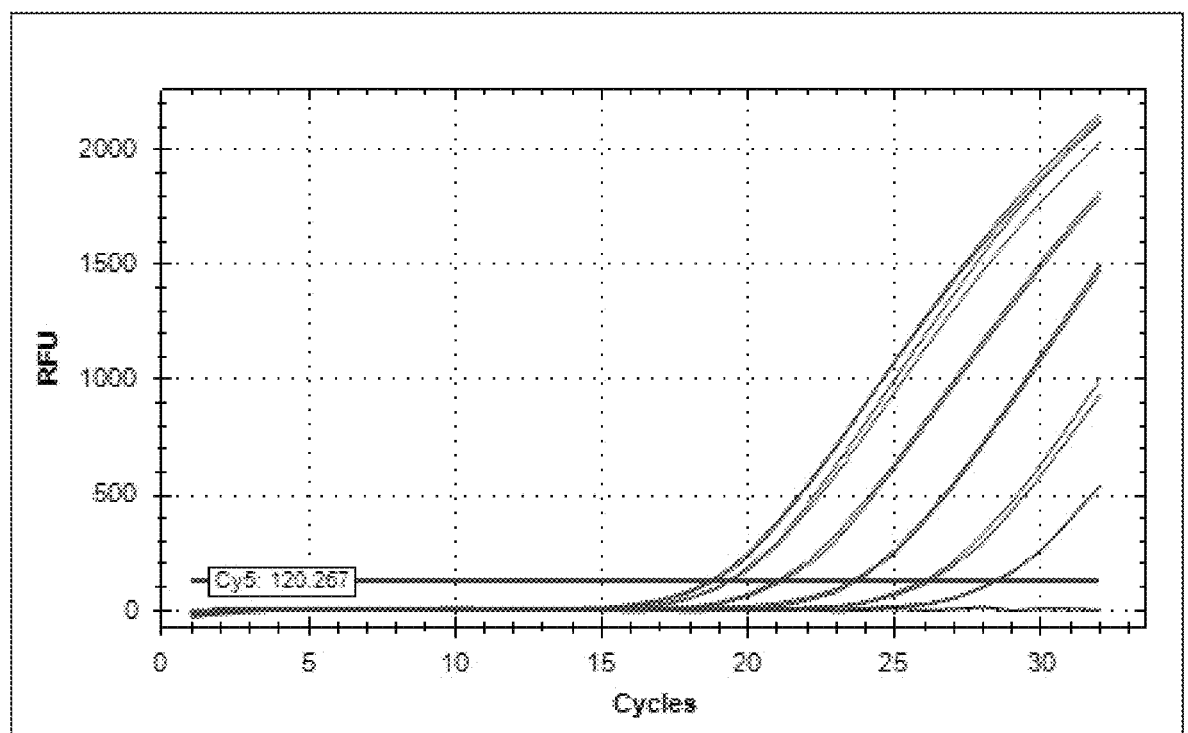

FIG. 34C shows an amplification plot for the SVA-207 target of a real-time PCR multiplex of the Yb8-120 and SVA-207 targets, the quantification of DNA in each sample being determined by use of a calibration curve with serial dilutions (1 ng, 200 pg, 40 pg, 8 pg, and 1.6 pg), with amplification of the SVA-207 target in purple, positive control in red and no template control in black.

Figure 34D:
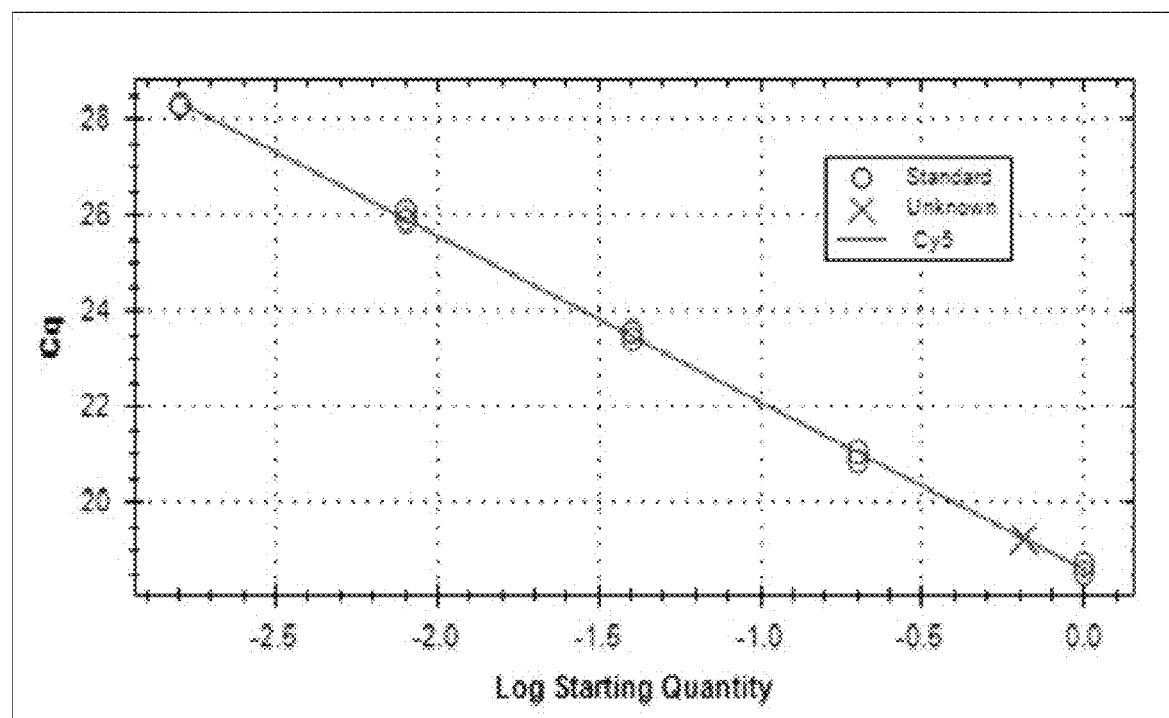

FIG. 34D shows a standard curve for the SVA-207 target of a real-time PCR multiplex of the Yb8-120 and SVA-207 targets. Efficiency: 93.5%; $R^2$: 0.999; slope: −3.487; y-intercept: 18.612.

Figure 34E:
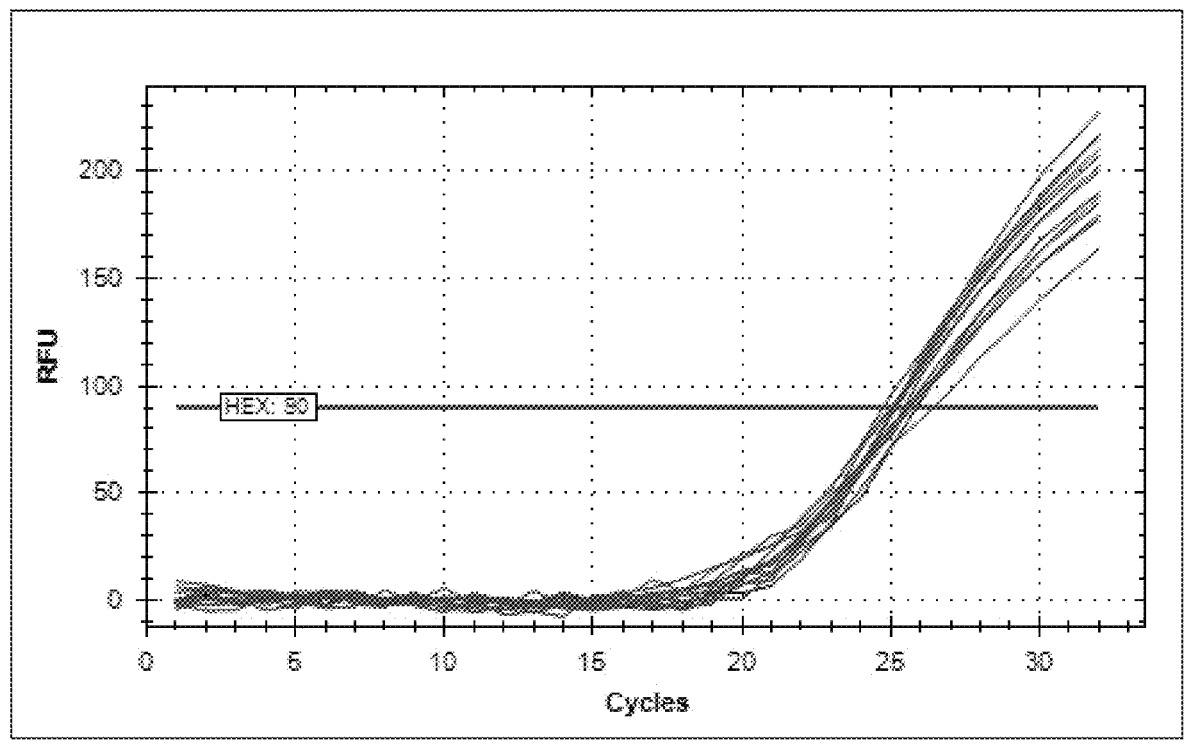

FIG. 34E shows an amplification plot of the internal positive control target within a real-time PCR multiplex of the Yb8-120 and SVA-207 targets, with amplification of the internal positive control target in blue.

Figure 35A:
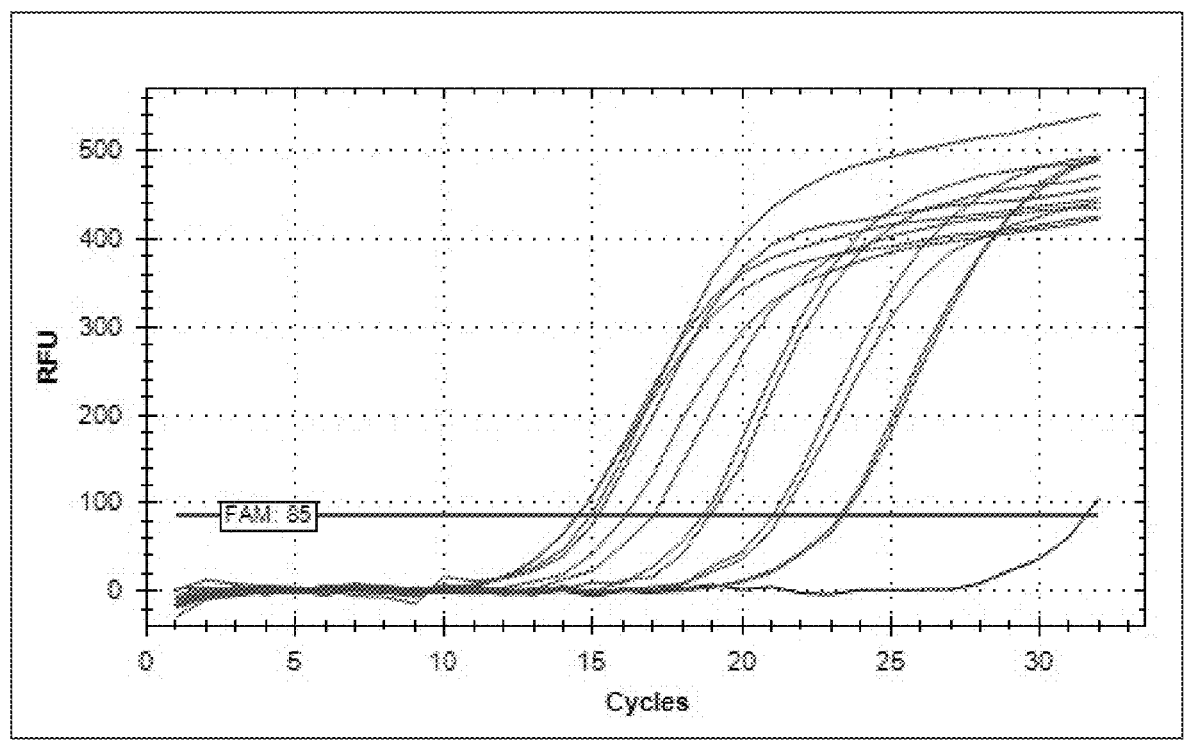

FIG. 35A shows an amplification plot for the Yb8-120 target of a real-time PCR multiplex of the Yb8-120 and SVA-257 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.

Figure 35B:
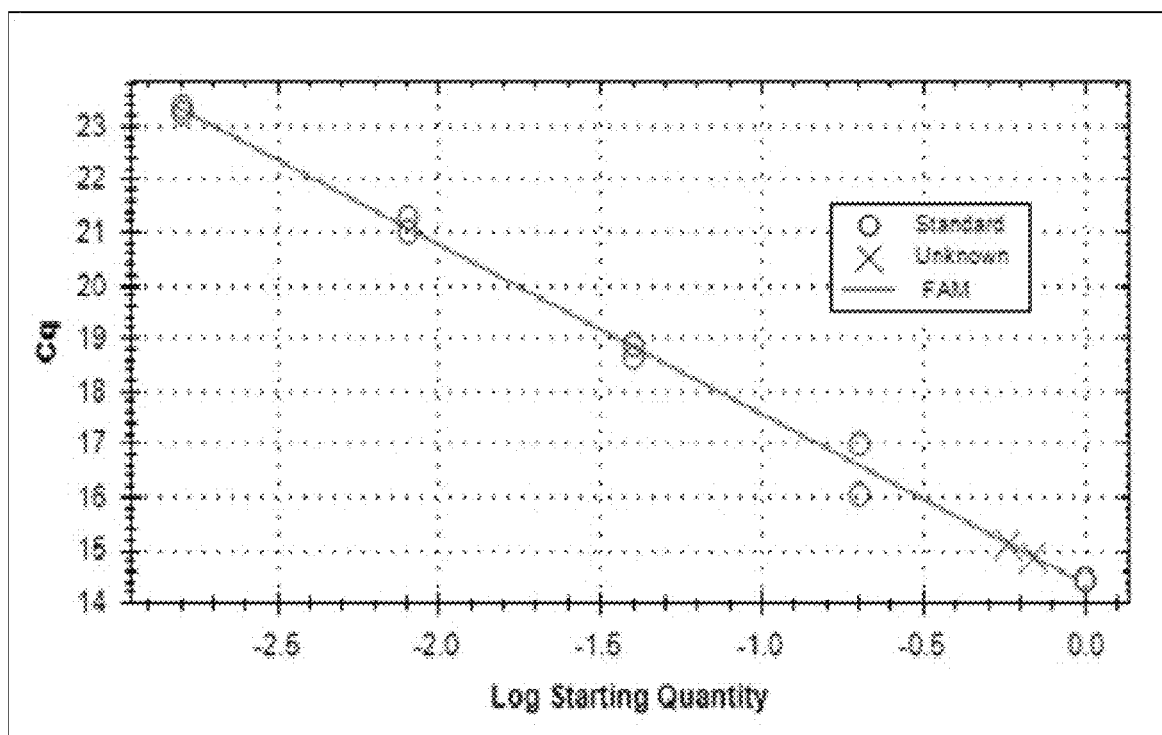

FIG. 35B shows a standard curve for the Yb8-120 target of a real-time PCR multiplex of the Yb8-120 and SVA-257 targets. Efficiency: 105.3%; $R^2$: 0.994; slope: −3.201; y-intercept: 14.369.

Figure 35C:
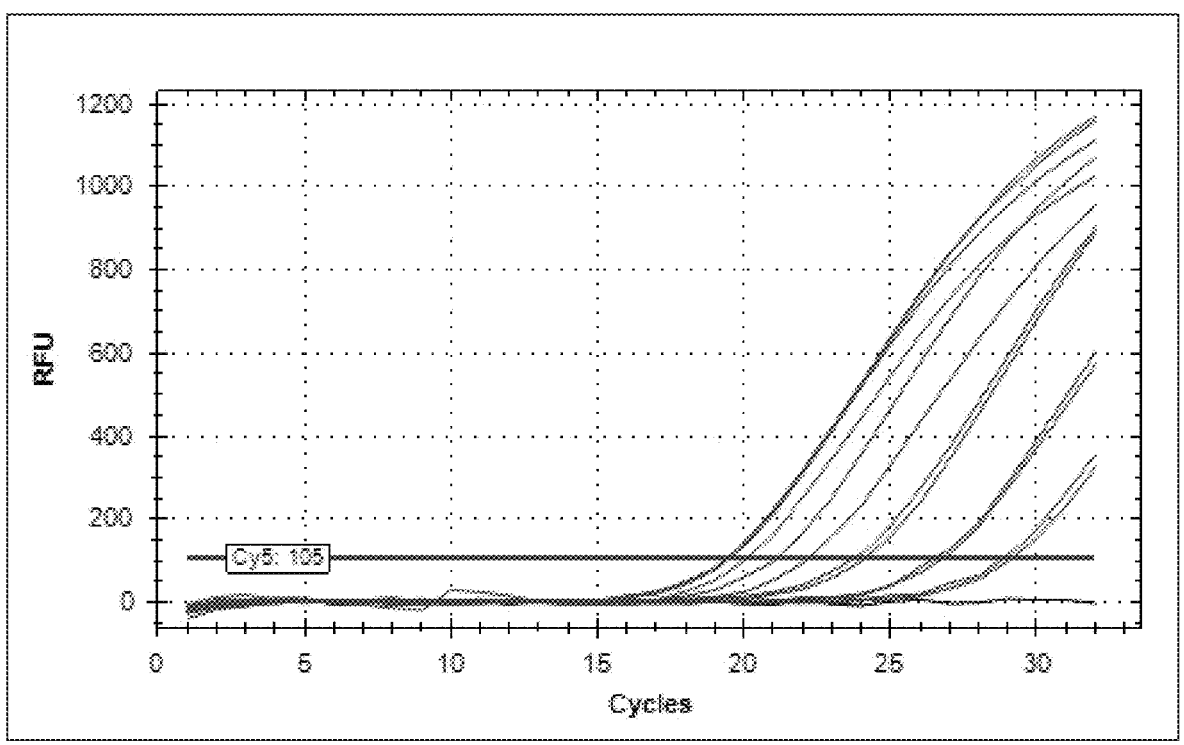

FIG. 35C shows an amplification plot for the SVA-257 target of a real-time PCR multiplex of the Yb8-120 and SVA-257 targets, the quantification of DNA in each sample being determined by use of a calibration curve with serial dilutions (1 ng, 200 pg, 40 pg, 8 pg, and 1.6 pg), with amplification of the SVA-257 target in purple, positive control in red and no template control in black.

Figure 35D:
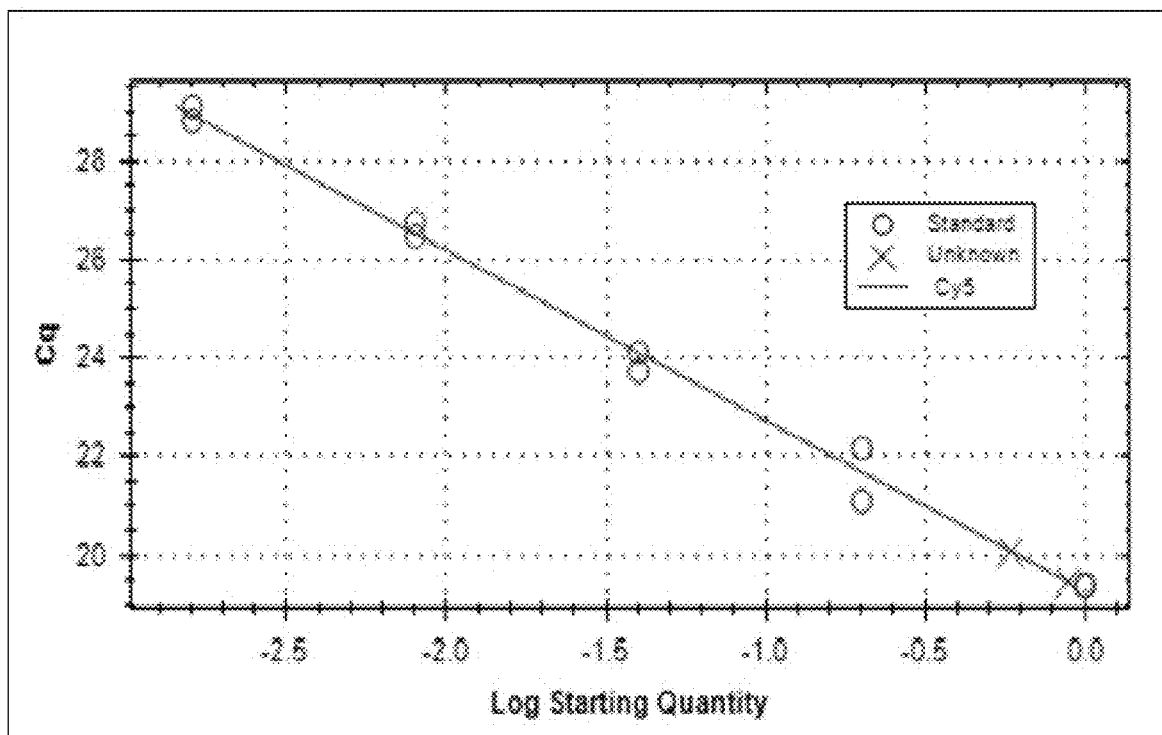

FIG. 35D shows a standard curve for the SVA-257 target of a real-time PCR multiplex of the Yb8-120 and SVA-257 targets. Efficiency: 95.0%; R2: 0.993; slope: −3.447; y-intercept: 19.287.

Figure 35E:
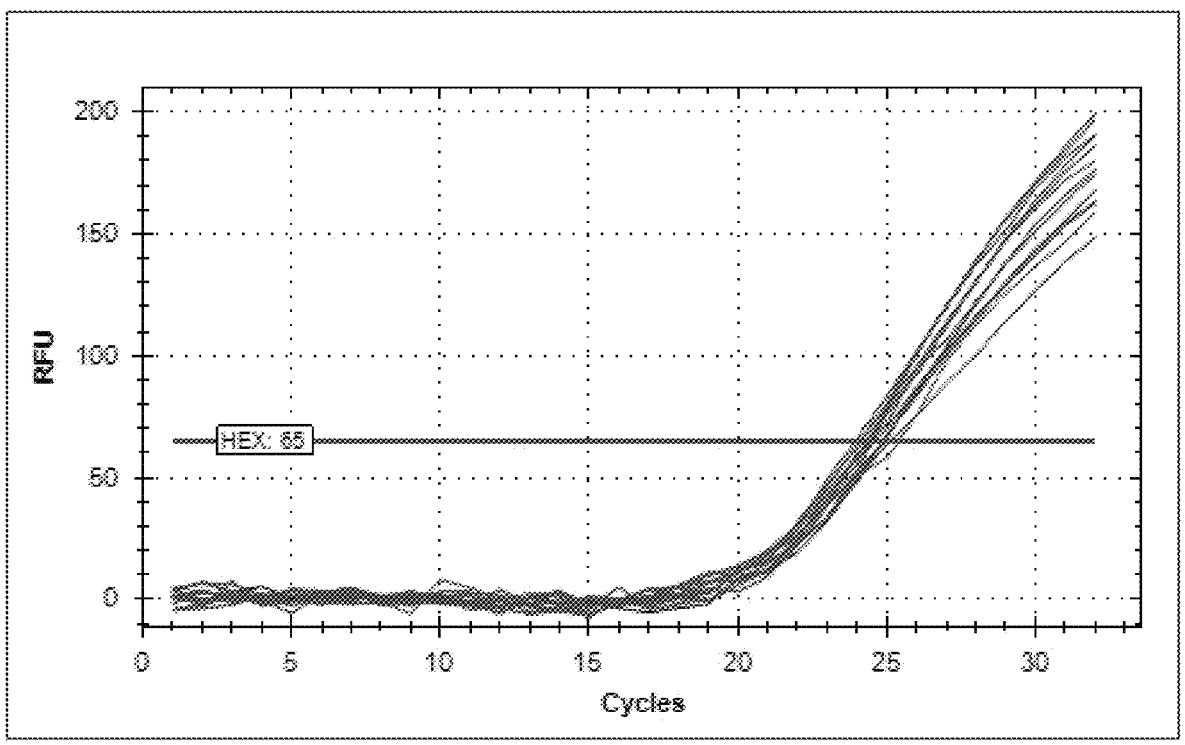

FIG. 35E shows an amplification plot of the internal positive control target within a real-time PCR multiplex of the Yb8-120 and SVA-257 targets, with amplification of the internal positive control target in blue.

Figure 36A:
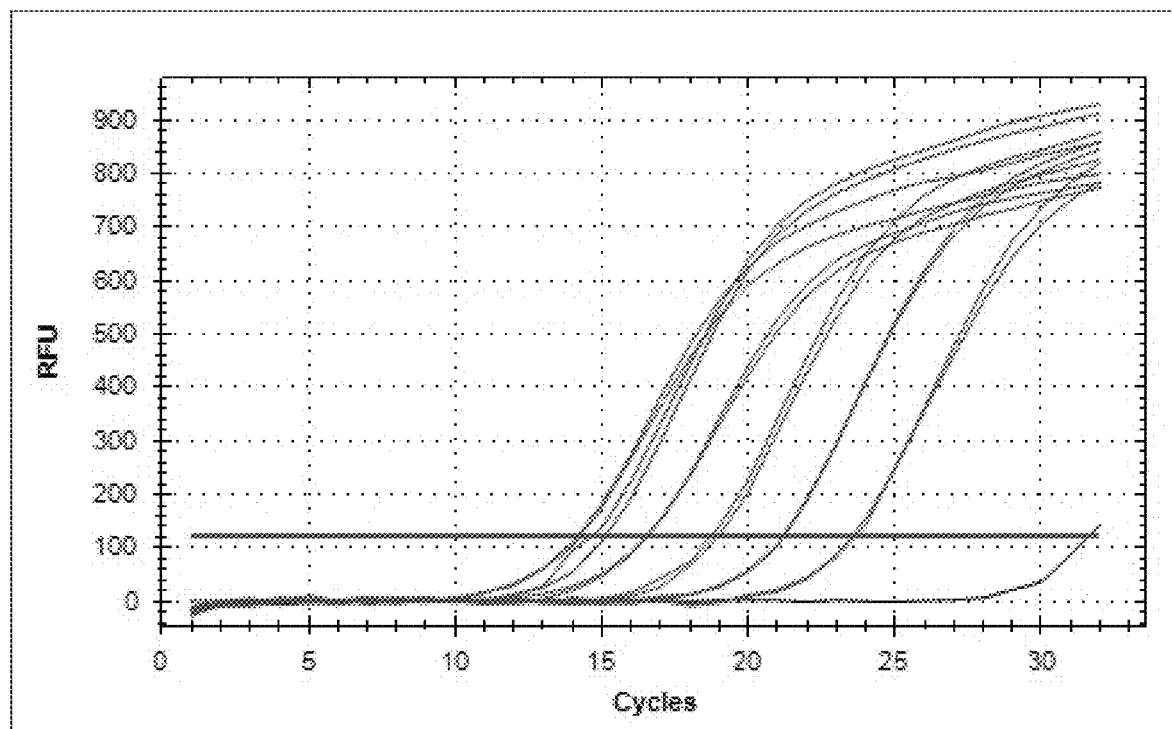

FIG. 36A shows an amplification plot for the Yb8-120 target of a real-time PCR multiplex of the Yb8-120 and SVA-265 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.

Figure 36B:
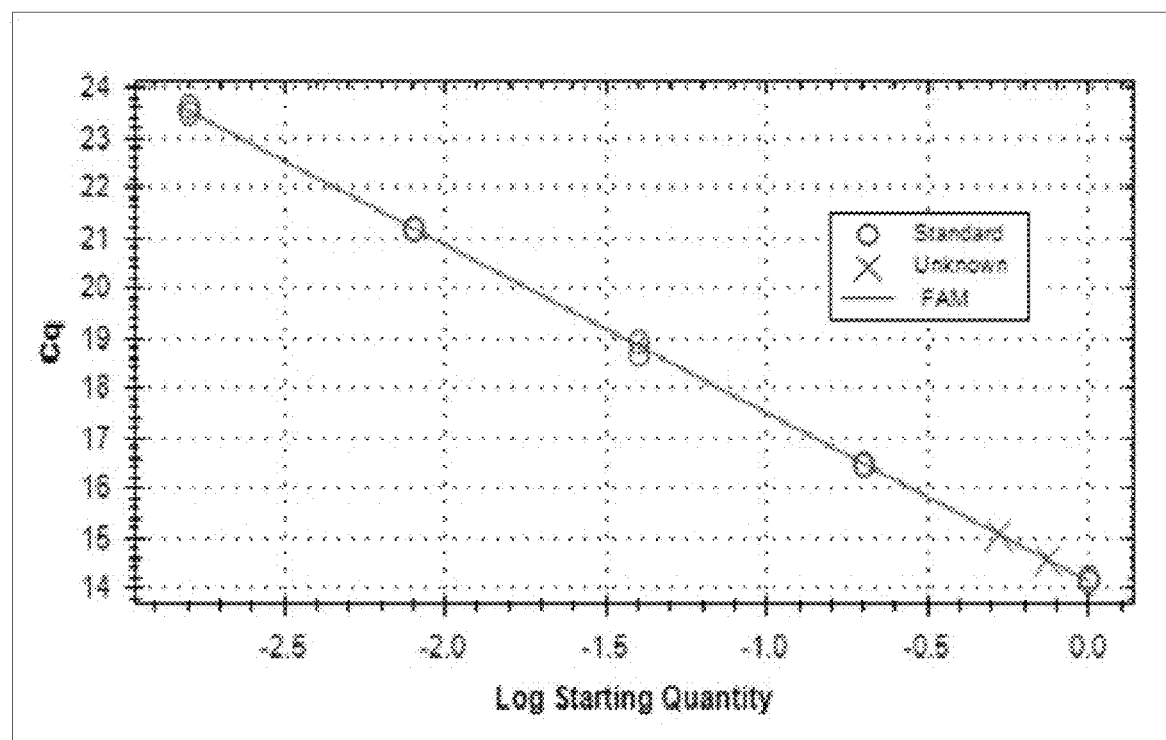

FIG. 36B shows a standard curve for the Yb8-120 target of a real-time PCR multiplex of the Yb8-120 and SVA-265 targets. Efficiency: 98.7%; $R^2$: 1.000; slope: −3.353; y-intercept: 14.152.

Figure 36C:
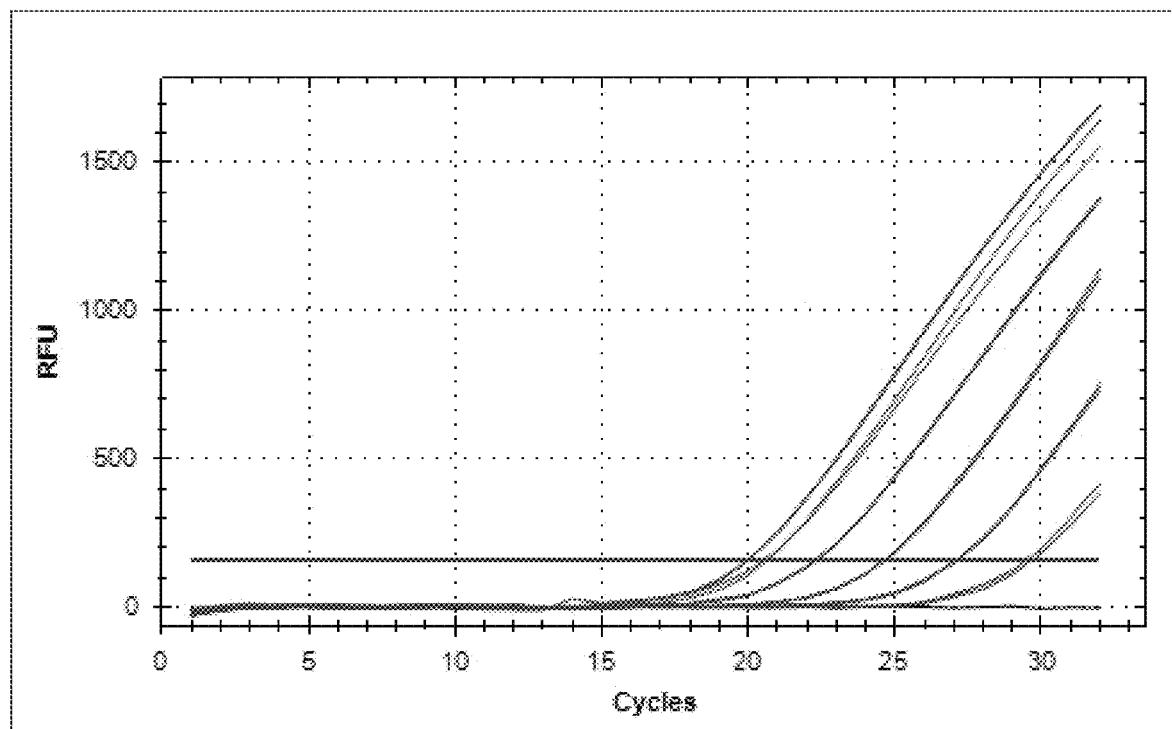

FIG. 36C shows an amplification plot for the SVA-265 target of a real-time PCR multiplex of the Yb8-120 and SVA-265 targets, the quantification of DNA in each sample being determined by use of a calibration curve with serial dilutions (1 ng, 200 pg, 40 pg, 8 pg, and 1.6 pg), with amplification of the SVA-265 target in purple, positive control in red and no template control in black.

Figure 36D:
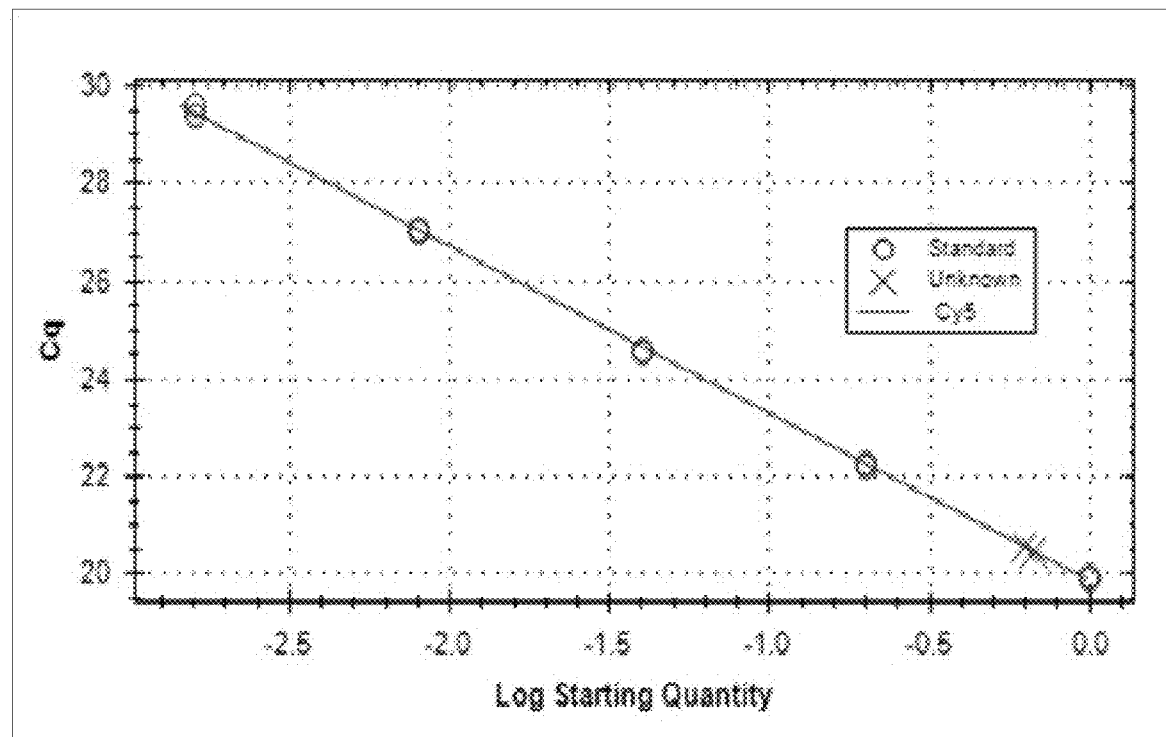

FIG. 36D shows a standard curve for the SVA-265 target of a real-time PCR multiplex of the Yb8-120 and SVA-265 targets. Efficiency: 95.9%; $R^2$: 0.999; slope: −3.425; y-intercept: 19.879.

Figure 36E:
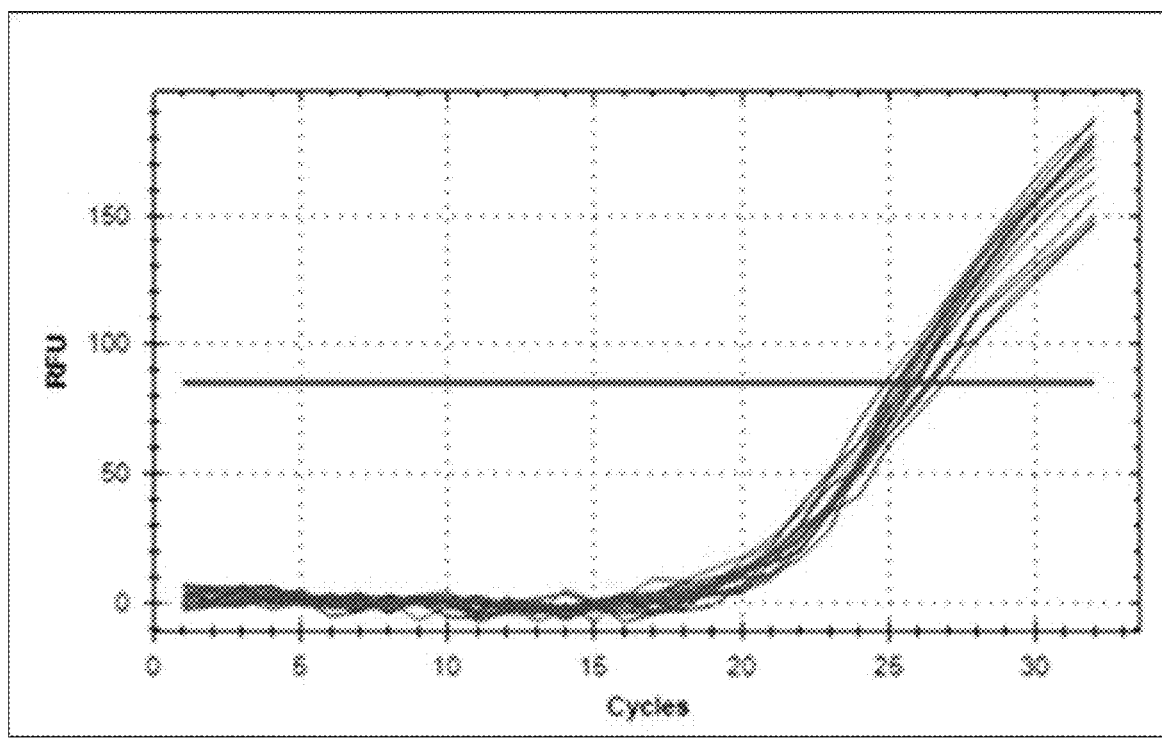

FIG. 36E shows an amplification plot of the internal positive control target within a real-time PCR multiplex of the Yb8-120 and SVA-265 targets, with amplification of the internal positive control target in blue.

Figure 37A:
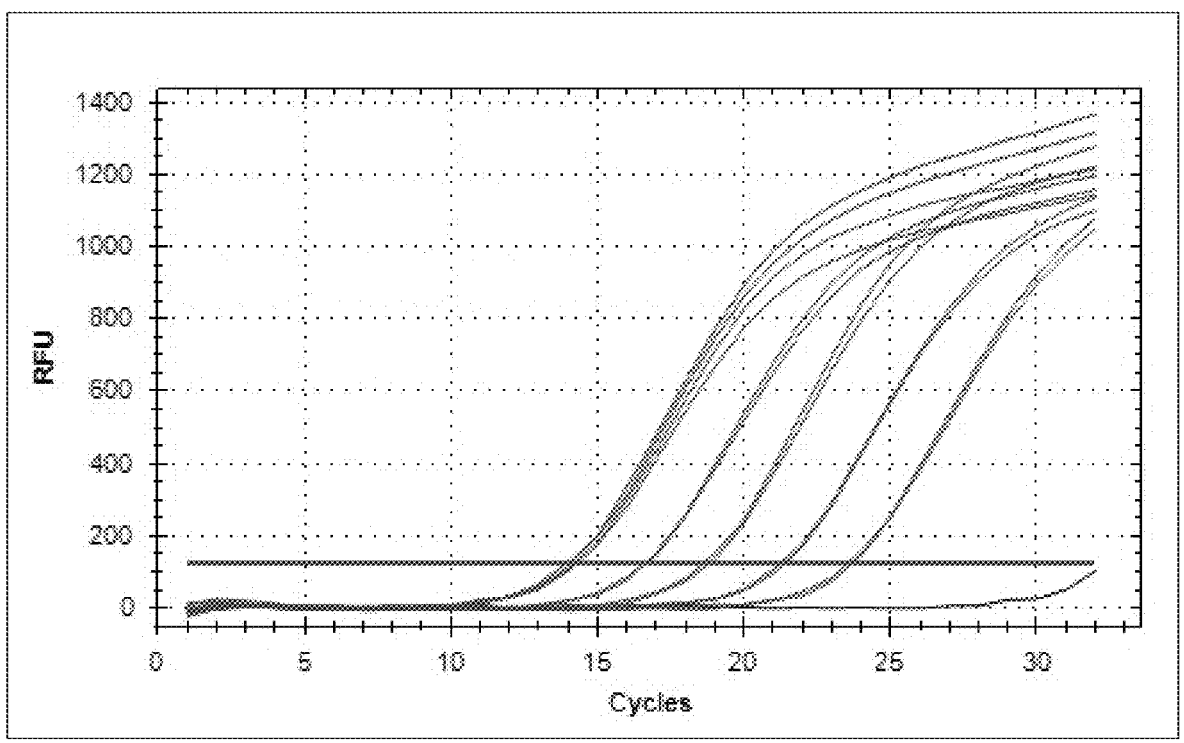

FIG. 37A shows an amplification plot for the Yb8-120 target of a real-time PCR multiplex of the Yb8-120 and SVA-290 targets, the quantification of DNA in each sample being determined by use of a calibration curve with serial dilutions (1 ng, 200 pg, 40 pg, 8 pg, and 1.6 pg), with amplification of the Yb8-120 target in green, positive control in red and no template control in black.

Figure 37B:
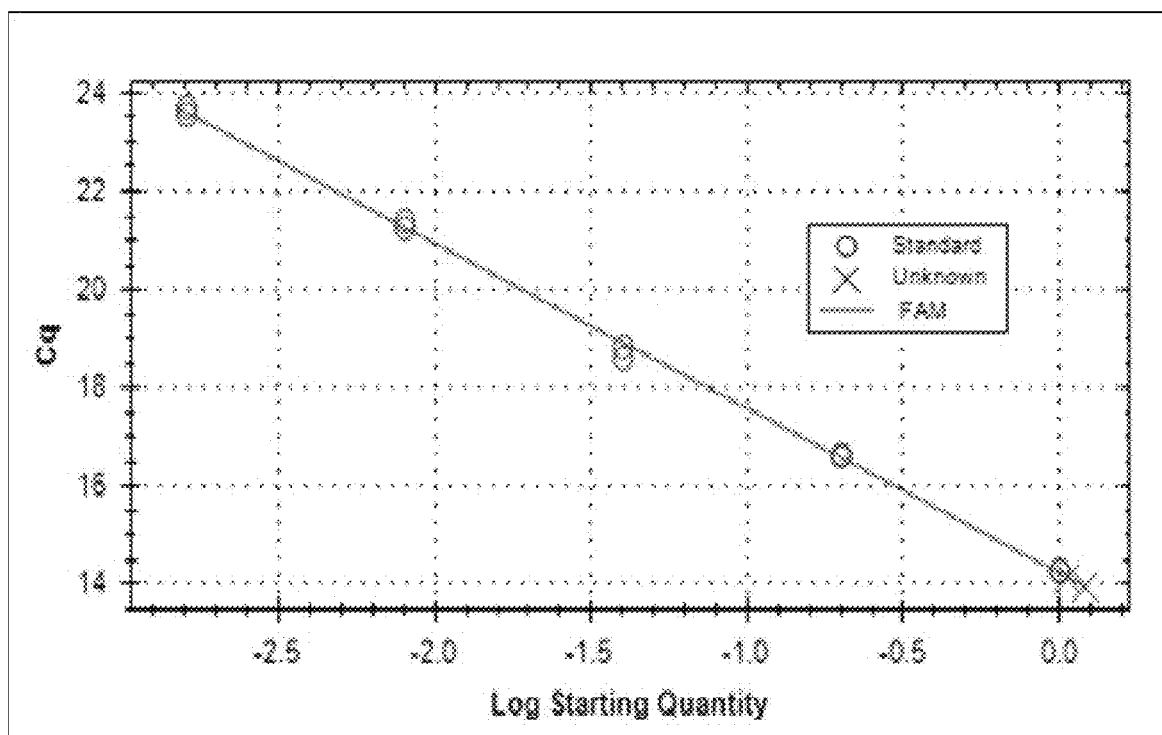

FIG. 37B shows a standard curve for the Yb8-120 target of a real-time PCR multiplex of the Yb8-120 and SVA-290 targets. Efficiency: 99.0%; $R^2$: 0.999; slope: −3.346; y-intercept: 14.247.

Figure 37C:
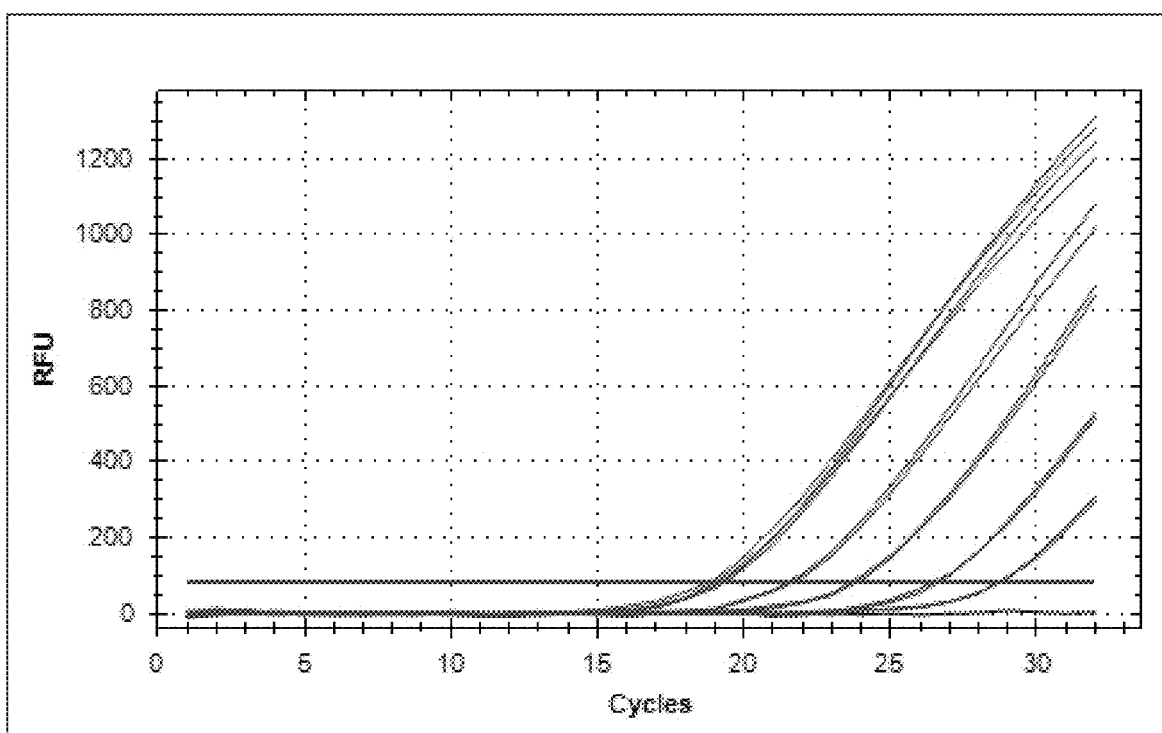

FIG. 37C shows an amplification plot for the SVA-290 target of a real-time PCR multiplex of the Yb8-120 and SVA-290 targets, the quantification of DNA in each sample being determined by use of a calibration curve with serial dilutions (1 ng, 200 pg, 40 pg, 8 pg, and 1.6 pg), with amplification of the SVA-290 target in purple, positive control in red and no template control in black.

Figure 37D:
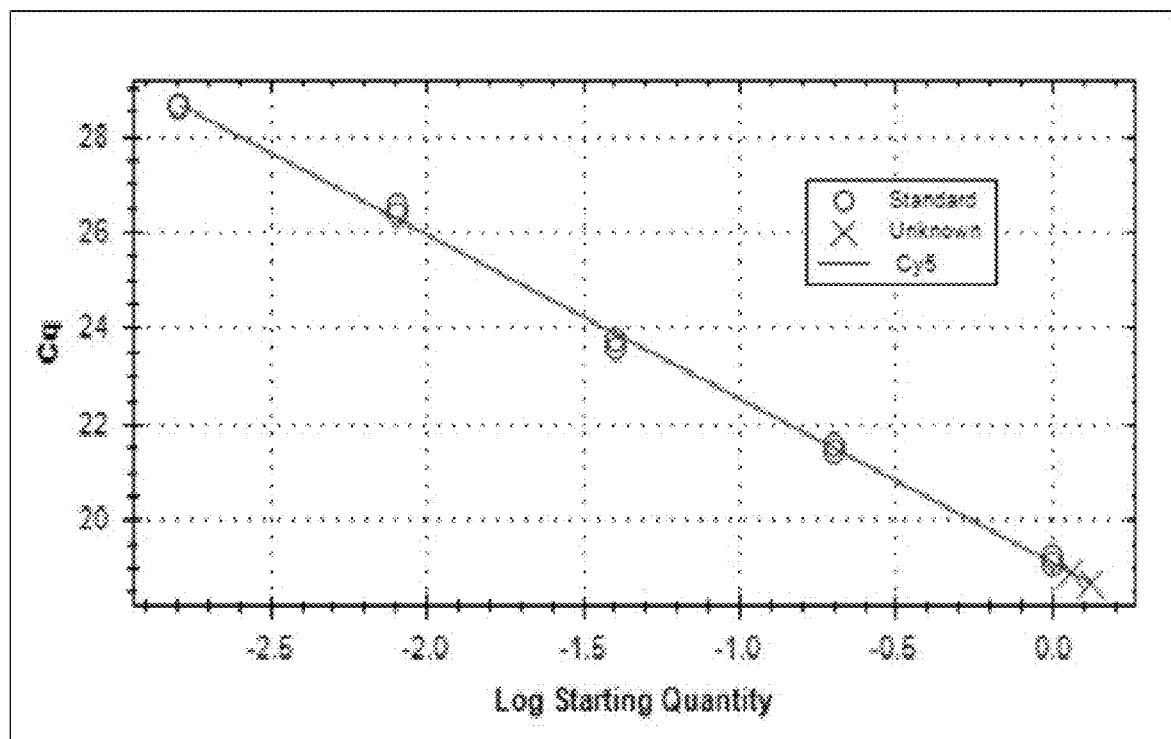

FIG. 37D shows a standard curve for the SVA-290 target of a real-time PCR multiplex of the Yb8-120 and SVA-290 targets. Efficiency: 96.3%; $R^2$: 0.998; slope: −3.413; y-intercept: 19.130.

Figure 37E:
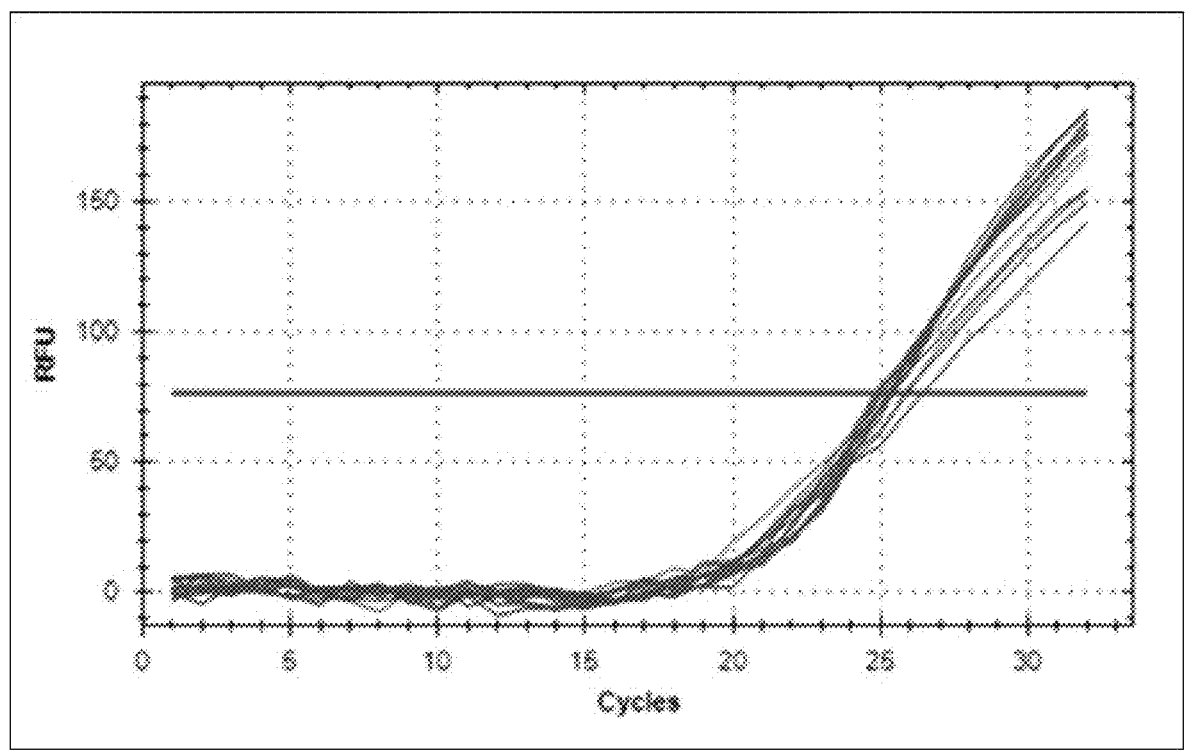

FIG. 37E shows an amplification plot of the internal positive control target within a real-time PCR multiplex of the Yb8-120 and SVA-290 targets, with amplification of the internal positive control target in blue.

DETAILED DESCRIPTION OF THE INVENTION

Definitions

Engraftment—For solid tumors, ctDNA analyses can indicate whether tumors are growing before they are large enough to measure. Can also be used in liquid tumor PDX. Similar to humanization, except the human cells circulating are diseased. Includes leukemia and myeloma models derived from human cells, both of which are very active areas for drug discovery.

Humanization—Use of normal human immune cells to replace mouse bone marrow. End-product is a mouse with circulating human immune cells in blood stream. Not PDX per se, but these mice are increasingly used for studies of immuno-oncology (IO) agents, and have therefore generated great interest among researchers. Many technical failures; optimization of the technique is hampered by the length of time required to see success by fluorescence-activated cell sorting (FACS).

PDX—Comprises both patient-derived-xenografting of primary tumor tissue and injection of human tumor cells lines (i.e., National Cancer Institute's NCI-60 panel) for tumor growth in mice. Cell line xenografting is done universally in research; patient-derived xenografting is much more expensive, and is generally done in drug discovery by companies.

PDX Mice

Animal models have been used in predicting efficacy and evaluating toxicity for cancer chemotherapeutic agents for the last two decades. Morton, et al., *Establishment of human tumor xenografts in immunodeficient mice*, Nature Protocols 2007, 2(2): 247-50. Many different animal models have been developed over the years to accomplish these tasks of predicting efficacy and evaluating toxicity. The discovery of T-cell deficient nude athymic mice made it possible to allow transplantation and propagation of human tumor tissues (xenografts) in mice. Several types of immune-deficient mice have been established using either various tumor cell lines or patient derived human tumor tissues obtained from biopsy or autopsy.

A patient derived xenograft (PDX) mouse is created when cancerous tissue from a patient's primary tumor is implanted directly into an immunodeficient mouse. Early PDX models provided solutions to the challenges that researchers faced in cancer drug research, such as by providing positive tumor responses in mouse models, but these successes were frequently not reflected in successful treatment of human cancers. The development of the immune-deficient nude mouse was a key factor in reversing this trend. Today, PDX cancer models are popular models for use in cancer drug research. PDX models offer a powerful tool for studying tumor biology and evaluating oncologic therapy and are useful for preclinical research, screening platforms for clinical drug trials, personalized cancer therapy ("Mouse Avatars"), and enabling the discovery of biomarkers predicting oncologic drug sensitivity and resistance.

The NOD ("non-obese diabetic") mouse was introduced in the early 1980s by Shionogi Pharmaceuticals. Although these mice harbor mutations that confer a predisposition to Type 1 diabetes, they also express a unique polymorphic variant of the signal regulatory protein alpha (SIRPα). SIRPα is a protein expressed on macrophages that interacts with CD47 ("Cluster of Differentiation 47," a transmembrane protein) on the surface of cells to communicate a "don't eat me" signal. The variant of SIRPα found in NOD mice has high affinity for human CD47, which helps engrafted cells of human origin evade being engulfed by the host macrophages. Other mouse strains, such as C57BL/6 and BALB/c, express alternative variants of SIRPα with lower affinity for human CD47. In these strains, macrophages more readily recognize introduced human cells as foreign, leading to higher rates of graft rejection.

Figure 1:
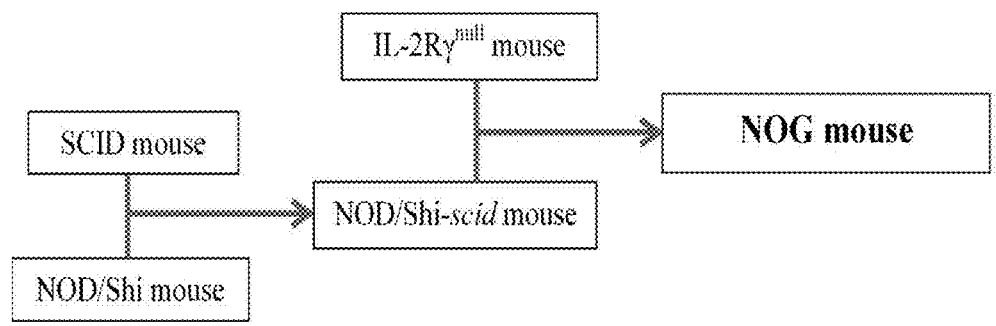
FIG. 1 shows how PDX mice were bred to provide more and more suitable mice, including ultimately the NOG mouse.

Several types of immunodeficient mice can be used to establish PDX models, including athymic nude mice, severely compromised immune deficient (SCID) mice, non-obese diabetic (NOD)-SCID mice, recombination-activating gene 2 (Rag2)-knockout mice (IL-2R$\gamma^{null}$) and NOD/Shi-SCID/IL-2R$\gamma^{null}$ (NOG). Id. FIG. 1 shows how these various mice were bred to produce more and more suitable mice. The mice used must be immunocompromised to prevent transplant rejection. The NOD-SCID mouse is considered more immunodeficient than the nude mouse because the NOD-SCID mouse does not produce Natural Killer cells, which have an immune function, so the NOD-SCID mouse is more commonly used for PDX models. Siolas, et al., *Patient-derived tumor xenografts: transforming clinical samples into mouse models*, Cancer Research (Perspectives) 2013, 73(17): 5315-19. Recently, the circulating tumor cells in plasma have been harvested from patients and have been successfully used in place of tissue biopsies to create more predictive PDX mouse models. These models are referred to as CDX mouse models.

One significant shortcoming of PDX mouse models is that they are created using highly immunodeficient mice to prevent rejection of implanted human tumor cells. Thus the resulting PDX models lack a critical component of the known tumor microenvironment that exists in the patient, the capability to deliver an immunochemical response to the tumor. As a consequence of this, immunotherapies and anti-cancer agents that target the human immune system cannot be studied. To overcome this issue, humanized-xenograft mouse models are created by engrafting human CD34+(Cluster of Differentiation 34," a transmembrane protein), hematopoietic stem cells, or a patient's bone marrow cells into NOG or similar highly immune deficient mice. Eswaraka, et al., define "humanized" mice as "highly immune-deficient mice that generate a functional human immune system through engraftment with human primary hematopoietic cells and human fetal tissues or engineered expression of human cytokine genes." Eswaraka, et al., *Humanized mice and PDX models*, in Patient Derived Tumor Xenograft Models: Promise, Potential and Practice, R. Uthamanthil and P. Tinkey, eds., E. de Stanchina, assoc. ed., London: Elsevier, 2017, p. 76 (referring to Shultz, et al.,

*Humanized mice for immune system investigation: progress, promise and challenges*, Nat. Rev. Immunol. 2012, 12: 786-98).

The variety of PDX mouse types may be used to produce many different types of PDX mouse models. Patient-derived primary tumor tissue may be xenografted into a PDX mouse, circulating human tumor cells may be injected into a PDX mouse, and human tumor cell lines (i.e., NCI60 panel) may be injected for tumor growth in mice. Cell line xenografting is performed widely in research settings; patient-derived xenografting is much more expensive than is cell line xenografting and is generally conducted as part of drug discovery by pharmaceutical companies.

Problems with the Use of PDX Mice in Research, Monitoring and Treatment of Cancers Even with a commercial scale and successful PDX infrastructure in place, in some cancers like prostate, tumor take rates in mice vary widely, from 10% to 54%, depending on the mouse strain. Maykel, et al., *NOD-scidIl2rg (tml Wjl) and NOD-Rag1 (null) Il2rg (tml Wjl): a model for stromal cell-tumor cell interaction for human colon cancer*, Dig. Dis. Sci. 2014, 59(6): 1169-79, Epub 6 May 2014. In some cancers, tissue implants are expected to fail to engraft into immunocompromised mice over 70% of the time. To operationalize methods with a high failure rate in a commercial environment, new quality management tools are needed. Ideally in industry, quality management is utilized to identify defective materials in real-time before additional resources are expended. In the context of high risk PDX modeling, identification of implantation failures is operationally useful. For example, Hodgkinson waited more than 12 months in the hope of achieving successful engraftment of tumors from lung circulating tumor cells (CTCs). Hodgkinson, et al., *Tumorigenicity and genetic profiling of circulating tumor cells in small-cell lung cancer*, Nature Medicine 2014, 20(8): 897-905. Four successful models developed palpable tumors in approximately 2-5 months; two attempts failed based on the absence of tumors after more than 12 months. No procedure was available to discriminate between success and failure, other than obvious success. Hlrenallur-Shanthappa, et al., and Mattar, et al., discuss the low engraftment success rates for many tumors and the fact that the time to tumor establishment can be lengthy. Hlrenallur-Shanthappa, et al., *Immunodeficient mice: the backbone of patient-derived tumor xenograft models*, in R. Uthamanthil and P. Tinkey, eds., referenced supra, pages 68-70; Mattar, et al., *Methodologies for developing and maintaining patient-derived xenograft mouse models*, in R. Uthamanthil and P. Tinkey, eds., referenced supra, pages 130-131 (referencing Moro, et al., *Patient-derived xenografts of non small cell lung cancer: resurgence of an old model for investigation of modern concepts of tailored therapy and cancer stem cells*, J. Biomed. Biotechnol. 2012, 2012: 568567).

The above difficulties in no small part account for the fact that "The U.S. Food and Drug Administration approval rate for targeted therapies against cancer-driving proteins is only 5-7%" and the fact that "the average time from discovery to therapy is 12 years with an average cost of US $0.5-2 billion." Hlrenallur-Shanthappa, et al., referenced supra, p. 57 (referencing Day, et al., *Preclinical mouse cancer models: a maze of opportunities and challenges*, Cell 2015, 163: 39-53). New ways to reduce the time required for and cost of development of new cancer therapies are needed.

Blood contains extra-cellular DNA that is shed by living and dying cells. This DNA is termed cell-free DNA (cfDNA). In patients with cancer, a sub-set of the cfDNA is derived from the tumor; the tumor-derived sub-fraction of cell-free DNA is circulating tumor DNA, or ctDNA. Cheng, et al., *A promising biomarker in the liquid biopsy of cancer*, Oncotarget 2016, 7(30): 48332-41. So-called "liquid biopsy" techniques interrogate cell-free DNAs to identify specific, low-frequency cancer-causing mutations in human patients. Pollack, *Liquid cancer test offers hope for alternative to painful biopsies*, New York Times, published online 4 Jun. 2016, with related version in print, New York Times (New York edition), 5 Jun. 2016, page A4; Qin, et al., *Cell free circulating tumor DNA in cancer*, Chinese Journal of Cancer 2016, 35: 36; Hegemann, et al., *Liquid biopsy: ready to guide therapy in advanced prostate cancer?*, BJU Int. 2016, 118: 855-863. In humans, methods must discriminate between human cfDNA and human ctDNA; many of the sequences are identical and high sensitivity is required. One approach to assess tumor engraftment is the use of liquid biopsy techniques to evaluate simply the absence or presence of circulating human tumor DNA in PDX mice. Applying this concept to mice with human tumors has a technical advantage over doing such testing in humans because DNA from different species can easily be distinguished by common molecular methods. However, a mouse has a total blood volume of about 2 mL, and if human ctDNA needs to be detected without killing the mouse, a small volume of typically 100 microliters of mouse blood is used, and the method has to be highly sensitive and quantitative. One goal of the presently described invention is to provide a new way to characterize PDX mice by detecting human ctDNA against a background of mouse cfDNA in mouse blood using a qPCR multiplex.

To this end, an efficient method that enables quantitative measurement of circulating human tumor cells or other human derived cellular material within a host mouse at serial time points is important. This requires evaluation of mouse blood samples without killing the mouse. Confirmation of successful engraftment using solely external physical methods (i.e., calipers or imaging techniques) is less useful. Early detection of engraftment success or failure would increase the cost-effectiveness of building PDX models dramatically.

Presently, there is no easy and cost-effective method to serially measure and monitor the amount of circulating tumor DNA (ctDNA) within the living mouse's vascular system. ctDNA is commonly assessed in patients as a proxy of tumor burden and tumor viability following drug treatment; parallel tools do not exist for PDX models. The ctDNA level would be expected to be an important indicator for the efficacy of the oncologic drug being studied in a PDX model, as it is in human patients.

Inghirami, et al., in summarizing important future challenges relating to the use of PDX mice, conclude that "it is now evident that we need to establish very large libraries of cancer-specific PDXs" and that "These libraries must include detailed clinical and molecular annotation," acknowledging that this will be a "monumental task." Inghirami, et al., *Patient-derived tumor xenograft: present and future challenges and applications*, in R. Uthamanthil and P. Tinkey, eds., referenced supra, page 433. A qPCR method used in multiplex format could provide a way to gather much useful data from the DNA samples derived from PDX mouse blood. As further described below, such a method is capable of providing information about an extent of fragmentation/degradation of one or more subject DNA samples as well as their quantitation. Thierry, et al., found that "[colorectal carcinoma] tumor growth seems to lead to higher ctDNA fragmentation in both mice and patients . . . " and made reference to the use of extent of DNA degradation as an indicator of apoptosis as a source of ctDNA. Thierry, et al., *Origin and quantification of circulating DNA in mice with human colorectal cancer xenografts*, Nucleic Acids Research 2010, 38(18): 6159-6175, abstract; p. 6173, penultimate sentence of col. 1. Notation of an extent of degradation as well as quantitation of ctDNAs from PDX mouse blood samples would generally aid researchers and would be a useful addition to future PDX mouse libraries.

Liquid biopsies utilized to detect ctDNA are predicated on the knowledge that ctDNA is labile and is continuously produced by metabolically active tumors. Cheng, et al., referenced supra; Qin, et al., referenced supra; Hegemann, et al., referenced supra; Bettegowda, et al., *Detection of circulating tumor DNA in early-and late-stage human malignancies*, Sci. Transl. Med. 2014, 6(224): 224ra24. Published work serendipitously demonstrated that metastatic colon cell line PDX models do have detectable human ctDNA in their blood. Mouliere, et al., *High fragmentation characterizes tumour-derived circulating DNA*, PLoS ONE 2011, 6(9): e23418. Mouliere, et al., utilized PDX models as a means to demonstrate ctDNA fragmentation as a function of tumor burden. Human DNA sequences were detected at low sensitivity by qPCR. However, the mice were exsanguinated (blead to death) to provide enough DNA for the study. Monitoring tumor derived DNA by measuring genetic mutation works well but since this DNA is present in such low levels, the single copy SNP genotyping requires several milliliters of blood, and this blood volume can only be obtained after sacrificing the mouse. The work of Mouliere shows that the amount of human ctDNA detected in the PDX mice correlated to the tumor burden, where larger tumors produced increasingly larger quantities of ctDNA. Smaller tumors produced less total ctDNA. The work of Mouliere demonstrates that tumors implanted into mice can generate ctDNA, and it shows that liquid biopsy tools are applicable to PDX models. Current methods to detect and enumerate circulating tumor cells (CTCs) or ctDNA in PDX models require the entire blood volume of the mouse and are therefore lethal. Mouliere, et al., supra; Roy, et al., *Feasibility of assessing circulating tumor cells in patient-derived xenograft tumor models*, American Association for Cancer Research, Annual Meeting, New Orleans, La., USA, Apr. 16-20, 2016, abstract 646/25; Guiliano, et al., *Circulating and disseminated tumor cells from breast cancer patient-derived xenograft-bearing mice as a novel model to study metastasis*, Breast Cancer Research 2015, 17(3): 1-9. To be a useful liquid biopsy tool, a method that is non-lethal and more sensitive than are the current methods is required to detect ctDNA. The present invention uses a high copy number *Alu* target, which provides high sensitivity and overcomes this problem.

Human-specific *Alu* based DNA probes are used for high-sensitivity in situ hybridization of mixed tissues, including in PDX models. Van der Horst, et al., *Taqman-based quantification of invasive cells in the chick embryo metastasis assay*, BioTechniques 2004, 37: 940-946; Allard, et al., *Immunohistochemical toolkit for tracking and quantifying xenotransplanted human stem cells*, Regen. Med. 2014, 9(4): 437-452. The high copy number of *Alu*, as compared to a typical somatic locus that has two copies per cell, increases the sensitivity of the *Alu* test by at least 5,000-fold in qualitative assay. However, the present invention, which monitors the progression of a human tumor in a PDX mouse using a multiplex qPCR system with above 90% PCR efficiency to accurately quantitate the mouse and human DNA from microliter quantities of PDX mouse blood, either with or without purification of the DNA by extraction from the blood sample, without killing the mouse, has not been previously reported. PCR efficiencies as high as 99% have been seen in this work.

Quantitation and Assessment of the Integrity of Cell-Free DNA in Biological Fluids for Cancer Diagnosis, Prognosis and Surveillance Many current diagnostic procedures are invasive, expensive and unpleasant. In multiple recent published studies, circulating cell-free DNA (cfDNA) concentration and integrity (fragmentation pattern) has shown promise as a highly sensitive and specific, minimally invasive blood biomarker for multiple cancer types (see, e.g., Hao, T B, et al., *Circulating cell-free DNA in serum as a biomarker for diagnosis and prognostic prediction of colorectal cancer*, British Journal of Cancer 2014: 1-2, doi 10.1038/bjc.2014.470; Gonzalez-Masia, et al., *Circulating nucleic acids in plasma and serum (CNAPS): applications in oncology*, Onco. Targets Ther. 6:819-832 (2013); Yu, J, et al., *Recent advances in clinical applications of circulating cell-free DNA integrity*, Lab Med. 45(1): 6-12 (2014)). A number of these studies have indicated the utility of a highly sensitive assay to measure cfDNA integrity (fragmentation pattern) and concentration based on quantitation of an ALU element, the most common type of retrotransposable elements (RE) in the human genome (Table 1). RE-based methods for quantitating DNA are attractive due to their superior sensitivity (multi-copy representation in the genome) and robustness.

The most commonly employed cfDNA integrity/concentration assessment I1 method, the ALU 247/115 bp index, targets sequences of a single ALU element, and thus the two fragments analyzed are not independent. This precludes use of these targets in a single multiplexed assay for maximum accuracy, efficiency and practical clinical use. This prior art method poses several particular problems. First, evaluating the first target and the second target separately rather than multiplexing into a single reaction mixture introduces well-to-well variability into the results. Every PCR reaction is somewhat different from every other PCR reaction, and experimental variation in set-up steps, such as variation in pipetting volumes, introduces error and can impact the results. Secondly, data presented herein demonstrates that the primers used in prior art studies to amplify these specific 247 bp/115 bp targets show poor primer specificity, with false signals being generated from non-template controls. Thirdly, single-plex amplification prohibits the incorporation of an internal PCR control. The use of an internal PCR control is critical for confirming the success of the reaction and for providing confidence that other experimental factors such as the presence of PCR inhibitors in the sample have not interfered. Additionally, single-plex amplification of each target is cumbersome, more labor-intensive and less cost effective than is running a multiplexed amplification.

One of the cancer types studied using cell free DNA integrity is colorectal cancer (CRC). The current gold-standard for CRC diagnosis and staging is colonoscopy and subsequent histological examination. While specific and accurate, colonoscopy is invasive, expensive, and poses some risks; all of which decrease patient compliance to screening recommendations and discourage routine monitoring. In CRC and a few other cancer types, tissue biopsy is supplemented with detection of cancer protein biomarkers in blood serum, e.g. carcinoembryonic antigen (CEA). Such assays have the significant advantage of being minimally invasive and also do not require immediate localization of the tumor. Nevertheless, these assays suffer from limited sensitivity. CEA, one component of the current standard of care for CRC post-treatment monitoring, has relatively low sensitivity and specificity for early (stages I and II) and late (stages III and IV) disease (early: 36% sensitivity and 87% specificity; late: 74% sensitivity and 83% specificity) (Fakih, M. G.; Padmanabhan, A., *CEA Monitoring in Colorectal Cancer*, Oncology 20(6): 579-587 (2006)). Given this performance, CEA is not recommended for CRC diagnosis according to the National Comprehensive Cancer Network guidelines for CRC (Ms-PSEE, Hunt, S., NCCN, Clinical Practice Guidelines in Oncology (NCCN Guidelines®) Colon Cancer, 2013).

Biology and Physiology of Cell-Free DNA

Characterization of cell-free DNA (cfDNA), DNA found in circulation in human blood plasma and serum, has emerged as an exciting prospect for a new generation of blood-based tools for cancer detection, monitoring and surveillance. Nucleic acid circulation in human blood plasma was first reported in 1948 (Mandel P; Metals P., *Les acides nucleiues du plasma sanguin chez l'Homme*, C. R. Acad. Sci. Paris 142: 241-243 (1948)). Leon, et al., (1977) were the first to report that mean cfDNA levels were significantly higher in the serum of patients with malignant cancers versus healthy patients (Leon, S A; Shapiro, B; Sklaroff, D M; Yaros, M J, *Free DNA in the Serum of Cancer Patients and the Effect of Therapy*, Cancer Research 1977: 646-650). In the past two decades, many details of cfDNA biology, and the relationship between cfDNA and disease, have been elucidated. A brief primer of these studies is provided below, with emphasis on aspects of cfDNA biology that are pertinent to our specific application.

Circulating cfDNA is derived from both the nuclear and mitochondrial genomes of normal and tumor cells (Mandel and Matais 1948, referenced supra; Zhong, S; Ng, MCY; Lo, Y M D; Chan, J C N; Johnson, P J; Kong H., Presence of mitochondrial tRNALeu (UUR>A to G 3243 mutation in DNA extracted from serum and plasma of patients with type 2 diabetes mellitus, J. Clin. Pathol. 53: 466-469 (2000)). Both coding and noncoding portions of the genome are represented among circulating cfDNA (Bettegowda, C, et al., Detection of Circulating Tumor DNA in Early- and Late-Stage Human Malignancies, Sci. Transl. Med. 6(224): 224ra24 (2014), doi: 10. I 126/scitranslmed.3007094.Detection). Although several mechanisms are believed to contribute to the circulating cfDNA pool, including spontaneous release of free, exosome-encapsulated, and microvesicle-encapsulated DNA into the bloodstream, cell death is the major generator of circulating cfDNAs (Jahr, S; Hentze, H; Englisch, S; Hardt, D; Fackelmayer, F O; Hesch, R, DNA Fragments in the Blood Plasma of Cancer Patients: Quantitations and Evidence for Their Origin from Apoptotic and Necrotic Cells, Cancer Research 61:1659-1665(2001)). Cell turnover in normal cells is ordinarily due to apoptosis, which results in stereotyped sized fragments of DNA: a monomeric form composed of ~180 bp fragments of DNA and associated nucleosomes, and reduced amounts of oligomeric forms. Id. Alternatively, tumor cells turn over using a diversity of cell death pathways, not only apoptosis, but also necrosis, autophagy, and mitotic catastrophe (Jin, Z; EI-Deiry, WS, Overview of Cell Death Signaling Pathways, Cancer Biology & Therapy 4(2): 139-163 (2005), available at flybay.net/(accessed 15 Dec. 2014)). Non-apoptotic pathways non-specifically and incompletely degrade DNA, generating substantially longer DNA fragments, up to 21 kilobases in the case of necrosis (Jahr, S., cited supra). Differences in the rate of cell death and type of cell death pathway utilized between normal and cancer cells lead to distinct characteristics of cfDNA pools that distinguish patients with and without cancer. cfDNAs have variable half-life within the body, ranging from minutes to hours (Lo Y M D; Zhang J; Leung T N; Lau T K; Chang A M Z; Hjelm N M, Rapid clearance of fetal DNA from maternal plasma, Am. J. Hum. Genet. 64: 218-224 (1999); Emlen W; Mannik M., Effect of DNA size and strandedness on the in vivo clearance and organ localization of DNA, Clin. Exp. Immunol. 56(1): 185-192 (1984)). Short half-life implies that circulating cfDNA levels provide a dynamic measure of the physiological and pathological state of an individual. Finally, there is evidence that a small fraction of circulating cfDNA from blood is able to pass the kidney barrier and enter urine. These cfDNAs are called 'trans-renal' cfDNAs (Su Y-H, et al., Human Urine Contains Small, 150 to 250 Nucleotide-Sized, Soluble DNA Derived from the Circulation and May Be Useful in the Detection of Colorectal Cancer, J. Molecular Diagnostics, 6(2): 101-107 (2004); Botezatu I, et al., Genetic analysis of DNA excreted in urine: A new approach for detecting specific genomic DNA sequences from cells dying in an organism, Clin. Chem. 46(8): 1078-1084 (2000)). The specific physiology of trans-renal cfDNAs awaits detailed exploration.

Cell-Free DNA and Cancer

Circulating cfDNAs from patients with and without cancer differ in a number of ways. Tumor genomes harbor specific genetic and epigenetic alterations that distinguish them from normal genomes, and these differences are reflected in cfDNAs. Nonspecific characteristics of cfDNA, such as concentration and integrity, differ between cancer patients and control subjects due to the specific mechanisms of cfDNA release into the blood by normal versus tumor cells. cfDNA concentration and integrity have often been found to be elevated in patients with cancer due to high rate of tumor cell death (reviewed in Schwarzenbach H; Hoon D S B; Pantel K., *Cell free nucleic acids as biomarkers in cancer patients*, Nature Reviews Cancer 11: 426-437 (2011), doi:10.1038/nrc3066; González-Masiá , JA; Garciá-Olmo, D; Garciá-Olmo, D C, *Circulating nucleic acids in plasma and serum (CNAPS): Applications in oncology*, Onco. Targets. Ther. 6: 819-832 (2013)). However, absolute cfDNA concentration significantly varies among currently employed assays, significantly hampering the ability to compare results across studies. There is currently no standardized, validated, commercially available cfDNA concentration and integrity assay. There are no reports in the prior art of using a multiplexed qPCR system of the kind described herein for accurate simultaneous measurement of concentration and integrity of Cell Free DNA.

cfDNA integrity has emerged as a particularly promising method for detecting and monitoring cancer. This method is based on the fact that normal and tumor cells undergo different types of cell death, leading to different size cfDNA products in the blood, as explained above. cfDNA in patients with cancer is expected to be, on average, longer, and therefore of higher integrity than in patients without cancer. While some studies established an integrity index based on one or a small number of genes, Umetani, et al., pioneered the use of an ALU retrotransposon-based integrity index for cfDNA assessment (Umetani N, et al., *Increased integrity of free circulating DNA in sera of patients with colorectal or periampullary cancer: Direct quantitative PCR for ALU repeats*, Clin. Chem. 52(6): 1062-1069 (2006), doi:10.1373/ clinchem.2006.068577; denoted Umetani 2006b in Table 1; Hoon, et al., *Use of free circulating DNA for diagnosis, prognosis, and treatment of cancer funding*, US 2009/0280479 A1). They defined integrity as the ratio of a 247 bp fragment (ALU 247) versus 115 bp fragment (ALU 115) of a single ALU element. ALU 115 measures the total cfDNA concentration and ALU 247 measures tumor-derived cfDNA. Using their ALU 247/115 integrity index, Umetani, et al., demonstrated that DNA integrity and concentration were significantly higher in patients with CRC, periampullary cancer, and breast cancer compared to healthy controls (Id.; Umetani, N, et al., *Prediction of breast tumor progression by integrity of free circulating DNA in serum*, J. Clin. Oncol. 24(26): 4270-4276 (2006), doi:10.1200/JCO.2006.05.9493; denoted Umetani 2006a in Table 1). They also showed that disease prognosis was predicted by cfDNA integrity in each of these cases. Subsequently, several authors have reported significant increases in cfDNA integrity in patients with cancer versus those without using the ALU 247/115 measure (summarized in Table 1 below).

The ALU-based method is highly sensitive due to the multi-copy nature of the ALU target (discussed more extensively below). Importantly, this enables development of a rapid, high-throughput, and cost effective assay due to the relative simplicity of the test. It utilizes real-time PCR, a standard DNA quantitation method compatible with multiple commonly used instrument platforms.

TABLE 1

Detection of cfDNA integrity using the ALU 247/115 index in different cancer types from serum or plasma samples. Area Under the Curve (AUC) from Receiver Operator Characteristic (ROC) curves presented. AUC assess diagnostic potential and ranges from 0.5 (not useful) to 1.0 (most useful).

| Cancer Type | Comparison Groups | AUC | Reference |
|---|---|---|---|
| Prostate | Benign prostate hyperplasia vs. prostate cancer | 0.91 | Feng 2013 |
| Colorectal | Healthy control (clean colon) vs. rectal cancer | 0.91 | Agostini 2011 |
| Colorectal | Normal control vs. primary colorectal cancer | 0.89 | Hao 2014 |
| Pleural effusion | No malignant pleural mesothelioma vs. malignant pleural effusion | 0.823 | Sriram 2012 |
| Breast | No lymph node metastasis vs. lymph node metastasis | 0.81 | Umetani 2006a |
| Periampullary | Healthy control vs. periampullary cancer (st. I-IV) | 0.8 | Umetani 2006b |
| Breast | Healthy control vs. preoperative breast cancer (st. II-IV) | 0.79 | Umetani 2006a |
| Colorectal | Healthy control vs. colorectal cancer (st. I-IV) | 0.78 | Umetani 2006b |
| Colorectal | Normal control vs. colorectal cancer | 0.772 | Mead 2011 |
| Pleural effusion | No malignant pleural effusion vs. malignant pleural effusion | 0.766 | Sriram 2012 |
| Colorectal | Response vs. non-response to chemoradiotherapy | 0.76 | Agostini 2011 |
| Hepatocellular Carcinoma | Hepatocellular carcinoma (HCC) vs. HCC with Hepatitis C viral infection | 0.75 | El-Shazly 2010 |
| Colorectal | Healthy control vs. colorectal cancer | 0.74 | Leszinski 2014 |

Overview of Retrotransposable Elements

Retrotransposable Elements (REs) are mobile element insertion polymorphisms that are essentially homoplasy-free characters, identical by descent and easy to genotype (reviewed in Batzer M A; Deininger, P L, *Alu repeats and human genomic diversity*, Nat. Rev. Genet. 3(5): 370-9 (2002), doi:10.1038/nrg798). ALUs are REs that are approximately 300 bp insertions and are distributed throughout the human genome in large copy number. In addition to the major retrotransposon families, REs include smaller families of transposons such as SVA or long interspersed element ("LINE"). SVA elements, named after its main components, short interspersed element ("SINE"), variable number tandem repeat ("VNTR") and Alu element ("ALU"), contain the hallmarks of retrotransposons, in that they are flanked by target site duplications ("TSDs"), terminate in a poly(A) tail and they are occasionally truncated and inverted during their integration into the genome (Ono, M; Kawakami, M; Takezawa, T, *A novel human nonviral retroposon derived from an endogenous retrovirus*. Nucleic Acids Res. 15(21): 8725-8737 (1987); Wang, H, et al., *SVA elements: A hominid-specific retroposon family*, J. Mol. Biol. 354(4): 994-1007 (2005), doi:10.1016/j.jmb.2005.09.085). Long-Interspersed Elements (LINE1) are similar to ALU and SVA in that they also contain the hallmarks of retrotransposons and are high copy number, but differ in size, being up to several kilobases in length (Deininger, P L; Batzer, M A, *Mammalian Retroelements. Genome Res.* 12(10):1455-65 (2002), doi:10.1101/gr.282402).

RE-Based DNA Quantitation

RE-based quantitation methods are advantageous when compared to current, commercially available systems due to the presence of a large number of fixed insertions. With a high copy number of subfamily-specific RE repeats within the human genome, these human-specific DNA assays have a very sensitive dynamic range of 1 pg to 100 ng (Nicklas, J A; Buel, E., *Development of an Alu-based, Real-Time PCR Method for Quantitation of Human DNA in Forensic Samples*, J. Forensic Sci. 48(5): 1-9 (2003)). For example, the ALU Yb lineage contains approximately 1800 copies per genome and SVA contains approximately 1700 full length element copies per genome (Wang, H., referenced supra; Carter, A B, et al., *Genome-wide analysis of the human Alu Yb-lineage*, Hum. Genomics 1(3): 167-178 (2004)). This large copy number minimizes the effect of variation between individuals, resulting in highly reproducible quantitation values.

U. S. Patent Publication 2014/0051075 A1, to Sudhir K. Sinha, is entitled "Development of a Highly Sensitive Quantification System for Assessing DNA Degradation and Quality in Forensic Samples" and describes the detection of DNA quality with a multiplex reaction using ALU and SVA for human DNA quantification. Though very useful for forensic purposes, the described method does not detail specific application to cell free DNA from plasma and/or serum. The amplicon sizes needed for a cfDNA assay are different from those needed for forensic applications, and other details of the two methods such as amplification conditions and primer/probe concentrations differ as well.

There is a clear need in cancer management, and CRC treatment specifically, for a standardized and validated blood test to sensitively and robustly quantitate cfDNA integrity and concentration. The present application addresses this need by creating a multiplex qPCR assay for quantitating cfDNA integrity and concentration based on REs.

The most commonly employed method conducted by others in the field of cfDNA integrity and concentration assessment for cancer detection and monitoring is qPCR using the ALU 247/115 index. This method has shown promise in multiple studies; however, there is a strong need for a standardized, validated multiplex that can simultaneously and accurately measure cfDNA concentration, integrity and PCR inhibition from plasma and serum.

Figure 2:
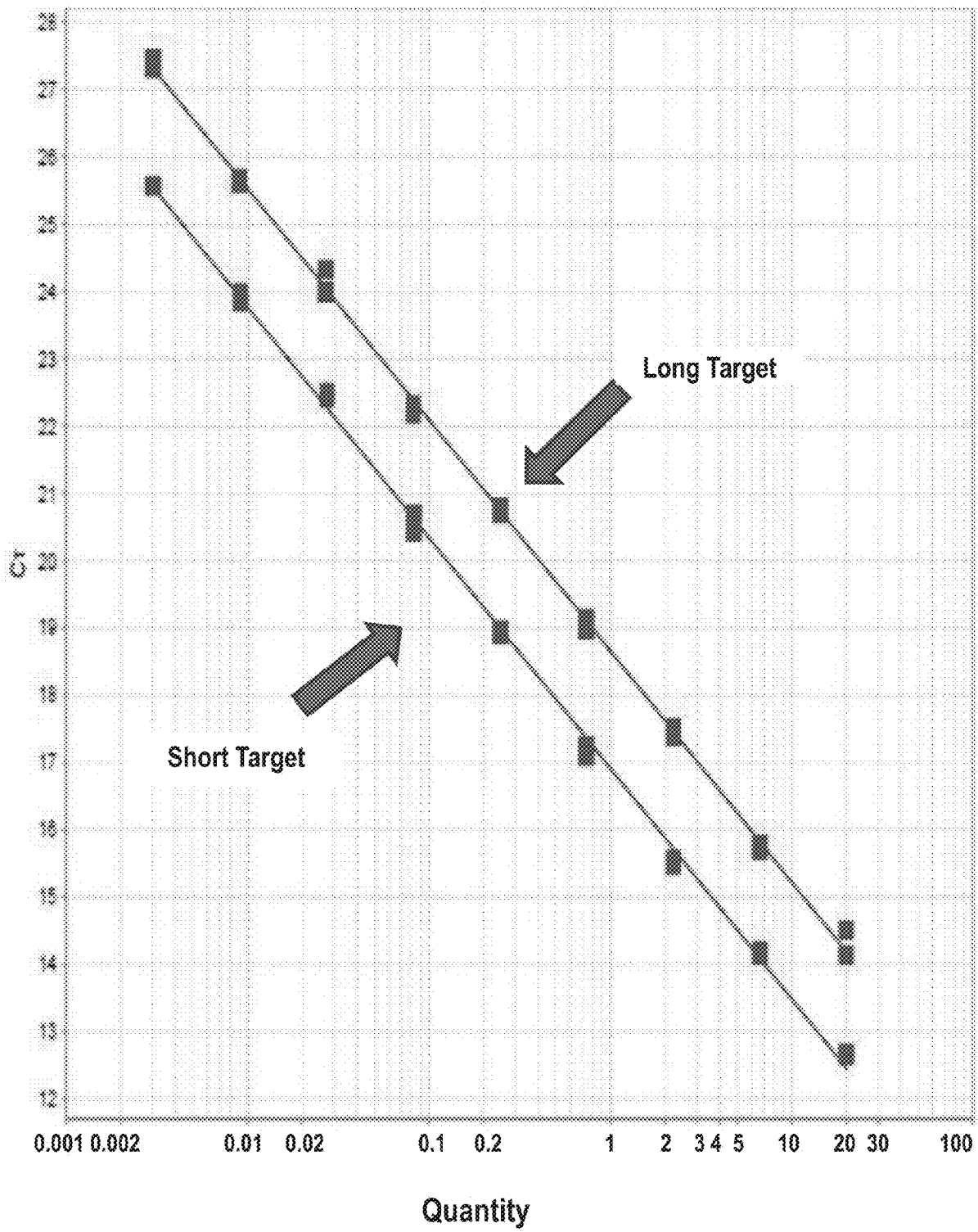
FIG. 2 shows standard curves for long and short targets of a three target multiplex RE-qPCR assay for cfDNA concentration and DNA integrity in a biological fluid sample.

In one embodiment, the developed multiplex uses two independent retrotransposable element genomic targets, an ALU element in the Yb8 subfamily of 80 bp in size and an SVA element of 207 bp in size, in a multiplex based, real-time qPCR assay for the detection of two sized targets to assess the extent of DNA integrity. The multiplex exhibits high PCR efficiencies for both targets (see FIG. 2). The system also incorporates an internal positive control target synthetic sequence of 172 bp in size to monitor and enable the detection of PCR inhibitors in forensic samples. The system is highly sensitive due to its multi-copy nature, and the system is highly reproducible and accurate due to the high copy number (>1000 copies per genome) of the selected targets.

A pilot study with serum and plasma samples tested with the qPCR multiplex of 207 bp and 80 bp target sizes has been performed. Serum and plasma samples from normal healthy individuals were processed both with DNA purification and without purification (direct qPCR). The data shows several interesting observations. First, it is observed that the short target produces a quantification value as low as 0.3 picograms of cfDNA (Table 2). It should be noted that in this pilot study, the PCR was performed at 32 PCR cycles (a literature search reveals cfDNA qPCR assays are typically performed as low as 35 cycles). Even with 32 cycles, the ability of the RE-qPCR multiplex to detect cfDNA at very low levels is demonstrated. Cycle numbers and other PCR parameters may be further optimized.

Secondly, it is observed from this pilot study that the main challenge to overcome is the complete inhibition or lack of detection of the long target with serum and plasma samples processed using direct qPCR without DNA purification. This can be overcome in part by testing fragments of cfDNA of varying sizes and selecting the most sensitive and accurate targets. The use of robust enzymes and PCR additives may be of primary importance in overcoming the problem of lack of detection of the long target. This pilot study demonstrates that the basic concept in this effort of using the high copy number retrotransposon targets Yb8 and SVA in a multiplex qPCR system to detect DNA integrity for the application of colorectal cancer diagnosis and prognosis is feasible.

purified DNA from serum and plasma, no PCR inhibition is noted, as indicated by the acceptable IPC Ct values. On the other hand, the direct qPCR of both serum and plasma samples without DNA purification exhibits PCR inhibition as indicated by the failure of the IPC target to amplify as expected (see IPC amplification plots in FIGS. 3A, 3B and IPC Ct values in Table 2). This work demonstrates the challenge in performing direct qPCR on serum and plasma samples.

Real-Time Polymerase Chain Reaction (PCR) Methods

In the last recent years, real-time polymerase chain reaction (PCR) chemistry has become the standard for reliably quantifying the amount of genomic and amplifiable DNA in a forensic sample. Commonly used systems include the assessment of total human and male DNA. Examples are Quantifiler® from Life Technologies Corporation, Plexor® from Promega Corporation and Quantiplex® from Qiagen. Currently there are several different approaches used for fluorescence-based quantification assays, including SYBR® Green, Plexor®, TaqMan®, AmpliFluor®, Quantifiler® and Quantiplex®.

Interest has recently grown in using real-time PCR methods to evaluate the extent of degradation of a DNA sample. This may be done using two nuclear DNA targets: a short multi-copy sequence and a long multi-copy sequence. Because the long target sequence will degrade more rapidly than will the short target sequence as a sample is compromised, the ratio of the quantity of the short target to the long target will provide an assessment of the extent of degradation in the sample. Studies on the assessment of degraded DNA in a forensic sample have been published using Alu or mini-satellite targets. However, the assays of previous studies either lack in sensitivity or do not exhibit high PCR efficiencies. Forensic samples vary widely in quantity and quality, making the goal of developing and validating a real-time PCR system for the purposes of quantitating the DNA in these samples and determining the extent of their degradation a challenging one.

The recent advances in mini short tandem repeat (STR) analysis systems have now made it possible to analyze

TABLE 2

RE qPCR on purified and direct qPCR serum and plasma samples from normal individuals.

|  | ALU 80; Short (ng/µL) | SVA 207; Long (ng/µL) | DNA Integrity (SVA207/ALU80) | IPC Ct$_{(acceptable\ range\ from\ 18\text{-}22)}$ |
|---|---|---|---|---|
| Whole serum 1 (direct) | 0.002 | 0 | 0 | Undetermined+ |
| Whole serum 2 (direct) | 0.022 | 0 | 0 | Undetermined+ |
| Whole serum 3 (direct) | 0.009 | 0 | 0 | Undetermined+ |
| Purified serum 1 | 0.020 | 0.009 | 0.45 | 20.2 |
| Purified serum 2 | 0.733 | 0.421 | 0.57 | 19.7 |
| Purified serum 3 | 0.045 | 0.013 | 0.29 | 20.2 |
| Whole plasma 4 (direct)* | 0.0003 | 0 | 0 | 24.9 |
| Whole plasma 5 (direct)* | 0.002 | 0 | 0 | 25.1 |
| Whole plasma 6 (direct)* | 0.0004 | 0 | 0 | 23.5 |
| Purified plasma 4 | 0.056 | 0.019 | 0.33 | 21.38 |
| Purified plasma 5 | 0.409 | 0.032 | 0.08 | 21.04 |
| Purified plasma 6 | 0.080 | 0.020 | 0.24 | 21.10 |

Breitbach 2014 method used for direct qPCR of plasma (The plasma was diluted in sterile water in a 1:40 ratio for direct qPCR measurement).
+Did not cross the cycle threshold at 32 PCR cycles.
Bold font indicates internal positive control Ct values outside of the acceptable range.

Furthermore, the utility of the internal positive control (IPC) with direct qPCR serum and plasma samples is shown by the results of this pilot study. It is observed that with highly compromised samples. Investigators have made great strides in the development of STR amplicons that, compared with traditional STR amplicons, are reduced in size and can be used effectively on DNA samples that have been significantly degraded (see, e.g., J. M. Butler, et al., *The development of reduced size STR amplicons as tools for analysis of degraded DNA*, J. Forensic Sci. 2003, 48(5): 1054-1064; T. J. Parsons, et al., *Application of novel "mini-amplicon" STR multiplexes to high volume casework on degraded skeletal remains*, Forensic Science International: Genetics 1, 2007, 175-179).

Useful DNA Target Sequences

Alu are Short Interspersed Elements (SINE), approximately 300 bp insertions which are distributed throughout the human genome in large copy number. The evolution of Alu elements in the human genome over time has made Alu elements well suited for the task of distinguishing human DNA from non-human DNA and for doing testing that is desired to be specific to human DNA. A recent study reports an evaluation of the quality assessment of degraded DNA samples using a Ya5-lineage Alu genetic element. J. A. Nicklas, et al., *Development of a real-time method to detect DNA degradation in forensic samples*, J. Forensic Sci. 2012, 57(2): 466-471. A multi-copy intra-Alu based approach for quantifying human specific DNA in an evidence sample has been successfully used to obtain DNA quantification with high sensitivity. J. A. Walker, et al., *Multiplex polymerase chain reaction for simultaneous quantitation of human nuclear, mitochondrial, and male Y-chromosome DNA: application in human identification*, Anal. Biochem. 2005, 337: 89-97.

The average age of Yb-lineage subfamily elements is estimated as 2.39 million years. It is estimated that the human genome contains over 1800 Alu Yb family elements and, out of those, approximately 50% are from the Yb8 subfamily. The Alu Yb8 system is known for the presence of a large number of fixed insertions. It has been reported that only 20% of the Yb-lineage Alu elements are polymorphic for insertion presence or absence in the human genome. Carter, et al., *Genome-wide analysis of the human Alu Yb-lineage*, Human Genomics 2004, 1(3): 167-178. Because a large number of these fixed elements are present in every human genome, the individual specific variation possible when using a multi-copy target quantification system is minimized.

In 1994, Shen, et al., identified a new composite retroposon when they studied the structure of the retinitis pigmentosa (RP) gene. Shen, et al., *Structure and genetics of the partially duplicated gene RP located immediately upstream of the complement C4A and the C4B genes in the HLA class III region. Molecular cloning, exon-intron structure, composite retroposon, and breakpoint of gene duplication*, J. Biol. Chem. 1994, 269(11): 8466-8476. This new retroposon consisted of the SINE-R element together with a stretch of sequence that shares sequence similarity with Alu sequences. Thus, it was named "SVA" after its main components, Short Interspersed Elements (SINE), Variable Number Tandem Repeats (VNTR) and Alu. SVA elements contain the hallmarks of retrotransposons, in that they are flanked by target site duplications (TSDs), terminate in a poly(A) tail and are occasionally truncated and inverted during their integration into the genome.

Method for Measuring Tumor Burden in Patient Derived Xenograft (PDX) Mice

In an embodiment, the present invention provides a quick and easy tool to predict in vivo human cancer cell survival in PDX mouse models, and accordingly enables the quantitative measurement of tumor burden and growth intensity in PDX mice. A highly sensitive quantitative polymerase chain reaction (qPCR) multiplexed method to determine the mouse vs. human DNA concentration in PDX mice has been developed. This assay can monitor the successful tumor engraftment and/or successful humanization of immunodeficient mice and has the capacity to quantify levels of mouse and human components in various applications.

In one embodiment of the invention, the inventive method utilizes a multiplexed real-time polymerase chain reaction (PCR) system that produces fluorescent labeled amplicons, where one target is a human Alu retrotransposon high-copy target and the other target is a mouse specific genomic sequence. The primers and probes utilized are specific for human and mouse DNA and do not exhibit any cross reactivity, so that they can be used to accurately and simultaneously quantitate the two species' DNA. This approach utilizes DNA from a small volume of mouse blood that can be routinely collected without harming the mice (typically 50-100 microliters). The use of a high copy number Alu target, as compared to a typical somatic locus that has two copies per cell, increases the sensitivity of the Alts (est by at least 5,000-fold. The proposed approach to monitor successful tumor engraftment, tumor burden and metabolic response to therapy through the use of a multiplex qPCR system with greater than 90% PCR efficiency to accurately and simultaneously quantitate mouse and human DNA from a small amount of PDX mouse blood, either after DNA extraction or directly from blood, and without killing the mouse, has not been previously reported. PCR efficiencies as high as 99% have been noted in this work.

In an embodiment of the principles of the present invention, the qPCR method described herein determines quantitatively the mouse vs. human DNA concentration in mouse blood and therefore is indicative of the extent to which human DNA/cells survived in the mouse model. This assay provides a quick and easy tool to assess in vivo human cancer cell survival in mouse models and thus enables the quantitative measurement of the tumor burden in PDX mice. Ideally, human cancer cell survival in mouse models is, in turn, predictive of cancer cell viability in human patients.

In another embodiment of the principles of the present invention, the qPCR method described herein can monitor patient derived tumor cell growth even in a humanized mouse, which was created by implantation of human immune cells and hence contained human DNA in its plasma before the patient derived cancer tissue was implanted. This may be done by selectively monitoring specific patient DNA markers in order to discriminate the implanted human tumor tissue DNA from the DNA of the human immune cells implanted in the mouse prior to implantation of the tumor.

In another embodiment of the principles of the present invention, the qPCR method described herein can monitor patient derived tumor cell metastatic processes in a humanized mouse. This may be done by quantitating the tumor patient DNA derived from tumor cells metastasizing by way of the PDX mouse bloodstream. In this embodiment, tumor DNA is measured from actual tumor cells, not from cell-free DNA. This allows a determination of tumor growth in the PDX mouse.

In another embodiment of the principles of the present invention, the qPCR method described herein saves time and cost by allowing the selection of an appropriate mouse during the early stages of the humanization process through monitoring the DNA derived from the immune cell transplant. The inventive method can monitor both the humanization process during preparation of an immune compromised mouse and the tumor burden in the humanized mouse after implantation of human tumor tissue.

In another embodiment of the principles of the present invention, patient derived tumor burden in a humanized mouse may be monitored. A humanized mouse contains human immune cells such as CD 34+ implanted in a NOG or other immunocompromised mouse. The retrotransposon insertion polymorphic markers of the human cells used for humanization can be typed (discerned), and then a mixture of polymorphic insertion or no insertion alleles that are not present in the humanization human cell DNA but are present in the human implanted tumor cell DNA can be selected. Utilizing qPCR primers and probes corresponding to these markers, where all selected alleles of the ctDNA are labeled with the same fluorophore, a multi copy high sensitivity system may be created to quantitate the patient circulating tumor DNA. Such a system allows monitoring of the growth of the human patient tumor in the mouse using samples of mouse blood that are small enough in volume that the mouse can be kept alive for future sampling and measurements.

The principles of the present invention contemplate monitoring tumor progression in a PDX mouse in which a multiplexed real-time PCR system that produces fluorescent labeled amplicons is utilized, where one of the target DNA sequences comprises an Alu retrotransposon multi-copy target found in human DNA and another target DNA sequence is a mouse specific genomic sequence. The primers and probes utilized are specific for human and mouse DNA, respectively, and do not exhibit any cross reactivity. These primers and probes can therefore be used to accurately and simultaneously quantitate the two species' DNA from a small amount of mouse blood (typically 50-100 microliters) with high sensitivity.

Because the principles of the present invention contemplate utilizing a multiplexed real-time PCR system and making use of a multicopy Alu target to perform qPCR, the sensitivity of the assay is very high, the assay can quantitate human DNA from only two microliters of mouse blood and the assay can be performed using direct qPCR (qPCR performed on a mouse blood sample without purification of the DNA in the mouse blood) utilizing inhibitor resistant polymerase and optimized PCR conditions. One advantage of this method is that it provides the ability to monitor tumor burden over different time intervals in the PDX mouse and can provide a method for investigating the utility of specific cancer drugs suitable for that particular patient's cancer or for more general drug discovery needs.

A highly sensitive, novel qPCR multiplexed method to determine the mouse vs. human DNA concentration in humanized engrafted mice has been developed. This assay can monitor the successful humanization of mice and also has predictive capacity (predictive for the human patient) based on the extent to which human tumor DNA/cells survived in the mouse model. This assay provides a quick and easy tool to predict in vivo human cancer cell survival in mouse models.

Proof-of-principal liquid biopsy qPCR was performed on human immune system (HIS) CD34+ engrafted mice with both human and mouse cells in the blood circulation. Human Alu-specific and mouse-specific qPCR assays performed on DNA extracted from whole blood from two candidate HIS mice demonstrate the power of inter Alu qPCR detection. These candidate engrafted mice have at least ten times more mouse cells than human cells in the blood samples, according to fluorescence-activated cell sorting (FACS) data. Under the same qPCR conditions, from the same DNA preparation, with the same quantity of input DNA (the equivalent of 5 µL of mouse blood), the massive-copy Alu assay and the two copy mouse assay were compared head-to-head. The qPCR results for the mouse blood DNA samples show the human Alu amplification crossed the threshold much sooner than the two copy per genome mouse qPCR target amplification. During PCR, the products double with each cycle; therefore a difference of one cycle corresponds to a two-fold difference in copy number (i.e., $2^1$). A ten cycle difference (27-17) thus corresponds to a 1024-fold difference in copy number ($2^{10}$). This cycle difference, combined with the fact that the human cells were present at a starting concentration 10-fold lower than mouse cells shows that the Alu amplicon has massive sensitivity, on the order of 10,000 times (10×1024) as much as a two copy per genome DNA target. Also, the primers and probes selected to produce the human Alu qPCR amplicon have no cross-reactivity to mouse DNA as determined by negative blank using mouse DNA.

The qPCR technique described allows the identification of tumors that are growing based on the presence of human ctDNA and/or human ctcDNA in the corresponding xenograft models. This technique will be integral in the decision making relating to how long to keep the PDX mouse models waiting for tumors to grow. This assay will provide information to actively manage scientific decisions based on existing and new quality management parameters. The result will build a new process to build PDX models. The liquid biopsy assay described herein provides a non-lethal test for the presence of human ctDNA to identify PDX models that are actively growing, and therefore provides a quantitative model to monitor tumor growth.

Kits

The above-described method for monitoring an implanted patient derived tumor in a humanized mouse may be carried out with a kit that enables monitoring of a tumor burden from an implanted patient derived tumor in a humanized mouse that was produced by introduction of human immune cells into an immunocompromised mouse, the kit comprising a first primer/probe mixture including a primer/probe set corresponding to each of a first group of retrotransposon insertion polymorphic genetic markers found in the human genome, each primer/probe set comprising a forward primer, a reverse primer and a probe, each primer/probe set of the first primer/probe mixture including one of a plurality of fluorescent labels and facilitating simultaneous amplification of the corresponding genetic markers using a real-time polymerase chain reaction system to produce an amplicon corresponding to each marker of the first group, the fluorescent labels facilitating identification of each amplicon with a genetic marker of the first group according to a distinct combination of size and fluorescent label; a primer/probe collection including a primer/probe set corresponding to each of the first group of retrotransposon insertion polymorphic genetic markers, each primer/probe set comprising a forward primer, a reverse primer and a probe, each primer/probe set of the primer/probe collection including the same fluorescent label, the primer/probe collection being customizable to form a second primer/probe mixture, the second primer/probe mixture including a selected subset of the primer/probe sets of the first primer/probe mixture, the second primer/probe mixture corresponding to a second group of retrotransposon insertion polymorphic genetic markers, the second group of markers being selected for failing to amplify in template DNA from the human immune cells that were used to produce the humanized mouse; and instructions indicating use of the first primer/probe mixture with the real-time polymerase chain reaction system to amplify DNA from the human immune cells to obtain a DNA profile, selection of the second group of markers, the second group of markers consisting of those markers that do not amplify in the generation of the DNA profile, formation of the second primer/probe mixture, using the second primer/probe mixture and the real-time polymerase chain reaction system to amplify DNA from a sample taken from the humanized mouse, and use of a resulting fluorescence level as an indication of a tumor burden in the humanized mouse.

The above-described method for measuring an extent of degradation of ctDNA in PDX mouse models may be carried out using a kit, the kit comprising: a third primer/probe mixture including a primer/probe set corresponding to an Alu element found in the human genome and a primer/probe set corresponding to an SVA element of the human retinitis pigmentosa (RP) gene, each primer/probe set comprising a forward primer, a reverse primer and a probe and producing a corresponding amplicon with a real-time polymerase chain reaction system; and instructions indicating use of the third primer/probe mixture with the real-time polymerase chain reaction system to amplify ctDNA, determination of quantitative amounts of DNA in a sample taken from the PDX mouse, the quantitative amounts based separately on amplification of the Alu element and amplification of the SVA element, calculation of a ratio of the quantity of DNA based on amplification of the Alu element to the quantity of DNA based on amplification of the SVA element, and use of said ratio as a measure of an extent of degradation of ctDNA in the PDX mouse.

The above-described kit for measuring an extent of degradation of ctDNA in PDX mouse models may comprise a primer/probe set corresponding to the Alu element, the primer/probe set including a forward primer having a structure defined as 5'-GGAAGCGGAGCTTGCAGTGA-3' (SEQ ID NO: 5), a reverse primer having a structure defined as 5'-AGACGGAGTCTCGCTCTGTCGC-3' (SEQ ID NO: 6) and a probe including a structure defined as 5'-AGATTGCGCCACTGCAGTCCGCAGT-3' (SEQ ID NO: 36).

The above-described method for measuring tumor burden in a patient derived xenograft (PDX) mouse may be carried out with a kit, the kit comprising: a primer/probe mixture including a primer/probe set corresponding to an Alu element found in the human genome and a primer/probe set corresponding to a mouse retrotransposon interspersed element being found in the genome of the mouse, each primer/probe set comprising a forward primer, a reverse primer and a probe and forming a corresponding amplicon with a real-time polymerase chain reaction system; and instructions indicating use of the fourth primer/probe mixture with the real-time polymerase chain reaction system for amplifying DNA from a sample taken from the PDX mouse, determination of a quantitative amount of DNA based separately on amplification of the Alu element and amplification of the mouse retrotransposon interspersed element, determination of a quantitative amount of DNA based separately on amplification of the Alu element and amplification of the mouse retrotransposon interspersed element, calculation of a ratio of the quantity of DNA based on amplification of the Alu element to the quantity of DNA based on amplification of the mouse retrotransposon interspersed element, and use of said ratio as a measure of a tumor burden in the PDX mouse.

Human DNA Quantitation and Determination of an Extent of DNA Degradation

One embodiment of the principles of the present invention contemplates a process for quantitating a human DNA in a sample in order to assess the extent of degradation of the DNA therein, the process comprising the steps of providing a sample to be analyzed, using a real time PCR system to separately quantitate within the sample a first retrotransposon interspersed element and a second retrotransposon interspersed element, the first retrotransposon interspersed element being an Alu element, the second retrotransposon interspersed element being an SVA element of the RP gene, and calculating a ratio of an occurrence within the sample of the first retrotransposon interspersed element to an occurrence of the second retrotransposon interspersed element.

In other embodiments of the principles of the present invention, the second retrotransposon interspersed element used as a target for quantitation with a real time PCR system may comprise at least two times or at least three times as many base pairs as are comprised by the first retrotransposon interspersed element.

In other embodiments of the principles of the present invention, the first retrotransposon interspersed element may be a target sequence that has about 80 base pairs and is an Alu element of subfamily Yb8, and the second retrotransposon interspersed element may be a target sequence that has about 257 base pairs or has about 290 base pairs and is an SVA element of the RP gene.

In another embodiment of the principles of the present invention, the inventive processes may be used to determine the extent of admixture of male and female DNA in a test sample. This embodiment is enabled by the existence of a male specific target sequence having about 90 base pairs, the male specific target sequence being deleted on the human X-chromosome in an X-Y chromosome homologous region and being therefore specific to male DNA. As explained in the disclosure of Walker, et al., U.S. Pat. No. 7,405,044 (hereinafter 'Walker'), which is hereby incorporated by reference in its entirety, sex chromosome assays may be designed around a 90 bp deletion on the human X-chromosome in the X-Y homologous region (col. 5, ln 42-44). In FIG. 3 of Walker, the relevant primers are shown in bold font and the chromosome specific probes are shown in lower case underlined font. The deletion starts at X position 89810740 as determined by BLAT (The BLAST like Alignment Tool) (Walker, col. 5, ln 44-47).

A process in conformance with the principles of the invention may further contemplate steps for providing a first probe, the first probe comprising a first moiety capable of fluorescence at a first diagnostic wavelength and a first quencher capable of quenching the first moiety fluorescence, the first probe being targeted to the first retrotransposon interspersed element, providing a second probe, the second probe comprising a second moiety capable of fluorescence at a second diagnostic wavelength and a second quencher capable of quenching the second moiety fluorescence, the second probe being targeted to the second retrotransposon interspersed element, providing at least one primer that is useful in a real-time polymerase chain reaction system, the system being capable of amplification of a DNA sample, providing a Taq polymerase enzyme capable of catalyzing the formation of a nucleic acid sequence that is complimentary to one present in the sample, the Taq polymerase enzyme being capable both of cleaving the first probe to separate the first fluorescent moiety from the first quencher and of cleaving the second probe to separate the second fluorescent moiety from the second quencher, treating the sample with the first probe and the second probe, amplifying the sample using the at least one primer and the Taq polymerase enzyme by means of the real-time polymerase chain reaction system, illuminating the sample during each real time polymerase chain reaction cycle using an excitation source capable of inducing fluorescence in both the first moiety and the second moiety, measuring the fluorescence emitted from the first moiety and the fluorescence emitted from the second moiety for each real time polymerase chain reaction cycle, determining a threshold cycle number for the first retrotransposon interspersed element and the second retrotransposon interspersed element, and comparing the determined threshold cycle numbers with standard curves (threshold cycle number vs. quantity of DNA) for each of the first retrotransposon interspersed element and the second retrotransposon interspersed element to determine a concentration for each of the first retrotransposon interspersed element and the second retrotransposon interspersed element within the sample.

In other embodiments of the principles of the present invention, the goal of determining the extent of degradation present in a DNA sample may be realized by using two independent genomic targets, obtaining quantification of a short DNA fragment having about 79 base pairs and a long DNA fragment having either about 257 base pairs or about 290 base pairs in a degraded DNA sample. A multi-copy intra Alu based approach has been developed using these target fragments to quantify human specific DNA in a sample and has been successfully used to obtain DNA quantification with high sensitivity. The use of internal primers to amplify DNA segments including that of an Alu element allows for human specificity as well as high sensitivity when compared to a single copy target.

The method for quantifying the extent of degradation of a human DNA sample relies on the fact that the integrity of the longer insertion sequences will be disrupted at a faster pace than will the integrity of the shorter insertion sequences as the DNA sample degrades in the environment. As the polymerization of the PCR reaction proceeds and the two TaqMan fluorescent probes are cleaved, the respective fluorescent signals are monitored during each PCR cycle, and a threshold cycle, the cycle upon which the signal is first detectable, is determined for each target. Using the log linear relationship between threshold cycle and DNA concentration, a concentration for each target sequence may be determined, and the concentration ratio of the respective target sequences in the DNA sample may be determined. This ratio will be an indication of the extent of degradation of the sample.

In an embodiment of the principles of the invention, primers and TaqMan probes are designed using two independent insertion targets. The first is a relatively short (50-150 base pairs) retrotransposon interspersed element insertion, whereas the second is a relatively longer (150-500 base pairs) retrotransposon interspersed element insertion. In other embodiments, the first insertion target has 60-125 base pairs, 75-85 base pairs, or 79 base pairs, and the second insertion target has 200-400 base pairs, 220-320 base pairs, 280-300 base pairs, or 290 base pairs.

The retrotransposon target elements of the present invention must be selected with care. Experimentation with a multiplex composed of Yb8 (80 bp) and Ya5 (250 bp) targets exhibited cross reactivity due to the sequence similarities of these targets. Quantitation values of samples amplified with individual targets Yb8 and Ya5 were discrepant when compared to quantitation values of the same samples amplified in a multiplex reaction containing primers and probes for both the short (Yb8) and long (Ya5) targets in a single amplification due to this cross reactivity. For this study, two forward primers (SEQ ID NO: 1 and SEQ ID NO: 2), a reverse primer (SEQ ID NO: 3) and a probe (SEQ ID NO: 4) corresponding to the Ya5 250 base pair fragment were developed.

In certain embodiments of the principles of the present invention, the shorter retrotransposon interspersed element is a 79 base pair sequence from the Yb8 subfamily of Alu insertions, and the longer retrotransposon interspersed element is a 290 base pair sequence of an SVA element or a 257 base pair sequence of an SVA element. In one of these embodiments, a system was developed using the Yb8 Alu sequence of 79 bp in size for the short fragment labeled in 5-carboxyfluorescein (FAM) and the SINE-R region of SVA sequence (H. Wang, et. al, J. Mol. Biol. 354: 994-1007 (2005)) of 290 bp in size labeled in Cy5 for the long target. A synthetic sequence labeled with indocarbocyanine Cy3 dye was also used as an internal positive control (IPC) to assess the presence or absence of inhibitors in the sample. Another version of this embodiment includes a fourth, male DNA specific, target. In this system, the 79 bp Yb8 fragment was labeled in 2',7'-dimethoxy-4',5'-dichloro-6-carboxyfluorescein (JOE), the 290 bp SVA fragment was labeled in indocarbocyanine Cy5, the male DNA target sequence on the Y chromosome is a 76 bp fragment and was labeled in FAM, and the IPC sequence was labeled in indocarbocyanine Cy3. In other embodiments making use of similar approaches, other multi-copy retrotransposons, such as Long Interspersed Elements (LINE), may also be used.

Cy5, HEX, FAM and TAMRA are believed to have become generic trade names for fluorescent dyes that may be used as labels attached to probes that track the growth of amplicon concentrations during polymerase chain reaction (PCR) amplification. In some embodiments of the present invention, fluorescent dye labels that may be covalently attached to nucleic acid sequence probes may be selected from 6-carboxyfluorescein (sold as 6-FAM or FAM) 1,6-carboxytetramethylrhodamine (sold as TAMRA or TMR) 2,6-carboxy-X-rhodamine (sold as ROX) 3, hexachlorofluorescein (sold as HEX) 4, or a cyanine 5 such as 2-[5-[1,3-Dihydro-1-ethyl-3,3-dimethyl-2H-indol-2-ylidene]-1,3-pentadien-1-yl]-3,3-dimethyl-3H-indolium (sold as Cy5) 5. The "X" groups in the dye structures are "linker" groups that connect an oligonucleotide to a dye label. As is well known in the art, various amide or other groups may be used as linkers.

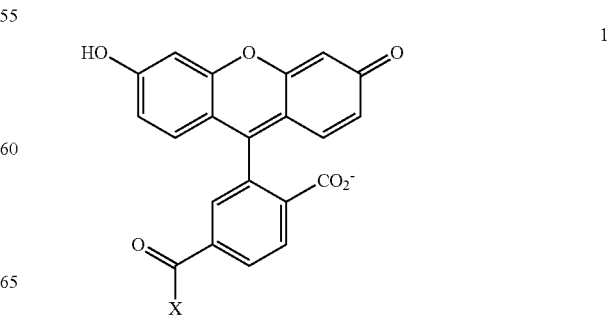

1

-continued

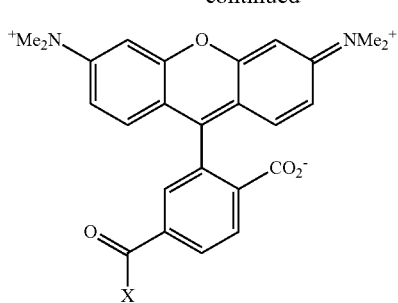

2

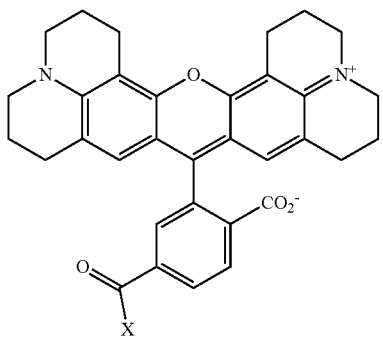

3

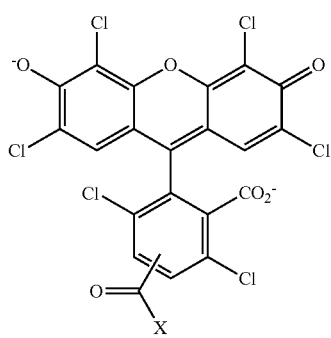

4

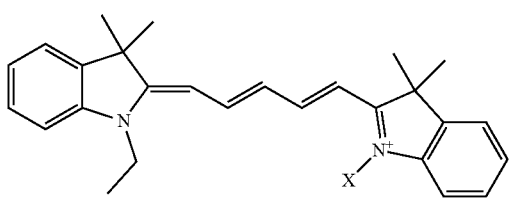

5

In some embodiments of the principles of the present inventions, use of a multi-copy target, two different size sequence markers along with a synthetic target as an Internal Positive Control (IPC) may provide an additional assessment for the presence of PCR inhibitors in the test sample. This is an important way of determining whether the sample matrix may be altering the operation of the test by providing assurance that the expected fluorescence ratios are obtainable under the test conditions.

The present invention will now be described more fully with reference to the accompanying drawing (FIG. 4), in which an exemplary embodiment of the invention is shown.

Figure 4:
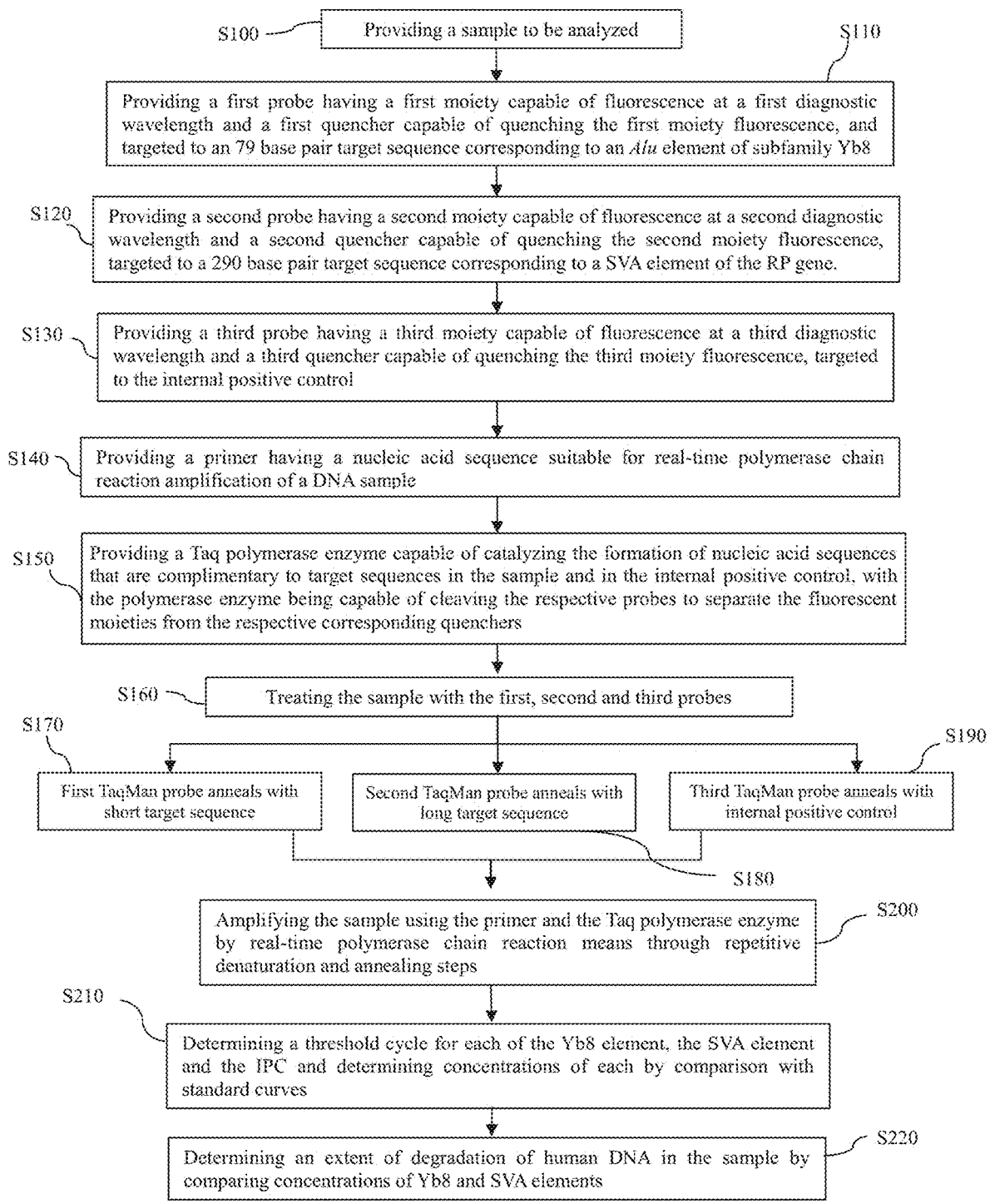
FIG. 4 is a flowchart illustrating a process for determining the extent of environmental degradation of a human DNA sample according to the present invention.

As shown in FIG. 4, a DNA sample (S100) is paired with three TaqMan probes (S110, S120, and S130), a real-time PCR primer (S140) and a Taq polymerase enzyme (S150), the Taq polymerase enzyme being capable of cleaving the TaqMan probes, separating each fluorescent moiety from its respective quencher. In the TaqMan procedure, the sample is treated with the first TaqMan probe, the second TaqMan probe and the third TaqMan probe (S160), the TaqMan probes anneal with one of the complimentary nucleic acid strands (S170, S180, S190), the sample is amplified using a standard real-time PCR technique, and the TaqMan probes corresponding to the target elements are cleaved to separate the three fluorophores from their respective quenchers during repetitive denaturation and annealing steps (S200). Illuminating the sample during each PCR cycle causes the fluorophores from both types of cleaved TaqMan probes to fluoresce. A threshold cycle for each of the Yb8 element, the SVA element and the internal positive control may then be determined, and concentrations of each of these may then be determined by comparison with standard curves (S210). The ratio of concentrations of the Yb8 element and the SVA element may be related to the extent of environmental degradation in the original DNA sample (S220). Comparison of the obtained concentration of the SVA element with a concentration obtained for the internal positive control provides information about the extent to which PCR inhibitors may be present in the sample.

The latter process is versatile and may be modified to provide additional useful information. One of skill in the art may readily envision modification of the above procedure to include a fourth probe corresponding to the male specific DNA target described above.

Precision and sensitivity studies have indicated that the process of the preferred embodiment of the present invention has a sensitivity threshold of about 0.6 pg. In other embodiments, the present invention may show a sensitivity of about 5 to about 9 pg, similar to sensitivities reported for other Alu-based quantification systems. The amount of synthetic IPC target may be adjusted to provide reproducible threshold cycle (Ct) values in the range from 18 to 22 cycles for samples with no inhibition.

Estimated quantitation for both 79 bp and 257 bp fragments obtained using the new primers and TaqMan probes were compared with STR analysis results obtained from DNA samples degraded using sonication, DNAse I and environmental degradation, and the correlation indicates that the process of the preferred embodiment of the present invention is a reliable one for determining the extent of degradation of a human DNA sample. In all instances, the STR results mirrored the degradation ratios calculated by this dual target quantification assay.

The present invention provides a quantification system that accurately assesses the quality of human DNA present in a forensic sample. Results demonstrate the preferred embodiment of the present invention to be specific to higher primates, sensitive down to 5-9 pg of DNA, reproducible, and a useful tool for assessing degradation in a biological sample. A DNA based qualitative/quantitative/inhibition assessment system that accurately predicts the status of a biological sample may serve as a valuable tool for deciding which DNA test kit to utilize when processing forensically compromised samples for DNA testing.

Examples Describing Methods for Measuring Tumor Burden in Patient Derived Xenograft (Pdx) Mice Using a Highly Sensitive Quantification System for Assessing DNA Degradation and Quality Preferred embodiments of the present invention may be better understood through the following characterizations of experimental methods, conditions, accuracy and precision of the process of the present invention and the associated examples that follow.

Example 1: Primers and Probes

Primers and probes that are useful in the described embodiments relating to a method for measuring tumor burden in PDX mice are shown in Table 3. An index of all primers and probes studied in relation to the present invention is shown in Table 4. An intra retrotransposable element (RE) primer design was used to target a Yb8 Alu sequence of 79 bp in size for the "short" fragment as well as a sequence in the SINE-R region of SVA of 290 bp in size for the "long" target in human DNA. An internal positive control (IPC) to assess the presence or absence of inhibitors in the sample was studied as well. IPC target synthetic sequences of 92 bp, 158 bp, 172 bp, and 192 bp were studied. Inhibition studies using inhibitors commonly found in forensic samples were performed on the 92 bp, 158 bp, and 172 bp IPC target sequences.

Two systems were developed: one three target system containing the Yb8 "short" Alu fragment labeled in FAM, the SVA "long" fragment labeled in Cy5, and a synthetic sequence labeled with Cy3 dye used as the IPC. A second system comprised of four targets was developed incorporating a male specific DNA target sequence to detect male DNA in the sample. In this system, the "short" 79 bp Yb8 fragment was labeled in JOE, the "long" 290 bp SVA fragment was labeled in Cy5, the male specific DNA target sequence on the Y chromosome is a 76 bp fragment and was labeled in FAM, and the IPC sequence was labeled in Cy3.

Figure 5:
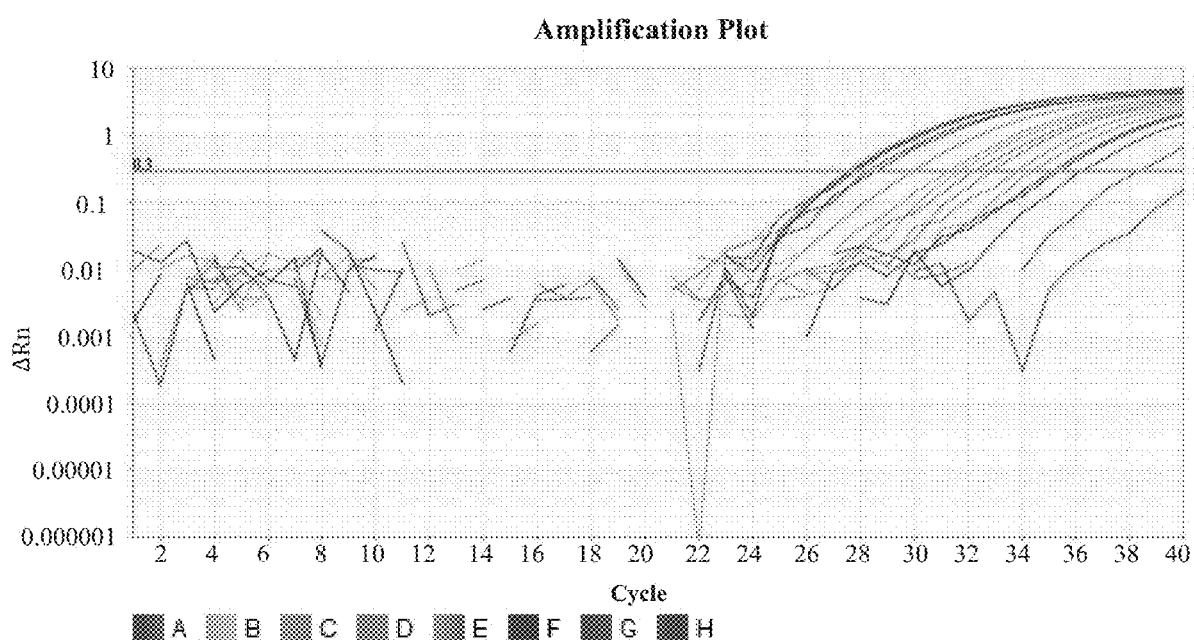
FIG. 5 shows the amplification plot of the Y chromosome target sequence in a single-plex reaction.

Primers and probes were designed for the Y chromosome marker to provide specificity to the Y chromosome target by placing the probe within the 90 bp X chromosome deletion. Single-plex reactions were run to verify the correct products formed. Because the copy number of this target sequence is not as high as the Yb8 or SVA copy number, a higher number of cycles were needed to produce amplification products. In a single reaction, 40 cycles produced a standard curve with 126% efficiency. See FIG. 5 for the real-time amplification plot of the single-plex Y reactions.

For purposes of determining human DNA in PDX mice, the Yb8 primers and probe (SEQ ID NOS. 5, 6, 7) have been found to work very well.

Mouse specific primers were created by comparing the human genome to the mouse genome of *Mus musculus* (lab mouse) and selecting a target area where no crossover between the two species occurred. Within the target sequence area, primer design was created using the Primer3® software to determine the most stable areas for the creation of the forward, reverse and probe primer targets for the qPCR assay to detect mouse DNA. The first attempt for primer design (not shown) resulted in primer cross-reactivity with human DNA, resulting in false positive results, and this primer set was not tested further. The design of another mouse primers and probe set was created and showed no relation to the human genome, as determined by utilizing the NCBI BLAST database for the target sequence. A set of primers and probe to be tested for detection of the mouse DNA (Table 3) was created again using the Primer3® software analysis. It was critical that, unlike previously reported primer pairs, the mouse specific primer had no cross reactivity with human DNA and, in the absence of mouse DNA, did not produce any signal over background with a sample including human DNA only. Table 4 provides an index of primers and probes that may be useful in the present invention, without limitation.

TABLE 3

Primer and probe sequences useful in PDX mouse studies

| Genetic Target: Target Size | Primer Type | Sequence (5'->3') | SEQ ID NO: |
|---|---|---|---|
| Mouse Beta-2 micro-globulin (B2m): 90 bp | Forward | GAC CAA GAC TCG TGA GGA TAA C | SEQ ID NO: 28 |
| | Reverse | CCA GTG TTG GGT CAG GTT TA | SEQ ID NO: 29 |
| | Probe | AGT CGT GGA GGT AGA AAT ATGGCA GAG A | SEQ ID NO: 30 |
| | Probe (labeled) | [Label]AGT CGT GGA GGT AGA AAT ATGGCA GAG A (Label = Cy5) | SEQ ID NO: 31 |
| Mouse L1Md-Tf18: 80 bp | Forward | CCTAAGCCACAGCAGCAG | SEQ ID NO: 32 |
| | Reverse | CCCTCTCACCTGTTCAGACTA | SEQ ID NO: 33 |
| | Probe | ATTTCCTAAGTTCGGCGGGTCCC | SEQ ID NO: 34 |
| | Probe (labeled) | [Label] ATTTCCTAAGTTCGGCGGGTCCC (Label = Cy5) | SEQ ID NO: 35 |
| Human Alu-Yb8: 80 bp | Forward | GGA AGC GGA GCT TGC AGT GA | SEQ ID NO: 5 |
| | Reverse | AGA CGG AGT CTC GCT CTG TCG C | SEQ ID NO: 6 |
| | Probe | AGA TTG CGC CAC TGC AGT CCG CAG T | SEQ ID NO: 36 |
| | Probe (labeled) | [Label] AGA TTG CGC CAC TGC AGT CCG CAG T (Label = HEX or FAM) | SEQ ID NO: 37 |
| Human SVA: 207 bp | Forward | CTG TGT CCA CTC AGG GTT AAA T | SEQ ID NO: 38 |
| | Reverse | GAG GGA AGG TCA GCA GAT AAA C | SEQ ID NO: 39 |
| | Probe | AAG GGC GGT GCA AGA TGT GCT TTG TT | SEQ ID NO: 10 |
| | Probe (labeled) | [Label] AAG GGC GGT GCA AGA TGT GCT TTG TT (Label = Cy5, HEX, or FAM) | SEQ ID NO: 40 |
| Human SVA: 257 bp | Forward | CCT GTG CTC TCT GAA ACA TGT GCT | SEQ ID NO: 41 |
| | Reverse | GAT TTG CAG GGT CA TGG GAC AAT | SEQ ID NO: 9 |
| | Probe | AAG GGC GGT GCA AGA TGT GCT TTG TT | SEQ ID NO: 10 |
| | Probe (labeled) | [Label]AAG GGC GGT GCA AGA TGT GCT TTG TT (Label = Cy5, HEX, or FAM) | SEQ ID NO: 40 |
| Human SVA: 265 bp | Forward | ATG TGC TGT GTC CAC TCA GGG TTA | SEQ ID NO: 11 |
| | Reverse | ATT CTT GGG TGT TTC TCA CAG AGG | SEQ ID NO: 13 |
| | Probe | AAG GGC GGT GCA AGA TGT GCT TTG TT | SEQ ID NO: 10 |
| | Probe (labeled) | [Label]AAG GGC GGT GCA AGA TGT GCT TTG TT (Label = Cy5, HEX, or FAM) | SEQ ID NO: 40 |

TABLE 3-continued

Primer and probe sequences useful in PDX mouse studies

| Genetic Target: Target Size | Primer Type | Sequence (5'->3') | SEQ ID NO: |
|---|---|---|---|
| Synthetic IPC: 172 bp | Forward | GCA TAA AGA TCC TGC CAA CAG | SEQ ID NO: 18 |
| | Reverse | GCCCGAACTTCCAACACTAT | SEQ ID NO: 22 |
| | Probe | ACAGTGTCAGGCAGAGATTGCACT | SEQ ID NO: 24 |
| | Probe (labeled) | [Label] ACAGTGTCAGGCAGAGATTGCACT (Label = HEX < ROX < or TMR) | SEQ ID NO: 42 |

TABLE 4

Index of primers, probes and IPC target studied

| Target Name | Primer or Probe Name (target bp) | Sequence (5'->3") | Sequence ID |
|---|---|---|---|
| Human Alu-Ya5 | Forward-1 | TCACGCCTGTAATCCCAGCACTT | SEQ ID NO: 1 |
| | Forward-2 | ACGCCTGTAATCCCAGCACTTTG | SEQ ID NO: 2 |
| | Reverse | TCTGTCGCCCAGGCTGGAT | SEQ ID NO: 3 |
| | Probe | ATCACGAGGTCAGGAGATCGAGACCAT | SEQ ID NO: 4 |
| Human Alu-Yb8 | Forward | GGAAGCGGAGCTTGCAGTGA | SEQ ID NO: 5 |
| | Reverse | AGACGGAGTCTCGCTCTGTCGC | SEQ ID NO: 6 |
| | Probe | AGATTGCGCCACTGCAGTCCGCAG | SEQ ID NO: 7 |
| Human SVA | Forward | TGGGATCCTGTTGATCTGTGACCT | SEQ ID NO: 8 |
| | Reverse | GATTTGGCAGGGTCATGGGACAAT | SEQ ID NO: 9 |
| | Probe | AAGGGCGGTGCAAGATGTGCTTTGTT | SEQ ID NO: 10 |
| | Forward-Q2F | ATGTGCTGTGTCCACTCAGGGTTA | SEQ ID NO: 11 |
| | Reverse-Q2R1 | TTCTTGGGTGTTTCTCACAGAGGG | SEQ ID NO: 12 |
| | Reverse-Q2R2 | ATTCTTGGGTGTTTCTCACAGAGG | SEQ ID NO: 13 |
| | Forward-Q3F | CCAACCCTGTGCTCTCTGAAAC | SEQ ID NO: 14 |
| | Reverse-Q3R | TTTGGCAGGGTCATGGGACAA | SEQ ID NO: 15 |
| Internal Positive Control (IPC) | Forward (90) | AAAGATCCTGCCAACAGGACAGTG | SEQ ID NO: 16 |
| | Reverse (90) | ACAGACGGTATAGAGACCAATCAG | SEQ ID NO: 17 |
| | IPCr7-Forward (158) | GCATAAAGATCCTGCCAACAG | SEQ ID NO: 18 |
| | IPCr7-Reverse (158) | ACCAAAGTGCTGCAGAAATAC | SEQ ID NO: 19 |
| | Probe | AGGCAGAGATTGCACTGCCTTAAAGTGG | SEQ ID NO: 20 |

TABLE 4-continued

Index of primers, probes and IPC target studied

| Target Name | Primer or Probe Name (target bp) | Sequence (5'->3") | Sequence ID |
|---|---|---|---|
| IPC-M (IPC for use with male specific sequence) | Forward | GCATAAAGATCCTGCCAACAG | SEQ ID NO: 21 |
| | Reverse (172) | GCCCGAACTTCCAACACTAT | SEQ ID NO: 22 |
| | Reverse (192) | ATTGTTCCTCCTGCCTGATT | SEQ ID NO: 23 |
| | Probe | ACAGTGTCAGGCAGAGATTGCACT | SEQ ID NO: 24 |
| | Target | GCA TAA AGA TCC TGC CAA CAG GAC AGT GTC AGG CAG AGA TTG CAC TGC CTT AAA GTG GAC TTA AGA TAA GTA CTG ATT GGT CTC TAT ACC GTC TGT ACC CTT TGA AAA CTG GCA CAA GAC AGG GAT GCC CTC TCT CAC CGC TCC TAT TCA ACA TAG TGT TGG AAG TTC GGG C | SEQ ID NO: 59 |
| Y chromosome | Forward | CAATGTG[CTAGGCTCTAG GAATAC | SEQ ID NO: 25 |
| | Reverse | AAGAGTGTCATGGCTCAAAGAG | SEQ ID NO: 26 |
| | Probe | AGAGAGTATGACAAACATGGCATGGGC | SEQ ID NO: 27 |
| Mouse Beta-2 microglobulin (B2m): 90 bp | Forward | GACCAAGACTCGTGAGGATAAC | SEQ ID NO: 28 |
| | Reverse | CCAGTGTTGGGTCAGGTTTA | SEQ ID NO: 29 |
| | Probe | AGTCGTGGAGGTAGAAATATGGCAGAGA | SEQ ID NO: 30 |
| | Probe (labeled) | [Label] AGTCGTGGAGGTAGAAATATGGCAGAGA (Label = Cy5) | SEQ ID NO: 31 |
| Mouse L1Md-Tf18: 80 bp | Forward | CCTAAGCCACAGCAGCAG | SEQ ID NO: 32 |
| | Reverse | CCCTCTCACCTGTTCAGACTA | SEQ ID NO: 33 |
| | Probe | ATTTCCTAAGTTCGGCGGGTCCC | SEQ ID NO: 34 |
| | Probe (labeled) | [Label] ATTTCCTAAGTTCGGCGGGTCCC (Label = Cy5) | SEQ ID NO: 35 |
| Human Alu-Yb8: 80 bp | Probe | AGATTGCGCCACTGCAGTCCGCAGT | SEQ ID NO: 36 |
| | Probe (labeled) | [Label] AGATTGCGCCACTGCAGTCCGCAGT (Label = HEX or FAM) | SEQ ID NO: 37 |
| Human SVA: 207 bp | Forward | CTGTGTCCACTCAGGGTTAAAT | SEQ ID NO: 38 |
| | Reverse | GAGGGAAGGTCAGCAGATAAAC | SEQ ID NO: 39 |
| | Probe (labeled) | [Label] AAGGGCGGTGCAAGATGTGCTTTGTT (Label = Cy5, HEX, or FAM) | SEQ ID NO: 40 |
| Human SVA: 257 bp | Forward | CCTGTGCTCTCTGAAACATGTGCT | SEQ ID NO: 41 |

TABLE 4-continued

Index of primers, probes and IPC target studied

| Target Name | Primer or Probe Name (target bp) | Sequence (5'->3") | Sequence ID |
|---|---|---|---|
| Human Alu: 119 bp | Forward | AGACCATCCTGGCTAACAA | SEQ ID NO: 42 |
| | Reverse | GCCATTCTCCTGCCTCA | SEQ ID NO: 43 |
| | Probe | TGTAGTCCCAGCTACTCGG GAG | SEQ ID NO: 44 |
| Human Alu: 120 bp | Forward | TGGATCATGAGGTCAGGAG AT | SEQ ID NO: 45 |
| | Reverse | CCGAGTAGCTGGGACTACA | SEQ ID NO: 46 |
| | Probe | ACCATCCTGGCTAACAAGG TGAAACC | SEQ ID NO: 47 |
| Human Alu: 123 bp | Forward | ATCCTGGCTAACAAGGTCA AA | SEQ ID NO: 48 |
| | Reverse | CGGGTTCACGCCATTCT | SEQ ID NO: 49 |
| Human SVA: 355 bp | Forward | GTTGCCGTGTCTGTGTAGA A | SEQ ID NO: 50 |
| | Reverse | ATGGGACAATAGTGGAGGG A | SEQ ID NO: 51 |
| Human SVA: 367 bp | Forward | CCGTGTCTGTGTAGAAAGA AGTAG | SEQ ID NO: 52 |
| | Reverse | GGGATTTGGCAGGGTCAT | SEQ ID NO: 53 |
| Human SVA: 399 bp | Forward | GGCGGCTTTGTGGAATAGA | SEQ ID NO: 54 |
| | Reverse | GAGGGAAGGTCAGCAGATA AAC | SEQ ID NO: 55 |
| | Probe | ATCAGGGACACAAACACTG CGGAA | SEQ ID NO: 56 |
| Human SVA: 411 bp | Forward | TGGAATAGAAAGGCAGGAA AGG | SEQ ID NO: 57 |
| | Reverse | GCAGGGTCATGGGACAATAG | SEQ ID NO: 58 |

Optimization of PCR conditions was carried out as described in Examples 2-5.

Example 2: Primer Dimerization and Cross Reactivity

Figure 6A:
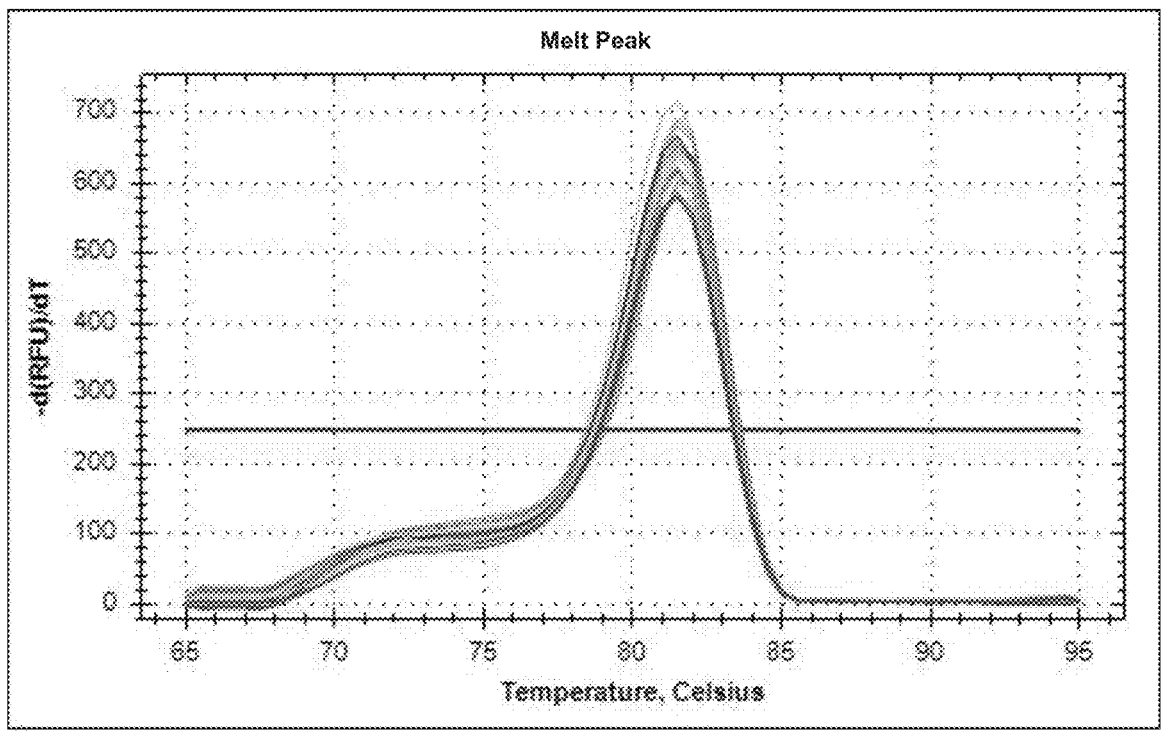
FIGS. 6A and 6B show melt curve analyses for the Yb8 and SVA targets, respectively.
Figure 6B:
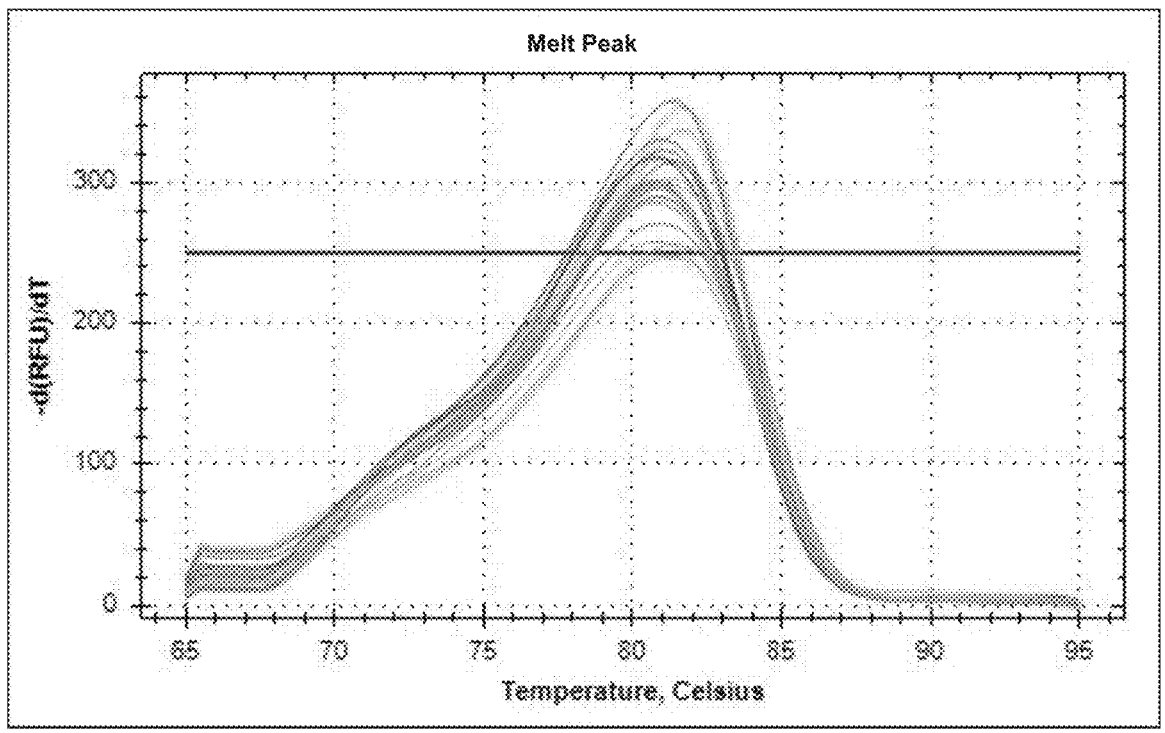

To verify the accuracy of the quantity obtained from each target and to rule out any cross reactivity between primers, a melt curve analysis and amplification artifacts from reactions containing the short target forward primer and the long target reverse primer, both human DNA sequences, were examined by fragment analysis. Melt curves exhibit the presence of a single peak for each of the Yb8 and SVA reactions, as expected. A slightly broad base was observed for both targets, indicating the presence of primer dimers. FIGS. 6A and 6B show melt curve analyses for the Yb8 and SVA targets respectively.

Fragment analysis confirmed the presence of the targeted fragment for each human DNA target sequence as well as the absence of any artifacts resulting from cross reactivity between the primers for the short and long human DNA target sequences (see Table 5). Some primer dimers were observed and one artifact at ~67 bp was also observed. Overall, the results of the melt curve analysis and the fragment analysis confirm the presence of the targeted fragments and the absence of artifacts.

TABLE 5

Fragment Analysis Results

| | Peaks Observed (size in base pairs) | | |
|---|---|---|---|
| | Primer Dimer | Expected Peak | Artifact |
| SVAF/R + Yb8F/R | 50 bp & 59/65 bp | 73 + 290 | |
| SVAF/R + Yb8R | ~50 bp | 290 | 67 |
| Yb8F/R + SVAR | 59/65 bp | 73 | |
| SVAF + Yb8R | | No peaks observed | 67 |
| Yb8F + SVAR | | No peaks observed | |

Figure 7A:
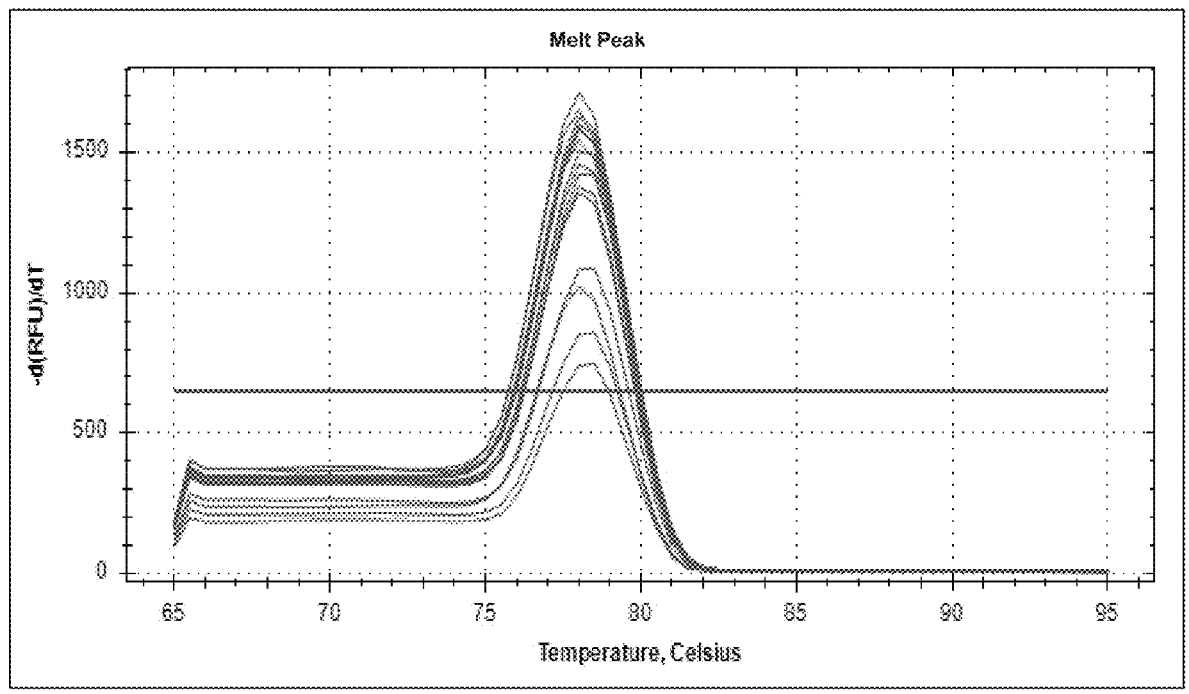
FIG. 7A shows melt curve analysis for the mouse primers.
Figure 7B:
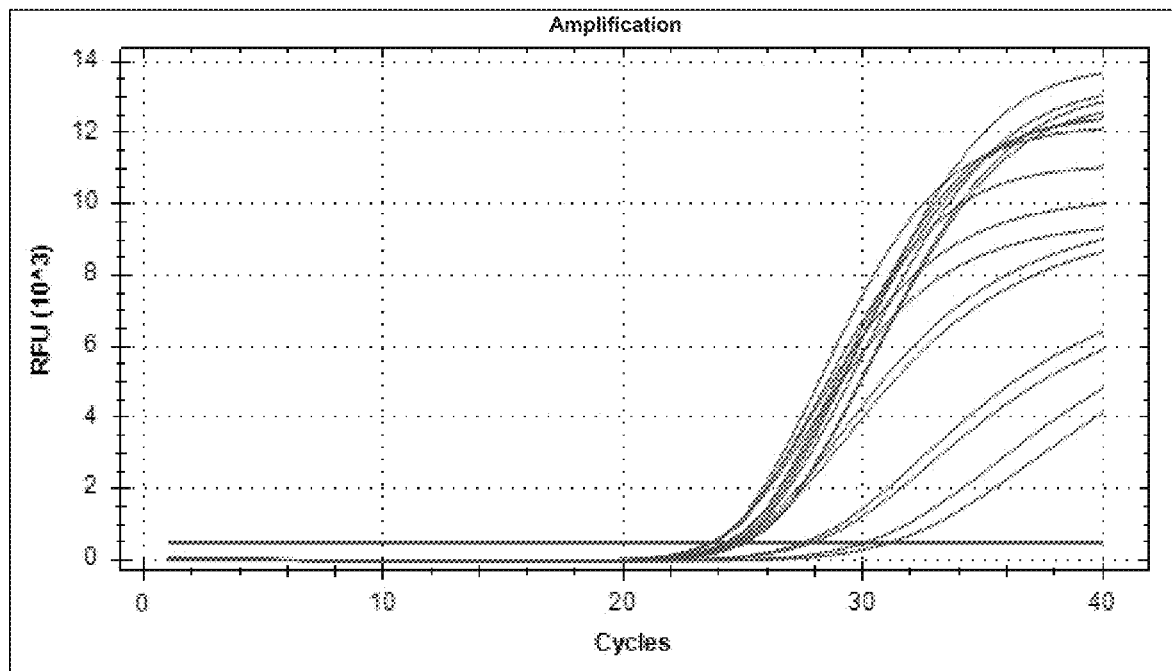
FIG. 7B shows optimization of annealing temperatures for the mouse primers, with annealing temperatures ranging from between 55° C. to 64° C.
Figure 8:
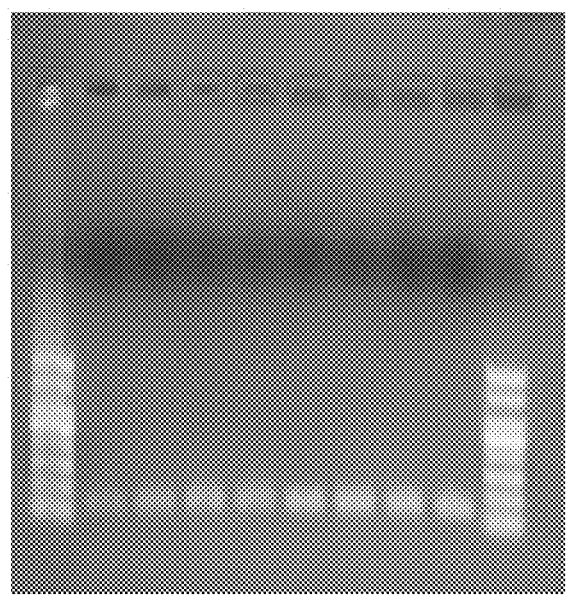
FIG. 8 shows an electrophoresis gel showing that a single product results from PCR amplification of the mouse primers.

The mouse primer sequence was tested for possible primer-dimer and multiple product formation by performing melt curve analysis with the SYBR Green qPCR Master Mix (ThermoFisher) to detect double stranded DNA. Parameters were set using the manufacturer's guidelines. Optimization of the annealing temperature for the primers was also performed ranging from 55-64° C. The melt curve and amplification curves for all annealing temperatures are shown in FIGS. 7A and 7B and in Table 8 below. The mouse primers showed no primer-dimer formation in the PCR cycling parameters using SYBR green and an optimized annealing temperature ~60.7° C. The electrophoresis gel (FIG. 8) shows the single PCR product for all annealing temperatures tested.

Figure 9:
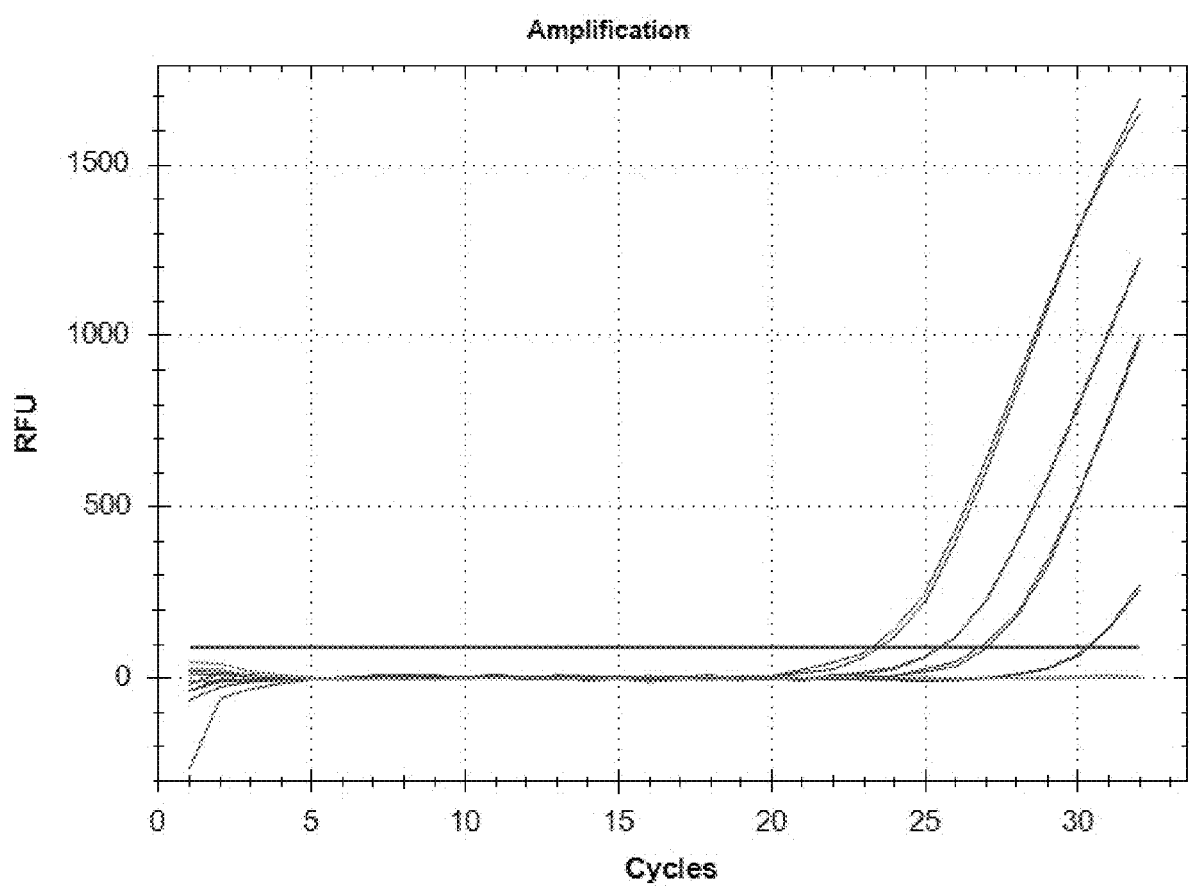
FIG. 9 shows a qPCR assay carried out with mouse primers. Purple curves correspond to the standard curve using mouse DNA. The red curve is a Naïve lab mouse representing ~1.4 ng/µL of mouse DNA in the sample. The green curves signify the CD34+ extracted human DNA showing no amplification after 32 cycles.

Further testing was performed to determine whether the mouse primers would show cross reactivity with human DNA. Human CD34+ cells were lysed and DNA was extracted using a QIAamp DNA Mini kit (Qiagen). The DNA was first quantified with the InnoQuant® Human DNA Quantification and Degradation Assessment Kit, which is available from InnoGenomics Technologies, LLC, New Orleans, La., to determine the concentration of human DNA in the sample. Using the sample of DNA thus obtained from human immune cells, a qPCR run using the mouse primers and probe was run under the same conditions as were used for the InnoQuant® kit run. FIG. 9 shows the amplification curve of the InnoQuant® run representing the human DNA and the mouse primer. The results show that the mouse DNA primers are specific to mouse DNA and do not form any cross-reactivity products with the CD34+ extracted human DNA.

Figure 10:
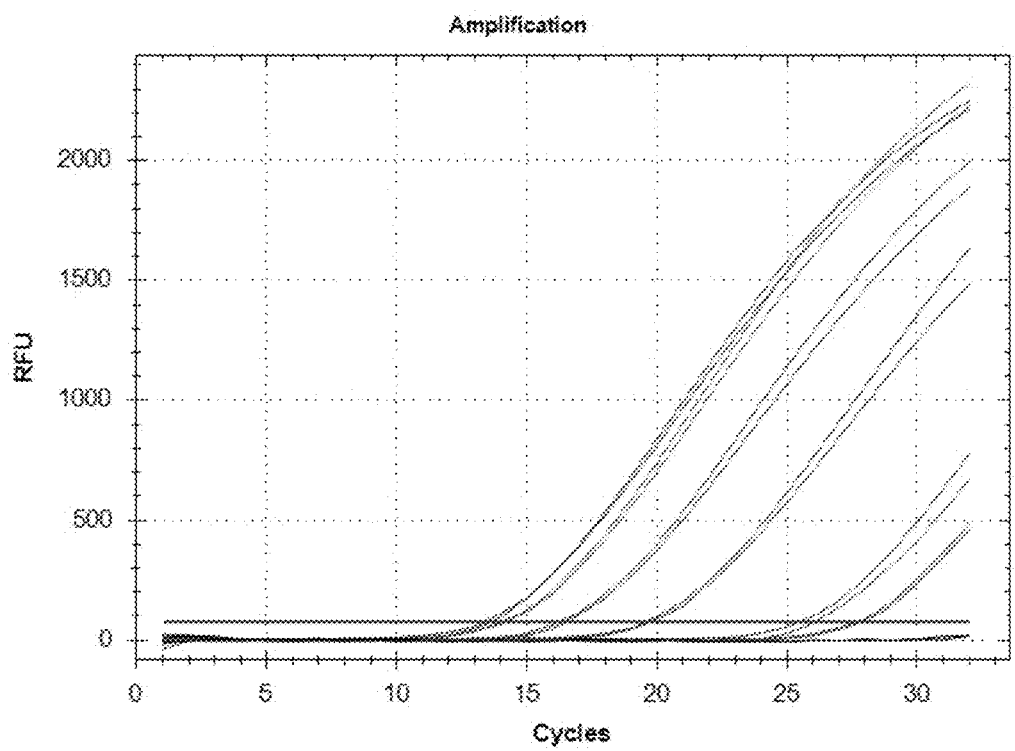
FIG. 10 shows a qPCR assay carried out with the InnoQuant® Kit and run with mouse DNA. Amplification curves are of the DNA standards (purple), CD34+ human immune cells (green), mouse DNA (red) and no target controls (NTCs) (black).

The human DNA quantification primers from the Yb8 region of inter Alu segment (13) were also tested to determine whether cross-reactivity with mouse samples was possible, and to determine the sensitivity of the Alu target for human CD34+ cells in mouse blood DNA samples. FIG. 10 shows the InnoQuant® amplification curves of the DNA standards (purple), CD34+ DNA (green), mouse DNA (red) and no target controls (NTCs) (black). Comparing the massive-copy Alu target and the two copy mouse target shows that the human Alu amplification plot (green curves in FIG. 10) signal crosses the threshold (horizontal bar) at approximately cycle 14. By contrast, the two copy per genome mouse qPCR target amplification plot (red curves in FIG. 10) signal crosses the threshold at approximately cycle 28. These results show the massive sensitivity of the Alu target in mouse blood DNA samples as well as the specificity that the Alu target exhibits to human DNA without any cross reactivity with mouse DNA.

Example 3: Testing Blood Samples of Mice Engrafted with Tumor Cells to Determine Successful Humanization of Mice Table 6 shows quantitative DNA testing results for both human and mouse DNA in a variety of PDX mice.

Two mouse samples (#M6 and #M7) were engrafted with tumor cells and allowed to incubate with the tumor cells for different amounts of time before blood was drawn from each of the specimens. Engraftment for mouse #M7 had previously been confirmed. Mouse #M6-Wk 4 was newly reconstituted with CD34+ cells, and engraftment had not been confirmed for this mouse. DNA controls for both mouse and human and a no-template control were also tested. All samples (mouse and controls) were tested by carrying out qPCR runs using the mouse primer assay and the InnoQuant® Kit. Table 7 shows the DNA quantification results for the mouse and human DNA for the mouse model specimens at various intervals following tumor engraftment and control samples. For both mouse models tested, various amounts of human DNA were detected. Even at DNA levels where engraftment could not be confirmed (mouse #M6-wk4), human DNA could be detected. In particular, mouse sample #M6-wk 10 from the previous test was again tested at ten weeks after engraftment and showed increased amounts of human DNA, showing a growth of the human DNA in the mouse sample and a decrease in the ratio of mouse:human DNA (Table 7). This data provides a quantitative measure of the humanization of the NOG mouse.

TABLE 6

PDx Mouse Sample Testing

| Tissue Type | Mouse # | Notes | DNA Concentration (ng DNA/μL Blood) | |
|---|---|---|---|---|
| | | | Human DNA | Mouse |
| Whole Blood | M1 | Low Engraftment <25% | 0.501 | 5.964 |
| Whole Blood | M2 | Low Engraftment <25% | 0.174 | 11.121 |
| Whole Blood | M3 | Successfully engrafted NOG w/ Human immune cells | 2.194 | 1.645 |
| Whole Blood | M4 | Successfully engrafted NOG w/ Human immune cells | 1.806 | 0.830 |
| Whole Blood | M5 | Successfully engrafted NOG w/ Human immune cells | 0.943 | 0.673 |
| Whole Blood | M6-10 Wk | NOG w/ CD34 cells, @ 10 wks | 0.566 | 1.155 |
| Whole Blood | Naïve NOG | — | 0.0006 | 0.324 |
| Water | NTC | No Template Control | UND | — |

TABLE 7

Time Course Comparison of Human DNA in engrafted mouse #M6

| Sample Category | Mouse # | DNA Sample (ng/uL) | | Mouse/Human Ratio |
|---|---|---|---|---|
| | | Mouse DNA | Human DNA | |
| Newly reconstituted NOG with CD34 cells (engraftment not confirmed) | M6-4 Wks | 9.375 | 0.482 | 19.426 |

TABLE 7-continued

Time Course Comparison of Human DNA in engrafted mouse #M6

| Sample Category | Mouse # | DNA Sample (ng/uL) | | Mouse/Human Ratio |
|---|---|---|---|---|
| | | Mouse DNA | Human DNA | |
| Previously newly reconstituted NOG w/ CD34 cells, now @ 10 wks | M6-10 Wks | 3.973 | 1.565 | 2.53 |

Human and Mouse primers run on the same qPCR plate
Concentrations are obtained from qPCR results for each run based on standard curves Initial experiments have demonstrated that mouse blood samples should be collected in the presence of ethylene diamine tetraacetic acid (EDTA), not heparin, as heparin reduces the efficiency of the polymerase chain reaction.

Example 4: Number of Cycles

The manufacturer recommendation for the QPCR Multiplex master mix is: 95° C. for 10 minutes followed by 40 cycles of 95° C. for 15 seconds and 60° C. for 60 seconds. To test the number of cycles that would be optimal for the dual target (short and long targets in degradation studies) quantification assay, the number of cycles was varied. Tests of 40 cycles and 32 cycles were carried out, and PCR efficiency values were examined. The results showed higher PCR efficiencies when 32 cycles were used.

Example 5: Annealing and Denaturation Times

The manufacturer recommendation for PCR conditions is: 95° C. for 10 minutes followed by 40 cycles of 95° C. for 15 seconds and 60° C. for 60 seconds. To test which PCR conditions would be optimal for the InnoQuant® Quantification Kit (InnoGenomics Technologies, LLC), a kit for quantitation of and determination of an extent of degradation of DNA, denaturation and annealing times were varied. Four annealing times were tested: 45, 60, 70, and 120 seconds; and two denaturation times were tested: 15 seconds and 30 seconds. PCR efficiency, $R^2$ values, and standard deviation of the triplicate quantitation values (three DNA extracts were run in triplicate) were examined.

Results indicate that, for the preferred embodiment of the DNA quantitation of the short and long targets to determine an extent of degradation, the longer second annealing time yields slightly improved PCR efficiencies and lower standard deviation of the triplicate quantification values than was achieved at shorter annealing times. A longer annealing time also provides more time for the enzyme to function properly with the longer targets. Additionally, results indicate that a 30 second denaturation time significantly decreases the $R^2$ value of the standard curve of both targets relative to that attained with the 15 second denaturation time. Therefore, the 15 second denaturation time and 120 second annealing time were selected for use with the preferred embodiment.

Example 6: Annealing Temperature

Annealing temperature was optimized for the mouse primers as shown in Table 8:

TABLE 8

Threshold cycle number ($C_T$) for optimizing annealing temperature of the mouse primers

|  | 64.0° C. | 63.5° C. | 62.5° C. | 60.7° C. | 58.6° C. | 56.8° C. | 55.6° C. | 55.0° C. |
|---|---|---|---|---|---|---|---|---|
| Forward Primer $C_T$ | 31.14 | 27.88 | 24.79 | 23.71 | 23.77 | 24.23 | 24.50 | 25.08 |
| Reverse Primer $C_T$ | 30.10 | 27.49 | 24.59 | 23.66 | 23.67 | 24.29 | 24.63 | 25.10 |
| $C_T$ Mean | 30.62 | 27.68 | 24.69 | 23.68 | 23.72 | 24.26 | 24.56 | 25.09 |

Three annealing temperatures were tested for the short and long human DNA amplifications: the manufacturer-recommended 60° C., 61° C., and 62° C. Efficiencies, $R^2$ values, and standard deviation of the sample triplicates were analyzed. The results are shown in Table 9.

TABLE 9

Annealing temperature runs

| Run date | Conditions | Yb8 Efficiency | Yb8 $R^2$ | Yb8 SD | SVA Efficiency | SVA $R^2$ | SVA SD |
|---|---|---|---|---|---|---|---|
| Oct. 30, 2012 | SVA/Yb8 0.3 IPC 0.2 stds at 20 ng 60° C. Annealing temp | 88% | 0.998 | 0.29 | 87% | 0.998 | 0.39 |
| Oct. 30, 2012 | SVA/Yb8 0.3 IPC 0.2 stds at 20 ng 61° C. Annealing temp | 95% | 0.993 | 0.16 | 85% | 0.994 | 0.24 |
| Oct. 31, 2012 | SVA/Yb8 0.3 IPC 0.2 stds at 20 ng 61° C. Annealing temp | 91% | 0.998 | 0.27 | 82% | 0.997 | 0.22 |
| Oct. 31, 2012 | SVA/Yb8 0.3 IPC 0.2 stds at 20 ng 62° C. Annealing temp | 86% | 0.996 | 1.51 | 84% | 0.997 | 0.98 |

A 62° C. annealing temperature exhibited wide standard deviation of the sample triplicates and a relatively low efficiency of the Yb8 target. Based on these results, an annealing temperature of 61° C. was selected due to the relatively high efficiency of the Yb8 target. The final PCR conditions selected for the preferred embodiment of the quantitation of the short and long targets for determination of an extent of degradation were as follows: 95° C. for 10 min, 32 cycles of: 95° C. for 15 seconds, 61° C. for 70 seconds.

Example 7: Primer and Probe Concentrations

The two targets (short and long) were tested individually to determine the best primer and probe concentrations. Once a determination was made from the individual runs, the two targets were multiplexed, and varying concentrations of each in combination were tested. At least two separate runs were performed for each parameter to ensure reproducibility of the results. Primer and probe concentrations were varied for the SVA (290 bp) and Yb8 targets. (The IPC primer/probe concentrations remained fixed at 150 nM final concentration in the reaction [0.2 µL put into reaction], and IPC template DNA amount remained fixed at 4.5 pg.) The average of the standard curve efficiencies and $R^2$ values, and standard deviation of the sample quantities (tested in triplicate) were examined. Based on the results, a final primer concentration of 0.3 µM (0.6 µl of a 10 µM stock) for SVA and 0.25 µM (0.5 µl of a 10 µM stock) for Yb8 in a total reaction volume of 20 µl was selected.

Example 8: Multiplex Sensitivity

The sensitivity study was designed such that a given set of measurements (threshold cycle, or $C_t$ value) could be evaluated at various input ranges using a log-linear relationship across the input amounts and to establish the lowest levels of sensitivity where the log-linear relationship was lost. For the Sensitivity Study, one plate of samples, standards, and negative controls, that were quantified with the InnoQuant® Quantification Kit and run on an Applied Biosystems 7500 Real-Time PCR System, were evaluated using the HID Real-Time PCR Analysis Software v. 1.1. Three serial dilutions of the standards (designated as STD1, STD2, and STD3) were made using Teknova DNA dilution buffer (10 mM Tris-0.1 mM EDTA) and run on the trays in duplicate. Different combinations of the DNA standards from the 2 quantification plates were used to determine the average $C_T$ and quantity of each standard when designated as "unknown". An extension of the DNA standard dilution STD3 was made two quantities above the highest standard and two quantities below the lowest standard at 100 ng/µl, 50 ng/µl, 0.0045 ng/µl and 0.0023 ng/µl concentrations. Using the different DNA standard configurations, an average $C_T$ and quantity were calculated for each standard labeled as an unknown. The $C_T$ vs. DNA quantity (ng/µl, on a logarithmic scale) for the unknown standard samples were plotted to demonstrate the linearity of the system. The same analysis was performed on other samples run during this validation, including the 100 ng/µl, 50 ng/µl, 0.0045 ng/µl and 0.0023 ng/µl extensions of the standard samples.

Example 9: Accuracy, Precision, Sensitivity and Linearity of DNA Determinations

Figure 11:
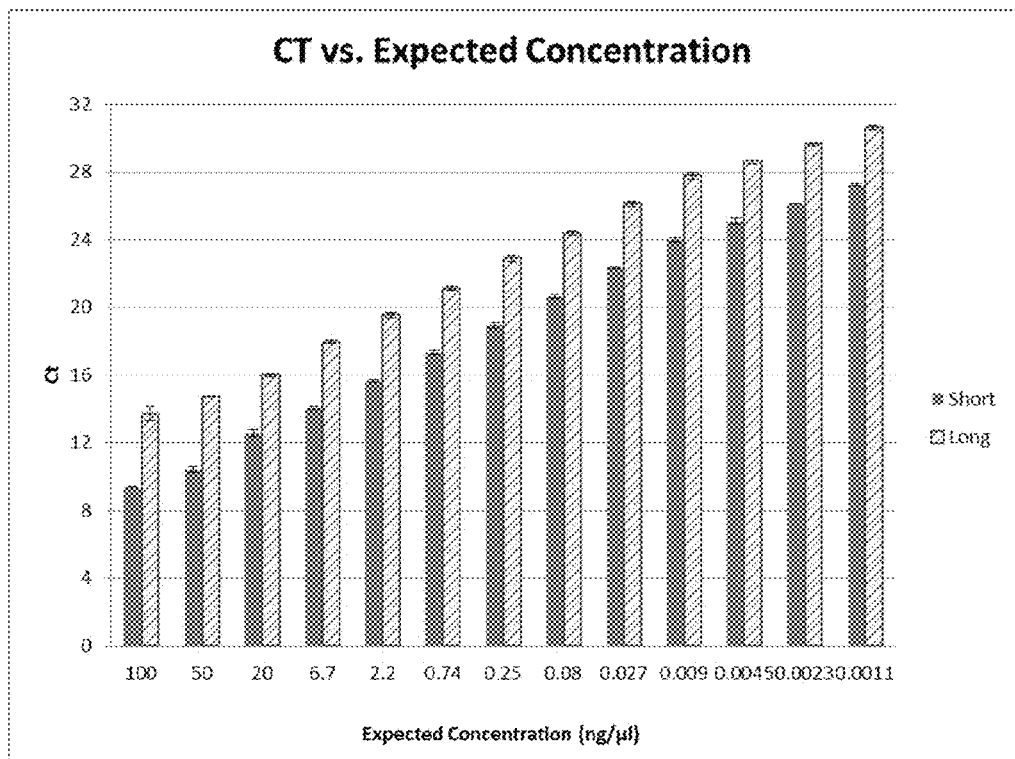
FIG. 11 shows observed threshold cycle values vs. expected concentrations of standards for the gDNA sensitivity standard dilutions.

Table 10 shows, for the short and long targets in the determination of degradation, the average quantity and $C_T$ values determined for the standard dilutions using the different combinations of the standard curves run on the plate. FIG. 11 is the graphical representation of the data in Table 10. Results demonstrate that the InnoQuant® Kit consistently detected all samples at as little as 2.3 pg of total input DNA. As the DNA concentration goes beyond the concentrations of the standard curve (20 ng/ul to 0.009 ng/ul), the variation from the expected quantities increases, and linearity is lost to an extent. However, these variations are minimal and would not have affected the ability to obtain full DNA profiles; the increase in variation can be expected with the lower concentrations (stochastic amplification effects). The average fold change between the quantity and the expected quantity is 1.13 for the short target and 1.07 for the long target, when all the dilutions are included. A 1.13 fold change of the human average quantity value would result in an approximate 13% variation in the quantity of the human quantifications. The two targets are amplified in a single reaction, but the small target quantity demonstrated slightly higher variation at several of the sensitivity dilutions. When examining the samples within the concentrations of the standard curve (20 ng/ul to 0.009 ng/ul), the fold changes decrease to an average of 1.04 for the short target and 1.06 for the long target. These fold changes in quantities would not significantly affect the Relative Fluorescent Units (RFU) seen in the electropherograms and are due to stochastic amplification effects. Higher fold differences were observed outside of the standard curve range and would be expected with the amount of template amplified.

The results for the 0.0045 ng and 0.0023 ng sample demonstrate the sensitivity of this dual target quantification assay to detect DNA samples below 9 pg. The reproducibility of such values is influenced by stochastic amplification effects associated with low template amplifications. The stochastic amplification effects can be seen in human or male amplifications and not necessarily at the same time. Samples at or near the ends of the standard curve are more susceptible to changes in slope of the standard curve. When samples quantify greater than 20 ng, the laboratory may consider diluting and re-quantifying samples to assure appropriate quantification value.

embodiment of the invention, and the Quantifiler® Human kit from Life Technologies. Quantifiler® human DNA concentrations averaged 140% of those calculated using the short target (Yb8) of this dual target assay. If differences were observed, in all instances, Quantifiler® human values were higher than dual target quantification assay values. These differences are attributed to differences in the DNA standards and differences in amplicon length (62 bp in Quantifiler® vs. 80 bp in dual target quantification assay system).

Figure 12:
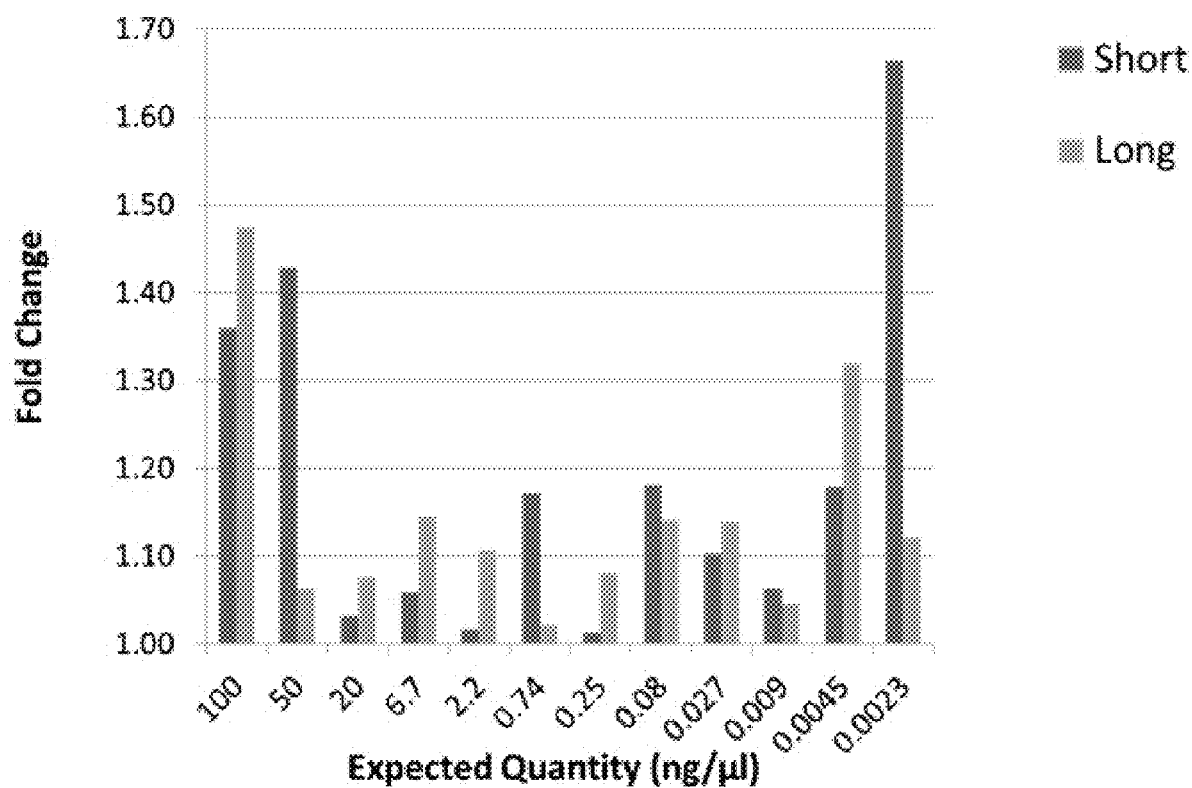
FIG. 12 shows fold changes between each replicate of the standard dilutions, based on at least 34 readings at each DNA concentration.
Figure 13A:
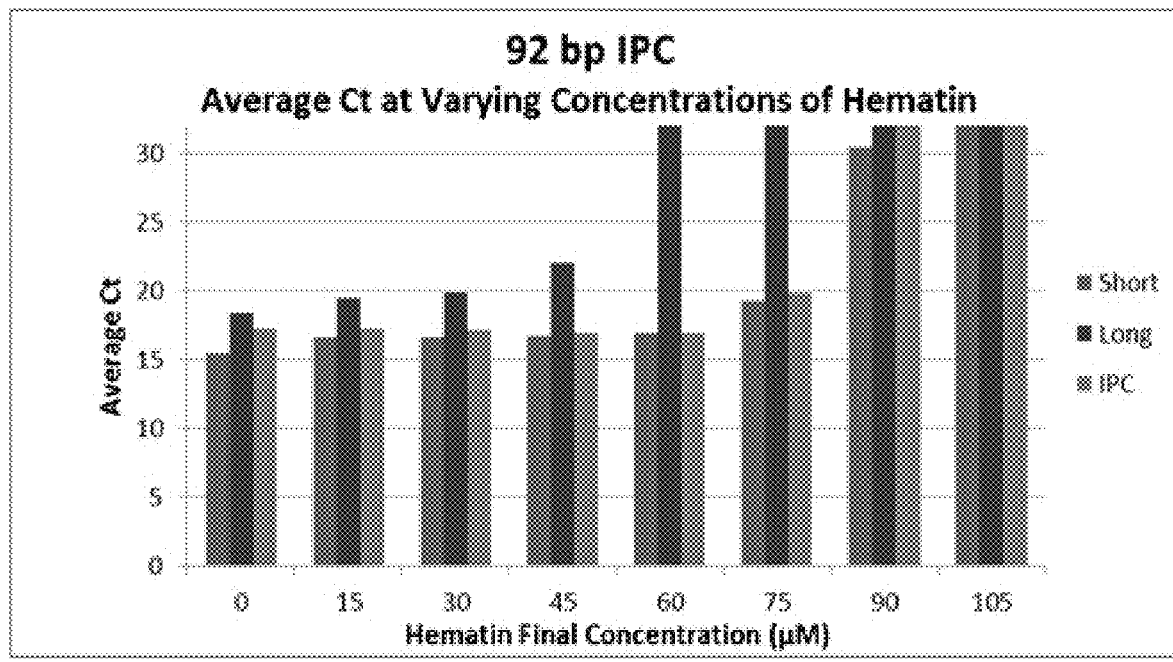
FIGS. 13A and 13B show observed threshold cycle values vs. hematin concentration for hematin inhibited samples using the 92 bp and the 172 bp internal positive controls (IPC's), respectively.
Figure 13B:
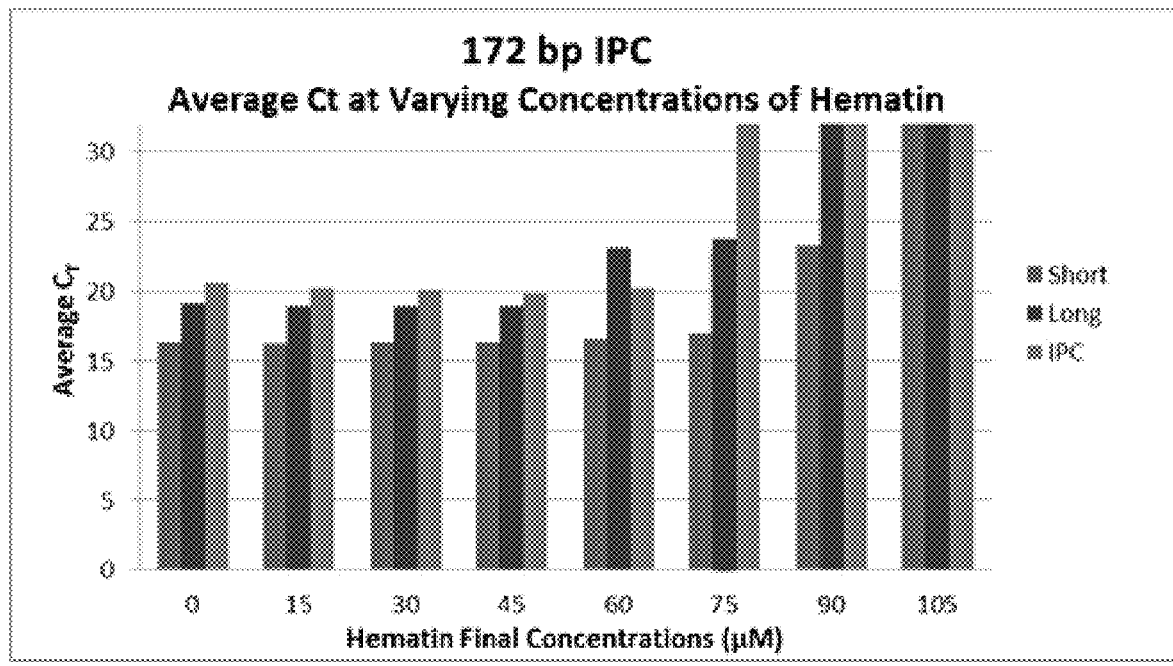
Figure 14A:
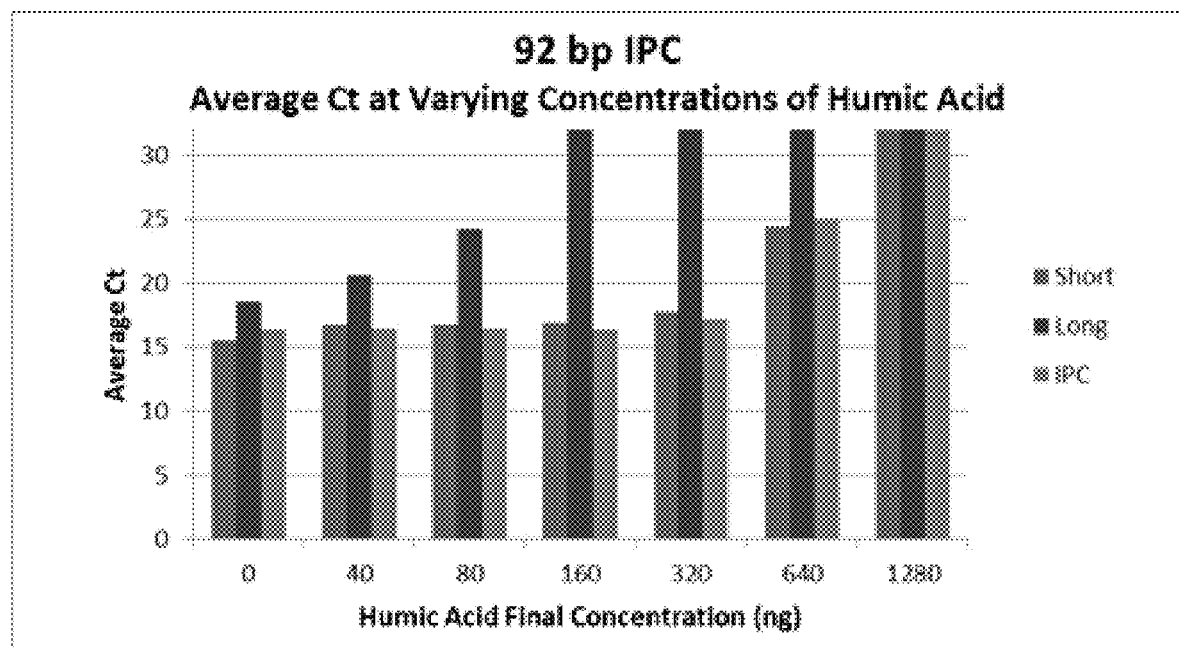
FIGS. 14A and 14B show observed threshold cycle values vs. humic acid concentration for humic acid inhibited samples using the 92 bp and the 172 bp IPC's, respectively.
Figure 14B:
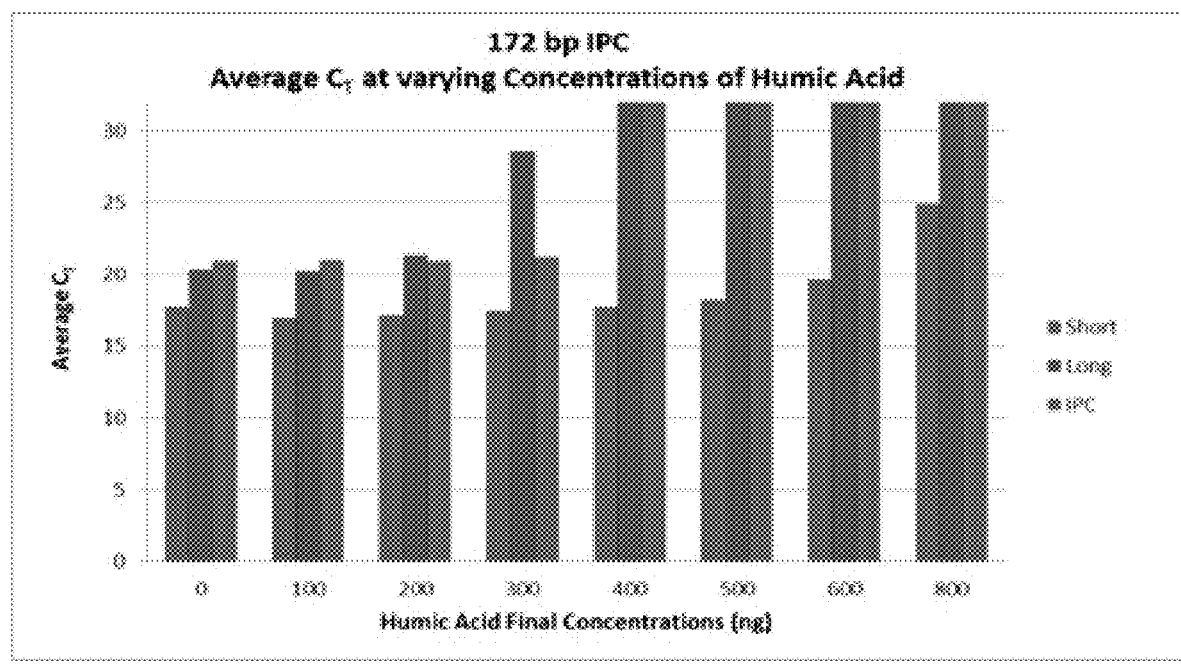
Figure 15:
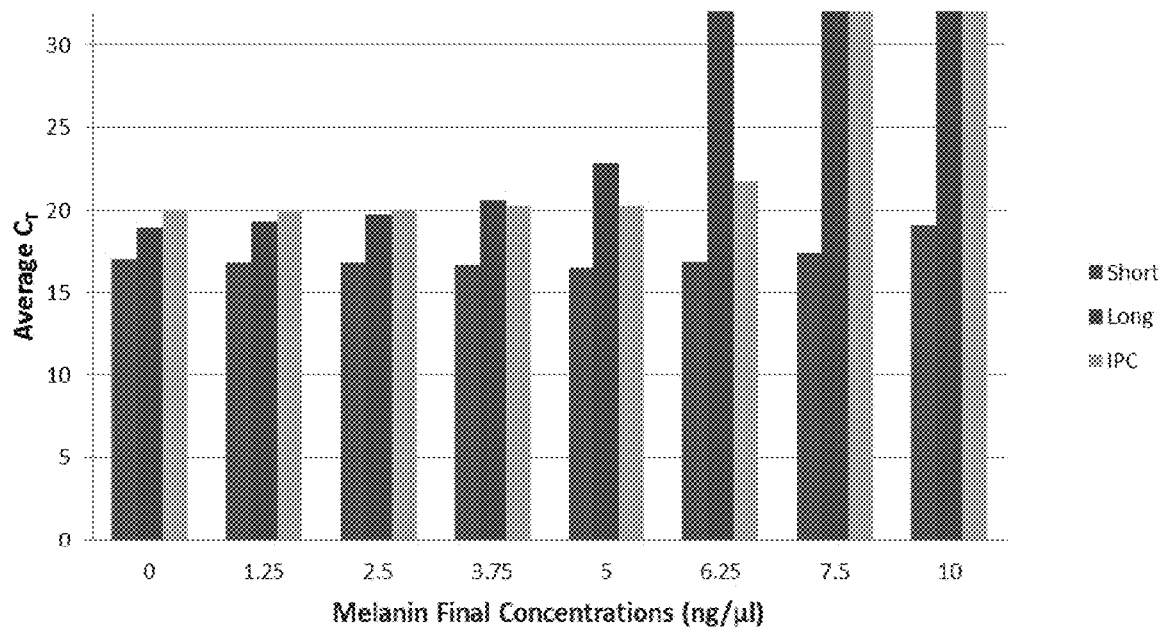
FIG. 15 shows the observed threshold cycle values vs. melanin concentration for melanin inhibited samples using the 172 bp IPC.
Figure 16:
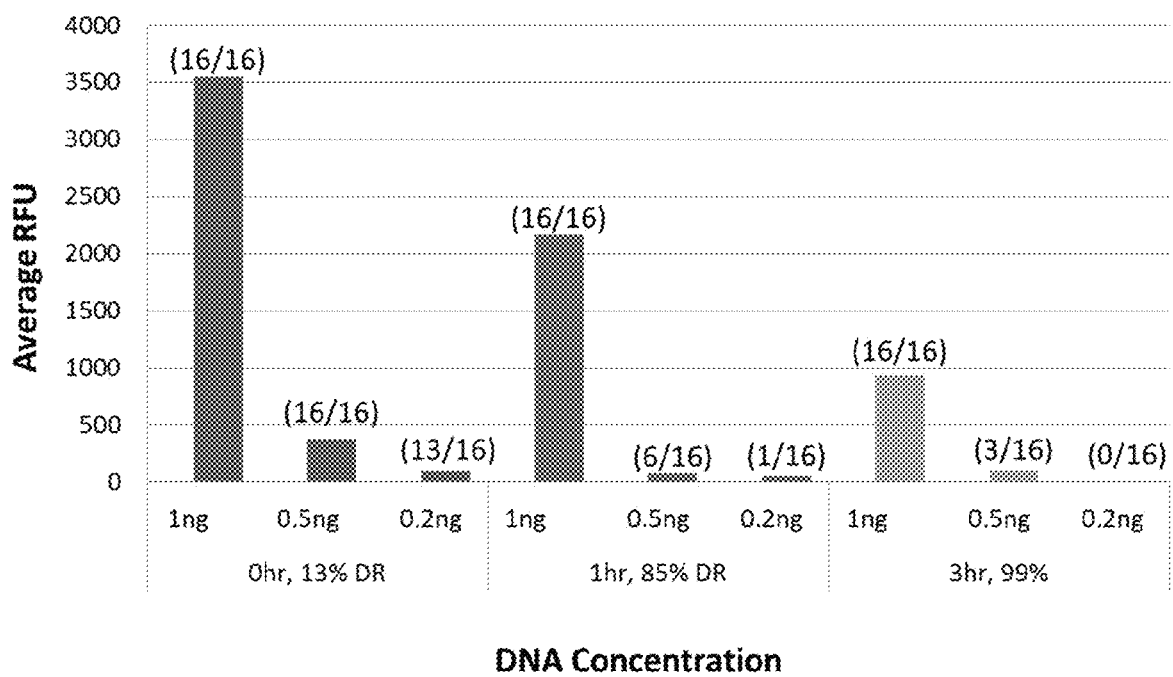
FIG. 16 shows the effects of mechanical degradation by sonication as plots of relative fluorescence units across three different DNA concentrations without degradation and for two degradation times.
Figure 17:
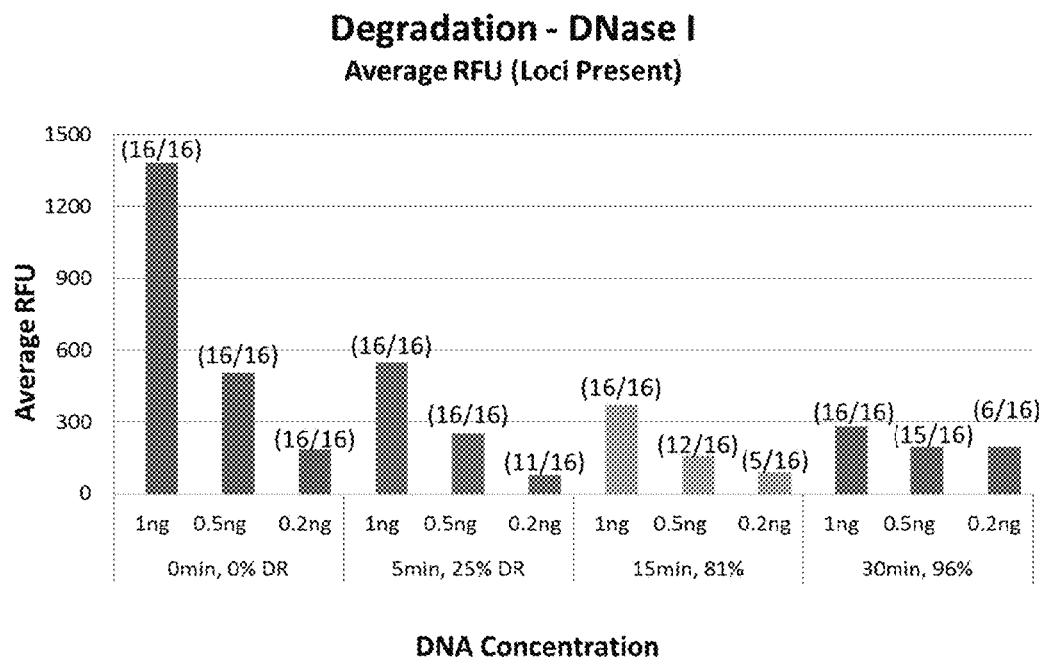
FIG. 17 shows the effects of chemical degradation by the action of DNase I as plots of relative fluorescence units across three different DNA concentrations without degradation and for three degradation times.
Figure 18:
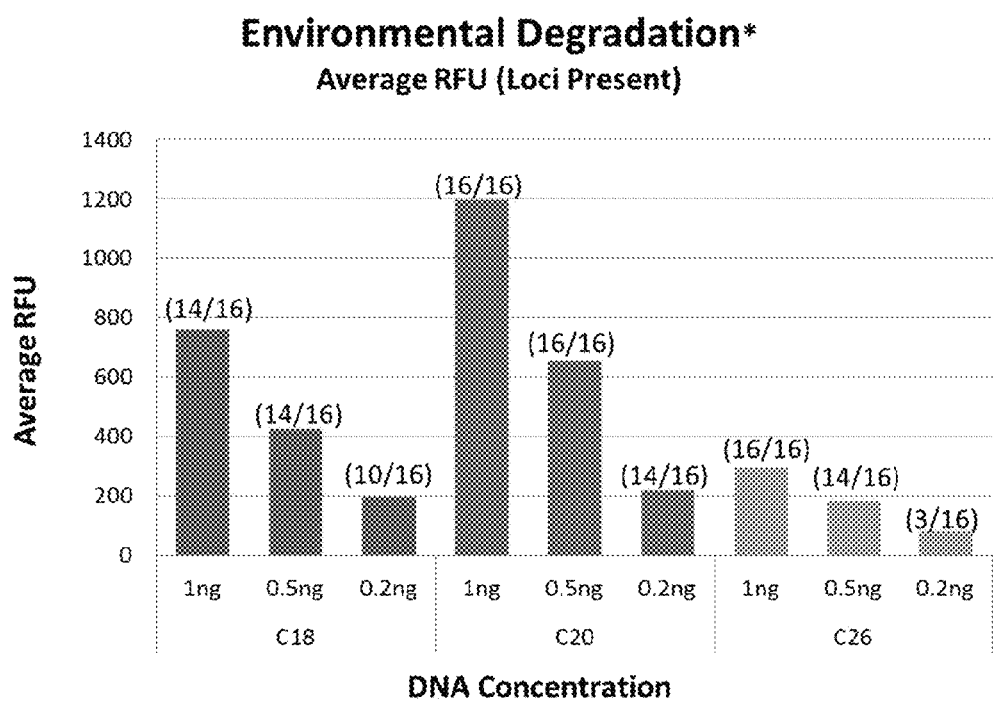
FIG. 18 shows the effects of environmental degradation by the action of ambient heat and humidity for a period of five years as plots of relative fluorescence units across three different DNA concentrations for three degradation times.

To test the reproducibility of the system across various DNA concentrations, the sensitivity data was examined for fold changes in concentration between the replicates. FIG. 12 shows the results of the fold changes between each replicate of the standard dilutions (at least 34 readings from each concentration). Results indicate that between the concentrations of the standards (20 ng to 9 pg), fold changes are all less than 1.20, which is equivalent to a 20% variation. As the concentrations go above or below the optimal range, fold changes increase, as expected.

Example 11: Effects of Inhibition

Varying concentrations of humic acid and hematin were used to inhibit samples using the 92 base pair IPC sequence and the 172 bp IPC sequence. Varying concentrations of melanin were used to inhibit samples using the 172 bp IPC sequence. This inhibitor was selected due to the prevalence of hair samples in forensic casework, where a determination of an extent of DNA degradation is important. The samples were quantified with the InnoQuant® Quantification Kit, and the $C_t$ values of the Yb8, SVA, and IPC targets were evaluated. FIGS. 13A, 13B, 14A, 14B and 15 show the results for the inhibitors tested.

A comparison of the $C_t$ values between the two sized IPC targets for the same inhibitor concentrations shows the 172 bp target is inhibited more readily, as expected due to its larger size. Results show a gradual increase in $C_t$ as the concentration of the inhibitor increases with both the 92 and the 172 bp targets. With the 92 bp IPC, it is observed that the Yb8 and IPC targets have similar reactions to inhibitors, and

TABLE 10

Average quantity and Ct values for the standard dilutions and the gDNA dilutions

| Sample Name (Expected Concentration) ng/ul | Observed Yb8 | | | Observed SVA | | |
| --- | --- | --- | --- | --- | --- | --- |
| | Ave. CT | Ave. Qty | Fold Change | Ave. CT | Ave. Qty | Fold Change |
| 100 | 9.41 | 153.8067 | 1.54 | 13.73 | 104.7562 | 1.05 |
| 50 | 10.43 | 78.2061 | 1.56 | 14.78 | 50.5777 | 1.01 |
| 20 | 12.57 | 18.7944 | 1.06 | 16.00 | 22.4396 | 1.12 |
| 6.7 | 14.08 | 6.7444 | 1.01 | 17.96 | 6.1197 | 1.09 |
| 2.2 | 15.66 | 2.3506 | 1.07 | 19.54 | 2.1496 | 1.02 |
| 0.74 | 17.33 | 0.7682 | 1.04 | 21.13 | 0.7456 | 1.01 |
| 0.25 | 18.93 | 0.2625 | 1.05 | 22.90 | 0.2318 | 1.08 |
| 0.08 | 20.64 | 0.0836 | 1.05 | 24.38 | 0.0866 | 1.08 |
| 0.027 | 22.34 | 0.0268 | 1.01 | 26.09 | 0.0278 | 1.03 |
| 0.009 | 24.00 | 0.0088 | 1.02 | 27.78 | 0.0091 | 1.02 |
| 0.0045 | 25.09 | 0.0043 | 1.06 | 28.61 | 0.0052 | 1.16 |
| 0.0023 | 29.66 | 0.0021 | 1.09 | 29.66 | 0.0026 | 1.13 |
| | Average Yb8 Fold Change | | 1.13 | Average SVA Fold Change | | 1.07 |

Example 10: Concordance and Reproducibility

Nineteen samples were quantified using the dual target assay for determining an extent of degradation, a preferred are affected at approximately the same level of inhibitor. SVA has a higher sensitivity to inhibitors and is the first target to be affected. In contrast, the 172 bp IPC target sequence is the first target of the three to be affected by inhibition. The 172 bp IPC target tracks with the SVA target, as both are affected similarly as the concentration of the inhibitor increases, whereas Yb8 is the last target to be affected as the concentration of the inhibitor increases. Due to the improved correlation of the 172 bp IPC with the short and long targets, this was selected to be incorporated into the multiplex comprising the short and long targets for determination of DNA degradation.

As with the other inhibitors tested, results of the melanin inhibitor show a gradual increase in the Ct of all three targets as the concentration of the inhibitor increases. In the case of melanin, the SVA long target is the first of the three targets to be affected, possibly due to a different mechanism of inhibition.

Figure 21:
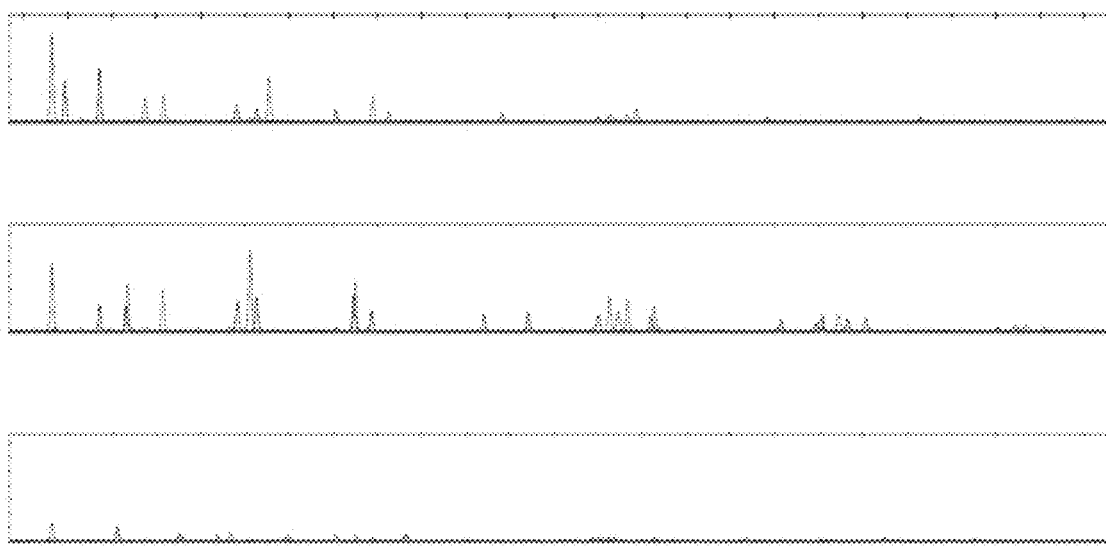
FIG. 21 shows STR results for 200 pg targeted environmentally degraded samples.

Example 12: Effects of Degradation on the Determination of Degradation Ratios or DNA Integrity Degradation studies were performed to assess the utility of this dual target quantification assay, the preferred embodiment of the present invention, with degraded samples. The experiments were designed to assess three types of degradation: mechanical (via sonication), chemical (via DNase I) and environmental degradation (samples placed in the outside elements [heat, humidity] for a period of 5 years). Degradation ratios based on the observed quantities of the long and short targets were expressed as a percentage=(1-[Long Qty/Short Qty])*100. Results are shown in FIGS. 19 through 21.

Downstream STR analysis of the degraded samples was performed using the Identifiler® Plus STR kit (Applied Biosystems/Life Technologies), targeting 3 different DNA concentrations: 1 ng (manufacturer recommended target amount), 500 pg, and 200 pg. In all instances, the STR results mirrored the degradation ratios calculated by this dual target quantification assay, the preferred embodiment of the present invention. As the degradation increased, the typical "ski slope" effect was observed in the STR results, until eventually, no results (or very partial, inconclusive results) were observed at the highest extent of the degradation. The extent of the degradation was observed to a much higher level at the low concentrations of DNA (500 pg and 200 pg). As expected, lower RFUs and in some instances, no results, were observed when the DNA was both degraded and low in amount. FIGS. 19 through 21 show the STR results of the degradation study.

Example 13: Species Specificity

A quantification system used for forensic DNA samples must not react to non-primate DNA, as the STR systems commonly used in crime laboratories are only reactive to human and primate DNA. Three primates, seven non-primate mammals, and five prokaryotic species were analyzed using the InnoQuant® Quantification Kit, the analyses including Yb8, SVA and the 172 bp IPC target. DNA purified from two species of dogs, two cats, deer, rat, mouse, mosquito, chicken, green monkey, chimpanzee, orangutan, *Escherichia coli, Ralstonia eutropha, Rhodococcus* rubber, yeast, and *Staphylococcus aureus* were run in duplicate. The DNA samples were at 5 ng/μl. A sample was considered "reactive" if >1 pg/μl of DNA was detected with the process of the present invention using a human DNA standard curve.

Figure 22:
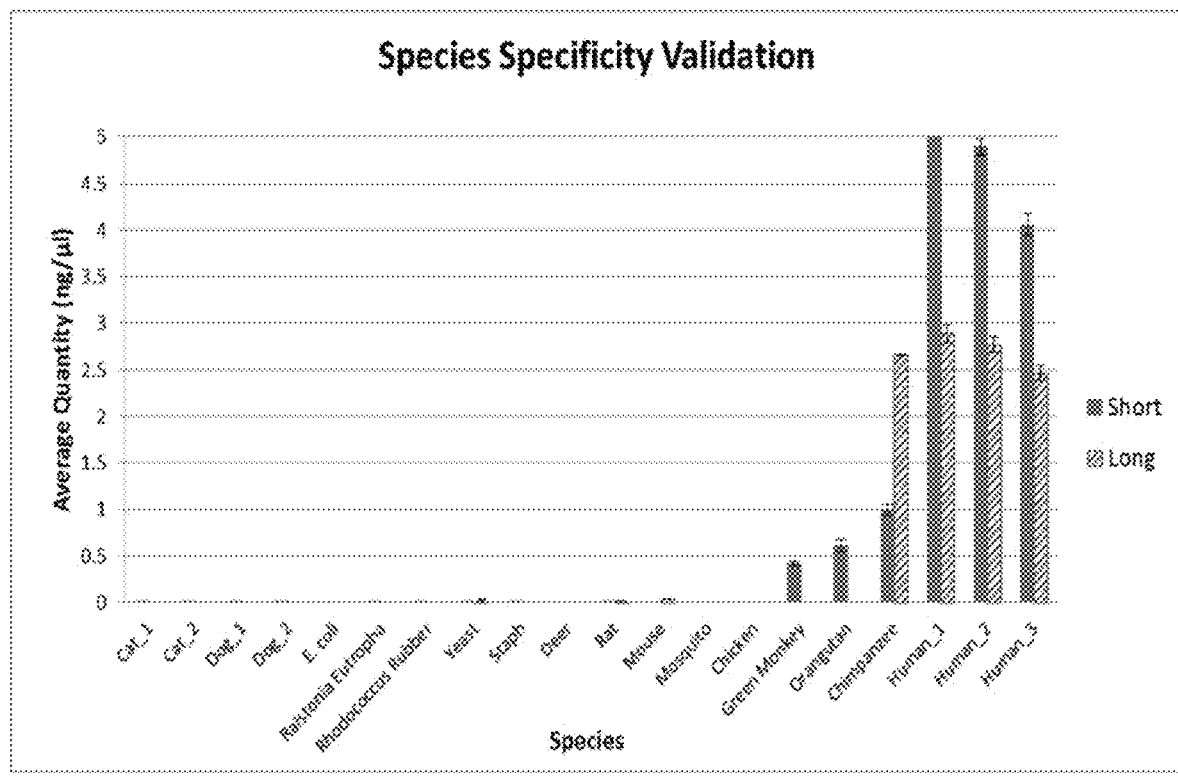
FIG. 22 shows species study results (striped red bars show long target SVA; solid blue bars show short target Yb8).

Of the species tested, only higher primate samples were reactive (FIG. 22). Cross reactivity of non-human primate species with the commonly used STR systems has been previously demonstrated. These results demonstrate that the process of the present invention is adequately species-specific for forensic use and does not yield quantitative results with non-primate samples.

Example 14: Four Target System (Yb8, SVA, Y Deletion, and IPC)

The addition of a male specific target to the real-time PCR quantitation multiplex is useful to detect the amount of male DNA in samples that contain large quantities of female DNA and low quantities of male DNA. A region of the human Y chromosome DNA containing a 90 base pair sequence which is deleted on the human X-chromosome in an X-Y chromosome homologous region was selected by using a primer pair specific to the human Y chromosome DNA in order to obtain amplified products (Walker, et al., Anal. Biochem. 337(1): 89-97 (2005)).

Example 15: Multiplex Reaction

When used in a multiplex, the mouse fragment can be labeled in Cy5, the human Alu target can be labeled in HEX or FAM, the second human target SVA can be labeled in Cy5, HEX, or FAM, and the internal positive control (IPC) to assess the presence or absence of inhibitors, can be labeled in Cy5, HEX, or FAM. The multiplex reactions tested included variations of these fluors, including mouse labeled in Cy5, Alu in FAM, and IPC in HEX.

Figure 23A:
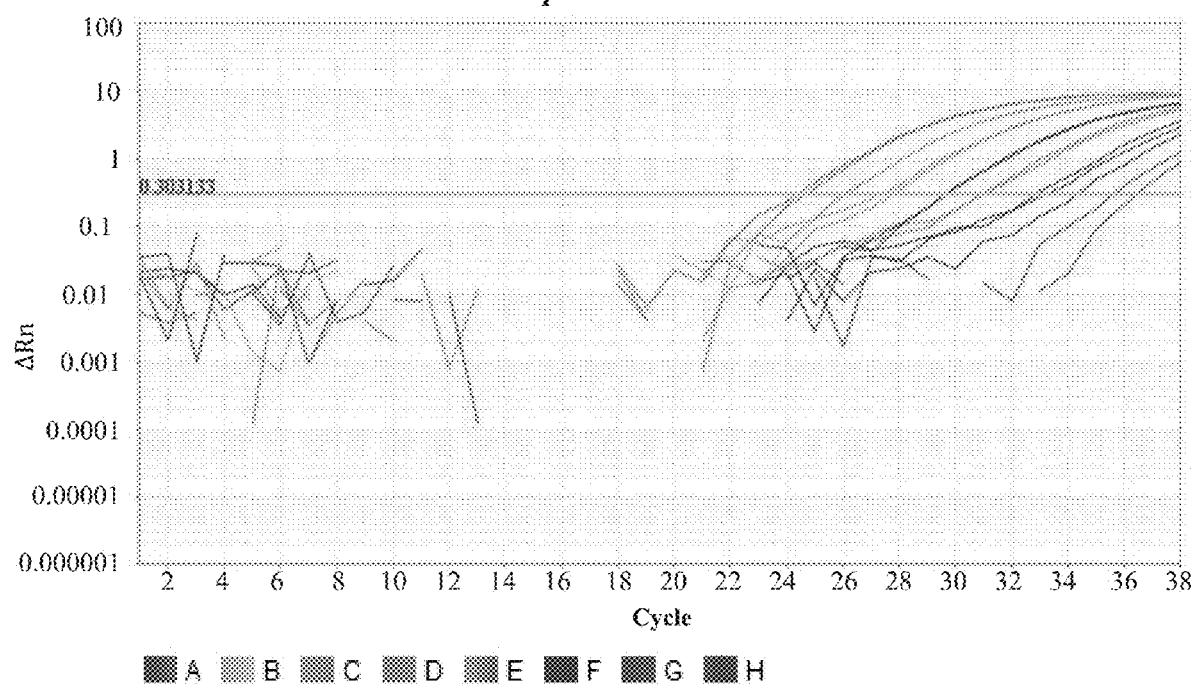
FIG. 23A shows the amplification plot of the Y chromosome target in a four-target multiplex reaction.
Figure 23B:
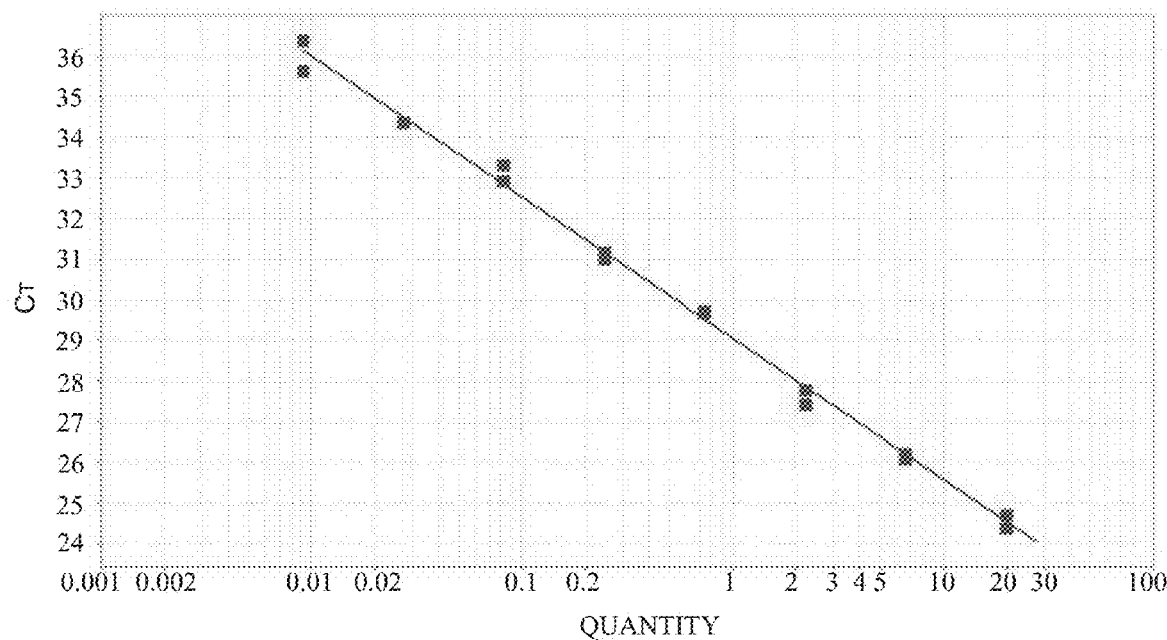
FIG. 23B shows the standard curve of the Y chromosome target in a four-target multiplex reaction. Target: Y; slope: −3.48; y-intercept: 29.047; $R^2$: 0.996; efficiency: 93.805%.

When added to the multiplex including the human Alu target, the human SVA (290 bp) target and the internal positive control (IPC), the male specific fragment is labeled in FAM, the "short" Yb8 fragment in JOE, the "long" SVA fragment in Cy5 and the 158 bp internal positive control (IPC) to assess the presence or absence of inhibitors in the sample in Cy3. The cycle number of the multiplex was increased from 32 to 35 and 38. Thirty-eight cycles produced adequate results, with efficiencies of the three targets, SVA, Yb8, and Y, at 88%, 99%, and 94%, respectively. See FIGS. 23A and 23B for the amplification plot and standard curve, respectively, of the Y chromosome target in a four-target multiplex reaction.

Example 16: Detection of Circulating Tumor DNA (ctDNA) in PDX Mouse Plasma

Mouse and Human Standard DNA Amplifications

The multiplex assays were optimized for use on the Applied Biosystems 7500 Real Time PCR instrument with Agilent Technologies' Brilliant Multiplex QPCR Master Mix and amplified in a 20 μL reaction volume that includes 5.7 μL of primer mix, 0.3 μL of the ROX reference standard diluted to 2 μM, 10 μL of Agilent Brilliant Multiplex QPCR Master Mix, and 4 μL of standard or unknown extracted DNA. The primer mixes contained primers and probes of Human, Mouse, and IPC target, and PCR enhancer additives.

The assays were run on an Applied Biosystems 7500 Real Time PCR instrument and data collection utilizing the HID Real-Time PCR Analysis Software v 1.2 (Applied Biosystems). The PCR conditions were one enzyme activation cycle for 10 min at 95° C., followed by 45 cycles of 2-step qPCR (15 seconds at 95° C. and 2 min at 61° C. combined annealing/extension time) at maximum ramp speed. To correct for well-to-well variations in background fluorescence on the 7500, the ROX-labeled passive reference dye was used (from the Agilent Technologies Brilliant QPCR Master Mix and per manufacturer instructions).

Figure 24A:
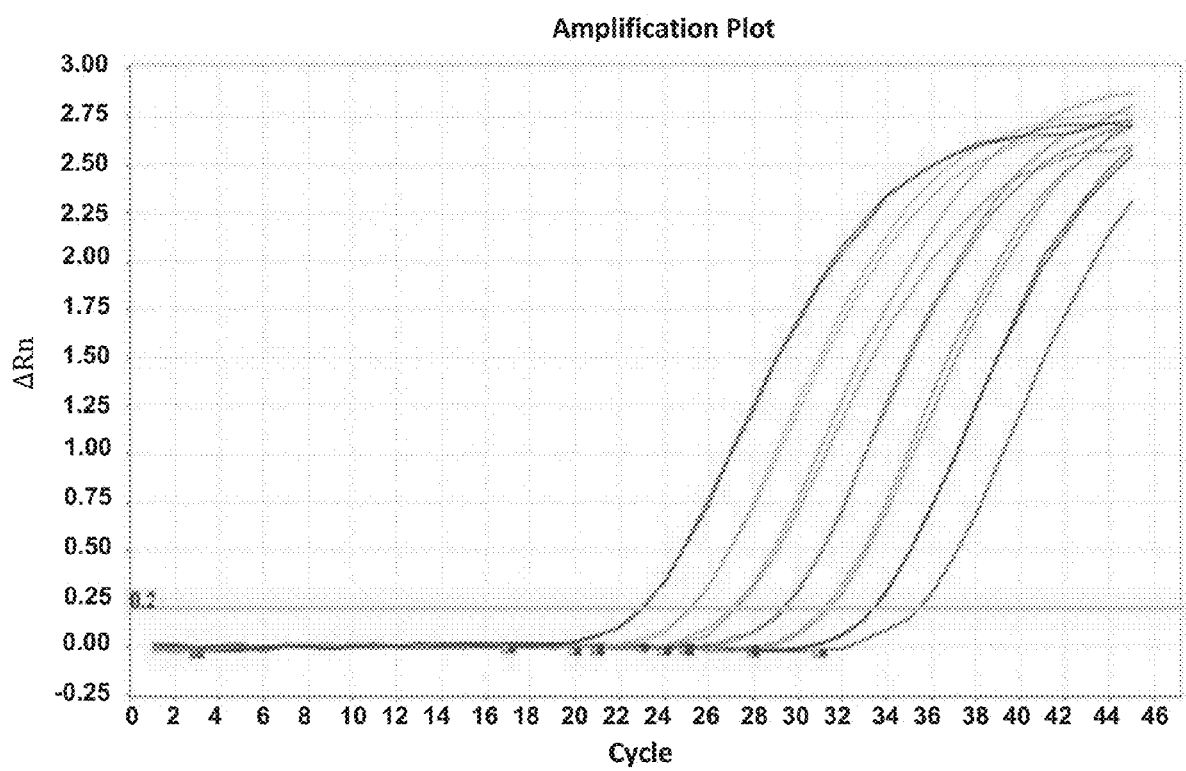
FIG. 24A shows amplification plots for the DNA standard for the mouse target sequence.
Figure 24B:
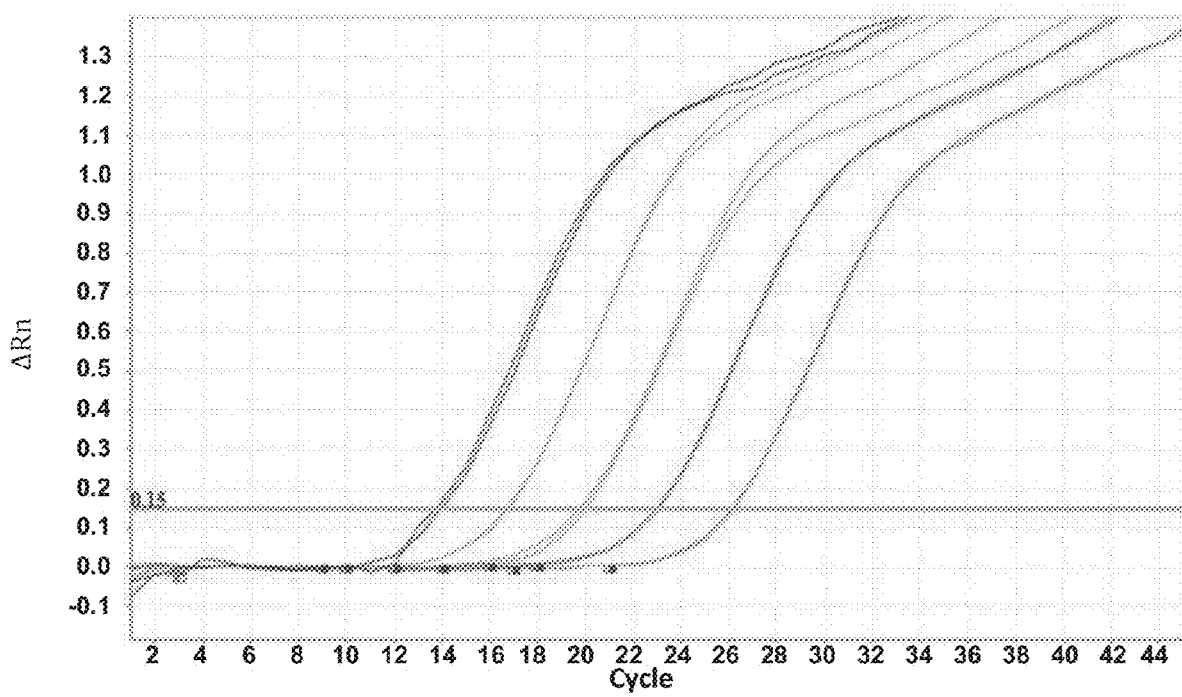
FIG. 24B shows amplification plots for the DNA standard for the human target sequence.
Figure 24C:
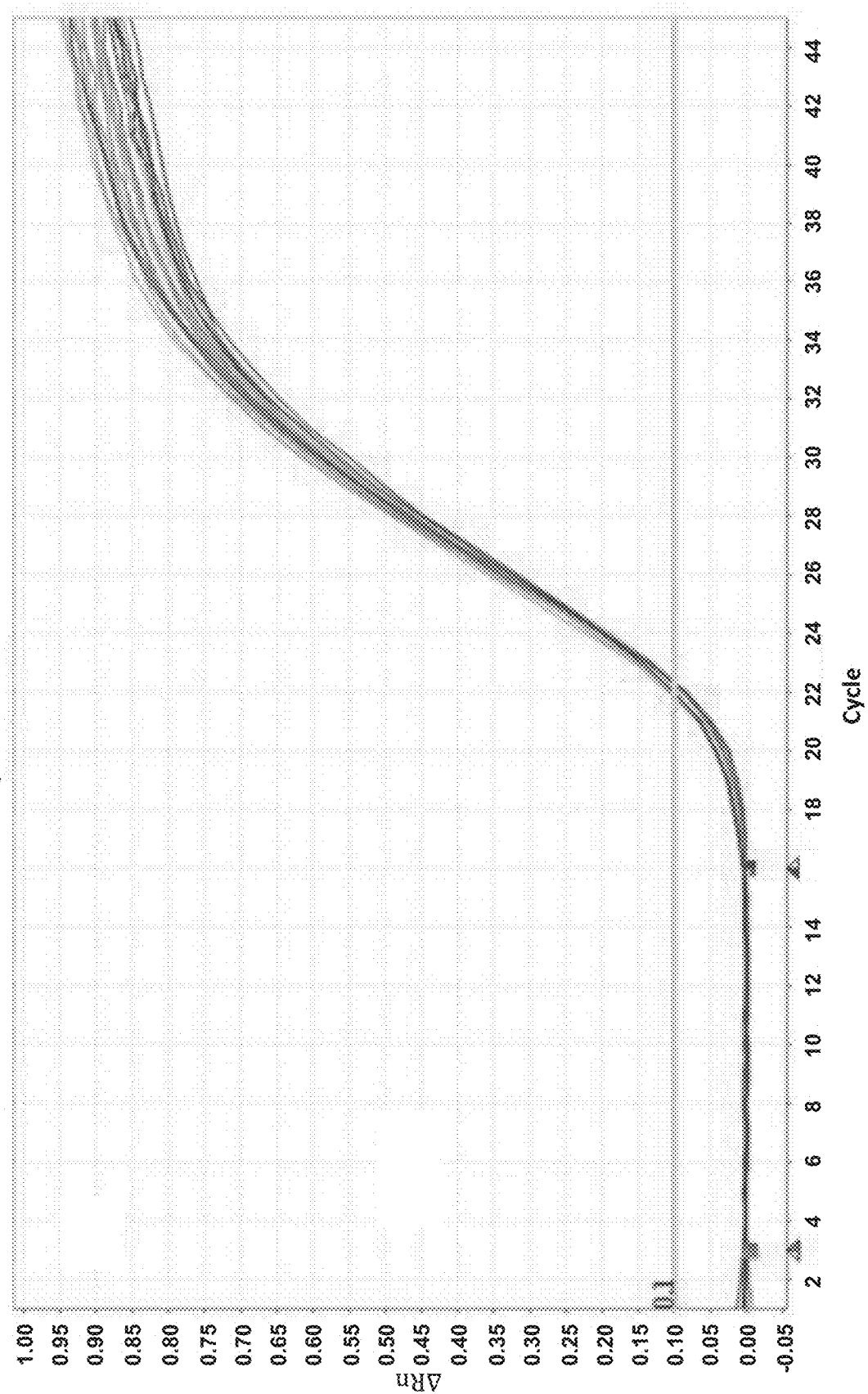
FIG. 24C shows amplification plots for the internal positive control (IPC) target.
Figure 24D:
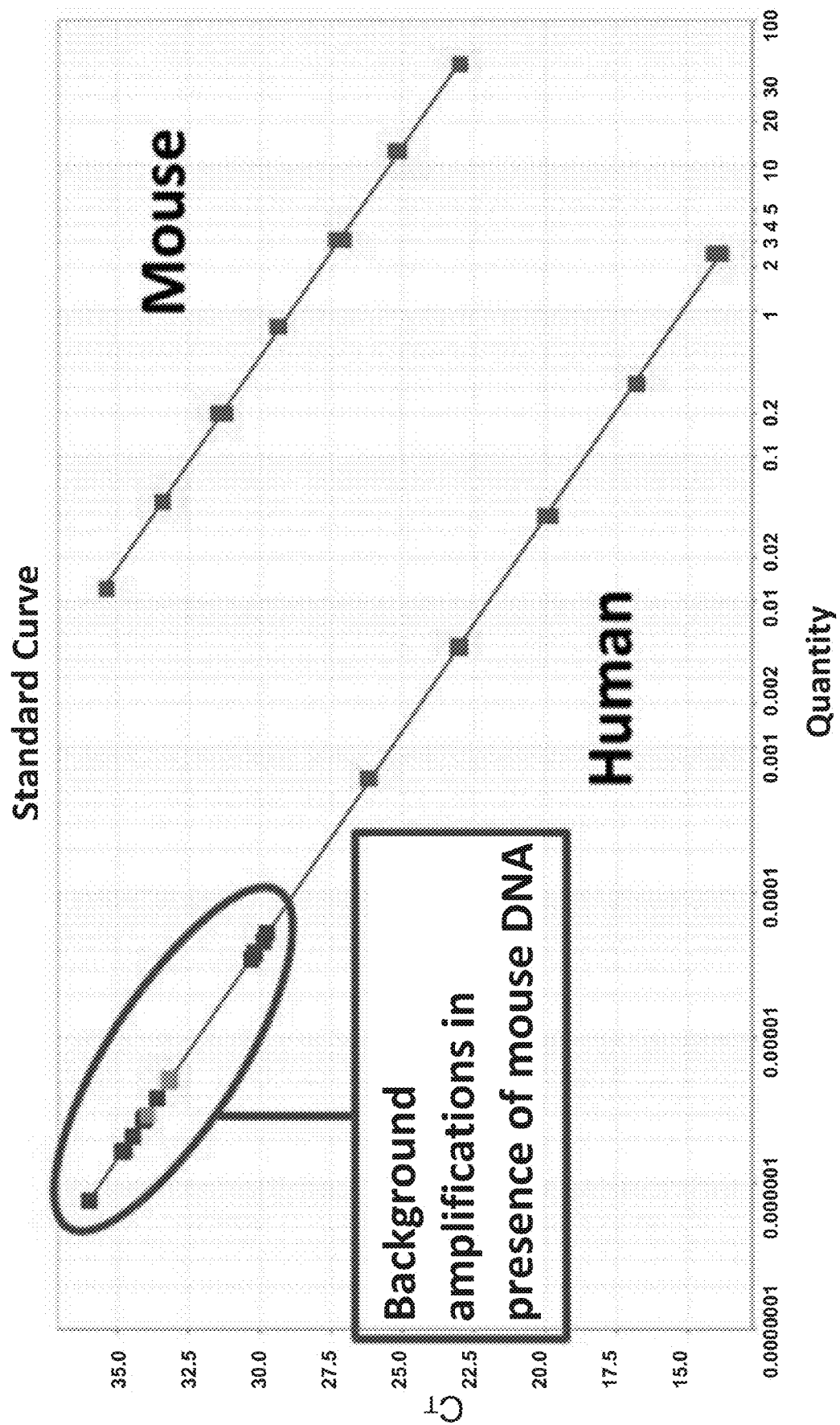
FIG. 24D shows standard curve plots for amplification of dilutions. Target: Mouse; slope: −3.437; y-intercept: 28.906.

Data analysis was performed utilizing the automatic baseline feature of the HID software. A freshly prepared 8-fold serial dilution of high molecular weight standard human DNA (2.5 ng/µL, 0.3125 ng/µL, 0.039 ng/µL, 0.005 ng/µL, and 0.0006 ng/µL) and 4-fold serial dilution of mouse standard DNA (50 ng/µL, 12.5 ng/µL, 3.125 ng/µL, 0.781 ng/µL, 0.195 ng/µL, 0.049 ng/µL, and 0.012 ng/µL) were run in duplicate to generate the standard curve. The standard curves were plotted, Ct vs. Delta Rn (the fluorescence emission intensity of the reporter dye divided by the fluorescence emission intensity of the passive reference dye). Resultant DNA quantitation values were interpolated from the resulting linear standard curves, using the HID software. At least one negative Non-Template Control (NTC) was run on each plate. Quality metrics of the Short and Long were assessed, including PCR efficiencies (i.e. slope) and $R^2$ values and verification of no true amplification in negative controls. Human and mouse standard curves have above 95% efficiencies. FIG. 24A shows a representative example of the amplification plots for mouse standard DNA targeting the mouse genetic target B1m. FIG. 24B shows a representative example of the amplification plots for human standard DNA targeting Alu-Yb8. FIG. 24C shows a representative example of the amplification plots for the internal positive control (IPC). FIG. 24D shows typical standard curves of the three-target multiplex assay across the range of DNA concentrations of the standards. The mouse B1m primers do not have cross reactivity with human DNA when less than or equal to 20 ng/µL is present. The human Alu-Yb8 primers have a little cross reactivity with mouse DNA. FIG. 24D shows the background amplification of Alu-Yb8 primers for human in the presence of mouse DNA. Although some signals from the mouse DNA contribute to human Alu-Yb8 amplifications, the contribution is negligible since the highest background signal from the 50 ng/µL mouse DNA is separated by >3 Ct from the lowest human standard point of 0.0006 ng/µL. Hence, the human DNA quantification is reliable when sample quantification values fall within the human standard range.

Detection of Circulating Tumor DNA (ctDNA) and Circulating Tumor Cell DNA (CTC-DNA) in PDX Mouse Plasma Three PDX models were tested in this experiment. A description of tumor growth in each PDX mouse is as follows:

PDX-Model#1—This is a human epidermal growth factor receptor 2 negative (HER2−), estrogen receptor positive (ER+), progesterone receptor positive (PR+) PDX model that has a D538G mutation in the estrogen receptor (ER) gene that makes the receptor constitutively active. This tumor was very aggressive in growth—it only took 14 days post-implantation for the tumor to reach over 4000 mm³ in volume. This PDX model, however, had the fewest number of liver lesions, but a higher number and area of lung lesions.

PDX-Model#2—This is a triple negative breast cancer (TNBC) PDX model derived from a patient. This tumor took 56 days to grow to a maximal volume of 1084 mm³. It was highly metastatic to the liver, and lowly metastatic in the lungs.

PDX-Model#3—This is also a TNBC PDX model derived from a patient. This mouse took 35 days to reach a peak volume of 3942 mm³. Two tumors were measured, both tumors being approximately the same size. It was highly metastatic to the liver (by far the most lesions) and less metastatic to the lungs.

Circulating Tumor DNA (ctDNA) in PDX Mouse Plasma

Mouse bloods were collected into EDTA tubes, and plasmas were separated by 2-step centrifugation. First, the whole blood was centrifuged at 2,500×g for 10 minutes, and plasma was recovered into a 0.2 mL tube. Then the recovered plasma was centrifuged for a second time at 16,000×g for 10 minutes at room temperature (15-25° C.). The plasma was then transferred into a new 1.5 mL low adhesion microcentrifuge tube leaving 5-10 µL of plasma at the bottom of the 0.2 mL tube to avoid any transfer of residual cells. DNA was extracted from the prepared plasma with Quick-cfDNA Serum & Plasma Kit (Zymo-Research). Duplicate extractions were performed for each sample. Table 11 lists the plasma volume used for DNA extraction and the final extraction elution volume. The extracted DNA samples were quantified for mouse cell-free DNA (cfDNA) and human ctDNA, and the resultant quantities, the plasma extraction volume, and the elution volume were used to calculate ctDNA and cfDNA in mouse plasma (Equation 1). Equation 1—conversion of absolute ctDNA/cfDNA concentration in plasma from quantification of extracted DNA:

Absolute ctDNA/cfDNA concentration in plasma($pg/mL$)=qPCR measured concentration($ng/\mu L$)× extraction elution volume($\mu L$)÷extraction volume of plasma($\mu L$)×1000.

Table 11 summarizes those results including the fraction of ctDNA among mouse cfDNA shown as human/mouse ratio (%). All of the extracted DNA samples exhibited human ctDNA quantity within the standard curve range, which confirmed the presence of ctDNA in plasma. These three metastatic PDX mice had ctDNA ranging from 1.3% to 17.6%. Two independent extractions of each sample did not show much variation.

TABLE 11

| | DNA extraction, qPCR quantification, and ctDNA in mouse plasma | | | | | | |
|---|---|---|---|---|---|---|---|
| PDX mouse | Plasma Extraction: Vol (uL) | Elution Final DNA Vol (uL) | Human ctDNA Quantity (ng/ul) | Mouse cfDNA Quantity (ng/ul) | ctDNA in plasma (pg/ul) | Mouse cfDNA in plasma (pg/ul) | Human/mouse ratio (%) |
| PDX-Model#1 | 59 | 8 | 0.0026 | 0.2025 | 0.350 | 27.460 | 1.3% |
|  | 50 | 8 | 0.0029 | 0.1798 | 0.467 | 28.761 | 1.6% |
| PDX-Model#2 | 15 | 11 | 0.0095 | 0.0539 | 6.950 | 39.555 | 17.6% |
|  | 20 | 9 | 0.0160 | 0.0994 | 7.221 | 44.722 | 16.1% |

TABLE 11-continued

DNA extraction, qPCR quantification, and ctDNA in mouse plasma

| PDX mouse | Plasma Extraction: Vol (uL) | Elution Final DNA Vol (uL) | Human ctDNA Quantity (ng/ul) | Mouse cfDNA Quantity (ng/ul) | ctDNA in plasma (pg/ul) | Mouse cfDNA in plasma (pg/ul) | Human/ mouse ratio (%) |
|---|---|---|---|---|---|---|---|
| PDX-Model#3 | 23 | 8 | 0.0302 | 0.2804 | 10.504 | 97.513 | 10.8% |
|  | 23 | 8 | 0.0293 | 0.2827 | 10.189 | 98.339 | 10.4% |

Example 17: Circulating Tumor Cell DNA (CTC-DNA) in PDX Mouse Plasma

Whole blood cell pellets were prepared from mouse blood collected in EDTA tube. 100 μL of whole blood was centrifuged at 2,500×g for 10 minutes at room temperature (15-25° C.). Then the supernatant (plasma) was removed without disturbing the pellets. The remaining cell pellets were washed with 150 μL of 1×PBS buffer for three times in order to remove the left over plasma and potentially contaminating ctDNA. The washing steps are as follows:

Add 150 μL of 1× phosphate-buffered saline (PBS) buffer (10 mM phosphate buffer concentration, 137 mM sodium chloride, 2.7 mM potassium chloride, 1.76 mM potassium phosphate, pH=7.4 @ 25° C.) into the 1.5 mL tube and pipette up and down several times.

Centrifuge at 3,300×g for 10 minutes in a microfuge at room temperature (15-25° C.).

Remove the top layer liquid without disturbing the cell pellet. The supernatant is discarded.

Repeat the above steps two more times to wash.

For DNA extraction, 1×PBS buffer was added to make the volume to 200 μL. The initial blood volume (before any centrifugation steps) and the final extraction elution volume were recorded. Duplicate extractions were performed for each sample. Table 11 lists the blood volume used for DNA extraction and the final extraction elution volume. The extracted DNA samples were quantified for mouse white blood cell (WBC) DNA and human circulating tumor cell (CTC) DNA. The resultant quantities, the blood extraction volume, and the elution volume were used to calculate CTC-DNA and mouse WBC-DNA in PDX mouse blood (Equation 2).

Equation 2—conversion of absolute CTC-DNA/WBC-DNA concentration in blood from quantification of extracted DNA:

Absolute *CTC-DNA/WBC-DNA* concentration in blood($pg/\mu L$ for *CTC-DNA*, $ng/\mu L$ for *WBC-DNA*)=qPCR measured concentration($ng/\mu L$)× extraction elution volume ($\mu L$)÷extraction volume of blood($\mu L$)×1000(only for *CTC-DNA* calculation).

The number of CTC and WBC was estimated (Equation 3) with the following assumptions. First, a human cell contains 6 pg of genomic DNA. Second, a mouse cell contains 5.5 pg of genomic DNA.

Equation 3—conversion of number of CTC/WBC in 100 μL of blood:

Number of *CTC/WBC*=qPCR measured concentration($ng/\mu L$)×extraction elution volume($\mu L$)÷genomic *DNA* weight per cell(0.006 $ng$ for *CTC* and 0.0055$ng$ for *WBC*).

Table 12 summarizes the CTC results. All of the tested PDX models exhibited the presence of CTC-DNA. The number of CTC in 100 μl, of blood was low for PDX-Model#1 compared to the other two PDX model mice, although PDX-Model#1 is also metastatic. This difference may be originated from the difference in metastatic lesion sites. PDX-Model#1 had the fewest number of liver lesions, but a higher number and area of lung lesions, and the others were highly metastatic to the liver and less metastatic to the lungs. We observed the higher variation between extractions in PDX-Model#3 blood. This may be because the aliquoted blood was not homogeneous.

TABLE 12

DNA extraction, qPCR quantification, and CTC-DNA in mouse plasma

| PDX mouse | Whole Blood Vol (uL) | Final Elute Vol (uL) | Human CTD-DNA Quantity (ng/ul) | Mouse WBC-DNA Quantity (ng/ul) | Human CTC-DNA in blood (pg/ul) | Mouse WBC-DNA in blood (ng/ul) | # of CTC in 100 uL of mouse blood | # of mouse WBC in 100 uL of blood |
|---|---|---|---|---|---|---|---|---|
| PDX-Model#1 | 100 | 91 | 0.0003 | 11.427 | 0.264 | 12.6 | 4.4 | 228317 |
|  | 100 | 94 | 0.0002 | 14.660 | 0.159 | 15.6 | 2.6 | 283566 |
| PDX-Model#2 | 100 | 95 | 0.0012 | 12.070 | 1.238 | 12.7 | 21.0 | 231005 |
|  | 100 | 94 | 0.0015 | 14.354 | 1.548 | 15.3 | 26.0 | 277640 |
| PDX-Model#3 | 100 | 95 | 0.0014 | 21.021 | 1.524 | 22.1 | 25.0 | 402309 |
|  | 100 | 92 | 0.0041 | 31.633 | 4.434 | 34.4 | 74.0 | 625165 |

TABLE 13

Quantitation and integrity of ctDNA in PDX mice

| Sample ID# | Plasma Extraction Vol (uL) | Elution Final DNA Vol (uL) | Human ctDNA Quantity (ng/ul) | Mouse cfDNA Quantity (ng/ul) | ctDNA in plasma (pg/ul) | Mouse cfDNA in plasma (pg/ul) | Human/ mouse ratio (%) | ctDNA DII-257/80 |
|---|---|---|---|---|---|---|---|---|
| PE-2881 | 60  | 12 | 0.0067 | 0.1957 | 1.330 | 39.141 | 3.40%  | 0.485 |
| PE-2884 | 50  | 14 | 0.0118 | 0.1493 | 3.308 | 41.796 | 7.92%  | 0.514 |
| PE-2888 | 120 | 14 | 0.0151 | 0.3581 | 1.765 | 41.774 | 4.23%  | 0.586 |
| PE-2904 | 50  | 12 | 0.0034 | 0.0605 | 0.827 | 14.523 | 5.69%  | 0.339 |
| PE-2905 | 70  | 11 | 0.0456 | 0.2257 | 7.163 | 35.471 | 20.19% | 0.485 |
| PE-2906 | 59  | 16 | 0.0100 | 0.0526 | 2.699 | 14.258 | 18.93% | 0.452 |
| PE-2908 | 60  | 13 | 0.0015 | 0.0463 | 0.330 | 10.035 | 3.29%  | 0.357 |
| PE-2915 | 50  | 13 | 0.0009 | 0.0205 | 0.230 | 5.324  | 4.31%  | 0.135 |

Example 18: Circulating Tumor DNA (ctDNA) and ctDNA DNA Integrity Index (DII) in PDX Mouse Plasma The use of the SVA long target in conjunction with the Alu target provides a measurement of the integrity of the ctDNA in PDX mice. Presence and integrity of ctDNA in PDX mouse plasma was assessed with eight PDX mouse plasma samples (Table 13). Blood collection, plasma preparation, and DNA extraction methods are the same as the above. The presence of ctDNA in plasma was confirmed with the ALU-Yb8 qPCR assay. Human/mouse ratios ranged from 3.4% to ~20%. DNA integrity index (DII) indicates fragmentation level of DNA, which expressed as Long target quantity/Short target quantity. DII of cell-free DNA in cancer patients' plasmas is lower than healthy individuals. DII can be also useful in monitoring cancer growth as well as cell-free DNA concentrations. The extracted DNA samples were also quantitated with human specific SVA-257 bp target, and DII-257/80 was obtained. The range of DII observed is from 0.135 to 0.586.

The designed primers targeting Alu-Yb8 and SVA can target human DNA and be used for human specific PCR amplification in the presence of excess amount of mouse DNA. From the assays described in Examples 14-16, we can obtain total amount of ctDNA, percent of ctDNA within circulating mouse cell-free DNA, and DNA integrity of ctDNA in PDX mouse plasma. Also, these primers can be used for monitoring circulating tumor cells (CTC) in PDX mouse plasma.

Further Examples Describing a Multiplexed Assay for Quantitating and Assessing Integrity of Cell-Free DNA in Biological Fluids

Example 19: Experimental Design

The objective of certain portions of this work was the development of a three target (one short RE target, one long RE target, and one internal positive control synthetic target) multiplex RE-qPCR assay to accurately and robustly obtain cell-free DNA (cfDNA) concentration and DNA integrity values from normal and CRC patients directly from plasma/ serum samples without DNA purification. The following process was used to address the goal of this work.

Step 1: Identification of Appropriate Multi Copy Targets (ALU, LINE, and/or SVA Element) for Accurate Quantitation of cfDNA Concentration.

Diagnostic potential of cfDNA integrity has been shown to be similar when different interspersed genetic elements are used (ALU and LINE1 in Madhavan, D, et al., *Plasma DNA integrity as a biomarker for primary and metastatic breast cancer and potential marker for early diagnosis*, Breast Cancer Res. Treat. 146(1): 163-74 (2014), doi: 10.1007/s10549-014-2946-2). Diagnostic potential is enhanced when multiple measures (e.g. concentration and integrity) are combined (Hao, T B, et al., *Circulating cell-free DNA in serum as a biomarker for diagnosis and prognostic prediction of colorectal cancer*, British Journal of Cancer 2014: 1-8, doi 10.1038/bjc.2014.470; Madhavan, et al., referenced supra). These results highlight the utility of evaluating different RE-based DNA quantitation methods for determining cfDNA concentration and integrity. In the case of the commonly employed ALU 247/115 protocol, targeted sequences of a single ALU element are used, and thus the two fragments analyzed are not independent. This can lead to less than accurate quantification values. As explained more fully above, the target sequences of the ALU 247/115 protocol cannot be multiplexed, and single-plexing is a much less advantageous experimental arrangement for the present purpose. The system of the present invention is one in which independent targets are used to accurately quantitate concentration and integrity within a single qPCR reaction.

For this application, a qPCR system employing two different sized targets has been assessed with blood serum and plasma samples. Additional targets may be assessed with the purpose of selecting the most accurate targets. Assessment included evaluating the ability of each tested target to accurately quantify DNA as compared to the known quantitation standard NIST SRM 2372 (Human DNA Quantitation Standard). The individual short RE target and long RE target that most accurately quantifies cfDNA and cfDNA integrity in the normal and CRC patient groups will be incorporated into the three-target multiplex. This step enables the identification of optimal targets for the accurate detection of cfDNA and cfDNA integrity.

Step 2: Creation of a Robust Three Target Multiplex Assay to Accurately Quantitate cfDNA Concentration and Integrity.

The two targets identified which most accurately quantify cfDNA concentration and integrity in the normal and CRC patient groups in a single-amplification multiplex reaction are used. The third target is a synthetic internal positive control (IPC) to monitor presence of inhibitors in the sample that can affect the accuracy of cfDNA measurement by qPCR. The approach to achieve the subject goal requires strategic planning as well as multiple attempts to optimize the reaction conditions. The task increases in complexity as one tries to multiplex more primers. There are several published reports that provide guidance to achieve successful PCR multiplexing (Markoulatos, P; Siafakas, N; Moncany, M, *Multiplex polymerase chain reaction: a practical approach*, J. Clin. Lab. Anal. 16(1): 47-51 (2002); Schoske, R; Vallone, P M; Ruitberg, C M; Butler, J M, *Multiplex PCR design strategy used for the simultaneous amplification of 10 Y chromosome short tandem repeat (STR) loci*, Anal. Bioanal. Chem. 375(3): 333-343 (2003); Henegariu, O; Heerema, N A; Dlouhy, S R; Vance, G H; Vogt, P H, *Multiplex PCR: critical parameters and step-by-step protocol*, Biotechniques 23(3): 504-511 (1997); Shuber, A P; Grondin, V J; Klinger, K W, *A simplified procedure for developing multiplex PCRs*, Genome Res. 5(5): 488-493 (1995), doi:10.1101/gr.5.5.488). The parameters to consider for developing a multiplexed PCR system are: 1) Primer length and sequence; 2) Melting temperature of each primer; 3) Relative concentration of primers; 4) Concentration of PCR buffer; 5) Balance between magnesium chloride and dNTP concentration; 6) Cycling Temperatures; 7) Cycling Times; and 8) Taqman probe design. Performance of the multiplex assay has been analyzed in the following ways: melt curve analyses to show sequence specificity of the primer sequences; quantitation of the NIST SRM 2372 human DNA quantitation standard to determine accuracy; and quantitation of a dilution series of the NIST standard to assess sensitivity. This step enables the development of an accurate, sensitive, reproducible, and robust multiplex qPCR assay to determine cfDNA concentration and integrity in a single reaction in less than 2 hours.

Step 3: Determine if and how PCR Inhibition Affects Accuracy of RE-qPCR from Human Blood Plasma and Serum.

Serum and plasma specimens are known to frequently contain PCR inhibitors, including hematin, Immunoglobulin G, and low molecular mass solutes and proteins (Al-Soud, W A; Jönsson, LJ; Rådström, P, *Identification and Characterization of Immunoglobulin G in Blood as a Major Inhibitor of Diagnostic PCR*, J. Clin. Microbiol. 38(1): 345-350 (2000)). These substances can significantly reduce PCR efficiency and cause false negative results. An important contribution of the present multiplex assay is the introduction of a synthetic DNA sequence used as an internal positive control (IPC) within each RE-qPCR reaction. This control evaluates PCR inhibition and determines successful PCR within a sample. Previous work has demonstrated that such a control increases reliability of PCR data by successfully identifying the effect of PCR inhibitors in a specimen (Pineda, G M; Montgomery, A H; Thompson, R; Indest, B; Carroll, M; Sinha, S K, *Development and validation of InnoQuant™, a sensitive human DNA quantitation and degradation assessment method for forensic samples using high copy number mobile elements Alu and SVA*, Forensic Sci. Int. Genet. 13: 224-235 (2014), doi:10.1016/j.fsigen.2014.08.007). Several studies show that the distribution of cfDNA concentration and integrity values from CRC patients and control subjects differ significantly, but the distributions of values are overlapping. It is possible that addressing inhibition may add resolution to these distributions. Incorporation of an IPC in the multiplex allows verification that the PCR reaction took place as expected without inhibitor or other adverse effects. IPC data has been analyzed from both purified DNA and direct RE-qPCR experiments to determine the extent of inhibition with respect to an empirically derived $C_T$ threshold. This step enables utilization of the developed multiplex in a direct qPCR reaction that includes verification of PCR success, while reducing false negative results.

Example 20: Protocol for Serum and Plasma Separation

Serum and plasma separation are performed according to the standard protocol and within four hours of collection, and stored at −80° C. until they are processed. Care is taken to avoid freeze-thaw cycles. For serum specimens, whole blood is collected in the commercially available red-topped test tube Vacutainer (Becton Dickinson). For plasma specimens, whole blood is collected in the commercially available anticoagulant-treated tubes e.g., EDTA-treated (lavender tops) or citrate-treated (light blue tops).

Example 21: Protocol for Direct DNA Quantitation

Two separate protocols have previously been described for direct DNA quantification from either human serum (Umetani, N., et al., *Increased integrity of free circulating DNA in sera of patients with colorectal or periampullary cancer—Direct quantitative PCR for ALU repeats*, Clin. Chem. 52(6): 1062-1069 (2006), doi:10.1373/clinchem.2006.068577) or plasma (Breitbach, S, et al., *Direct quantification of cell-free, circulating DNA from unpurified plasma*, PLOS One 9(3): e87838 (2014), doi: 10.1371/journal.pone.0087838). We have tested both of these methods on serum and plasma in order to compare amplification efficiency from both methods. The first method includes deactivation or elimination of proteins that bind to template DNA or DNA polymerase and might invalidate qPCR results. A volume of 20 µL of each serum or plasma sample is mixed with 20 µL of a preparation buffer that contains 25 mL/L Tween 20, 50 mM Tris, and 1 mM EDTA. This mixture is then digested with 16 µg of proteinase K solution (Qiagen) at 50° C. for 20 min, followed by 5 min of heat deactivation and insolubilization at 95° C. After subsequent centrifugation at 10,000 g for 5 min, 0.2 µL of the supernatant (containing 0.1-µL equivalent volume of serum/plasma) is used as a template for each direct RE-qPCR reaction. The second method bypasses the protein removal step and only requires 1:40 dilution of the serum/plasma sample with sterile $H_2O$.

Example 22: Procedure for DNA Purification

For comparison to and validation of direct quantification of cfDNA, RE-qPCR has been performed on isolated, purified cfDNA. cfDNA may be purified by magnetic bead extraction or by using the silica based membrane QIAamp DNA Investigator Kit (Qiagen).

Example 23: Design of Primers and TaqMan Probes

Primers and labeled probes used in the qPCR reactions may be obtained from Eurofins MWG/Operon, Integrated DNA Technologies, or a variety of other vendors. Primers for amplifying the ALU 115 and ALU 247 fragments and LINE1 79 and 300 fragments have been reported previously (Umetani N, et al., *Increased integrity of free circulating DNA in sera of patients with colorectal or periampullary cancer: Direct quantitative PCR for ALU repeats*, Clin. Chem. 52(6): 1062-1069 (2006), doi:10.1373/clinchem.2006.068577; Mead, R; Duku, M; Bhandari, P; Cree I A, *Circulating tumour markers can define patients with normal colons, benign polyps, and cancers*, Br. J. Cancer 105(2): 239-245 (2011), doi:10.1038/bjc.2011.230).

Primers for our proposed targets ALU Yb8 and SVA were designed and tested. Two short ALU primer sets designed to produce amplicon lengths of 80 bp and 120 bp, among others, were developed for use in the multiplexed assay of the present invention. Four primer sets designed to produce amplicon lengths of 207 bp, 257 bp, 265 bp and 290 bp, among others, were developed using Primer 3 software and an SVA retrotransposon sequence. Because the SVA sequences are truncated in many individuals and also have sequence similarities with ALU sequences in certain regions, the target SVA sequence was selected from the SVA-R region, which has no or minimal sequence similarity as compared with the ALU sequence. FIG. 25 shows a schematic representation of the relative positions of the forward and reverse primers and the double labeled probes for both ALU-Yb8 and SVA sequences for qPCR analysis. The primer sequences are shown in Table 2. Any additional primer design may be done using Primer 3 software (Koressaar, T; Remm, M, *Enhancements and modifications of primer design program Primer3*, Bioinformatics 23(10): 1289-91 (2007), doi:10.1093/bioinformatics/btm091; Untergasser A, et al., *Primer3—new capabilities and interfaces*, Nucleic Acids Res. 40(15): el 15 (2012), doi:10.1093/nar/gks596). Additionally, appropriate probes were developed for use in these amplifications. Probe sequences are also shown in Table 2.

Example 24: Optimization of Oligonucleotide Primers

Primers were evaluated by gel electrophoresis analysis of PCR products, noting the ability of each primer pair to produce a single PCR product when PCR amplification was carried out in the presence of human genomic DNA. Care was taken to ensure that no PCR amplification product was formed in the absence of genomic DNA. Primers were further evaluated using a SYBR green assay and melt curve analysis to examine the specificity of the PCR amplification. FIGS. 26A-26D and 27A-27D show exemplary SYBR green data in the form of an amplification plot, a standard curve, a melt curve and a melt peak (derivative melt curve) for the Yb8-119 and SVA-399 targets.

FIGS. 28A-28D and 29A-29D show the unacceptable SYBR green results obtained for the most common cell free DNA PCR biomarker, which includes ALU-115 and ALU-247 targets. Amplifications based on the ALU-115 and ALU-247 biomarkers were both unsuccessful as shown by primer dimer background in the no template controls.

Results obtained from SYBR green assays for particular primer pairs are summarized in Table 12 below:

TABLE 12

SYBR Green Assay Results for Individual Primer Pairs

| Primer Pair | Optimal Temperature | Results |
|---|---|---|
| Yb8-80 | 61° C. | High efficiency, low levels of DNA detected without any primer dimer background |
| Yb8-119 | 61° C. | Unsuitable due to high primer dimer background |
| Yb8-120 | 62.5° C. | High efficiency, low levels of DNA detected without any primer dimer background |
| SVA-207 | 61° C. | High efficiency, low levels of DNA detected without any primer dimer background |
| SVA-257 | 64° C. | High efficiency, low levels of DNA detected without any primer dimer background |
| SVA-265 | 57° C. | High efficiency, low levels of DNA detected without any primer dimer background |
| SVA-290 | 64° C. | High efficiency, low levels of DNA detected with very low levels of primer dimer background |
| SVA-367 | — | Unsuitable due to high primer dimer background |
| SVA-399 | — | Unsuitable due to high primer dimer background |
| SVA-411 | — | Unsuitable due to high primer dimer background |
| ALU-115 | 64° C. | Primer pairs reported in the prior art indicated high primer dimer background and therefore are not optimal for this application |
| ALU-147 | 64° C. | Primer pair reported in the prior art indicated high primer dimer background and therefore is not optimal for this application |

Example 25: Procedure for qPCR

The qPCR assays may be run on an Applied Biosystems 7500 Real Time PCR instrument and/or the Biorad CFX, but useful instrument platforms are not limited thereto. The qPCR assays of the present invention may be adapted to work on most Real-Time PCR instruments. To assess the concentration and integrity index of serum and plasma circulating cfDNA, both short and long fragments may be amplified and quantified. The short fragment primer sets may amplify the short (apoptotic) DNA fragments, whereas the long fragment primer sets may amplify the long (non-apoptotic) DNA fragments. The RE-qPCR multiplex reaction may contain three targets in a Taqman based assay: a short RE target, a long RE target, and a synthetic IPC sequence. The hybridization probes detecting each target may be labeled with different fluorophores (e.g. FAM, Cy5, or Cy3) to enable simultaneous detection. The following PCR conditions may be used, but they can be modified as necessary: 10 min 95° C. denaturation cycle, followed by 32 cycles of 2-step qPCR (15 s at 95° C. and 2 min at 61° C. combined annealing/extension time) at maximum ramp speed. Additional PCR parameters (i.e. cycle number, denaturation and annealing/extension times and temperatures) are investigated to obtain a robust, sensitive qPCR multiplex.

'Short' Yb8 and 'long' SVA primer pairs selected from those shown in Table 2 above were combined into eight different multiplex sets (Yb8-80 & SVA-207, Yb8-80 & SVA-257, Yb8-80 & SVA-265, Yb8-80 & SVA-290, Yb8-120 & SVA-207, Yb8-120 & SVA-257, Yb8-120 & SVA-265, and Yb8-120 & SVA-290). The optimal temperature for each multiplex was determined by a temperature gradient ranging from 64.0° C. to 55.0° C. The concentration of primers and additives including DMSO and additional MgCl$_2$ were optimized for each multiplex set.

The reaction mixture of each multiplex Yb8-SVA-qPCR included a template, forward primer, reverse primer, fluorescent probe, Brilliant Multiplex QPCR Master Mix (Agilent) and the additives bovine serum albumin ('BSA'), dimethyl sulfoxide ('DMSO'), and magnesium chloride ('MgCl$_2$'). Real-time PCR amplification was performed with pre-cycling heat activation of DNA polymerase at 95° C. for 10 min followed by 32 cycles of denaturation at 95° C. for 15 sec and extension at 61-62.5° C. (depending on the multiplex set) in a CFX96 Touch Real-Time PCR Detection System (Bio-Rad Laboratories). The quantification of DNA in each sample was determined by use of a calibration curve with serial dilutions (5 ng/µL to 1.6 pg/µL). Selected results are shown in FIGS. 30A-30E, 31A-31E, 32A-32E, 33A-33E, 34A-34E, 35A-35E, 36A-36E and 37A-37E.

Example 26: Procedure for qPCR Data Analysis and Quality Control

Data analysis may be performed utilizing the respective AB 7500 or BioRad CFX instrument software. Melt curve analysis may be generated using Qiagen's QuantiTect 1 SYBR1 Green PCR Kit (Cat#204141) and operated using the Applied Biosystems 7500 Real Time PCR instrument. For each experiment, a freshly prepared 3-fold serial dilution of high molecular weight standard DNA (ranging from 10 ng/µL to 0.004 ng/µL) was run in duplicate on each plate to generate standard curves for the long and short targets. The standard curves are plotted $C_T$ vs. Delta $R_n$ (the fluorescence emission intensity of the reporter dye divided by the fluorescence emission intensity of the passive reference dye). Resultant DNA quantitation values are interpolated from the resulting linear standard curves. At least one negative No Template Control (NTC) is run on each plate. The ratio between DNA concentration of the long target divided by DNA concentration of the short target provides an indication as to the degree of DNA integrity for the quantified sample. DNA integrity index is calculated as the ratio of concentrations ([concentration of long RE marker]/[concentration of short RE marker]). Quality metrics, including PCR efficiencies (i.e. slope) of both short and long targets, Y-intercept values, and verification of no true amplification in negative controls was assessed.

Efficiencies and integrity indices (long/short ratio) for some of the multiplex sets named above are shown in Table 13. As noted in Table 12, the primer pairs that performed exceptionally well individually in the SYBR green assay were Yb8-80, Yb8-120, SVA-207, SVA-257, SVA-265, and SVA-290.

TABLE 13

Efficiencies and Integrity Indices for Selected Multiplex Sets

| Short Target | Long Target | Efficiency Short Target | Efficiency Long Target | Integrity Index |
|---|---|---|---|---|
| Yb8-80 | SVA-207 | 101.8% | 101.7% | 0.995 |
| Yb8-80 | SVA-257 | 99.4 | 90.5 | 1.041 |
| Yb8-80 | SVA-265 | 99.9 | 98.3 | 1.069 |
| Yb8-80 | SVA-290 | 101.2 | 99.3 | 1.089 |
| Yb8-120 | SVA-207 | 99.9 | 93.5 | 0.786 |
| Yb8-120 | SVA-257 | 105.3 | 95.0 | 1.15 |
| Yb8-120 | SVA-265 | 98.7 | 95.9 | 1.046 |
| Yb8-120 | SVA-290 | 99.0 | 96.3 | 1.12 |

While the invention has been described in connection with specific and preferred embodiments thereof, it is capable of further modifications without departing from the spirit and scope of the invention. This application is intended to cover all variations, uses, or adaptations of the invention, following, in general, the principles of the invention and including such departures from the present disclosure as come within known or customary practice within the art to which the invention pertains, or as are obvious to persons skilled in the art, at the time the departure is made. It should be appreciated that the scope of this invention is not limited to the detailed description of the invention hereinabove, which is intended merely to be illustrative, but rather comprehends the subject matter defined by the following claims.

What is claimed is:

1. A method for assessing tumor burden in a patient-derived xenograft (PDX) mouse, the method comprising:
providing a sample taken from a patient-derived xenograft (PDX) mouse;
using a real-time polymerase chain reaction system to separately quantitate within the sample human DNA including a first retrotransposon interspersed element and mouse DNA including a mouse retrotransposon interspersed element, the first retrotransposon interspersed element being an Alu element found in the human genome or an SVA element of the human retinitis pigmentosa (RP) gene, the mouse retrotransposon interspersed element being found in the genome of the mouse;
the real-time polymerase chain reaction system comprising a second set of nucleic acid sequences for quantitation of the mouse retrotransposon interspersed element, the second set of nucleic acid sequences including a forward primer having a structure defined as 5'-GACCAAGACTCGTGAGGATAAC-3' (SEQ ID NO: 28), a reverse primer having a structure defined as 5'-CCAGTGTTGGGTCAGGTTTA-3' (SEQ ID NO: 29) and a probe including a structure defined as 5'-AGTCGTGGAGGTAGAAATATGGCAGAGA-3' (SEQ ID NO: 30); and
assessing a tumor burden based on said quantitations.

2. The method of claim 1, the sample being a blood sample.

3. The method of claim 2, a volume of the sample being about 200 μL or less.

4. The method of claim 3, the volume of the sample being from about 25 μL to about 100 μl.

5. The method of claim 1, the *Alu* element being an *Alu* Yb8 target genetic sequence.

6. The method of claim 5, the real-time polymerase chain reaction system making use of a first set of nucleic acid sequences for amplification of the Alu element or a first set of nucleic acid sequences for amplification of the human SVA element, the set of nucleic acid sequences for amplification of the Alu element including a forward primer having a structure defined as 5'-GGAAGCGGAGCTTGCAGTGA-3' (SEQ ID NO: 5), a reverse primer having a structure defined as 5'-AGACGGAGTCTCGCTCTGTCGC-3' (SEQ ID NO: 6) and a probe including a structure defined as 5'-AGATTGCGCCACTGCAGTCCGCAGT-3' (SEQ ID NO: 36), the set of nucleic acid sequences for amplification of the SVA element including one of the following groups of nucleic acid sequences, where one group includes a forward primer having a structure defined as 5'-CTGTGTCCACTCAGGGTTAAAT-3' (SEQ ID NO: 38), a reverse primer having a structure defined as 5'-GAGGGAAGGTCAGCAGATAAAC-3' (SEQ ID NO: 39) and a probe including a structure defined as 5'-AAGGGCGGTGCAAGATGTGCTTTGTT-3' (SEQ ID NO: 10), another group includes a forward primer having a structure defined as 5'-CCTGTGCTCTCTGAAACATGTGCT-3' (SEQ ID NO: 41), a reverse primer having a structure defined as 5'-GATTTGGCAGGGTCATGGGACAAT-3' (SEQ ID NO: 9) and a probe including a structure defined as 5'-AAGGGCGGTGCAAGATGTGCTTTGTT-3' (SEQ ID NO: 10), and another group includes a forward primer having a structure defined as 5'-ATGTGCTGTGTCCACTCAGGGTTA-3' (SEQ ID NO: 11), a reverse primer having a structure defined as 5'-ATTCTTGGGTGTTTCTCACAGAGG-3' (SEQ ID NO: 13) and a probe including a structure defined as 5'-AAGGGCGGTGCAAGATGTGCTTTGTT-3' (SEQ ID NO: 10).

7. The method of claim 1, where the first retrotransposon interspersed element and the mouse retrotransposon interspersed element do not exhibit any significant cross reactivity with respect to real-time polymerase chain reaction amplification.

8. The method of claim 1, the method further comprising:
determining a ratio of human DNA to mouse DNA in the sample using quantitation results provided by the real-time polymerase chain reaction system; and
considering the ratio as an indication of an extent of tumor growth intensity in the mouse.

9. The method of claim 8, the providing, using, determining and considering steps being performed multiple times in repetition over a time interval, the samples being taken serially from the same PDX mouse, the resulting ratios serving to characterize tumor growth in the mouse over time.

10. The method of claim 8, the providing, using, determining and considering steps being performed on each of a series of samples, each sample being taken from a different PDX mouse, the resulting ratios serving to assist a researcher in selecting one or more PDX mice for further study.

11. The method of claim 8, the method further comprising:
treating the PDX mouse with a putative or potential anti-cancer drug prior to the providing step; and
accepting the ratio as a predictor of likely efficacy of the drug in a human patient.

12. The method of claim 1, the mouse surviving the taking of the sample.

13. The method of claim 1, the quantitation of the human DNA and the quantitation of the mouse DNA being performed simultaneously.

14. The method of claim 1, where the sample is derived from circulating tumor cells metastasizing by way of the plasma in the PDX mouse, the assessed tumor burden being attributed to circulating tumor cells.

\* \* \* \* \*

SEQUENCE LISTING

<160> NUMBER OF SEQ ID NOS: 59

<210> SEQ ID NO 1
<211> LENGTH: 23
<212> TYPE: DNA
<213> ORGANISM: Artificial Sequence
<220> FEATURE:
<223> OTHER INFORMATION: A first forward primer for determining an
      approximately 250 base pair fragment in the alu Ya5 subfamily in a
      human nuclear DNA quantitation assay

<400> SEQUENCE: 1
tcacgcctgt aatcccagca ctt                                           23

<210> SEQ ID NO 2
<211> LENGTH: 23
<212> TYPE: DNA
<213> ORGANISM: Artificial Sequence
<220> FEATURE:

```
<223> OTHER INFORMATION: A second forward primer for determining an
      approximately 250 base pair fragment in the Alu Ya5 subfamily in a
      human nuclear DNA quantitation assay

<400> SEQUENCE: 2
acgcctgtaa tcccagcact ttg                                              23

<210> SEQ ID NO 3
<211> LENGTH: 20
<212> TYPE: DNA
<213> ORGANISM: Artificial Sequence
<220> FEATURE:
<223> OTHER INFORMATION: Reverse primer for determining an approximately
      250 base pair fragment in the Alu Ya5 subfamily in a human nuclear
      DNA quantitation assay

<400> SEQUENCE: 3
tctgtcgccc aggctggagt                                                  20

<210> SEQ ID NO 4
<211> LENGTH: 27
<212> TYPE: DNA
<213> ORGANISM: Artificial Sequence
<220> FEATURE:
<223> OTHER INFORMATION: Probe for an approximately 250 base pair
      fragment in the Alu Ya5 subfamily, the probe being useful in a
      human nuclear DNA quantitation assay

<400> SEQUENCE: 4
atcacgaggt caggagatcg agaccat                                          27

<210> SEQ ID NO 5
<211> LENGTH: 20
<212> TYPE: DNA
<213> ORGANISM: Artificial Sequence
<220> FEATURE:
<223> OTHER INFORMATION: Forward primer for an approximately 80 base
      pair fragment in the Yb8 Alu subfamily in a human nuclear DNA
      quantitation assay

<400> SEQUENCE: 5
ggaagcggag cttgcagtga                                                  20

<210> SEQ ID NO 6
<211> LENGTH: 22
<212> TYPE: DNA
<213> ORGANISM: Artificial Sequence
<220> FEATURE:
<223> OTHER INFORMATION: Reverse primer for an approximately 80 base
      pair fragment in the Yb8 Alu subfamily in a human nuclear DNA
      quantitation assay

<400> SEQUENCE: 6
agacggagtc tcgctctgtc gc                                               22

<210> SEQ ID NO 7
<211> LENGTH: 24
<212> TYPE: DNA
<213> ORGANISM: Artificial Sequence
<220> FEATURE:
<223> OTHER INFORMATION: Probe for an approximately 80 base pair
      fragment in the Yb8 Alu subfamily in a human nuclear DNA
      quantitation assay

<400> SEQUENCE: 7
agattgcgcc actgcagtcc gcag                                             24
```

```
<210> SEQ ID NO 8
<211> LENGTH: 24
<212> TYPE: DNA
<213> ORGANISM: Artificial Sequence
<220> FEATURE:
<223> OTHER INFORMATION: Forward primer for an approximately 290 base
      pair SVA fragment useful in a human nuclear DNA quantitation assay

<400> SEQUENCE: 8
tgggatcctg ttgatctgtg acct                                              24

<210> SEQ ID NO 9
<211> LENGTH: 24
<212> TYPE: DNA
<213> ORGANISM: Artificial Sequence
<220> FEATURE:
<223> OTHER INFORMATION: Reverse primer for an approximately 290 base
      pair SVA fragment useful in a human nuclear DNA quantitation assay

<400> SEQUENCE: 9
gatttggcag ggtcatggga caat                                              24

<210> SEQ ID NO 10
<211> LENGTH: 26
<212> TYPE: DNA
<213> ORGANISM: Artificial Sequence
<220> FEATURE:
<223> OTHER INFORMATION: Probe for an approximately 290 base pair SVA
      fragment useful in a human nuclear DNA quantitation assay

<400> SEQUENCE: 10
aagggcggtg caagatgtgc tttgtt                                            26

<210> SEQ ID NO 11
<211> LENGTH: 24
<212> TYPE: DNA
<213> ORGANISM: Artificial Sequence
<220> FEATURE:
<223> OTHER INFORMATION: Forward primer for an SVA fragment useful in a
      human nuclear DNA quantitation assay

<400> SEQUENCE: 11
atgtgctgtg tccactcagg gtta                                              24

<210> SEQ ID NO 12
<211> LENGTH: 24
<212> TYPE: DNA
<213> ORGANISM: Artificial Sequence
<220> FEATURE:
<223> OTHER INFORMATION: A first reverse primer for an SVA fragment
      useful in a human nuclear DNA quantitation assay

<400> SEQUENCE: 12
ttcttgggtg tttctcacag aggg                                              24

<210> SEQ ID NO 13
<211> LENGTH: 24
<212> TYPE: DNA
<213> ORGANISM: Artificial Sequence
<220> FEATURE:
<223> OTHER INFORMATION: A second reverse primer for an SVA fragment
      useful in a human nuclear DNA quantitation assay

<400> SEQUENCE: 13
attcttgggt gtttctcaca gagg                                              24

<210> SEQ ID NO 14
```

```
<211> LENGTH: 22
<212> TYPE: DNA
<213> ORGANISM: Artificial Sequence
<220> FEATURE:
<223> OTHER INFORMATION: Forward primer for an SVA fragment useful in a
      human nuclear DNA quantitation assay

<400> SEQUENCE: 14
ccaaccctgt gctctctgaa ac                                              22

<210> SEQ ID NO 15
<211> LENGTH: 21
<212> TYPE: DNA
<213> ORGANISM: Artificial Sequence
<220> FEATURE:
<223> OTHER INFORMATION: Reverse primer for an SVA fragment useful in a
      human nuclear DNA quantitation assay

<400> SEQUENCE: 15
tttggcaggg tcatgggaca a                                               21

<210> SEQ ID NO 16
<211> LENGTH: 24
<212> TYPE: DNA
<213> ORGANISM: Artificial Sequence
<220> FEATURE:
<223> OTHER INFORMATION: Forward primer for a 90 base pair internal
      positive control that is useful for determining an extent of
      inhibition in a human nuclear DNA quantitation assay

<400> SEQUENCE: 16
aaagatcctg ccaacaggac agtg                                            24

<210> SEQ ID NO 17
<211> LENGTH: 24
<212> TYPE: DNA
<213> ORGANISM: Artificial Sequence
<220> FEATURE:
<223> OTHER INFORMATION: Reverse primer for a 90 base pair internal
      positive control that is useful for determining an extent of
      inhibition in a human nuclear DNA quantitation assay

<400> SEQUENCE: 17
acagacggta tagagaccaa tcag                                            24

<210> SEQ ID NO 18
<211> LENGTH: 21
<212> TYPE: DNA
<213> ORGANISM: Artificial Sequence
<220> FEATURE:
<223> OTHER INFORMATION: Forward primer for a 158 base pair internal
      positive control that
 is useful for determining an extent of inhibition in a human
      nuclear DNA quantitation assay

<400> SEQUENCE: 18
gcataaagat cctgccaaca g                                               21

<210> SEQ ID NO 19
<211> LENGTH: 21
<212> TYPE: DNA
<213> ORGANISM: Artificial Sequence
<220> FEATURE:
<223> OTHER INFORMATION: Reverse primer for a 158 base pair internal
      positive control that is useful for determining an extent of
      inhibition in a human nuclear DNA quantitation assay

<400> SEQUENCE: 19
```

```
accaaagtgc tgcagaaata c                                          21
```

<210> SEQ ID NO 20
<211> LENGTH: 28
<212> TYPE: DNA
<213> ORGANISM: Artificial Sequence
<220> FEATURE:
<223> OTHER INFORMATION: Probe for the internal positive control assay,
      the probe being useful in the assay including three targets--a
      "short" Yb8 Alu fragment, a "long" SVA fragment and the internal
      positive control

<400> SEQUENCE: 20

```
aggcagagat tgcactgcct taaagtgg                                   28
```

<210> SEQ ID NO 21
<211> LENGTH: 21
<212> TYPE: DNA
<213> ORGANISM: Artificial Sequence
<220> FEATURE:
<223> OTHER INFORMATION: Forward primer for an internal positive control
      that is useful for determining an extent of inhibition in a human
      nuclear DNA quantitation assay incorporating an assay for a male
      specific DNA target sequence to detect male DNA in the sample

<400> SEQUENCE: 21

```
gcataaagat cctgccaaca g                                          21
```

<210> SEQ ID NO 22
<211> LENGTH: 20
<212> TYPE: DNA
<213> ORGANISM: Artificial Sequence
<220> FEATURE:
<223> OTHER INFORMATION: Reverse primer for a 172 base pair internal
      positive control that is useful for determining an extent of
      inhibition in a human nuclear DNA quantitation assay incorporating
      an assay for a male specific DNA target sequence to detect male
      DNA in the sample

<400> SEQUENCE: 22

```
gcccgaactt ccaacactat                                            20
```

<210> SEQ ID NO 23
<211> LENGTH: 20
<212> TYPE: DNA
<213> ORGANISM: Artificial Sequence
<220> FEATURE:
<223> OTHER INFORMATION: Reverse primer for a 192 base pair internal
      positive control that is useful for determining an extent of
      inhibition in a human nuclear DNA quantitation assay incorporating
      an assay for a male specific DNA target sequence to detect male
      DNA in the sample

<400> SEQUENCE: 23

```
attgttcctc ctgcctgatt                                            20
```

<210> SEQ ID NO 24
<211> LENGTH: 24
<212> TYPE: DNA
<213> ORGANISM: Artificial Sequence
<220> FEATURE:
<223> OTHER INFORMATION: Probe for the internal positive control assay,
      the probe being useful in the assay including four targets--a
      "short" Yb8 fragment, a "long" SVA fragment, a male specific DNA
      target sequence to detect male DNA and the internal positive
      control

<400> SEQUENCE: 24

```
acagtgtcag gcagagattg cact                                       24
```

<210> SEQ ID NO 25
<211> LENGTH: 24
<212> TYPE: DNA
<213> ORGANISM: Artificial Sequence
<220> FEATURE:
<223> OTHER INFORMATION: Forward primer for male specific DNA target
sequence for detecting male DNA

<400> SEQUENCE: 25
caatgtgcta ggctctagga atac                                    24

<210> SEQ ID NO 26
<211> LENGTH: 22
<212> TYPE: DNA
<213> ORGANISM: Artificial Sequence
<220> FEATURE:
<223> OTHER INFORMATION: Reverse primer for the male specific DNA target
sequence for
detecting male DNA

<400> SEQUENCE: 26
aagagtgtca tggctcaaag ag                                      22

<210> SEQ ID NO 27
<211> LENGTH: 27
<212> TYPE: DNA
<213> ORGANISM: Artificial Sequence
<220> FEATURE:
<223> OTHER INFORMATION: Probe for the male specific DNA target sequence
for detecting male DNA

<400> SEQUENCE: 27
agagagtatg acaaacatgg catgggc                                 27

<210> SEQ ID NO 28
<211> LENGTH: 22
<212> TYPE: DNA
<213> ORGANISM: Artificial Sequence
<220> FEATURE:
<223> OTHER INFORMATION: Forward primer for mouse beta-2 microglobulin
(Bm2)

<400> SEQUENCE: 28
gaccaagact cgtgaggata ac                                      22

<210> SEQ ID NO 29
<211> LENGTH: 20
<212> TYPE: DNA
<213> ORGANISM: Artificial Sequence
<220> FEATURE:
<223> OTHER INFORMATION: Reverse primer for Mouse Beta-2 microglobulin
(B2m)

<400> SEQUENCE: 29
ccagtgttgg gtcaggttta                                         20

<210> SEQ ID NO 30
<211> LENGTH: 28
<212> TYPE: DNA
<213> ORGANISM: Artificial Sequence
<220> FEATURE:
<223> OTHER INFORMATION: Probe for mouse beta-2 microglobulin (B2m)

<400> SEQUENCE: 30
agtcgtggag gtagaaatat ggcagaga                                28

```
<210> SEQ ID NO 31
<211> LENGTH: 28
<212> TYPE: DNA
<213> ORGANISM: Artificial Sequence
<220> FEATURE:
<223> OTHER INFORMATION: Labeled probe for mouse beta-2 microglobulin
      (B2m), where n is adenine having Cy5 dye covalently bound
<220> FEATURE:
<221> NAME/KEY: misc_feature
<222> LOCATION: (1)..(1)
<223> OTHER INFORMATION: n is adenine having Cy5 dye covalently bound

<400> SEQUENCE: 31
ngtcgtggag gtagaaatat ggcagaga                                           28

<210> SEQ ID NO 32
<211> LENGTH: 18
<212> TYPE: DNA
<213> ORGANISM: Artificial Sequence
<220> FEATURE:
<223> OTHER INFORMATION: Forward primer for mouse L1Md-Tf18

<400> SEQUENCE: 32
cctaagccac agcagcag                                                      18

<210> SEQ ID NO 33
<211> LENGTH: 21
<212> TYPE: DNA
<213> ORGANISM: Artificial Sequence
<220> FEATURE:
<223> OTHER INFORMATION: Reverse primer for mouse L1Md-Tf18

<400> SEQUENCE: 33
ccctctcacc tgttcagact a                                                  21

<210> SEQ ID NO 34
<211> LENGTH: 23
<212> TYPE: DNA
<213> ORGANISM: Artificial Sequence
<220> FEATURE:
<223> OTHER INFORMATION: Probe for mouse L1Md-Tf18

<400> SEQUENCE: 34
atttcctaag ttcggcgggt ccc                                                23

<210> SEQ ID NO 35
<211> LENGTH: 23
<212> TYPE: DNA
<213> ORGANISM: Artificial Sequence
<220> FEATURE:
<223> OTHER INFORMATION: Labeled probe for mouse L1Md-Tf18, where the
      label is adenine bearing Cy5 dye covalently bound
<220> FEATURE:
<221> NAME/KEY: misc_feature
<222> LOCATION: (1)..(1)
<223> OTHER INFORMATION: n is adenine bearing Cy5 dye covalently bound

<400> SEQUENCE: 35
ntttcctaag ttcggcgggt ccc                                                23

<210> SEQ ID NO 36
<211> LENGTH: 25
<212> TYPE: DNA
<213> ORGANISM: Artificial Sequence
<220> FEATURE:
<223> OTHER INFORMATION: Probe for human Alu-Yb8

<400> SEQUENCE: 36
```
agattgcgcc actgcagtcc gcagt                                      25

<210> SEQ ID NO 37
<211> LENGTH: 25
<212> TYPE: DNA
<213> ORGANISM: Artificial Sequence
<220> FEATURE:
<223> OTHER INFORMATION: Labeled probe for human Alu-Yb8, where the
      label is adenine bearing either HEX or FAM dye covalently bound
<220> FEATURE:
<221> NAME/KEY: misc_feature
<222> LOCATION: (1)..(1)
<223> OTHER INFORMATION: n is adenine bearing either HEX or FAM dye
      covalently bound

<400> SEQUENCE: 37
ngattgcgcc actgcagtcc gcagt                                      25

<210> SEQ ID NO 38
<211> LENGTH: 22
<212> TYPE: DNA
<213> ORGANISM: Artificial Sequence
<220> FEATURE:
<223> OTHER INFORMATION: Forward primer for human SVA 207 bp

<400> SEQUENCE: 38
ctgtgtccac tcagggttaa at                                         22

<210> SEQ ID NO 39
<211> LENGTH: 22
<212> TYPE: DNA
<213> ORGANISM: Artificial Sequence
<220> FEATURE:
<223> OTHER INFORMATION: Reverse primer for human SVA 207 bp

<400> SEQUENCE: 39
gagggaaggt cagcagataa ac                                         22

<210> SEQ ID NO 40
<211> LENGTH: 26
<212> TYPE: DNA
<213> ORGANISM: Artificial Sequence
<220> FEATURE:
<223> OTHER INFORMATION: Labeled probe for human SVA 207 bp, where the
      label is adenine having either Cy5, HEX, or FAM dye covalently
      bound
<220> FEATURE:
<221> NAME/KEY: misc_feature
<222> LOCATION: (1)..(1)
<223> OTHER INFORMATION: n is adenine having either Cy5, HEX, or FAM dye
      covalently bound

<400> SEQUENCE: 40
nagggcggtg caagatgtgc tttgtt                                     26

<210> SEQ ID NO 41
<211> LENGTH: 24
<212> TYPE: DNA
<213> ORGANISM: Artificial Sequence
<220> FEATURE:
<223> OTHER INFORMATION: Forward primer for human SVA 257 bp

<400> SEQUENCE: 41
cctgtgctct ctgaaacatg tgct                                       24

<210> SEQ ID NO 42
<211> LENGTH: 19

```
<212> TYPE: DNA
<213> ORGANISM: Artificial Sequence
<220> FEATURE:
<223> OTHER INFORMATION: Forward primer for human Alu 119 bp

<400> SEQUENCE: 42
agaccatcct ggctaacaa                                                    19

<210> SEQ ID NO 43
<211> LENGTH: 17
<212> TYPE: DNA
<213> ORGANISM: Artificial Sequence
<220> FEATURE:
<223> OTHER INFORMATION: Reverse primer for human Alu 119 bp

<400> SEQUENCE: 43
gccattctcc tgcctca                                                      17

<210> SEQ ID NO 44
<211> LENGTH: 22
<212> TYPE: DNA
<213> ORGANISM: Artificial Sequence
<220> FEATURE:
<223> OTHER INFORMATION: Probe for human Alu 119 bp

<400> SEQUENCE: 44
tgtagtccca gctactcggg ag                                                22

<210> SEQ ID NO 45
<211> LENGTH: 21
<212> TYPE: DNA
<213> ORGANISM: Artificial Sequence
<220> FEATURE:
<223> OTHER INFORMATION: Forward primer for human Alu 120 bp

<400> SEQUENCE: 45
tggatcatga ggtcaggaga t                                                 21

<210> SEQ ID NO 46
<211> LENGTH: 19
<212> TYPE: DNA
<213> ORGANISM: Artificial Sequence
<220> FEATURE:
<223> OTHER INFORMATION: Reverse primer for human Alu 120 bp

<400> SEQUENCE: 46
ccgagtagct gggactaca                                                    19

<210> SEQ ID NO 47
<211> LENGTH: 26
<212> TYPE: DNA
<213> ORGANISM: Artificial Sequence
<220> FEATURE:
<223> OTHER INFORMATION: Probe for human Alu 120 bp

<400> SEQUENCE: 47
accatcctgg ctaacaaggt gaaacc                                            26

<210> SEQ ID NO 48
<211> LENGTH: 21
<212> TYPE: DNA
<213> ORGANISM: Artificial Sequence
<220> FEATURE:
<223> OTHER INFORMATION: Forward primer for human Alu 123 bp

<400> SEQUENCE: 48
```

```
atcctggcta acaaggtcaa a                                              21
```

<210> SEQ ID NO 49
<211> LENGTH: 17
<212> TYPE: DNA
<213> ORGANISM: Artificial Sequence
<220> FEATURE:
<223> OTHER INFORMATION: Reverse primer for human Alu 123 bp

<400> SEQUENCE: 49

```
cgggttcacg ccattct                                                   17
```

<210> SEQ ID NO 50
<211> LENGTH: 20
<212> TYPE: DNA
<213> ORGANISM: Artificial Sequence
<220> FEATURE:
<223> OTHER INFORMATION: Forward primer for human SVA 355 bp

<400> SEQUENCE: 50

```
gttgccgtgt ctgtgtagaa                                                20
```

<210> SEQ ID NO 51
<211> LENGTH: 20
<212> TYPE: DNA
<213> ORGANISM: Artificial Sequence
<220> FEATURE:
<223> OTHER INFORMATION: Reverse primer for human SVA 355 bp

<400> SEQUENCE: 51

```
atgggacaat agtggaggga                                                20
```

<210> SEQ ID NO 52
<211> LENGTH: 24
<212> TYPE: DNA
<213> ORGANISM: Artificial Sequence
<220> FEATURE:
<223> OTHER INFORMATION: Forward primer for human SVA 367 bp

<400> SEQUENCE: 52

```
ccgtgtctgt gtagaaagaa gtag                                           24
```

<210> SEQ ID NO 53
<211> LENGTH: 18
<212> TYPE: DNA
<213> ORGANISM: Artificial Sequence
<220> FEATURE:
<223> OTHER INFORMATION: Reverse primer for human SVA 367 bp

<400> SEQUENCE: 53

```
gggatttggc agggtcat                                                  18
```

<210> SEQ ID NO 54
<211> LENGTH: 19
<212> TYPE: DNA
<213> ORGANISM: Artificial Sequence
<220> FEATURE:
<223> OTHER INFORMATION: Forward primer for human SVA 399 bp

<400> SEQUENCE: 54

```
ggcggctttg tggaataga                                                 19
```

<210> SEQ ID NO 55
<211> LENGTH: 22
<212> TYPE: DNA
<213> ORGANISM: Artificial Sequence

```
<220> FEATURE:
<223> OTHER INFORMATION: Reverse primer for human SVA 399 bp

<400> SEQUENCE: 55
gagggaaggt cagcagataa ac                                              22

<210> SEQ ID NO 56
<211> LENGTH: 24
<212> TYPE: DNA
<213> ORGANISM: Artificial Sequence
<220> FEATURE:
<223> OTHER INFORMATION: Probe for human SVA 399 bp

<400> SEQUENCE: 56
atcagggaca caaacactgc ggaa                                            24

<210> SEQ ID NO 57
<211> LENGTH: 22
<212> TYPE: DNA
<213> ORGANISM: Artificial Sequence
<220> FEATURE:
<223> OTHER INFORMATION: Forward primer for human SVA 411 bp

<400> SEQUENCE: 57
tggaatagaa aggcaggaaa gg                                              22

<210> SEQ ID NO 58
<211> LENGTH: 20
<212> TYPE: DNA
<213> ORGANISM: Artificial Sequence
<220> FEATURE:
<223> OTHER INFORMATION: Reverse primer for human SVA 411 bp

<400> SEQUENCE: 58
gcagggtcat gggacaatag                                                 20

<210> SEQ ID NO 59
<211> LENGTH: 172
<212> TYPE: DNA
<213> ORGANISM: Artificial Sequence
<220> FEATURE:
<223> OTHER INFORMATION: Synthetic target sequence for use as an
      internal positive control

<400> SEQUENCE: 59
gcataaagat cctgccaaca ggacagtgtc aggcagagat tgcactgcct taaagtggac      60
ttaagataag tactgattgg tctctatacc gtctgtaccc tttgaaaact ggcacaagac    120
agggatgccc tctctcaccg ctcctattca acatagtgtt ggaagttcgg gc            172
```